United States Patent
Bagaev et al.

(10) Patent No.: US 10,636,514 B2
(45) Date of Patent: *Apr. 28, 2020

(54) USING SUBJECT SEQUENCING DATA AND A DATABASE OF THERAPY BIOMARKER DISTRIBUTIONS TO DETERMINE NORMALIZED BIOMARKER SCORES AND THERAPY SCORES

(71) Applicant: BostonGene Corporation, Waltham, MA (US)

(72) Inventors: Alexander Bagaev, Moscow (RU); Feliks Frenkel, Moscow (RU); Ravshan Ataullakhanov, Moscow (RU)

(73) Assignee: BostonGene Corporation, Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/676,375

(22) Filed: Nov. 6, 2019

(65) Prior Publication Data

US 2020/0075131 A1 Mar. 5, 2020

Related U.S. Application Data

(63) Continuation of application No. 16/662,280, filed on Oct. 24, 2019, which is a continuation of application No. 16/456,370, filed on Jun. 28, 2019, now Pat. No. 10,504,615, which is a continuation of application No. 16/006,279, filed on Jun. 12, 2018, now Pat. No. 10,340,030, application No. 16/676,375, which is a continuation of application No. 16/456,462, filed on Jun. 28, 2019, which is a continuation of application No. 16/006,340, filed on Jun. 12, 2018, now Pat. No. 10,340,031.

(60) Provisional application No. 62/598,440, filed on Dec. 13, 2017, provisional application No. 62/518,787, filed on Jun. 13, 2017.

(51) Int. Cl.

| | | |
|---|---|---|
| *G16B 45/00* | (2019.01) | |
| *G16H 20/00* | (2018.01) | |
| *G16H 50/20* | (2018.01) | |
| *G06F 17/18* | (2006.01) | |
| *C12Q 1/6886* | (2018.01) | |
| *G16H 70/20* | (2018.01) | |
| *G06F 16/28* | (2019.01) | |
| *G16H 20/10* | (2018.01) | |
| *G16H 50/30* | (2018.01) | |
| *G16B 40/00* | (2019.01) | |
| *G16H 50/70* | (2018.01) | |
| *G16H 50/50* | (2018.01) | |
| *G16B 20/00* | (2019.01) | |
| *G16H 20/40* | (2018.01) | |
| *G16H 10/20* | (2018.01) | |
| *G16B 50/00* | (2019.01) | |
| *G16B 5/00* | (2019.01) | |

(52) U.S. Cl.
CPC .......... *G16B 45/00* (2019.02); *C12Q 1/6886* (2013.01); *G06F 16/285* (2019.01); *G06F 17/18* (2013.01); *G16B 5/00* (2019.02); *G16B 20/00* (2019.02); *G16B 40/00* (2019.02); *G16B 50/00* (2019.02); *G16H 10/20* (2018.01); *G16H 20/00* (2018.01); *G16H 20/10* (2018.01); *G16H 20/40* (2018.01); *G16H 50/20* (2018.01); *G16H 50/30* (2018.01); *G16H 50/50* (2018.01); *G16H 50/70* (2018.01); *G16H 70/20* (2018.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 10,311,967 B2 | 6/2019 | Bagaev et al. |
| 10,340,030 B2 | 7/2019 | Bagaev et al. |

(Continued)

FOREIGN PATENT DOCUMENTS

| | | |
|---|---|---|
| WO | WO 2015/073896 A2 | 5/2015 |
| WO | WO 2017/013436 A1 | 1/2017 |
| WO | WO 2017/093764 A1 | 6/2017 |

OTHER PUBLICATIONS

U.S. Appl. No. 16/006,340 Applicant Remarks Made in an Amendment filed Apr. 11, 2019, 11 pages.*

(Continued)

*Primary Examiner* — G Steven Vanni
(74) *Attorney, Agent, or Firm* — Wolf, Greenfield & Sacks, P.C.

(57) ABSTRACT

Techniques for determining therapy scores for at least two of an anti-PD1 therapy, an anti-CTLA4 therapy, an IL-2 therapy, an IFN alpha therapy, an anti-cancer vaccine therapy, an anti-angiogenic therapy, and an anti-CD20 therapy. The techniques include determining, using sequencing data for the subject and information indicating distribution of biomarker values across one or more reference populations, a first set of normalized biomarker scores for a first set of biomarkers associated with a first therapy; and a second set of normalized biomarker scores for a second set of biomarkers associated with a second therapy; providing the first set of normalized biomarker scores as input to a statistical model to obtain a first therapy score for the first therapy; and providing the second set of normalized biomarker scores as input to the statistical model to obtain a second therapy score for the second therapy.

30 Claims, 25 Drawing Sheets

(56) References Cited

U.S. PATENT DOCUMENTS

| | | | |
|---|---|---|---|
| 10,340,031 | B2 | 7/2019 | Bagaev et al. |
| 10,504,615 | B2 | 12/2019 | Bagaev et al. |
| 2006/0127928 | A1 | 6/2006 | Bacus et al. |
| 2007/0172844 | A1 | 7/2007 | Lancaster et al. |
| 2008/0153098 | A1 | 6/2008 | Rimm et al. |
| 2009/0105167 | A1 | 4/2009 | Potti et al. |
| 2014/0220580 | A1 | 8/2014 | Brown et al. |
| 2014/0342924 | A1 | 11/2014 | Harkin et al. |
| 2016/0123964 | A1 | 5/2016 | Tumeh et al. |
| 2016/0312286 | A1 | 10/2016 | Brandon et al. |
| 2018/0357361 | A1 | 12/2018 | Frenkel et al. |
| 2018/0357372 | A1 | 12/2018 | Bagaev et al. |
| 2018/0357373 | A1 | 12/2018 | Bagaev et al. |
| 2018/0357374 | A1 | 12/2018 | Bagaev et al. |
| 2018/0357376 | A1 | 12/2018 | Bagaev et al. |
| 2018/0358118 | A1 | 12/2018 | Bagaev et al. |
| 2018/0358125 | A1 | 12/2018 | Bagaev et al. |
| 2018/0358128 | A1 | 12/2018 | Bagaev et al. |
| 2018/0358132 | A1 | 12/2018 | Bagaev et al. |
| 2019/0179998 | A9 | 6/2019 | Frenkel et al. |
| 2019/0243943 | A9 | 8/2019 | Bagaev et al. |
| 2019/0325993 | A1 | 10/2019 | Bagaev et al. |
| 2019/0332744 | A9 | 10/2019 | Bagaev et al. |

OTHER PUBLICATIONS

International Search Report and Written Opinion for International Application No. PCT/US2018/037008 dated Sep. 21, 2018.
International Search Report and Written Opinion for International Application No. PCT/US2018/037018 dated Sep. 21, 2018.
International Search Report and Written Opinion for International Application No. PCT/US2018/037017 dated Sep. 25, 2018.
[No Author Listed] Atezolizumab (TECENTRIQ). FDA U.S. Food & Drug Administration. https://www.fda.gov/drugs/informationondrugs/approveddrugs/ucm525780.htm Last updated Oct. 19, 2016. Last accessed Jul. 26, 2018. 2 pages.
[No Author Listed] Bevacizumab. FDA U.S. Food & Drug Administration. https://web.archive.org/web/20170111231723/https://www.fda.gov/Drugs/InformationOnDrugs/ApprovedDrugs/ucm336763.htm Last updated Oct. 9, 2015. Last accessed via WayBackMachine Jul. 26, 2018. 1 page.
[No Author Listed] Elotuzumab. FDA U.S. Food & Drug Administration. https://web.archive.org/web/20170118085702/http://www.fda.gov/Drugs/InformationOnDrugs/ApprovedDrugs/ucm474719.htm Last updated Nov. 30, 2015. Last accessed via WayBackMachine Jul. 26, 2018. 1 page.
[No Author Listed] Nivolumab (Opdivo). FDA U.S. Food & Drug Administration. https://web.archive.org/web/20170118085700/https://www.fda.gov/Drugs/InformationOnDrugs/ApprovedDrugs/ucm436566.htm Last updated Apr. 6, 2015. Last accessed via WayBackMachine Jul. 26, 2018. 1 page.
[No Author Listed] Olaratumab (LARTRUVO). FDA U.S. Food & Drug Administration. https://www.fda.gov/Drugs/InformationOnDrugs/ApprovedDrugs/ucm526087.htm Last updated Oct. 20, 2016. Last accessed Jul. 26, 2018. 2 pages.
[No Author Listed] Osimertinib. FDA U.S. Food & Drug Administration. https://web.archive.org/web/20170227152135/https://www.fda.gov/Drugs/InformationOnDrugs/ApprovedDrugs/ucm472565.htm Last updated Nov. 13, 2015. Last accessed via WayBackMachine Jul. 26, 2018. 1 page.
[No Author Listed] Pembrolizumab (KEYTRUDA) Checkpoint Inhibitor. FDA U.S. Food & Drug Administration. https://www.fda.gov/Drugs/InformationOnDrugs/ApprovedDrugs/ucm526430.htm Last updated Oct. 25, 2016. Last accessed Jul. 26, 2018. 2 pages.
[No Author Listed] Rituximab Infusion. FDA U.S. Food & Drug Administration. https://web.archive.org/web/20161211125252/http://www.fda.gov:80/Drugs/InformationOnDrugs/ApprovedDrugs/ucm324890.htm Last updated May 4, 2016. Last accessed via WayBackMachine Jul. 26, 2018. 1 page.

[No Author Listed], A Phase 3 Study of Pembrolizumab + Epacadostat or Placebo in Subjects With Unresectable or Metastatic Melanoma (Keynote-252 / ECHO-301). Clinical Trials. https://clinicaltrials.gov/ct2/show/NCT02752074 Last updated May 8, 2018. Last accessed Jul. 26, 2018. 7 pages.
[No Author Listed], A Pilot Study to Evaluate the Safety of a 3 Weeks Sitagliptin Treatment in HCC Patients Undergoing Liver Resection (HCC-DPPIV). Clinical Trials. https://clinicaltrials.gov/ct2/show/NCT02650427 Last updated Sep. 28, 2017. Last accessed Jul. 26, 2018. 7 pages.
[No Author Listed], Combination of Interferon-gamma and Nivolumab for Advanced Solid Tumors. Clinical Trials. https://clinicaltrials.gov/ct2/show/NCT02614456 Last updated Feb. 7, 2018. Last accessed Jul. 26, 2018. 8 pages.
[No Author Listed], Evaluation of MGN1703 Maintenance Treatment in Patients with mCRC With Tumor Reduction During Induction Treatment (IMPALA). Clinical Trials. https://clinicaltrials.gov/ct2/show/NCT02077868 Last updated Jun. 23, 2017. Last accessed Jul. 26, 2018. 7 pages.
[No Author Listed], FDA Approves Merck's KEYTRUDA® (pembrolizumab) as First-Line Combination Therapy with Pemetrexed and Carboplatin for Patients with Metastatic Nonsquamous Non-Small Cell Lung Cancer (NSCLC), Irrespective of PD-L1 Expression. Merck. http://investors.merck.com/news/press-release-details/2017/FDA-Approves-Mercks-KEYTRUDA-pembrolizumab-as-First-Line-Combination-Therapy-with-Pemetrexed-and-Carboplatin-for-Patients-with-Metastatic-Nonsquamous-Non-Small-Cell-Lung-Cancer-NSCLC-Irrespective-of-PD-L1-Expression/default.aspx May 10, 2017. Last accessed Jul. 27, 2018.
[No Author Listed], FDA grants accelerated approval to pembrolizumab for first tissue/site agnostic indication. FDA U.S. Food & Drug Administration. https://www.fda.gov/drugs/informationondrugs/approveddrugs/ucm560040.htm Last updated May 30, 2017. Last accessed Jul. 27, 2018. 2 pages.
[No Author Listed], Immunotherapy Combination Study in Advanced Previously Treated Non-Small Cell Lung Cancer. Clinical Trials. https://clinicaltrials.gov/ct2/show/NCT02460367 Last updated Feb. 4, 2016. Last accessed Jul. 26, 2018. 9 pages.
[No Author Listed], L-NMMA Plus Docetaxel in Refractory Locally Advanced or Metastatic Triple Negative Breast Cancer Patients. Clinical Trials. https://clinicaltrials.gov/ct2/show/NCT02834403 Last updated Mar. 29, 2018. Last accessed Jul. 26, 2018. 10 pages.
[No Author Listed], NHS-IL12 for Solid Tumors. Clinical Trials. https://clinicaltrials.gov/ct2/show/NCT01417546 Last updated Jul. 6, 2018. Last accessed Jul. 26, 2018. 11 pages.
[No Author Listed], Ph2 NK Cell Enriched DCIs w/wo RLR9 Agonist, DUK-CPG-001 From Donors Following Allogeneic SCT (NK-DCI). Clinical Trials. https://clinicaltrials.gov/ct2/show/NCT02452697 Last updated Jul. 25, 2018. Last accessed Jul. 26, 2018. 10 pages.
[No Author Listed], Provenge Followed by Docetaxel in Castration-Resistant Prostate Cancer. Clinical Trials. https://clinicaltrials.gov/ct2/show/NCT02793219 Last updated Oct. 30, 2017. Last accessed Jul. 26, 2018. 11 pages.
[No Author Listed], SABR-ATAC: A Trial of TGF-beta Inhibition and Stereotactic Ablative Radiotherapy for Early Stage Non-small Cell Lung Cancer. Clinical Trials. https://clinicaltrials.gov/ct2/show/NCT02581787 Last updated May 7 04, 2018. Last accessed Jul. 26, 2018. 8 pages.
[No Author Listed], Study Evaluating the Safety and Pharmacokinetics of JCAR017 in B-cell Non-Hodgkin Lymphoma (TRANSCEND-NHL-001). Clinical Trials. https://clinicaltrials.gov/ct2/show/NCT02631044 Last updated Jun. 8, 2018. Last accessed Jul. 26, 2018. 12 pages.
[No Author Listed], Study of AM0010 With FOLFOX Compared to FOLFOX Alone Second-line Tx in Pts With Metastatic Pancreatic Cancer (Sequoia). Clinical Trials. https://clinicaltrials.gov/ct2/show/NCT02923921 Last updated Jul. 17, 2018. Last accessed Jul. 26, 2018. 6 pages.
[No Author Listed], The R Project for Statistical Computing. Getting Started. https://www.r-project.org/ last accessed Jul. 26, 2018. 5 pages.

(56) References Cited

OTHER PUBLICATIONS

[No Author Listed], Trial of TRX518 (Anti-GITR mAb) in Stage III or IV Malignant Melanoma or Other Solid Tumors (TRX518-001). Clinical Trials. https://clinicaltrials.gov/ct2/show/NCT01239134 Last updated Mar. 3, 2017. Last accessed Jul. 26, 2018. 9 pages.
Akbani et al., Genomic Classification of Cutaneous Melanoma. Cell. Jun. 18, 2015;161(7):1681-96. doi: 10.1016/j.cell.2015.05.044.
Aran et al., Systematic pan-cancer analysis of tumour purity. Nat Commun. Dec. 4, 2015;6:8971. doi: 10.1038/ncomms9971. 11 pages.
Attard et al., Prostate cancer. Seminar. Lancet. 2016;387:70-82.
Ayers et al., Relationship between immune gene signatures and clinical response to PD-1 blockade with pembrolizumab (MK-3475) in patients with advanced solid tumors. Journal for Immuno Therapy of Cancer. 2015;3(22):1-2.
Bao et al., AbsCN-seq: a statistical method to estimate tumor purity, ploidy and absolute copy numbers from next-generation sequencing data. Bioinformatics. 2014;30(8):1056-063.
Barbie et al., Systematic RNA interference reveals that oncogenic KRAS-driven cancers require TBK1. Nature. 2009. 462. 108-12.
Becht et al., Estimating the population abundance of tissue-infiltrating immune and stromal cell populations using gene expression. Genome Biol. Oct. 20, 2016;17(1):218.
Beck et al., Significance Analysis of Prognostic Signatures. PLOS Computational Biology. 2013;9(1):1-17.
Blank et al., The "cancer immunogram" Science. 2016;352:658-60.
Blondel et al., Fast unfolding of communities in large networks. J Stat Mech Theory Exp. 2008. P10008. 12 pages.
Bolotin et al., Antigen receptor repertoire profiling from RNA-seq data. Nat Biotechnol. Oct. 11, 2017;35(10):908-911. doi: 10.1038/nbt.3979.
Bray et al. Near-optimal probabilistic RNA-seq quantification. Nature Biotechnology vol. 34, pp. 525-527 (2016).
Brown et al., Regression of Glioblastoma after Chimeric Antigen Receptor T-Cell Therapy. The New England Journal of Medicine. 2016. 9 pages.
Burke, Predicting Clinical Outcomes Using Molecular Biomarkers. Biomarkers in Cancer. 2016;8:89-99.
Cantoni et al., NK Cells, Tumor Cell Transition, and Tumor Progression in Solid Malignancies: New Hints for NK-Based Immunotherapy. Journal of Immunology Research. 2016. 13 pages.
Carter et al., Absolute quantification of somatic DNA alterations in human cancer. Nat Biotechnol. May 2012; 30(5): 413-421.
Chanmee et al., Tumor-associated macrophages as major players in the tumor microenvironment. Cancers (Basel). Aug. 13, 2014;6(3):1670-90. doi: 10.3390/cancers6031670.
Charoentong et al., Pan-cancer Immunogenomic Analyses Reveal Genotype-Immunophenotye Relationships and Predictors of Response To Checkpoint Blockade. Cell Rep. Cold Spring Harbor Labs Journals. 2017;18:248-62.
Chaudhary et al., Regulatory T Cells in the Tumor Microenvironment and Cancer Progression: Role and Therapeutic Targeting. Vaccines (Basel). Aug. 6, 2016;4(3). pii: E28. doi: 10.3390/vaccines4030028. 25 pages.
Ding, Visualization and Integrative Analysis of Cancer Multi-Omics Data. Dissertation. The Ohio State University. 2016. 150 pages.
Feng et al., Differentially expressed genes between primary cancer and paired lymph node metastases predict clinical outcome of node-positive breast cancer patients. Breast Cancer Research and Treatment. 2007;103:319-29.
Filatenkov et al., Ablative Tumor Radiation Can Change the Tumor Immune Cell Microenvironment to Induce Durable Complete Remissions. Clin Cancer Res. Aug. 15, 2015;21(16):3727-39. doi: 10.1158/1078-0432.CCR-14-2824. Epub Apr. 13, 2015.
Finak et al., Stromal gene expression predicts clinical outcome in breast cancer. Nature Medicine. 2008;14:518-527.
Gordon et al., Using gene expression ratios to predict outcome among patients with mesothelioma. J Natl Cancer Inst. Apr. 16, 2003;95(8):598-605.
Grossman et al., Toward a Shared Vision for Cancer Genomic Data. Perspective. Sep. 22, 2016. 4 pages.
Guo et al., Translational progress on tumor biomarkers. Invited Review. Thoracic Cancer. 2015;6:665-71.
Gyorffy et al., An online survival analysis tool to rapidly assess the effect of 22,277 genes on breast cancer prognosis using microarray date of 1,809 patients. Breast Cancer Research and Treatment. 2010;123:725-31.
Haabeth et al., Inflammation driven by tumour-specific Th1 cells protects against B-cell cancer. Nat Commun. 2011;2:240. doi: 10.1038/ncomms1239. 12 pages.
Hagberg et al., Exploring network structure, dynamics, and function using NetworkX. Proceedings of the 7th Python in Science Conference (SciPy 2008). 5 pages.
Hanzelmann et al., GSVA: gene set variation analysis for microarray and RNA-seq data. BMC Bioinformatics. Jan. 16, 2013;14:7. doi: 10.1186/1471-2105-14-7.
Hermann et al., Analysis and Visualization of Gene Expression Data. Dissertation. Tubingen. 2011. 180 pages.
Hua et al., Accumulation of FoxP3+ T regulatory cells in the tumor microenvironment of human colorectal adenomas. Pathol Res Pract. Feb. 2016;212(2):106-12. doi: 10.1016/j.prp.2015.12.002. Epub Dec. 14, 2015.
Hugo et al., Genomic and Transcriptomic Features of Response to Anti-PD-1 Therapy in Metastatic Melanoma. Cell. 2016;165(1):35-44.
Hunter, Matplotlib: A 2D Graphics Environment. Comput Sci Eng. 2007;9:90-5.
Inoue et al., Novel Molecular Markers for Breast Cancer. Biomarkers in Cancer. 2016;8:25-42.
Jacquelot et al., Predictors of responses to immune checkpoint blockade in advanced melanoma. Nature Communications. 2017. 13 pages.
Jansen et al., Molecular Classification of Tamoxifen-Resistant Breast Carcinomas by Gene Expression Profiling. Jorunal of Clinical Oncology. 2005;23(4):732-40.
Ji et al., An immune-active tumor microenvironment favors clinical response to ipilimumab. Cancer Immunology, Immunotherapy. 2012;61(7):1019-31.
Kandoth et al., Mutational landscape and significance across 12 major cancer types. Nature. Oct. 17, 2013;502(7471):333-339. doi: 10.1038/nature12634.
Kaporis et al., Human basal cell carcinoma is associated with Foxp3+ T cells in a Th2 dominant microenvironment. J Invest Dermatol. Oct. 2007;127(10):2391-8. Epub May 17, 2007.
Kemper et al., BRAF(V600E) Kinase Domain Duplication Identified in Therapy-Refractory Melanoma Patient-Derived Xenografts. Cell Rep. Jun. 28, 2016;16(1):263-277. doi: 10.1016/j.celrep.2016.05.064. Epub Jun. 16, 2016.
Le et al., PD-1 Blockade in Tumors with Mismatch-Repair Deficiency. N Engl J Med. Jun. 25, 2015;372(26):2509-20. doi: 10.1056/NEJMoa1500596. Epub May 30, 2015.
Lu et al., Identification of Gene Expression Biomarkers for Predicting Radiation Exposure. Sci Rep 2015;4(1):6293. 7 pages.
Ludwig et al., Biomarkers in cancer staging, prognosis and treatment selection. Nature Reviews Cancer. 2005;5:845-56.
Marvel et al., Myeloid-derived suppressor cells in the tumor microenvironment: expect the unexpected. J Clin Invest. Sep. 2015;125(9):3356-64. doi: 10.1172/JCI80005. Epub Jul. 13, 2015.
Mcart et al., PICan: An integromics framework for dynamic cancer biomarker discovery. Molecular Oncology. 2015;9(6):1234-40.
McKinney, Data Structures for Statistical Computing in Python. Proc. of the 9th Python in Science Conf. SCIPY 2010;51.
Merico et al., Enrichment Map: A Network-Based Method for Gene-Set Enrichment Visualization and Interpretation. Plos One. 2010;5(11):1-12.
Mustacchi et al., Identification and Validation of a New Set of Five Genes for Prediction of Risk in Early Breast Cancer. International Journal of Molecular Science. 2013;14:9686-702.
Nam et al., A pathway-based approach for identifying biomarkers of tumor progression to trastuzumab-resistant breast cancer. Cancer Letters. 2015;356:880-90.

(56) References Cited

OTHER PUBLICATIONS

Nathanson et al., Somatic Mutations and Neoepitope Homology in Melanomas Treated with CTLA-4 Blockade. Cancer Immunology Research. 2017. 9 pages.
Newman et al., Robust enumeration of cell subsets from tissue expression profiles. Nat Methods. May 2015;12(5):453-7. doi: 10.1038/nmeth.3337. Epub Mar. 30, 2015.
Noguera et al., Extracellular matrix, biotensegrity and tumor microenvironment. An update and overview. Histol Histopathol. Jun. 2012;27(6):693-705. doi: 10.14670/HH-27.693.
O'Leary et al., Reference sequence (RefSeq) database at NCBI: current status, taxonomic expansion, and functional annotation. Nucleic Acids Res. Jan. 4, 2016;44(D1):D733-45. doi: 10.1093/nar/gkv1189. Epub Nov. 8, 2015.
Palmieri et al., Genetic instability and increased mutational load: which diagnostic tool best direct patients with cancer to immunotherapy? J Transl Med. 2017; 15: 17. 4 pages.
Panse et al., Chemokine CXCLI3 is overexpressed in the tumor tissue and in the peripheral blood of breast cancer patients. British Journal of Cancer. 2008;99:930-38.
Papageorgis, TGFβ Signaling in Tumor Initiation, Epithelial-to-Mesenchymal Transition, and Metastasis. J Oncol. 2015;2015:587193. doi: 10.1155/2015/587193. Epub Mar. 25, 2015. 15 pages.
Pardoll, The blockade of immune checkpoints in cancer immunotherapy. Nature Reviews Cancer. 2012;12(4):252-64.
Passiglia et al., PD-L1 expression as predictive biomarker in patients with NSCLC: a pooled analysis. Oncotarget. Apr. 12, 2016;7(15):19738-47. doi: 10.18632/oncotarget.7582.
Pedregosa et al., Scikit-learn: Machine Learning in Python. J Mach Learn Res. 12(Oct):2825-2830, 2011.
Quail et al., Microenvironmental regulation of tumor progression and metastasis. Nat Med. Nov. 2013;19(11):1423-37. doi: 10.1038/nm.3394.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.
Rizvi et al., Cancer immunology. Mutational landscape determines sensitivity to PD-1 blockade in non-small cell lung cancer. Science. Apr. 3, 2015;348(6230):124-8. doi: 10.1126/science.aaa1348. Epub Mar. 12, 2015.
Roh et al., Integrated molecular analysis of tumor biopsies on sequential CTLA-4 and PD-1 blockade reveals markers of response and resistance. Cancer. Sci Transl Med. 2017. 13 pages.
Sato et al., Integrated molecular analysis of clear-cell renal cell carcinoma. Nat Genet. Aug. 2013;45(8):860-7. doi: 10.1038/ng.2699. Epub Jun. 24, 2013.
Schumacher et al., Editorial overview: Cancer immunology: genomics & biomarkers: Cancer immunity through the prism of genomics and proteomics. Curr Opin Immunol. Aug. 2016;41:ix-x. doi: 10.1016/j.coi.2016.07.006. Epub Aug. 6, 2016.
Senbabaoglu et al., Tumor immune microenvironment characterization in clear cell renal cell carcinoma identifies prognostic and immunotherapeutically relevant messenger RNA signatures. Genome Biol. Nov. 17, 2016;17(1):231. 25 pages.
Shalapour et al., Immunosuppressive plasma cells impede T-cell-dependent immunogenic chemotherapy. Nature. May 7, 2015;521(7550):94-8. doi: 10.1038/nature14395. Epub Apr. 29, 2015.
Shannon et al., Cytoscape: a software environment for integrated models of biomolecular interaction networks. Genome Res. Nov. 2003;13(11):2498-504.
Shiga et al., Cancer-Associated Fibroblasts: Their Characteristics and Their Roles in Tumor Growth. Cancers (Basel). Dec. 11, 2015;7(4):2443-58. doi: 10.3390/cancers7040902.
Singel et al., Neutrophils in the tumor microenvironment: trying to heal the wound that cannot heal. Immunol Rev. Sep. 2016;273(1):329-43. doi: 10.1111/imr.12459.
Snyder et al., Genetic Basis for Clinical Response to CTLA-4 Blockade in Melanoma. N Engl J Med. 2014;371(23):2189-99.
Sturm et al., Discovering Medical Knowledge Using Visual Analytics. Eurographics Workshop on Visual Computing for Biology and Medicine. 2015. 10 pages.
Subramanian et al., Gene set enrichment analysis: a knowledge-based approach for interpreting genome-wide expression profiles. Proc Natl Acad Sci U S A. Oct. 25, 2005;102(43):15545-50. Epub Sep. 30, 2005.
Tamburini et al., Gene expression profiling identifies inflammation and angiogenesis as distinguishing features of canine hemangiosarcoma. BMC Cancer. 2010;10(1):619. 16 pages.
Tappeiner et al., TIminer: NGS data mining pipeline for cancer immunology and immunotherapy. Bioinformatics. Oct. 1, 2017;33(19):3140-3141. doi: 10.1093/bioinformatics/btx377.
Tirosh et al., Dissecting the multicellular ecosystem of metastatic melanoma by single-cell RNA-seq. Science. Apr. 8, 2016;352(6282):189-96. doi: 10.1126/science.aad0501.
Umansky et al., Tumor microenvironment and myeloid-derived suppressor cells. Cancer Microenviron. Aug. 2013;6(2):169-77. doi: 10.1007/s12307-012-0126-7. Epub Dec. 16, 2012.
Van Allen et al., Genomic correlates of response to CTLA-4 blockade in metastatic melanoma. Science. Oct. 9, 2015;350(6257):207-211. doi: 10.1126/science.aad0095. Epub Sep. 10, 2015.
Van Der Auwera et al., Increased Angiogenesis and Lymphangiogenesis in Inflammatory versus Noninflammatory Breast Cancer by Real-Time Reverse Transcriptase-PCR Gene Expression Quantification. Clinical Cancer Research. 2004;10:7965-971.
Van Der Maaten, Accelerating t-SNE using Tree-Based Algorithms. Journal of Machine Learning Research. 2014;15:3221-3245.
Van Der Maaten, Visualizing Data using t-SNE. Journal of Machine Learning Research. 2008;9:2579-2605.
Van Der Walt et al., The NumPy Array: A Structure for Efficient Numerical Computation. Computing in Science and Engineering. 2011;13(2):22-30.
Vilgelm et al,. Combinatorial approach to cancer immunotherapy: strength in numbers. JLB. 2016. 16 pages.
Vuaroqueaux et al. Low E2F1 transcript levels are a stron determinant of favorable breast cancer outcome. Breast Cancer Research 2007. 2007;9:1-10.
Wargo et al., Monitoring immune responses in the tumor microenvironment. Curr Opin Immunol. Aug. 2016;41:23-31. doi: 10.1016/j.coi.2016.05.006. Epub May 27, 2016.
West et al., Tumor-infiltrating lymphocytes predict response to anthracycline-based chemotherapy in estrogen receptor-negative breast cancer. Breast Cancer Research. 2011;12:13 pages.
Yiu et al., Biomarkers in Colorectal Cancer. Anticancer Research. 2016;36:1093-102.
Yu et al., Cancer-associated fibroblasts induce epithelial-mesenchymal transition of breast cancer cells through paracrine TGF-β signalling. Br J Cancer. Feb. 4, 2014;110(3):724-32. doi: 10.1038/bjc.2013.768. Epub Dec. 12, 2013.
Zhang et al., Starved and Asphyxiated: How Can CD8(+) T Cells within a Tumor Microenvironment Prevent Tumor Progression. Front Immunol. Feb. 10, 2016;7:32. doi: 10.3389/fimmu.2016.00032. eCollection 2016.

\* cited by examiner

US 10,636,514 B2

USING SUBJECT SEQUENCING DATA AND A DATABASE OF THERAPY BIOMARKER DISTRIBUTIONS TO DETERMINE NORMALIZED BIOMARKER SCORES AND THERAPY SCORES

RELATED APPLICATIONS

This application claims the benefit under 35 U.S.C. § 119(e) of the filing date of U.S. provisional patent application Ser. No. 62/518,787, entitled "Systems and Methods for Identifying Cancer Treatments from Sequence Data", filed Jun. 13, 2017 and U.S. provisional patent application Ser. No. 62/598,440, entitled "Systems and Methods Identifying Cancer Treatments from Sequence Data," filed Dec. 13, 2017, the entire contents of each of which are incorporated herein by reference.

This application is filed on the same day as International Application No.: PCT/US18/37017, entitled "SYSTEMS AND METHODS FOR GENERATING, VISUALIZING AND CLASSIFYING MOLECULAR FUNCTIONAL PROFILES"; International Application No.: PCT/US18/37018, entitled "SYSTEMS AND METHODS FOR IDENTIFYING RESPONDERS AND NON-RESPONDERS TO IMMUNE CHECKPOINT BLOCKADE THERAPY"; and International Application No.: PCT/US18/37008, entitled "SYSTEMS AND METHODS FOR IDENTIFYING CANCER TREATMENTS FROM NORMALIZED BIOMARKER SCORES", the entire contents of each of which are incorporated herein by reference.

FIELD

Aspects of the technology described herein relate to predicting treatment efficacy based on subject (e.g., patient) specific information such as a subject's (e.g., patient's) biomarkers.

Some aspects of the technology described herein relate to determining therapy scores (for one or more potential treatments) and determining therapy scores before and after a treatment. Some aspects of the technology described herein relate to generating a graphical user interface (GUI) for visualizing therapy scores.

Some aspects of the technology described herein relate to determining impact scores (for treatments). Some aspects of the technology described herein relate to generating a graphical user interface for visualizing impact scores.

Some aspects of the technology described herein relate to determining normalized biomarker scores for a subject. Some aspects of the technology described herein relate to identifying the subject as a member of one or more cohorts using normalized biomarkers scores. Some aspects of the technology described herein relate to outputting such information (e.g., to one or more users). Some aspects of the technology described herein relate to potential inclusion or exclusion of a subject from a clinical trial.

BACKGROUND

Correctly selecting one or more effective therapies for a subject (e.g., a patient) with cancer or determining the effectiveness of a treatment can be crucial for the survival and overall wellbeing of that subject. Advances in identifying effective therapies and understanding their effectiveness or otherwise aiding in personalized care of patients with cancer are needed.

SUMMARY

Provided herein, inter alia, are systems and methods for determining therapy scores for multiple therapies based on normalized biomarker scores. Such information, in some embodiments, is output to a user in a graphical user interface (GUI).

Systems and methods for determining therapy scores for multiple therapies based on normalized biomarker scores comprises, in some embodiments, accessing sequence data for a subject, accessing biomarker information indicating distribution of values for biomarkers associated with multiple therapies, determining normalized biomarker scores for the subject using sequencing data and biomarker information, and determining therapy scores for the multiple therapies based on normalized biomarker scores.

Provided herein, inter alia, are systems and methods for determining impact score for a candidate therapy using first and second normalized biomarker scores. Such information, in some embodiments, is output to a user in a graphical user interface (GUI).

Systems and methods for determining impact score for a candidate therapy using first and second normalized biomarker scores comprises, in some embodiments, obtaining first sequencing data for a subject prior to administration of candidate therapy, obtaining second sequencing data for a subject subsequent to administration of candidate therapy, accessing biomarker information indicating distribution of values for a biomarker associated with the candidate therapy, determining first and second biomarker scores for the subject using first sequencing data, second sequencing data, and biomarker information, and determining impact score for the candidate therapy using first and second normalized biomarker scores.

Provided herein, inter alia, are systems and methods for determining therapy scores for at least two selected therapies based on normalized biomarker scores for the at least three biomarkers. Such information, in some embodiments, is output to a user in a graphical user interface (GUI).

Systems and methods for determining therapy scores for at least two selected therapies based on normalized biomarker scores for the at least three biomarkers comprises, in some embodiments, obtaining sequencing data for a subject, accessing biomarker information for at least three biomarkers associated with at least two selected therapies, determining first and second sets of normalized biomarker scores for the subject using sequencing data and biomarker information, and determining therapy scores for the at least two selected therapies based on normalized biomarker scores for the at least three biomarkers.

Provided herein, inter alia, are systems and methods for obtaining first and second therapy scores for first and second therapies. Such information, in some embodiments, is output to a user in a graphical user interface (GUI).

Systems and methods for obtaining first and second therapy scores for first and second therapies comprises, in some embodiments, obtaining sequence data for a subject, accessing biomarker information indicating distribution of values for biomarkers associated with multiple therapies, determining first and second sets of normalized biomarker scores for the subject using sequencing data and biomarker information, and obtaining first and second therapy scores for first and second therapies.

Provided herein, inter alia, are systems and methods for identifying a subject as a member of a cohort using normalized biomarker scores. Such information, in some embodiments, is output to a user in a graphical user interface (GUI).

Systems and methods for identifying a subject as a member of a cohort using normalized biomarker scores comprises, in some embodiments, obtaining sequencing data for a subject, accessing biomarker information indicating distribution of values for biomarkers associated with multiple therapies, determining normalized biomarker scores for the subject using sequencing data and biomarker information, and identifying the subject as a member of a cohort using normalized biomarker scores.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information, a normalized score for each biomarker in at least a subject subset of the plurality of biomarkers to obtain a set of normalized biomarker scores for the subject, wherein the subject subset of the plurality of biomarkers is a subset of the reference subset of the plurality of biomarkers; and determining, using the set of normalized biomarker scores for the subject, therapy scores for the plurality of therapies, each of the therapy scores indicative of predicted response of the subject to administration of a respective therapy in the plurality of therapies.

In one aspect provided herein is at least one non-transitory computer-readable storage medium storing processor-executable instructions that, when executed by at least one computer hardware processor, cause the at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information, a normalized score for each biomarker in at least a subject subset of the plurality of biomarkers to obtain a set of normalized biomarker scores for the subject, wherein the subject subset of the plurality of biomarkers is a subset of the reference subset of the plurality of biomarkers; and determining, using the set of normalized biomarker scores for the subject, therapy scores for the plurality of therapies, each of the therapy scores indicative of predicted response of the subject to administration of a respective therapy in the plurality of therapies.

In one aspect provided herein is a method, comprising: using at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information, a normalized score for each biomarker in at least a subject subset of the plurality of biomarkers to obtain a set of normalized biomarker scores for the subject, wherein the subject subset of the plurality of biomarkers is a subset of the reference subset of the plurality of biomarkers; and determining, using the set of normalized biomarker scores for the subject, therapy scores for the plurality of therapies, each of the therapy scores indicative of predicted response of the subject to administration of a respective therapy in the plurality of therapies.

In one aspect provided herein is a system comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining first sequencing data about at least one biological sample of a subject prior to administration of a candidate therapy; obtaining second sequencing data about at least one other biological sample of the subject subsequent to administration of the candidate therapy; accessing, in the at least one database, biomarker information indicating a distribution of values for each biomarker, across a respective group of people, in at least a reference subset of a plurality of biomarkers; determining, using the first and second sequencing data and the biomarker information, a first set of normalized biomarker scores for the subject and a second set of normalized biomarker scores for the subject; and determining, using the first and second sets of normalized biomarker scores for the subject, an impact score for the candidate therapy, wherein the impact score is indicative of response of the subject to administration of the candidate therapy.

In one aspect provided herein is at least one non-transitory computer-readable storage medium storing processor-executable instructions that, when executed by at least one computer hardware processor, cause the at least one computer hardware processor to perform: obtaining first sequencing data about at least one biological sample of a subject prior to administration of a candidate therapy; obtaining second sequencing data about at least one other biological sample of the subject subsequent to administration of the candidate therapy; accessing, in at least one database, biomarker information indicating a distribution of values for each biomarker, across a respective group of people, in at least a reference subset of a plurality of biomarkers; determining, using the first and second sequencing data and the biomarker information, a first set of normalized biomarker scores for the subject and a second set of normalized biomarker scores for the subject; and determining, using the first and second sets of normalized biomarker scores for the subject, an impact score for the candidate therapy, wherein the impact score is indicative of response of the subject to administration of the candidate therapy.

In one aspect provided herein is a method, comprising: using at least one computer hardware processor to perform: obtaining first sequencing data about at least one biological sample of a subject prior to administration of a candidate therapy; obtaining second sequencing data about at least one other biological sample of the subject subsequent to administration of the candidate therapy; accessing, in at least one database, biomarker information indicating a distribution of values for each biomarker, across a respective group of people, in at least a reference subset of a plurality of biomarkers; determining, using the first and second sequencing data and the biomarker information, a first set of normalized biomarker scores for the subject and a second set of normalized biomarker scores for the subject; and determining, using the first and second sets of normalized biomarker scores for the subject, an impact score for the candidate therapy, wherein the impact score is indicative of response of the subject to administration of the candidate therapy.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information: a first set of normalized scores for a first set of biomarkers associated with a first therapy in the plurality of therapies; and a second set of normalized scores for a second set of biomarkers associated with a second therapy in the plurality of therapies, wherein the first set of biomarkers is different from the second set of biomarkers; providing the first set of normalized scores as input to a statistical model to obtain a first therapy score for the first therapy; providing the second set of normalized scores as input to the statistical model to obtain a second therapy score for the second therapy; generating a graphical user interface (GUI), wherein the GUI comprises: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In one aspect provided herein is at least one non-transitory computer-readable storage medium storing processor-executable instructions that, when executed by the at least one computer hardware processor, cause the at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information: a first set of normalized scores for a first set of biomarkers associated with a first therapy in the plurality of therapies; and a second set of normalized scores for a second set of biomarkers associated with a second therapy in the plurality of therapies, wherein the first set of biomarkers is different from the second set of biomarkers; providing the first set of normalized scores as input to a statistical model to obtain a first therapy score for the first therapy; providing the second set of normalized scores as input to the statistical model to obtain a second therapy score for the second therapy; generating a graphical user interface (GUI), wherein the GUI comprises: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In one aspect provided herein is a method, comprising using the at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information: a first set of normalized scores for a first set of biomarkers associated with a first therapy in the plurality of therapies; and a second set of normalized scores for a second set of biomarkers associated with a second therapy in the plurality of therapies, wherein the first set of biomarkers is different from the second set of biomarkers; providing the first set of normalized scores as input to a statistical model to obtain a first therapy score for the first therapy; providing the second set of normalized scores as input to the statistical model to obtain a second therapy score for the second therapy; generating a graphical user interface (GUI), wherein the GUI comprises: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker, across a respective group of people, in at least a reference subset of the plurality of biomarkers, each of the plurality of biomarkers being associated with at least one therapy in a plurality of therapies; determining, using the sequencing data and the biomarker information: a first set of normalized biomarker scores for a first set of biomarkers associated with a first therapy in the plurality of therapies; and a second set of normalized biomarker scores for a second set of biomarkers associated with a second therapy in the plurality of therapies, wherein the first set of biomarkers is different from the second set of biomarkers; providing the first set of normalized biomarker scores as input to a statistical model to obtain a first therapy score for the first therapy; providing the second set of normalized biomarker scores as input to the statistical model to obtain a second therapy score for the second therapy; wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

In one aspect provided herein is at least one non-transitory computer-readable storage medium storing processor-executable instructions that, when executed by at least one computer hardware processor, cause the at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one therapy in a plurality of therapies; determining, using the sequencing data and the biomarker information: a first set of normalized biomarker scores for a first set of biomarkers associated with a first therapy in the plurality of therapies; and a second set of normalized biomarker scores for a second set of biomarkers associated with a second therapy in the plurality of therapies, wherein the first set of biomarkers is different from the second set of biomarkers; providing the first set of normalized biomarker scores as input to a statistical model to obtain a first therapy score for the first therapy; providing the second set of normalized biomarker scores as input to the statistical model to obtain a second therapy score for the second therapy; wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

In one aspect provided herein is a method, comprising using at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one therapy in a plurality of therapies; determining, using the sequencing data and the biomarker information: a first set of normalized biomarker scores for a first set of biomarkers associated with a first therapy in the plurality of therapies; and a second set of normalized biomarker scores for a second set of biomarkers associated with a second therapy in the plurality of therapies, wherein the first set of biomarkers is different from the second set of biomarkers; providing the first set of normalized biomarker scores as input to a statistical model to obtain a first therapy score for the first therapy; providing the second set of normalized biomarker scores as input to the statistical model to obtain a second therapy score for the second therapy; wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker, across a respective group of people, in at least a reference subset of the plurality of biomarkers, each of the plurality of biomarkers being associated with at least one candidate therapy; determining, using the sequencing data and the biomarker information, a normalized score for each biomarker in at least a subject subset of the plurality of biomarkers to obtain a set of normalized biomarkers for the subject; identifying the subject as a member of one or more cohorts based on the set of normalized biomarker scores for the subject, wherein each of the one or more cohorts is associated with a positive or negative outcome of the at least one candidate therapy; and outputting an indication of the one or more cohorts in which the subject is a member.

In one aspect provided herein is at least one non-transitory computer-readable storage medium storing processor-executable instructions that, when executed by at least one computer hardware processor, cause the at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one candidate therapy; determining, using the sequencing data and the biomarker information, a normalized score for each biomarker in at least a subject subset of the plurality of biomarkers to obtain a set of normalized biomarkers for the subject; identifying the subject as a member of one or more cohorts based on the set of normalized biomarker scores for the subject, wherein each of the one or more cohorts is associated with a positive or negative outcome of the at least one candidate therapy; and outputting an indication of the one or more cohorts in which the subject is a member.

In one aspect a method comprising using at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one candidate therapy; determining, using the sequencing data and the biomarker information, a normalized score for each biomarker in at least a subject subset of the plurality of biomarkers to obtain a set of normalized biomarkers for the subject; identifying the subject as a member of one or more cohorts based on the set of normalized biomarker scores for the subject, wherein each of the one or more cohorts is associated with a positive or negative outcome of the at least one candidate therapy; and outputting an indication of the one or more cohorts in which the subject is a member.

BRIEF DESCRIPTION OF THE DRAWINGS

Various aspects and embodiments will be described with reference to the following figures. The figures are not necessarily drawn to scale.

DETAILED DESCRIPTION

Figure 1A:
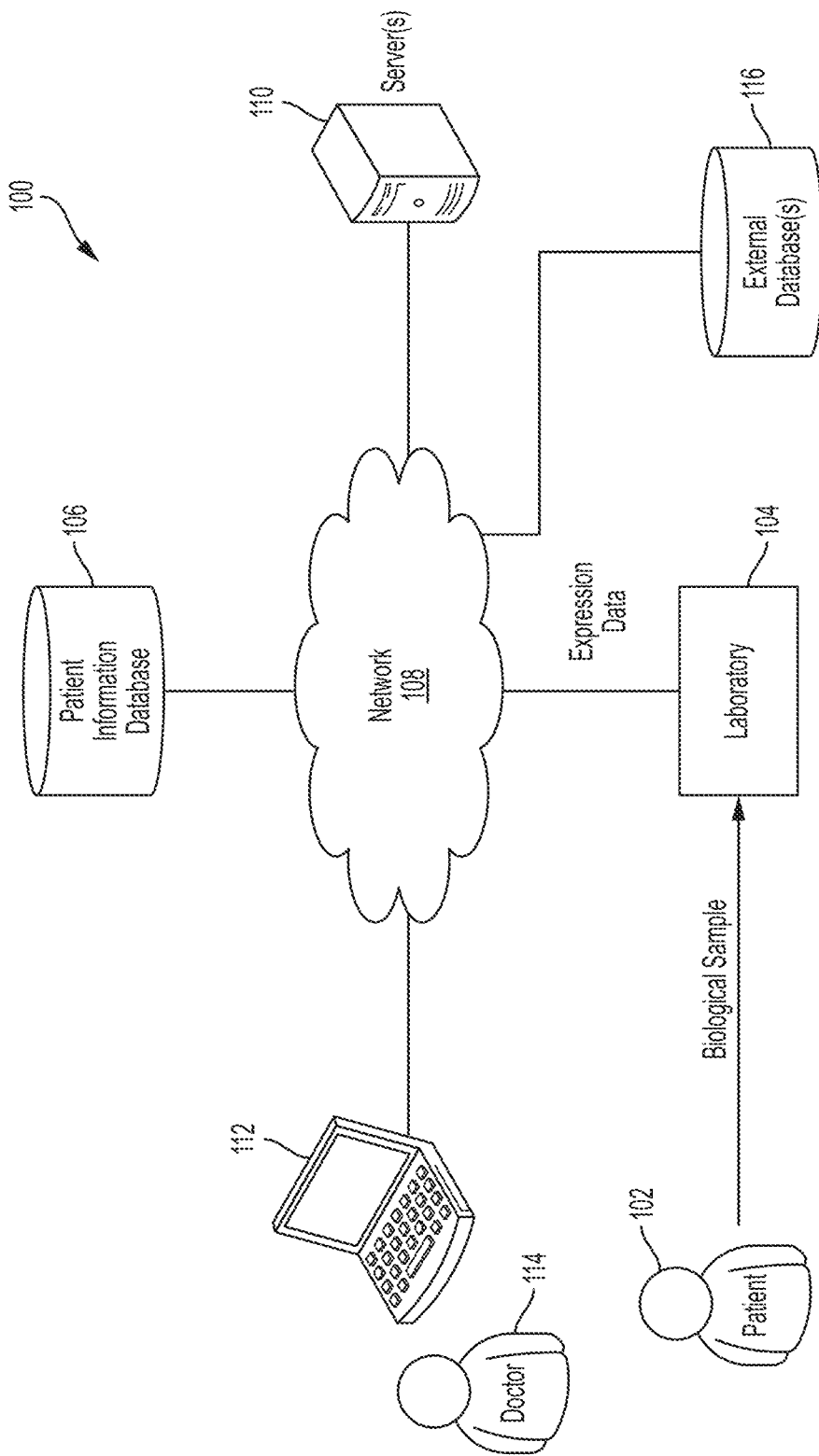
FIG. 1A is a diagram of an illustrative process for obtaining patient data and providing that data to a doctor, in accordance with some embodiments of the technology described herein.

Currently, certain conventional therapy selection methods allow for selection of a therapy based on a single parameter (or biomarker) of an individual patient or tumor, the presence or absence of which is correlated with treatment response or patient survival. The inventors have appreciated that there are several problems with this type of single-parameter methodology. The first problem of such conventional therapy selection methods is their weak predictive power when evaluating potential candidate therapies. While a particular individual biomarker may be predictive of the efficacy of a candidate therapy for one cohort (or group) of subjects (e.g., patients), it may fail to do so for a second or further cohorts (or groups). A second biomarker may be predictive of the efficacy of the candidate therapy for a second or further cohorts (or groups) of subjects (e.g., patients), but fail to do so for the first cohort (or group). Thus, different individual biomarkers may suggest different courses of action. As a result, using a single biomarker to determine the efficacy of a candidate treatment is problematic for many patients. Even if a single biomarker having the highest correlation with response for a candidate treatment were chosen, it may still have a weak predictive capability without taking into account the full scope of each patient's case and personal condition.

Another problem with conventional single-parameter methodology is the heterogeneity of a biomarker's values. Due to the variation in measurements of different clinics and clinical trials, potential biomarkers become incomparable between subjects (e.g., patients) from different hospitals or clinical settings. The biomarker values defined in one study could significantly differ from the results of the same measurements performed at a different site or on different equipment. While the relative meaning of a biomarker may remain unchanged—for example, a "high" biomarker value is bad or "low" value is good for predicting therapy efficacy—experimental cut-off or threshold values for "high" or "low" definitions often significantly vary among studies.

The inventors have developed techniques for predicting the efficacy of therapies for a subject that address (e.g., mitigate or avoid) the above-described problems of conventional single-biomarker approaches. In particular, the inventors have developed techniques of predicting therapy efficacy using multiple biomarkers (e.g., biomarkers associated with positive therapeutic response or non-positive therapeutic response to a particular therapy or type of therapy). The inventors have appreciated that different biomarkers may have values in vastly different ranges. In order to use multiple such biomarkers in a single common quantitative framework for predicting therapy efficacy, the inventors have developed a technique for normalizing the values of the biomarkers relative to their variation in reference populations, thereby placing them on a common scale. The inventors have also recognized that comparing biomarker scores of a patient to those of other patients may be used to compute normalized biomarker scores. Further, such normalized biomarker scores may be utilized to more accurately predict a patient's response to a therapy. The inventors have specifically developed techniques for simultaneous analysis of the normalized biomarkers as described herein.

Additionally, recent advances in personalized genomic sequencing and cancer genomic sequencing technologies have made it possible to obtain patient-specific information about cancer cells (e.g., tumor cells) and cancer microenvironments from one or more biological samples obtained from individual patients. This information can be used to determine a large number of parameters (or biomarkers) for each patient and, potentially, use this information to identify effective therapies and/or select one or more effective therapies for the subject (e.g., the patient). This information may also be used to determine how a subject (e.g., a patient) is responding over time to a treatment and, if necessary, to select a new therapy or therapies for the subject (e.g., the patient) as necessary. This information may also be used to determine whether the subject (e.g., the patient) should be included or excluded from participating in a clinical trial.

Global comparison of different types and groupings of biomarkers using normalization as described herein was not known in the art, and the integration of such normalized biomarkers in a coherent and quantitative manner with therapy or impact scores calculated therefrom provide more accurate predictions (greater predictive capacity) of a patient's response to a therapy than might be seen by the use of any single marker or less complex combination of elements. The methods, systems, and graphical user interfaces (GUIs) based on such a wide variety of biomarkers as described herein are newly available and not previously described techniques or methods existed to perform the elements of these techniques. Further, techniques for combining various types of biomarkers in a single analytical tool had not been developed because these biomarkers were from different origins (i.e., different studies, hospitals, and treatment centers) and were of vastly differing scales.

The inventors have recognized that several of the elements described herein add something more than what is well understood, routine, or conventional activity proposed by others in the field. These meaningful non-routine steps result in the improvements seen in the methods, systems, and GUIs described herein and include, but are not limited to: the normalization of different biomarker types to a common scale; the combination(s) of biomarker types provided herein; the determination of therapy scores from different biomarker types; technical improvements in analyses that allow for more accurate prediction of a patient's response to a therapy and resulting improvements in outcome for the patient; and the creation of improved graphical user interfaces to aid in the selection of a therapy.

Therefore, aspects of the technology described herein relate to systems and methods and for predicting a patient's response to a therapy based on patient specific information such as a patient's biomarker values. In some embodiments, predicting a patient's response to a therapy comprises determining normalized biomarker scores (also described as "normalized scores") using sequencing data and biomarker information. In some embodiments, predicting a patient's response to a therapy comprises determining therapy scores for the multiple therapies based on normalized biomarker scores. A therapy score for a therapy is a numerical value that may provide a quantitative measure of the therapy's predicted efficacy in treating a subject. In some embodiments, determining a patient's response to a therapy comprises determining an impact score based on normalized biomarker scores. An impact score for a therapy is a numerical value that may provide a quantitative measure of the therapy's current efficacy (impact) in treating a subject.

Such methods and systems may be useful for clinical purposes including, for example, selecting a treatment, evaluating suitability of a patient for participating in a clinical trial, or determining a course of treatment for a subject (e.g., a patient).

The methods and systems described herein may also be useful for non-clinical applications including (as a non-limiting example) research purposes such as, e.g., studying the biological pathways and/or biological processes targeted by a therapy, and developing new therapies for cancer based on such studies.

Further, systems which present this information in a comprehensive and useable format will be needed to facilitate treatment of patients with such conditions. Therefore, provided herein are systems and methods for analyzing patient specific information that result in a prediction of a patient's response or lack thereof to a treatment.

Such an analysis takes into consideration a global view of patient information to make a prediction regarding the patient's response to a therapy that is well-informed and comprehensive. The analysis described herein, in some embodiments, is a global analysis of patient specific information. Certain aspects of the described methods take into account biological data generated from analysis of at least one biological sample of a subject. Other aspects of the described methods take into account patient specific information related to the overall health and/or lifestyle of a patient (e.g., personal habits, environmental factors) that may play a role in whether a patient responds to a therapy.

Generally, techniques described herein provide for improvements over conventional computer-implemented techniques for analysis of medical data such as evaluation of expression data (e.g., RNA expression data) and determining whether one or more therapies (e.g., targeted therapies, radiotherapies, and/or immunotherapies) will be effective in treating the subject. Such improvements include, but are not limited to, improvements in predictive power regarding the effectiveness of candidate treatments for a subject over conventional single biomarker treatments. Additionally, some embodiments of the technology provided herein are directed to graphical user interfaces that present oncological data in a new way which is compact and highly informative. These graphical user interfaces not only reduce the cognitive load on a user (e.g., a doctor or other medical professional) working with them, but may serve to reduce clinician errors and improve the functionality of a computer by providing all needed information in a single interactive interface. This could eliminate the need for a user (e.g., a clinician) to consult different sources of information (e.g., view multiple different webpages, use multiple different application programs, etc.), which would otherwise place an additional burden on the processing, memory, and communications resources of the computer(s) used by such a user (e.g., a clinician).

Biomarkers

The methods described are based on in part on the analysis of anthropometric, clinical, tumor, and/or cancerous cell microenvironment parameters, and tumor and/or cancerous cell parameters of a subject (e.g., a patient), along with accompanying disease information. For such analyses, sequence data such as that from transcriptome, exome, and/or genome sequencing of a patient's tumor biopsy, or from other tissues of the patient are suitable although any type of sequence data may be used. Additional data concerning other patient, cancerous cell, or tumor parameters, or microenvironment parameters may also be considered including, but not limited to: tumor and/or cancerous cell proteomic analysis; immunohistochemistry staining; flow cytometry; standard clinical measurements of blood, urine and other biological fluids; biopsies of one or more tumors and organs; images obtained by any methods, including X-ray, ultrasonic, sonic, or magnetic resonance imaging scintillation studies, etc. In these terms, all features that distinguish one patient from another including, but not limited to, disease stage, sex, age, tumor mutations, cancerous cell mutations, blood analysis, IHC of biopsy, etc. are called patient parameters and may be included in the algorithm. The parameters of the subject (e.g., the patient), the type of tumor, or the type of cancerous cell may have been identified in group clinical trials that were published in scientific journals or actively used in clinically approved analyses, guidelines of treatment options (FDA, NIH, NCCN, CPIC, etc.) or elsewhere. These parameters are biomarkers, the presence or absence of which and/or levels of which may be statistically significantly correlated (e.g., the correlation may be at least a threshold amount away from zero) with treatment response or patient survival.

Certain techniques described herein are designed to use any reliable and available information about discovered biomarkers to simultaneously analyze individual biomarkers of the patient and may use any number of pre-defined biomarker combinations. This method generally considers several parameters concerning the patient and/or the cancerous tissues and/or cells of the patient and does not classify the patient to a one-biomarker group, such as high or low PDL1 expression. Certain techniques described herein may be based on the simultaneous analysis of tens or hundreds of biomarkers.

In some embodiments, the techniques described herein provide a way to generate "thresholds" for pre-defined biomarkers based on (e.g., large volumes of) data obtained from large numbers of patients, such as TCGA, ICGC, Human Protein Atlas, etc., allowing for the creation of a normalized score for each of the biomarkers. Combinations of normalized biomarker scores for the patient may be used to analyze one more defined therapies (creating therapy scores) providing information that allows the selection of one or more therapies for each patient based on their personal parameters.

Types of Biomarkers

Aspects of the present disclosure relate to systems and methods for predicting efficacy of a cancer treatment from a plurality of biomarkers. As used herein, the term "biomarker" refers to any information (or any parameter) of a biomolecule (e.g., a gene or a protein), a cancer (e.g., tumor type) or a subject (e.g., age of a subject) that may be used to predict an effect of a therapy or lack thereof in the subject. Accordingly, "biomarker information" or "biomarker value" as used herein, refers to any information relating to a biomarker. As a non-limiting example, if a biomarker is age, a biomarker value (e.g., information about the biomarker) may be 32 for a patient that is 32 years of age.

A biomarker as described herein may be associated with at least one therapy and/or at least one cancer. As used herein, the term "associated with" indicates that a biomarker has been found to be relevant (e.g., in one or more studies such as those described in a paper or journal article) to and/or involved with the associated therapy and/or the associated cancer. It should be appreciated that a biomarker, in some embodiments, may be directly linked to a therapy and/or cancer or indirectly linked to a therapy and/or a cancer (e.g., that the biomarker has been found to directly or indirectly effect or modulate a biological process related to the therapy and/or the cancer). As a set of non-limiting examples, biomarkers for use with the methods and systems described herein may include any group or subset of biomarkers listed herein, including those listed in the Tables (e.g., in Table 2). Such a group or subset of biomarkers may include at least 3, at least 4, at least 5, at least 6, at least 7, at least 8, at least 9, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, or at least 1000 biomarkers. Such a group or subset of biomarkers may include up to 3, up to 4, up to 5, up to 6, up to 7, up to 8, up to 9, up to 10, up to 20, up to 30, up to 40, up to 50, up to 60, up to 70, up to 80, up to 90, up to 100, up to 200, up to 300, up to 400, up to 500, up to 600, up to 700, up to 800, up to 900, or up to 1000 biomarkers.

A biomarker as described herein, in some embodiments, may be associated with multiple therapies. In some embodiments, a biomarker may be associated with at least 2, at least 3, at least 4, at least 5, at least 6, at least 7, at least 8, at least 9, at least 10, at least 20, at least 30, at least 40, at least 50, at least 60, at least 70, at least 80, at least 90, or at least 100 different therapies. In some embodiments, a biomarker may be associated with up to 2, up to 3, up to 4, up to 5, up to 6, up to 7, up to 8, up to 9, up to 10, up to 20, up to 30, up to 40, up to 50, up to 60, up to 70, up to 80, up to 90, or up to 100 different therapies.

A biomarker as described herein, in some embodiments, may be associated with multiple cancers. In some embodiments, a biomarker may be associated with at least 2, at least 3, at least 4, at least 5, at least 6, at least 7, at least 8, at least 9, at least 10, at least 20, at least 30, at least 40, at least 50, at least 60, at least 70, at least 80, at least 90, or at least 100 different cancers. In some embodiments, a biomarker may be associated with up to 2, up to 3, up to 4, up to 5, up to 6, up to 7, up to 8, up to 9, up to 10, up to 20, up to 30, up to 40, up to 50, up to 60, up to 70, up to 80, up to 90, or up to 100 different cancers.

Biomarkers as provided herein may be associated with any biomolecule. Examples of a biomolecule include, but are not limited to, a growth factor, a hormone, a steroid, a saccharide, a lipid, a heterocyclic compound, an elementary compound (e.g., iron), a metabolite, a vitamin, a neurotransmitter, and fatty acids. Such biomarkers may be referred to by the biomolecule that they are associated with. For example, a biomarker associated with a saccharide may be referred to as a saccharide biomarker; a biomarker associated with a lipid may be referred to as a lipid biomarker; a biomarker associated with a heterocyclic compound may be referred to as a heterocyclic biomarker, and a biomarker associated with an elementary compound may be referred to as an elementary compound biomarker.

A "genetic biomarker," as used herein, is a biomarker associated with a gene or any product thereof (e.g., RNA, protein). Examples of a genetic biomarker include, but are not limited to, a gene expression level (e.g., an increased expression level or a decreased expression level), a gene mutation, a gene insertion, a gene deletion, a gene fusion, a single nucleotide polymorphism (SNPs), and a gene copy number variation (CNV).

A genetic biomarker as described herein may be associated with any gene. In some embodiments, genes are group by a related function and/or other property. Examples of gene groups include, but are not limited to, the fibroblasts group, the angiogenesis group, the tumor properties group, the anti-tumor immune microenvironment group, the tumor-promoting immune microenvironment group, the cancer associated fibroblasts group, the proliferation rate group, the PI3K/AKT/mTOR signaling group, the RAS/RAF/MEK signaling group, the receptor tyrosine kinases expression group, the tumor suppressors group, the metastasis signature group, the anti-metastatic factors group, the mutation status group, the antigen presentation group, the cytotoxic T and NK cells group, the B cells group, the anti-tumor microenvironment group, the checkpoint inhibition group, the Treg group, the MDSC group, the granulocytes group, the tumor-promotive immune group, the receptor tyrosine kinases expression group, the growth factors group, the tumor suppressors group, the metastasis signature group, the anti-metastatic factors group, the mutation status group, the MHCI group, the MHCII group, the coactivation molecules group, the effector cells group, the NK cells group, the T cell traffic group, the T cells group, the M1 signatures group, the Th1 signature group, the antitumor cytokines group, the checkpoint inhibition group, the M2 signature group, the Th2 signature group, the protumor cytokines group, and the complement inhibition group.

In some embodiments, a genetic biomarker may be associated with some (e.g., at least three) genes from one or more of the following groups: the fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the tumor properties group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, MCM6, PIK3CA, PIK3CB, PIK3CG, PIK3CD, AKT1, MTOR, PTEN, PRKCA, AKT2, AKT3, BRAF, FNTA, FNTB, MAP2K1, MAP2K2, MKNK1, MKNK2, ALK, AXL, KIT, EGFR, ERBB2, FLT3, MET, NTRK1, FGFR1, FGFR2, FGFR3, ERBB4, ERBB3, BCR-ABL, PDGFRA, PDGFRB, NGF, CSF3, CSF2, FGF7, IGF1, IGF2, IL7, FGF2, TP53, SIK1, PTEN, DCN, MTAP, AIM2, RB1, ESRP1, CTSL, HOXA1, SMARCA4, SNAI2, TWIST1, NEDD9, PAPPA, HPSE, KISS1, ADGRG1, BRMS1, TCF21, CDH1, PCDH10, NCAM1, MITF, APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL; the anti-tumor immune microenvironment group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, CD28, IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, TRAT1, CD19, MS4A1, TNFRSF13C, CD27, CD24, CR2, TNFRSF17, TNFRSF13B, CD22, CD79A, CD79B, BLK, NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the tumor-promoting immune microenvironment group: PDCD1, CD274, CTLA4, LAG3, PDCD1LG2, BTLA, HAVCR2, VSIR, CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, CCL28, IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, CXCL8, CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, CTSG, IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1; the cancer associated fibroblasts group: LGALS1, COL1A1, COL1A2, COL4A1, COL5A1, TGFB1, TGFB2, TGFB3, ACTA2, FGF2, FAP, LRP1, CD248, COL6A1, COL6A2, and COL6A3; the angiogenesis group: VEGFA, VEGFB, VEGFC, PDGFC, CXCL8, CXCR2, FLT1, PIGF, CXCL5, KDR, ANGPT1, ANGPT2, TEK, VWF, CDH5, NOS3, KDR, VCAM1, MMRN1, LDHA, HIF1A, EPAS1, CA9, SPP1, LOX, SLC2A1, and LAMP3; the proliferation rate group: MKI67, ESCO2, CETN3, CDK2, CCND1, CCNE1, AURKA, AURKB, CDK4, CDK6, PRC1, E2F1, MYBL2, BUB1, PLK1, CCNB1, MCM2, and MCM6; the PI3K/AKT/mTOR signaling group: PIK3CA, PIK3CB, PIK3CG, PIK3CD, AKT1, MTOR, PTEN, PRKCA, AKT2, and AKT3; the RAS/RAF/MEK signaling group: BRAF, FNTA, FNTB, MAP2K1, MAP2K2, MKNK1, and MKNK2; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL; the antigen presentation group: HLA-A, HLA-B, HLA-C, B2M, TAP1, TAP2, HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, HLA-DRB6, CD80, CD86, CD40, CD83, TNFRSF4, ICOSLG, and CD28; the cytotoxic T and NK cells group: IFNG, GZMA, GZMB, PRF1, LCK, GZMK, ZAP70, GNLY, FASLG, TBX21, EOMES, CD8A, CD8B, NKG7, CD160, CD244, NCR1, KLRC2, KLRK1, CD226, GZMH, GNLY, IFNG, KIR2DL4, KIR2DS1, KIR2DS2, KIR2DS3, KIR2DS4, KIR2DS5, CXCL9, CXCL10, CXCR3, CX3CL1, CCR7, CXCL11, CCL21, CCL2, CCL3, CCL4, CCL5, EOMES, TBX21, ITK, CD3D, CD3E, CD3G, TRAC, TRBC1, TRBC2, LCK, UBASH3A, and TRAT1; the B cells group: CD19, MS4A1, TNFRSF13C, CD27, CD24, CR2, TNFRSF17, TNFRSF13B, CD22, CD79A, CD79B, and BLK; the anti-tumor microenvironment group: NOS2, IL12A, IL12B, IL23A, TNF, IL1B, SOCS3, IFNG, IL2, CD40LG, IL15, CD27, TBX21, LTA, IL21, HMGB1, TNF, IFNB1, IFNA2, CCL3, TNFSF10, and FASLG; the checkpoint inhibition group: PDCD1, CD274, CTLA4, LAG3, PDCD1LG2, BTLA, HAVCR2, and VSIR; the Treg group: CXCL12, TGFB1, TGFB2, TGFB3, FOXP3, CTLA4, IL10, TNFRSF1B, CCL17, CXCR4, CCR4, CCL22, CCL1, CCL2, CCL5, CXCL13, and CCL28; the MDSC group: IDO1, ARG1, IL4R, IL10, TGFB1, TGFB2, TGFB3, NOS2, CYBB, CXCR4, CD33, CXCL1, CXCL5, CCL2, CCL4, CCL8, CCR2, CCL3, CCL5, CSF1, and CXCL8; the granulocytes group: CXCL8, CXCL2, CXCL1, CCL11, CCL24, KITLG, CCL5, CXCL5, CCR3, CCL26, PRG2, EPX, RNASE2, RNASE3, IL5RA, GATA1, SIGLEC8, PRG3, CMA1, TPSAB1, MS4A2, CPA3, IL4, IL5, IL13, SIGLEC8, MPO, ELANE, PRTN3, and CTSG; the tumor-promotive immune group: IL10, VEGFA, TGFB1, IDO1, PTGES, MRC1, CSF1, LRP1, ARG1, PTGS1, MSR1, CD163, CSF1R, IL4, IL5, IL13, IL10, IL25, GATA3, IL10, TGFB1, TGFB2, TGFB3, IL22, MIF, CFD, CFI, CD55, CD46, and CR1; the receptor tyrosine kinases expression group: ALK, AXL, KIT, EGFR, ERBB2, FLT3, MET, NTRK1, FGFR1, FGFR2, FGFR3, ERBB4, ERBB3, BCR-ABL, PDGFRA, and PDGFRB; the growth factors group: NGF, CSF3, CSF2, FGF7, IGF1, IGF2, IL7, and FGF2; the tumor suppressors group: TP53, SIK1, PTEN, DCN, MTAP, AIM2, and RB1; the metastasis signature group: ESRP1, CTSL, HOXA1, SMARCA4, SNAI2, TWIST1, NEDD9, PAPPA, and HPSE; the anti-metastatic factors group: KISS1, ADGRG1, BRMS1, TCF21, CDH1, PCDH10, NCAM1, and MITF; the mutation status group: APC, ARID1A, ATM, ATRX, BAP1, BRAF, BRCA2, CDH1, CDKN2A, CTCF, CTNNB1, DNMT3A, EGFR, FBXW7, FLT3, GATA3, HRAS, IDH1, KRAS, MAP3K1, MTOR, NAV3, NCOR1, NF1, NOTCH1, NPM1, NRAS, PBRM1, PIK3CA, PIK3R1, PTEN, RB1, RUNX1, SETD2, STAG2, TAF1, TP53, and VHL; the MHCI group: HLA-A, HLA-B, HLA-C, B2M, TAP1, and TAP2; the MHCII group: HLA-DRA, HLA-DRB1, HLA-DOB, HLA-DPB2, HLA-DMA, HLA-DOA, HLA-DPA1, HLA-DPB1, HLA-DMB, HLA-DQB1, HLA-DQA1, HLA-DRB5, HLA-DQA2, HLA-DQB2, and HLA-DRB6; the coactivation molecules group: CD80, CD86, CD40, CD83, TNFRSF4, ICOSLG, and CD28; the effector cells group: IFNG, GZMA, GZMB, PRF1, LCK, GZMK, ZAP70, GNLY, FASLG, TBX21, EOMES, CD8A, and CD8B; the NK cells group: NKG7, CD160, CD244, NCR1, KLRC2, KLRK1, CD226, GZMH, GNLY, IFNG, KIR2DL4, KIR2DS1, KIR2DS2, KIR2DS3, KIR2DS4, and KIR2DS5; the T cell traffic group: CXCL9, CXCL10, CXCR3, CX3CL1, CCR7, CXCL11, CCL21, CCL2, CCL3, CCL4, and CCL5; the T cells group: EOMES, TBX21, ITK, CD3D, CD3E, CD3G, TRAC, TRBC1, TRBC2, LCK, UBASH3A, and TRAT1; the M1 signatures group: NOS2, IL12A, IL12B, IL23A, TNF, IL1B, and SOCS3; the Th1 signature group: IFNG, IL2, CD40LG, IL15, CD27, TBX21, LTA, and IL21; the antitumor cytokines group: HMGB1, TNF, IFNB1, IFNA2, CCL3, TNFSF10, and FASLG; the M2 signature group: IL10, VEGFA, TGFB1, IDO1, PTGES, MRC1, CSF1, LRP1, ARG1, PTGS1, MSR1, CD163, and CSF1R; the Th2 signature group: IL4, IL5, IL13, IL10, IL25, and GATA3;

the protumor cytokines group: IL10, TGFB1, TGFB2, TGFB3, IL22, and MIF; and the complement inhibition group: CFD, CFI, CD55, CD46, and CR1.

A "protein biomarker," as used herein, is a biomarker associated with a protein. Examples of a protein biomarker include, but are not limited to, a protein expression level (e.g., an increased expression level or a decreased expression level), a protein activity level (e.g., an increased activity level or a decreased activity level), a protein mutation, and a protein truncation.

A protein biomarker as described herein may associated with any protein. Examples of proteins related to protein biomarkers include, but are not limited to, interferons, cytotoxic proteins, enzymes, cell adhesion proteins, extracellular matrix proteins, transcription factor proteins, intracellular signaling proteins, cytokines, chemokines, chemokine receptors, and interleukins. Such biomarkers may be referred to by the biomolecule for which they are related to, for example, interferon biomarker, cytotoxic protein biomarker, enzyme biomarker, cell adhesion protein biomarker, extracellular matrix protein biomarker, transcription factor protein biomarker, intracellular signaling protein biomarker, cytokine biomarker, chemokine biomarker, chemokine receptor biomarker, and interleukin biomarker. Such protein biomarkers may include products of, for example, any of the genes listed or referred to herein.

A "cellular biomarker," as used herein, is a biomarker associated with a cell. Examples of cellular biomarkers include, but are not limited to, numbers of types of one or more cells, percentage of one or more types of cells, location of one or more cells, and structure or morphology of one or more cells.

A cellular biomarker as described herein may be associated with any cell. Examples of cells include, but are not limited to, malignant cancer cells, leukocytes, lymphocytes, stromal cells, vascular endothelial cells, vascular pericytes, and myeloid-derived suppressor cells (MDSCs).

An "expression biomarker," as used herein, is a biomarker associated with an expression of a gene or a product thereof (e.g., RNA, protein). Examples of expression biomarkers include, but are not limited to, an increased expression level of a gene or product thereof, a decreased expression level of a gene or product thereof, expression of a truncated gene or product thereof, and expression of a mutated gene or product thereof.

By comparing the expression level of a biomarker in a sample obtained from a subject to a reference (or control), it can be determined whether the subject has an altered expression level (e.g., increased or decreased) as compared to the reference (or control). For example, if the level of a biomarker in a sample from a subject deviates (e.g., is increased or decreased) from the reference value (by e.g., 1%, 5%, 10%, 20%, 30%, 40%, 50%, 60%, 70%, 80%, 90%, 100%, 150%, 200%, 300%, 400%, 500% or more from a reference value), the biomarker might be identified as an expression biomarker.

An "imaging biomarker," as used herein, is a biomarker associated with imaging data. Examples of imaging biomarkers include, but are not limited to, expression levels obtained from imaging data, numbers of types of one or more cells obtained from imaging data, and cancer location and/or progression obtained from imaging data.

An imaging biomarker as described herein may be associated with any imaging data. Examples of imaging data include, but are not limited to, histological imaging data, immunohistological imaging data, magnetic resonance imaging (MRI) data, ultrasound data, and x-ray data.

A "disease-state biomarker," as used herein, is a biomarker associated with a state of a disease (e.g., cancer). Examples of disease-state biomarkers include, but are not limited to, metastasis status (e.g., absence or presence of metastasis), remission status (e.g., number of previous remissions, current remission), disease progression (e.g., low, moderate, or high disease progression), and cancer stage (e.g., stage 1, stage 2, stage 3, or stage 4).

Biomarkers as used herein encompasses any patient specific information that may be used to predict that patient's response to a therapy. For example, a personal habit of a patient (e.g., smoking) may be used as a biomarker to predict whether the patient is a responder or non-responder to a therapy.

A "personal habit biomarker," as used herein, is a biomarker associated with a personal habit of a subject. Examples of personal habit biomarkers include, but are not limited to, smoking (e.g., status as a smoker or non-smoker), frequency of exercise, alcohol use (e.g., low, moderate, high use of alcohol), and drug use (e.g., low, moderate, high use of drugs).

In another example, a cultural or environmental factor experienced by a patient may play a role in whether the patient responds to a therapy. Such factors are used in systems and methods described herein to predict a patient's response to a therapy.

An "anthropological biomarker," as used herein, is a biomarker associated with a culture and/or an environment of a subject. Examples of anthropological biomarkers include, but are not limited to, stress (e.g., low, moderate, or high stress levels), economic status (e.g., low, moderate, or high economic status), mental health (e.g., depression or anxiety), and relationship status (e.g., married, single, divorced, or widowed).

From Biomarker Values to Normalized Biomarker Scores

Aspects of the present disclosure provide systems and methods that normalize biomarker scores to a common scale, thereby allowing comparison of biomarker scores across different cell populations and/or among different subjects.

Normalized biomarker scores may be determined for any number of biomarkers as described herein. As used herein, the term "normalized biomarker score" refers to a biomarker value that has been adjusted (e.g., normalized) to a common scale according to the techniques described herein.

In some embodiments, biomarker values are normalized to create normalized biomarker scores based on a respective distribution of values for each biomarker in a reference subset of biomarkers. In some embodiments, the reference subset of biomarkers comprises biomarker information from any number of reference subjects. In one embodiment, a "reference subset" is a subset of biomarkers from one or more reference subjects, the values of which may be used to normalize a biomarker of a subject.

As a non-limiting example, data may be available for up to 4,000 biomarkers for a group of subjects. In this group of 4,000 biomarkers, 1,000 biomarkers may be associated with a particular therapy (thus creating a reference subset of 1,000 biomarkers). If, for a particular subject being analyzed using the methods and systems described herein, values for 723 of these biomarkers are available (thus creating a subject subset of 723 biomarkers), a normalized biomarker score for each of the 723 biomarkers may be computed using the distribution of values for each particular biomarker. As another non-limiting example, in this group of 4,000 biomarkers, 10 biomarkers may be associated with a particular therapy (thus creating a reference subset of 10 biomarkers).

If, for a particular subject being analyzed using the methods and systems described herein, values for 7 of these biomarkers are available (thus creating a subject subset of 7 biomarkers), a normalized biomarker score for each of the 7 biomarkers may be computed using the distribution of values for each particular biomarker.

In some embodiments, the reference subset of biomarkers comprises biomarker information from any number of subjects. In some embodiments, the reference subset of biomarkers comprises biomarker information from at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, or at least 1000 subjects. In some embodiments, the reference subset of biomarkers comprises biomarker information from up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 25, up to 30, up to 35, up to 40, up to 45, up to 50, up to 55, up to 60, up to 65, up to 70, up to 75, up to 80, up to 85, up to 90, up to 95, up to 100, up to 200, up to 300, up to 400, up to 500, or up to 1000 subjects.

A reference subset of biomarkers may comprise any number of biomarkers. In some embodiments, the reference subset of biomarkers comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, or at least 1000 biomarkers. In some embodiments, the reference subset of biomarkers comprises up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 25, up to 30, up to 35, up to 40, up to 45, up to 50, up to 55, up to 60, up to 65, up to 70, up to 75, up to 80, up to 85, up to 90, up to 95, up to 100, up to 200, up to 300, up to 400, up to 500, or up to 1000 biomarkers.

In some embodiments, biomarker values are normalized to create normalized biomarker scores based on a respective distribution of values for each biomarker in a subject subset of biomarkers. As used herein, the "subject subset" of biomarkers comprises biomarker information from a single subject. A subject subset of biomarkers may comprise any number of biomarkers. In some embodiments, the subject subset of biomarkers comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, or at least 1000 biomarkers. In some embodiments, the subject subset of biomarkers comprises up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 25, up to 30, up to 35, up to 40, up to 45, up to 50, up to 55, up to 60, up to 65, up to 70, up to 75, up to 80, up to 85, up to 90, up to 95, up to 100, up to 200, up to 300, up to 400, up to 500, or up to 1000 biomarkers. In some embodiments, the subject subset of biomarkers is identical to the reference subset of biomarkers (i.e., for a given calculation, system, or method described herein).

Systems and methods described herein provide for determining any number of normalized biomarker scores using sequencing data and biomarker information. In some embodiments, systems and methods described herein provide for determining at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, or at least 1000 normalized biomarker scores. In some embodiments, systems and methods described herein provide for determining up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 25, up to 30, up to 35, up to 40, up to 45, up to 50, up to 55, up to 60, up to 65, up to 70, up to 75, up to 80, up to 85, up to 90, up to 95, up to 100, up to 200, up to 300, up to 400, up to 500, or up to 1000 normalized biomarker scores.

Systems and methods described herein, in some embodiments, provide for determining normalized biomarker scores for biomarkers associated with a particular therapy. In some embodiments, systems and methods described herein provide for determining normalized biomarker scores for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500, or at least 1000 biomarkers associated with a particular therapy. In some embodiments, systems and methods described herein provide for determining normalized biomarker scores for up to 1, up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 25, up to 30, up to 35, up to 40, up to 45, up to 50, up to 55, up to 60, up to 65, up to 70, up to 75, up to 80, up to 85, up to 90, up to 95, up to 100, up to 200, up to 300, up to 400, up to 500, or up to 1000 biomarkers associated with a particular therapy.

Systems and methods for normalization of biomarkers as described herein may be applied to biomarkers for any cancer (e.g., any tumor). Exemplary cancers include, but are not limited to, adrenocortical carcinoma, bladder urothelial carcinoma, breast invasive carcinoma, cervical squamous cell carcinoma, endocervical adenocarcinoma, colon adenocarcinoma, esophageal carcinoma, kidney renal clear cell carcinoma, kidney renal papillary cell carcinoma, liver hepatocellular carcinoma, lung adenocarcinoma, lung squamous cell carcinoma, ovarian serous cystadenocarcinoma, pancreatic adenocarcinoma, prostate adenocarcinoma, rectal adenocarcinoma, skin cutaneous melanoma, stomach adenocarcinoma, thyroid carcinoma, uterine corpus endometrial carcinoma, any type of lymphoma, leukemia, and cholangiocarcinoma.

Obtaining Biomarker Information

Biomarker information as described herein may be obtained from a variety of sources. In some embodiments, biomarker information may be obtained by analyzing a biological sample from a patient. The biological sample may be analyzed prior to performance of the methods described herein for predicting the efficacy of one or more treatments for the patient. In some such embodiments, data obtained from the biological sample may stored (e.g., in a database) and accessed during performance of the techniques described herein for predicting the efficacy of one or more treatments for the patient. In some embodiments, biomarker information is obtained from a database containing biomarker information for at least one patient.

Biological Samples

Any biological sample from a subject (i.e., a patient or individual) may be analyzed as described herein to obtain biomarker information. In some embodiments, the biological sample may be any sample from a subject known or suspected of having cancerous cells or pre-cancerous cells.

The biological sample may be from any source in the subject's body including, but not limited to, any fluid [such as blood (e.g., whole blood, blood serum, or blood plasma), saliva, tears, synovial fluid, cerebrospinal fluid, pleural fluid, pericardial fluid, ascitic fluid, and/or urine], hair, skin (including portions of the epidermis, dermis, and/or hypodermis), oropharynx, laryngopharynx, esophagus, stomach, bronchus, salivary gland, tongue, oral cavity, nasal cavity, vaginal cavity, anal cavity, bone, bone marrow, brain, thymus, spleen, small intestine, appendix, colon, rectum, anus, liver, biliary tract, pancreas, kidney, ureter, bladder, urethra, uterus, vagina, vulva, ovary, cervix, scrotum, penis, prostate, testicle, seminal vesicles, and/or any type of tissue (e.g., muscle tissue, epithelial tissue, connective tissue, or nervous tissue).

The biological sample may be any type of sample including, for example, a sample of a bodily fluid, one or more cells, a piece of tissue, or some or all of an organ. In certain embodiments, one sample will be taken from a subject for analysis. In some embodiments, more than one (e.g., 2, 3, 4, 5, 6, 7, 8, 9, 10, 11, 12, 13, 14, 15, 16, 17, 18, 19, 20, or more) samples may be taken from a subject for analysis. In some embodiments, one sample from a subject will be analyzed. In certain embodiments, more than one (e.g., 2, 3, 4, 5, 6, 7, 8, 9, 10, 11, 12, 13, 14, 15, 16, 17, 18, 19, 20, or more) samples may be analyzed. If more than one sample from a subject is analyzed, the samples may be procured at the same time (e.g., more than one sample may be taken in the same procedure), or the samples may be taken at different times (e.g., during a different procedure including a procedure 1, 2, 3, 4, 5, 6, 7, 8, 9, 10 days; 1, 2, 3, 4, 5, 6, 7, 8, 9, 10 weeks; 1, 2, 3, 4, 5, 6, 7, 8, 9, 10 months, 1, 2, 3, 4, 5, 6, 7, 8, 9, 10 years, or 1, 2, 3, 4, 5, 6, 7, 8, 9, 10 decades after a first procedure). A second or subsequent sample may be taken or obtained from the same region (e.g., from the same tumor or area of tissue) or a different region (including, e.g., a different tumor). A second or subsequent sample may be taken or obtained from the subject after one or more treatments, and may be taken from the same region or a different region. As a non-limiting example, the second or subsequent sample may be useful in determining whether the cancer in each sample has different characteristics (e.g., in the case of samples taken from two physically separate tumors in a patient) or whether the cancer has responded to one or more treatments (e.g., in the case of two or more samples from the same tumor or different tumors prior to and subsequent to a treatment).

Any of the biological samples described herein may be obtained from the subject using any known technique. In some embodiments, the biological sample may be obtained from a surgical procedure (e.g., laparoscopic surgery, microscopically controlled surgery, or endoscopy), bone marrow biopsy, punch biopsy, endoscopic biopsy, or needle biopsy (e.g., a fine-needle aspiration, core needle biopsy, vacuum-assisted biopsy, or image-guided biopsy). In some embodiments, each of the at least one biological samples is a bodily fluid sample, a cell sample, or a tissue biopsy.

In some embodiments, one or more than one cell (i.e., a cell sample) may be obtained from a subject using a scrape or brush method. The cell sample may be obtained from any area in or from the body of a subject including, for example, from one or more of the following areas: the cervix, esophagus, stomach, bronchus, or oral cavity. In some embodiments, one or more than one piece of tissue (e.g., a tissue biopsy) from a subject may be used. In certain embodiments, the tissue biopsy may comprise one or more than one (e.g., 2, 3, 4, 5, 6, 7, 8, 9, 10, or more than 10) samples from one or more tumors or tissues known or suspected of having cancerous cells.

Sample Analysis

Systems and methods described herein are based, at least in part, on the identification and characterization of certain biomarkers of a patient and/or the patient's cancer. Such information may be obtained from a biological sample of the subject (e.g., the patient) as described herein.

Any type of analysis may be performed on a biological sample from a subject. In some embodiments, a blood analysis is performed on a biological sample from a subject. In some embodiments, a cytometry analysis is performed on a biological sample from a subject. In some embodiments, a histological analysis is performed on a biological sample from a subject. In some embodiments, a immunohistological analysis is performed on a biological sample from a subject.

Any type of sequencing data may be obtained from a biological sample of a subject. In some embodiments, the sequencing data is DNA sequencing data. In some embodiments, the sequencing data is RNA sequencing data. In some embodiments, the sequencing data is proteome sequencing data.

Such sequencing data may be obtained by any known technique. In some embodiments, the sequencing data is obtained from whole genome sequencing (WGS). In some embodiments, the sequencing data is obtained from whole exome sequencing (WES). In some embodiments, the sequencing data is obtained from whole transcriptome sequencing. In some embodiments, the sequencing data is obtained from mRNA sequencing. In some embodiments, the sequencing data is obtained from DNA/RNA-hybridization. In some embodiments, the sequencing data is obtained from microarray. In some embodiments, the sequencing data is obtained from DNA/RNA chip. In some embodiments, the sequencing data is obtained from PCR. In some embodiments, the sequencing data is obtained from single nucleotide polymorphism (SNP) genotyping.

Expression data (e.g., indicating expression levels) for a plurality of genes may be obtained from a biological sample. There is no limit to the number of genes which may be examined. For example, there is no limit to the number of genes for which the expression levels may be examined.

As a non-limiting example, four or more, five or more, six or more, seven or more, eight or more, nine or more, ten or more, eleven or more, twelve or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 40 or more, 50 or more, 60 or more, 70 or more, 80 or more, 90 or more, 100 or more, 125 or more, 150 or more, 175 or more, 200 or more, 225 or more, 250 or more, 275 or more, or 300 or more genes may be used for any evaluation described herein. As another set of non-limiting examples, at least four, at least five, at least six, at least seven, at least eight, at least nine, at least ten, at least eleven, at least twelve, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 125, at least 150, at least 175, at least 200, at least 225, at least 250, at least 275, or at least 300 genes may be used for any evaluation described herein. As a further set of non-limiting examples, up to four, up to five, up to six, up to seven, up to eight, up to nine, up to ten, up to eleven, up to twelve, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 40, up to 50, up to 60, up to 70, up to 80, up to 90, up to 100, up to 125, up to 150, up to 175, up to 200, up to 225, up to 250, up to 275, or up to 300 genes may be used for any evaluation described herein.

Any method may be used on a sample from a subject in order to acquire expression data (e.g., indicating expression levels) for the plurality of genes. As a set of non-limiting examples, the expression data may be RNA expression data, DNA expression data, or protein expression data.

DNA expression data, in some embodiments, refers to a level of DNA in a sample from a subject. The level of DNA in a sample from a subject having cancer may be elevated compared to the level of DNA in a sample from a subject not having cancer, e.g., a gene duplication in a cancer patient's sample. The level of DNA in a sample from a subject having cancer may be reduced compared to the level of DNA in a sample from a subject not having cancer, e.g., a gene deletion in a cancer patient's sample.

DNA expression data, in some embodiments, refers to data for DNA (or gene) expressed in a sample, for example, sequencing data for a gene that is expressed in a patient's sample. Such data may be useful, in some embodiments, to determine whether the patient has one or more mutations associated with a particular cancer.

RNA expression data may be acquired using any method known in the art including, but not limited to: whole transcriptome sequencing, total RNA sequencing, mRNA sequencing, targeted RNA sequencing, small RNA sequencing, ribosome profiling, RNA exome capture sequencing, and/or deep RNA sequencing. DNA expression data may be acquired using any method known in the art including any known method of DNA sequencing. For example, DNA sequencing may be used to identify one or more mutations in the DNA of a subject. Any technique used in the art to sequence DNA may be used with the methods and systems described herein. As a set of non-limiting examples, the DNA may be sequenced through single-molecule real-time sequencing, ion torrent sequencing, pyrosequencing, sequencing by synthesis, sequencing by ligation (SOLiD sequencing), nanopore sequencing, or Sanger sequencing (chain termination sequencing). Protein expression data may be acquired using any method known in the art including, but not limited to: N-terminal amino acid analysis, C-terminal amino acid analysis, Edman degradation (including though use of a machine such as a protein sequenator), or mass spectrometry.

In some embodiments, the expression data comprises whole exome sequencing (WES) data. In some embodiments, the expression data comprises whole genome sequencing (WGS) data. In some embodiments, the expression data comprises next-generation sequencing (NGS) data. In some embodiments, the expression data comprises microarray data.

Datasets

Any dataset containing information associated with a biomarker may be used to obtain biomarker information as described herein. In some embodiments, biomarker information may be obtained from one or more databases and/or any other suitable electronic repository of data. Examples of databases include, but are not limited to, CGP (Cancer Genome Project), CPTAC (Clinical Proteomic Tumor Analysis Consortium), ICGC (International Cancer Genome Consortium), and TCGA (The Cancer Genome Atlas). In some embodiments, biomarker information may be obtained from data associated with a clinical trial. In some embodiments, biomarker information may be predicted in association with a clinical trial based on one or more similar drugs (e.g., drugs of a similar class such as PD-1 inhibitors). In some embodiments, biomarker information may be obtained from a hospital database. In some embodiments, biomarker information may be obtained from a commercial sequencing supplier. In some embodiments, biomarker information may be obtained from a subject (e.g., a patient) and/or a subject's (e.g., a patient's) relative, guardian, or caretaker.

Assays

Any of the biological samples described herein can be used for obtaining expression data using conventional assays or those described herein. Expression data, in some embodiments, includes gene expression levels. Gene expression levels may be detected by detecting a product of gene expression such as mRNA and/or protein.

In some embodiments, gene expression levels are determined by detecting a level of a protein in a sample and/or by detecting a level of activity of a protein in a sample. As used herein, the terms "determining" or "detecting" may include assessing the presence, absence, quantity and/or amount (which can be an effective amount) of a substance within a sample, including the derivation of qualitative or quantitative concentration levels of such substances, or otherwise evaluating the values and/or categorization of such substances in a sample from a subject.

The level of a protein may be measured using an immunoassay. Examples of immunoassays include any known assay (without limitation), and may include any of the following: immunoblotting assay (e.g., Western blot), immunohistochemical analysis, flow cytometry assay, immunofluorescence assay (IF), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting a level of a protein provided herein will be apparent to those of skill in the art.

Such immunoassays may involve the use of an agent (e.g., an antibody) specific to the target protein. An agent such as an antibody that "specifically binds" to a target protein is a term well understood in the art, and methods to determine such specific binding are also well known in the art. An antibody is said to exhibit "specific binding" if it reacts or associates more frequently, more rapidly, with greater duration and/or with greater affinity with a particular target protein than it does with alternative proteins. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen. In some embodiments, a sample may be contacted, simultaneously or sequentially, with more than one binding agent that binds different proteins (e.g., multiplexed analysis).

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG, IgE, IgD, IgM (as well as subtypes thereof). Antibodies may be from any source including, but not limited to, primate (human and non-human primate) and primatized (such as humanized) antibodies.

In some embodiments, the antibodies as described herein can be conjugated to a detectable label and the binding of the detection reagent to the peptide of interest can be determined based on the intensity of the signal released from the detectable label. Alternatively, a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

It will be apparent to those of skill in the art that this disclosure is not limited to immunoassays. Detection assays that are not based on an antibody, such as mass spectrometry, are also useful for the detection and/or quantification of a protein and/or a level of protein as provided herein. Assays that rely on a chromogenic substrate can also be useful for the detection and/or quantification of a protein and/or a level of protein as provided herein.

Alternatively, the level of nucleic acids encoding a gene in a sample can be measured via a conventional method. In some embodiments, measuring the expression level of nucleic acid encoding the gene comprises measuring mRNA. In some embodiments, the expression level of mRNA encoding a gene can be measured using real-time reverse transcriptase (RT) Q-PCR or a nucleic acid microarray. Methods to detect nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

In some embodiments, the level of nucleic acids encoding a gene in a sample can be measured via a hybridization assay. In some embodiments, the hybridization assay comprises at least one binding partner. In some embodiments, the hybridization assay comprises at least one oligonucleotide binding partner. In some embodiments, the hybridization assay comprises at least one labeled oligonucleotide binding partner. In some embodiments, the hybridization assay comprises at least one pair of oligonucleotide binding partners. In some embodiments, the hybridization assay comprises at least one pair of labeled oligonucleotide binding partners.

Any binding agent that specifically binds to a desired nucleic acid or protein may be used in the methods and kits described herein to measure an expression level in a sample. In some embodiments, the binding agent is an antibody or an aptamer that specifically binds to a desired protein. In other embodiments, the binding agent may be one or more oligonucleotides complementary to a nucleic acid or a portion thereof. In some embodiments, a sample may be contacted, simultaneously or sequentially, with more than one binding agent that binds different proteins or different nucleic acids (e.g., multiplexed analysis).

To measure an expression level of a protein or nucleic acid, a sample can be in contact with a binding agent under suitable conditions. In general, the term "contact" refers to an exposure of the binding agent with the sample or cells collected therefrom for suitable period sufficient for the formation of complexes between the binding agent and the target protein or target nucleic acid in the sample, if any. In some embodiments, the contacting is performed by capillary action in which a sample is moved across a surface of the support membrane.

In some embodiments, an assay may be performed in a low-throughput platform, including single assay format. In some embodiments, an assay may be performed in a high-throughput platform. Such high-throughput assays may comprise using a binding agent immobilized to a solid support (e.g., one or more chips). Methods for immobilizing a binding agent will depend on factors such as the nature of the binding agent and the material of the solid support and may require particular buffers. Such methods will be evident to one of ordinary skill in the art.

Genes

The various genes recited herein are, in general, named using human gene naming conventions. The various genes, in some embodiments, are described in publically available resources such as published journal articles. The gene names may be correlated with additional information (including sequence information) through use of, for example, the NCBI GenBank® databases available at www <dot> ncbi <dot> nlm <dot> nih <dot> gov; the HUGO (Human Genome Organization) Gene Nomination Committee (HGNC) databases available at www <dot> genenames <dot> org; the DAVID Bioinformatics Resource available at www <dot> david <dot> ncifcrf <dot> gov. It should be appreciated that a gene may encompass all variants of that gene. For organisms or subjects other than human subjects, corresponding specific-specific genes may be used. Synonyms, equivalents, and closely related genes (including genes from other organisms) may be identified using similar databases including the NCBI GenBank® databases described above.

In some embodiments, gene AXL may be identified as GenBank® Accession number NM_199054.2 or NM_017572.3.; gene CCL2 may be identified as GenBank® Accession number NM_002982.3; gene CCL7 may be identified as GenBank® Accession number NM_006273.3; gene CCL8 may be identified as GenBank® Accession number NM_005623.2; gene CDH1 may be identified as GenBank® Accession number NM_004360.4, NM_001317184.1, NM_001317185.1, or NM_001317186.1; gene VEGFC may be identified as GenBank® Accession number NM_005429.4; gene EGFR may be identified as GenBank® Accession number NM_001346941.1, NM_005228.4, NM_001346898.1, NM_001346900.1, NM_001346899.1, NM_001346897.1, NM_201284.1, NM_201283.1 or NM_201282.1; gene ROR2 may be identified as GenBank® Accession number NM_004560.3 or NM_001318204.1; gene PTEN may be identified as GenBank® Accession number NM_001304717.2, NM_000314.6 or NM_001304718.1; gene TAGLN may be identified as GenBank® Accession number NM_001001522.2 or NM_003186.4.

Predicting Therapy Response

Normalized biomarker scores derived from a patient and/or a patient's biological sample as described herein may be used for various clinical purposes including, for example, identifying subjects suitable for a particular treatment (e.g., an immunotherapy), and/or predicting likelihood of a patient's response or lack thereof to a particular treatment. Accordingly, described herein are prognostic methods for predicting therapy efficacy, for example, an immunotherapy, based on a patient's biomarker values. Additionally, the systems and methods described herein may be used to predict whether a patient (subject) may or may not have one or more adverse reactions to a particular therapy, based on the patient's biomarker values (e.g., whether a subject is likely to have immune-mediated adverse reactions to checkpoint blockade therapy and/or not have immune-mediated adverse reactions to checkpoint blockade therapy).

To practice methods for predicting therapeutic efficacy as described herein, a therapy score for a patient may be determined for a particular therapy. As used herein, the term "therapy score" is calculated using multiple normalized biomarker scores for a patient that is indicative of a predicted response of that subject to a therapy. As a set of non-limiting examples, such a "therapy score" may be calculated using multiple normalized biomarker scores in one or more of the following ways: 1) as a sum; 2) as a weighted sum (e.g., in a regression model); 3) using any linear or generalized linear model taking the normalized biomarker scores as inputs and producing, based on the input normalized biomarker scores, an output indicative of a patient's predicted response to a therapy; 4) using any statistical model (e.g., a neural network model, a Bayesian regression model, an adaptive non-linear regression model, a support vector regression model, a Gaussian mixture model, random forest regression, and/or any other suitable type mixture model) taking the normalized biomarker scores as inputs and producing, based on the input biomarker scores, an output indicative of a patient's predicted response to a therapy.

A therapy score as described herein includes a therapy score calculated using any suitable number of normalized biomarker scores. In some embodiments, the therapy score may be calculated using at least 2 normalized biomarker scores. In some embodiments, the therapy score may be calculated using at least 3, at least 4, at least 5, at least 6, at least 7, at least 8, at least 9, at least 10, at least 20, at least 30, at least 40, at least 50, at least 60, at least 70, at least 80, at least 90, or at least 100 normalized biomarker scores.

In some embodiments, a therapy score is calculated using one or more normalized biomarker values which may be weighted by one or more respective weights as part of the calculation. A biomarker weight may be assigned to any biomarker. For example, an abundant biomarker may be assigned a higher weight for predicting a therapy response. Such weights may be determined, for example, using a machine learning technique. As a non-limiting set of examples, such weights may be determined by training a regression model (e.g., a linear regression model, a generalized linear model, a support vector regression model, a logistic regression model, a random forest regression model, a neural network model, etc.).

A therapy score for a therapy may be a positive value or a negative value. A positive therapy score, in some embodiments, is indicative of a positive response to a therapy. A negative therapy score, in some embodiments, is indicative of a negative response or no response to a therapy. A therapy score close to zero, in some embodiments, is indicative of little or no measurable response to a therapy.

A therapy score, in some embodiments, more accurately predicts a patient's response to a therapy when compared, for example, to using a single biomarker. For example, a patient's response to a therapy may be more accurately predicted as a therapy score positively increases in numeric value. In another example, a patient's lack of response to a therapy may be more accurately predicted as a therapy score negatively increases in numeric value.

The terms "subject" or "patient" may be used interchangeably and refer to a subject who needs the analysis as described herein. In some embodiments, the subject is a human or a non-human mammal (e.g., a non-human primate). In some embodiments, the subject is suspected to have cancer or is at risk for cancer. In some embodiments, the subject has (e.g., is known to have) cancer. Examples of cancer include, without limitation, adrenocortical carcinoma, bladder urothelial carcinoma, breast invasive carcinoma, cervical squamous cell carcinoma, endocervical adenocarcinoma, colon adenocarcinoma, esophageal carcinoma, kidney renal clear cell carcinoma, kidney renal papillary cell carcinoma, liver hepatocellular carcinoma, lung adenocarcinoma, lung squamous cell carcinoma, ovarian serous cystadenocarcinoma, pancreatic adenocarcinoma, prostate adenocarcinoma, rectal adenocarcinoma, skin cutaneous melanoma, stomach adenocarcinoma, thyroid carcinoma, uterine corpus endometrial carcinoma, one or more types of leukemia, and cholangiocarcinoma.

In some embodiments, the subject is a human patient having one or more symptom of a cancer. For example, the subject may have fatigue, pain, weakness or numbness, loss of bladder or bowel control, cough, blood-tinged saliva, anemia, breast lump or discharge, or a combination thereof. In some embodiments, the subject has a symptom of cancer or has a history of a symptom of cancer. In some embodiments, the subject has more than one symptom of cancer or has a history of more than one symptoms of cancer. In some embodiments, the subject has no symptom of cancer, has no history of a symptom of cancer, or has no history of cancer.

Such a subject may exhibit one or more symptoms associated with a cancer. Alternatively or in addition, such a subject may have one or more risk factors for cancer, for example, an environmental factor associated with cancer (e.g., geographic location or exposure to a mutagen), a family history of cancer, and/or a genetic predisposition to developing cancer.

Alternatively, the subject who needs the analysis described herein may be a patient having cancer or suspected of having cancer. Such a subject may currently be having a relapse, or may have suffered from the disease in the past (e.g., may be currently relapse-free), or may have cancer. In some examples, the subject is a human patient who may be on a treatment (i.e., the subject may be receiving treatment) for the disease including, for example, a treatment involving chemotherapy or radiation therapy. In other instances, such a human patient may be free of such a treatment.

Impact Scores

In some embodiments, the systems and methods described herein may be used to assess the effectiveness of a therapy over time. In some embodiments, aspects of the disclosure provide methods and systems for using normalized biomarker scores obtained from samples prior to and subsequent to administration of a candidate therapy to determine the efficacy of that therapy. In some embodiments, such methods may also be used to select a candidate therapy for use with a patient or subject. In certain embodiments, such methods may be used to assess the impact of a candidate therapy, which impact may be quantified by determining an impact score, in accordance with some embodiments described herein.

For example, some embodiments provide for determining, using a first and second set of normalized biomarker scores for a subject, an impact score for a candidate therapy, wherein the first and second set of normalized biomarker scores are determined using first sequencing data about at least one biological sample of a subject prior to administration of the candidate therapy, and second sequencing data about at least one biological sample of a subject subsequent to administration of the candidate therapy. Such an impact score would be indicative of response (e.g., a positive or negative response) of the subject to administration of the candidate therapy.

Computer Implemented Methods for Predicting or Describing Therapy Response

Aspects of the disclosure provide computer implemented methods for determining, using a set of normalized biomarker scores, biomarker scores for a subject indicative of a patient's response or lack thereof to a particular therapy.

In some embodiments, a software program may provide a user with a visual representation presenting information related to a patient's biomarkers scores (e.g., a biomarker score, and/or a therapy score, and/or an impact score), and predicted efficacy of a therapy. Such a software program may execute in any suitable computing environment including, but not limited to, a cloud-computing environment, a device co-located with a user (e.g., the user's laptop, desktop, smartphone, etc.), one or more devices remote from the user (e.g., one or more servers), etc.

For example, in some embodiments, the techniques described herein may be implemented in the illustrative environment 100 shown in FIG. 1A. As shown in FIG. 1A, within illustrative environment 100, one or more biological samples of a patient 102 may be provided to a laboratory 104. Laboratory 104 may process the biological sample(s) to obtain sequencing data (e.g., transcriptome, exome, and/or genome sequencing data) and provide it, via network 108, to at least one database 106 that stores information about patient 102.

Network 108 may be a wide area network (e.g., the Internet), a local area network (e.g., a corporate Intranet), and/or any other suitable type of network. Any of the devices shown in FIG. 1A may connect to the network 108 using one or more wired links, one or more wireless links, and/or any suitable combination thereof.

In the illustrated embodiment of FIG. 1A, the at least one database 106 may store sequencing data for the patient, expression data for the patient, medical history data for the patient, test result data for the patient, and/or any other suitable information about the patient 102. Examples of stored test result data for the patient include biopsy test results, imaging test results (e.g., MRI results), and blood test results. The information stored in at least one database 106 may be stored in any suitable format and/or using any suitable data structure(s), as aspects of the technology described herein are not limited in this respect. The at least one database 106 may store data in any suitable way (e.g., one or more databases, one or more files). The at least one database 106 may be a single database or multiple databases.

As shown in FIG. 1A, illustrative environment 100 includes one or more external databases 116, which may store information for patients other than patient 102. For example, external databases 116 may store expression data (of any suitable type) for one or more patients, medical history data for one or more patients, test result data (e.g., imaging results, biopsy results, blood test results) for one or more patients, demographic and/or biographic information for one or more patients, and/or any other suitable type of information. In some embodiments, external database(s) 116 may store information available in one or more publically accessible databases such as TCGA (The Cancer Genome Atlas), one or more databases of clinical trial information, and/or one or more databases maintained by commercial sequencing suppliers. The external database(s) 116 may store such information in any suitable way using any suitable hardware, as aspects of the technology described herein are not limited in this respect.

In some embodiments, the at least one database 106 and the external database(s) 116 may be the same database, may be part of the same database system, or may be physically co-located, as aspects of the technology described herein are not limited in this respect.

In some embodiments, information stored in patient information database 106 and/or in external database(s) 116 may be used to perform any of the techniques described herein related to determining a therapy score and/or impact score indicative of a patient's response to a therapy. For example, the information stored in the database(s) 106 and/or 116 may be accessed, via network 108, by software executing on server(s) 110 to perform any one or more of the techniques described herein in connection with FIGS. 2A, 2B, 2C, 2D and 2E.

For example, in some embodiments, server(s) 110 may access information stored in database(s) 106 and/or 116 and use this information to perform process 200, described with reference to FIG. 2A, for determining therapy scores for multiple therapies based on normalized biomarker scores.

As another example, server(s) 110 may access information stored in database(s) 106 and/or 116 and use this information to perform process 220, described with reference to FIG. 2B, for determining the effectiveness of a candidate therapy on a patient.

As another example, server(s) 110 may access information stored in database(s) 106 and/or 116 and use this information to perform process 240, described with reference to FIG. 2C, for determining therapy scores for at least two selected therapies based on normalized biomarker scores for at least three biomarkers for each of the therapies.

As another example, server(s) 110 may access information stored in database(s) 106 and/or 116 and use this information to perform process 260, described with reference to FIG. 2D, for obtaining first and second therapy scores for first and second therapies.

As yet another example, server(s) 110 may access information stored in database(s) 106 and/or 116 and use this information to perform process 280, described with reference to FIG. 2E, for identifying a subject as a member of a cohort using normalized biomarker scores.

In some embodiments, server(s) 110 may include one or multiple computing devices. When server(s) 110 include multiple computing devices, the device(s) may be physically co-located (e.g., in a single room) or distributed across multi-physical locations. In some embodiments, server(s) 110 may be part of a cloud computing infrastructure. In some embodiments, one or more server(s) 110 may be co-located in a facility operated by an entity (e.g., a hospital, research institution) with which doctor 114 is affiliated. In such embodiments, it may be easier to allow server(s) 110 to access private medical data for the patient 102.

As shown in FIG. 1A, in some embodiments, the results of the analysis performed by server(s) 110 may be provided to doctor 114 through a computing device 114 (which may be a portable computing device, such as a laptop or smartphone, or a fixed computing device such as a desktop computer). The results may be provided in a written report, an e-mail, a graphical user interface, and/or any other suitable way. It should be appreciated that although in the embodiment of FIG. 1A, the results are provided to a doctor, in other embodiments, the results of the analysis may be provided to patient 102 or a caretaker of patient 102, a healthcare provider such as a nurse, or a person involved with a clinical trial.

In some embodiments, the results may be part of a graphical user interface (GUI) presented to the doctor 114 via the computing device 112. In some embodiments, the GUI may be presented to the user as part of a webpage displayed by a web browser executing on the computing device 112. In some embodiments, the GUI may be presented to the user using an application program (different from a web-browser) executing on the computing device 112. For example, in some embodiments, the computing device 112 may be a mobile device (e.g., a smartphone) and the GUI may be presented to the user via an application program (e.g., "an app") executing on the mobile device.

The GUI presented on computing device 112 provides a wide range of oncological data relating to both the patient and the patient's cancer in a new way that is compact and highly informative. Previously, oncological data was obtained from multiple sources of data and at multiple times making the process of obtaining such information costly from both a time and financial perspective. Using the techniques and graphical user interfaces illustrated herein, a user can access the same amount of information at once with less demand on the user and with less demand on the computing resources needed to provide such information. Low demand on the user serves to reduce clinician errors associated with searching various sources of information. Low demand on the computing resources serves to reduce processor power, network bandwidth, and memory needed to provide a wide range of oncological data, which is an improvement in computing technology.

Figure 1B:
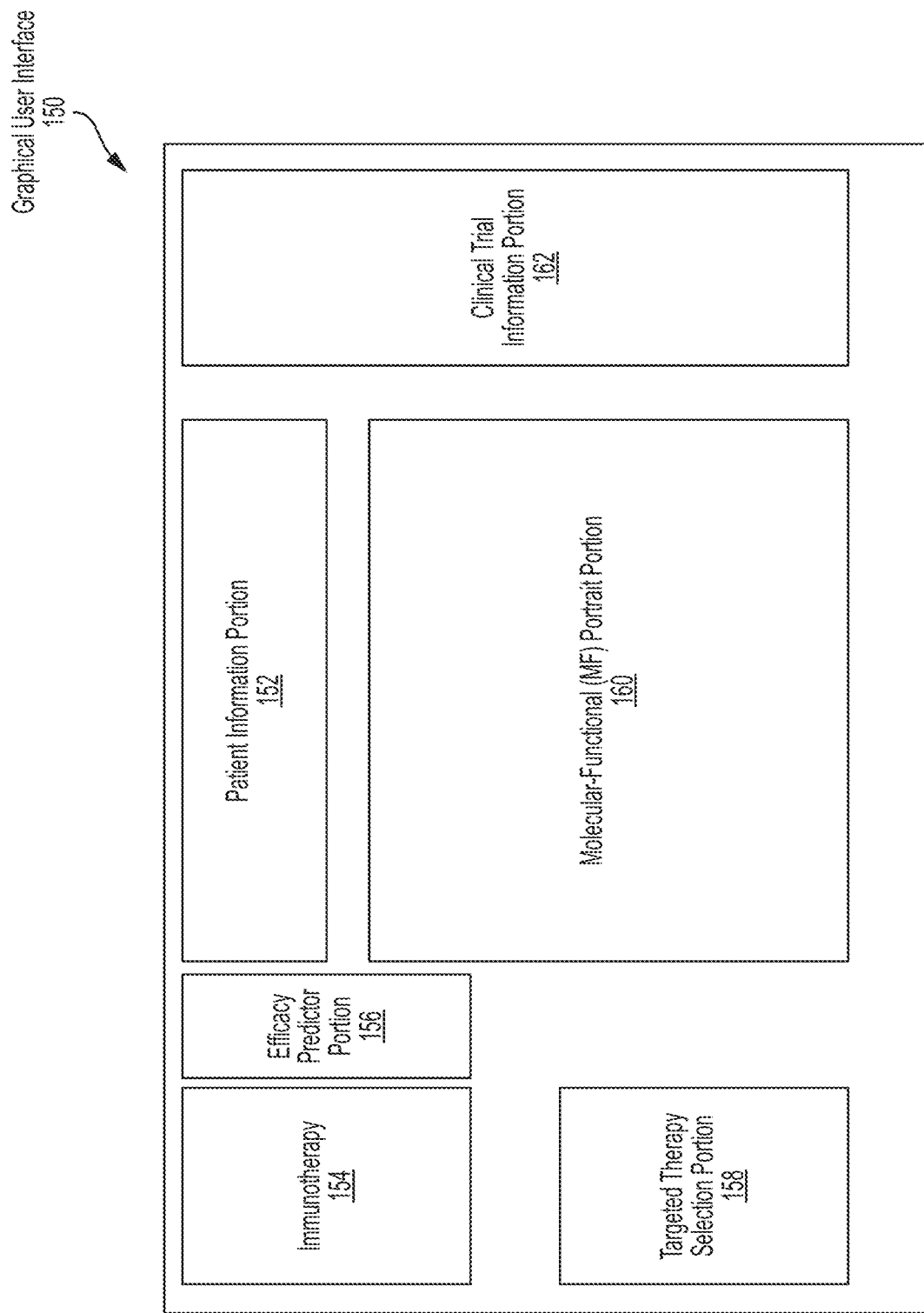
FIG. 1B is a block diagram of patient data that may be presented to a user, in accordance with some embodiments of the technology described herein.

FIG. 1B shows a block diagram of an illustrative GUI 150 containing information about patient 102. GUI 150 may include separate portions providing different types of information about patient 102. Illustrative GUI 150 includes the following portions: Patient Information Portion 152, Molecular-Functional (MF) Portrait Portion 160, Clinical Trial Information Portion 162, Immunotherapy Portion 154, Efficacy Predictor Portion 156, and Targeted Therapy Selection Portion 158.

Patient Information Portion 152 may provide general information about the patient and the patient's cancer. General information about the patient may include such information as the patient's name and date of birth, the patient's insurance provider, and contact information for the patient such as address and phone number. General information about the patient's cancer may include the patient's diagnosis, the patient's history of relapse and/or remission, and information relating to stage of the patient's cancer. Patient Information Portion 152 may also provide information relating to potential treatment options for the patient and/or previously administered treatments.

Molecular-Functional (MF) Portrait Portion 160 may include a molecular functional tumor portrait (MF profile) which refers to a graphical depiction of a tumor with regard to its molecular and cellular composition, and biological processes that are present within and/or surrounding the tumor. Further aspects relating to a patient's MF profile are provided in International patent application number PCT/US18/37017, entitled "Systems and Methods for Generating, Visualizing and Classifying Molecular Functional Profiles," filed Jun. 12, 2018, the entire contents of which are incorporated herein by reference.

Clinical Trial Information Portion 162 may include information relating to a clinical trial for a therapy that may be and/or will be administered to the patient. Clinical Trial Information Portion 162 may provide information about an ongoing clinical trial or a completed clinical trial. Information that may be provided in Clinical Trial Information Portion 162 may include information related to a therapy used in the clinical trial such as dosage and dosage regimen, number and diagnosis of patients participating in the clinical trial, and patient outcomes.

Immunotherapy Portion 154 may include patient specific information as it relates to an immunotherapy. Immunotherapy Portion 154 may provide such information for different immunotherapies, for example, immune checkpoint blockade therapies, anti-cancer vaccine therapies, and T cell therapies. Patient specific information relating to an immunotherapy may include information about the patient such as the patient's biomarkers associated with an immunotherapy and/or information about the patient's cancer such as composition of immune cells in the patient's tumor.

Efficacy Predictor Portion 156 may include information indicative of the patient's predicted response to an immunotherapy based on patient specific information presented in Immunotherapy Portion 154. Efficacy Predictor Portion 156 may provide predicted efficacy of an immunotherapy determined, in some embodiments, using a patient's biomarkers as described in herein. Additionally or alternatively, Efficacy Predictor Portion 156 may provide predicted efficacy of an immune checkpoint blockade therapy determined using patient specific information such as gene expression data as described in International patent application number PCT/US18/37018, entitled "Systems and Methods for Identifying Responders and Non-Responders to Immune Checkpoint Blockade Therapy," filed Jun. 12, 2018, the entire contents of which are incorporated herein by reference.

Targeted Therapy Selection Portion 158 may include patient specific information as it relates to a targeted therapy. Targeted Therapy Selection Portion 158 may provide such information for different targeted therapies, for example, a kinase inhibitor therapy, a chemotherapy, and anti-cancer antibody therapy. Patient specific information relating to an a targeted therapy may include information about the patient such as the patient's biomarkers associated with a targeted therapy and/or information about the patient's cancer such as whether a mutation is present in the patient's tumor.

Figure 1C:
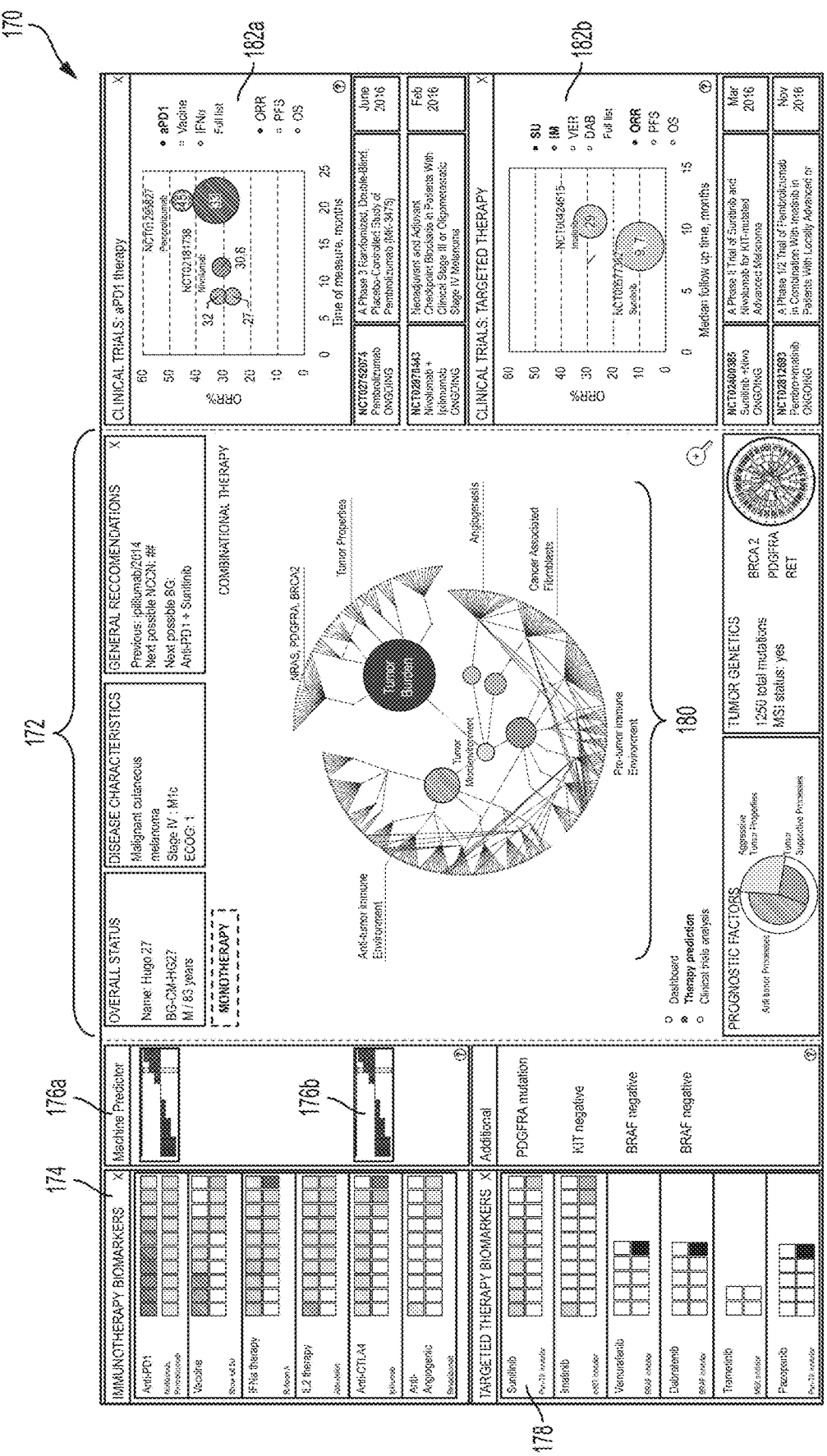
FIG. 1C is a graphical representation of patient data that may be presented to a user, in accordance with some embodiments of the technology described herein.

An illustrative example of the graphical user interface 150 of FIG. 1B is shown as graphical user interface 170 of FIG. 1C. As shown in FIG. 1C, Patient Information Portion 172 may provide different information in different panels, for example, Overall Status panel, Disease Characteristics panel, and General Recommendations panel. Overall Status panel, in some embodiments, may provide general information about the patient such as patient name and patient age. Disease Characteristics panel, in some embodiments, may provide information about the patient's cancer such as type of cancer and stage of cancer. General Recommendations panel, in some embodiments, may provide previous treatments and possible treatment options for the patient.

Clinical Trial Information Portion 182a provides information relating to a clinical trial for anti-PD1 therapy. Clinical Trial Information Portion 182a (as shown in the upper portion) shows a graph providing patient overall response rate (ORR) for anti-PD1 therapy and other therapies such as vaccine or IFNα therapies. A user may select portions of the Clinical Trial Information Portion 182a to access information related to patient progression-free survival (PFS) and/or patient overall survival (OS). Clinical Trial Information Portion 182a (as shown in the lower portion) provides information relating to different clinical trials that may be presented to a user including a brief description of the clinical trial.

Clinical Trial Information Portion 182b provides information relating to a clinical trial for different targeted therapies. Clinical Trial Information Portion 182b (as shown in the upper portion) shows a graph providing patient overall response rate (ORR) for different targeted therapies including sunitinib (SU), imatinib (IM), vemurafenib (VER) and dabrafenib (DAB). A user may select portions of the Clinical Trial Information Portion 182b to access information related to patient progression-free survival (PFS) and/or patient overall survival (OS). Clinical Trial Information Portion 182b (as shown in the lower portion) provides information relating to different clinical trials that may be presented to a user including a brief description of the clinical trial.

Immunotherapy Portion 174 provides patient specific information associated with an immunotherapy and information indicative of the patient's predicted response to that immunotherapy. Immunotherapy Portion 174 provides such information for anti-PD1 therapy, a therapeutic cancer vaccine, IFNα therapy, IL2 therapy, anti-CTLA4 therapy, and anti-angiogenic therapy. Patient specific information shown in Immunotherapy Portion 174 includes the patient's biomarker information relating to various immunotherapies and the patient's therapy scores calculated from their biomarkers.

Efficacy Predictor Portion 176a provides information indicative of the patient's predicted response to anti-PD1 therapy based on patient specific information presented in Immunotherapy Portion 174. Efficacy Predictor Portion 176b provides information indicative of the patient's predicted response to anti-CTLA4 therapy based on patient specific information presented in Immunotherapy Portion 174.

Targeted Therapy Selection Portion 178 provides patient specific information associated with a targeted therapy and information indicative of the patient's predicted response to the targeted therapy. Targeted Therapy Selection Portion 178 provides such information for sunitinib (SU), imatinib (IM), vemurafenib (VER), dabrafenib (DAB), trametinib, and pazopanib. Patient specific information shown in Targeted Therapy Selection Portion 178 includes a patient's biomarker information relating to various targeted therapies and the patient's therapy scores calculated from their biomarkers.

Figure 15:
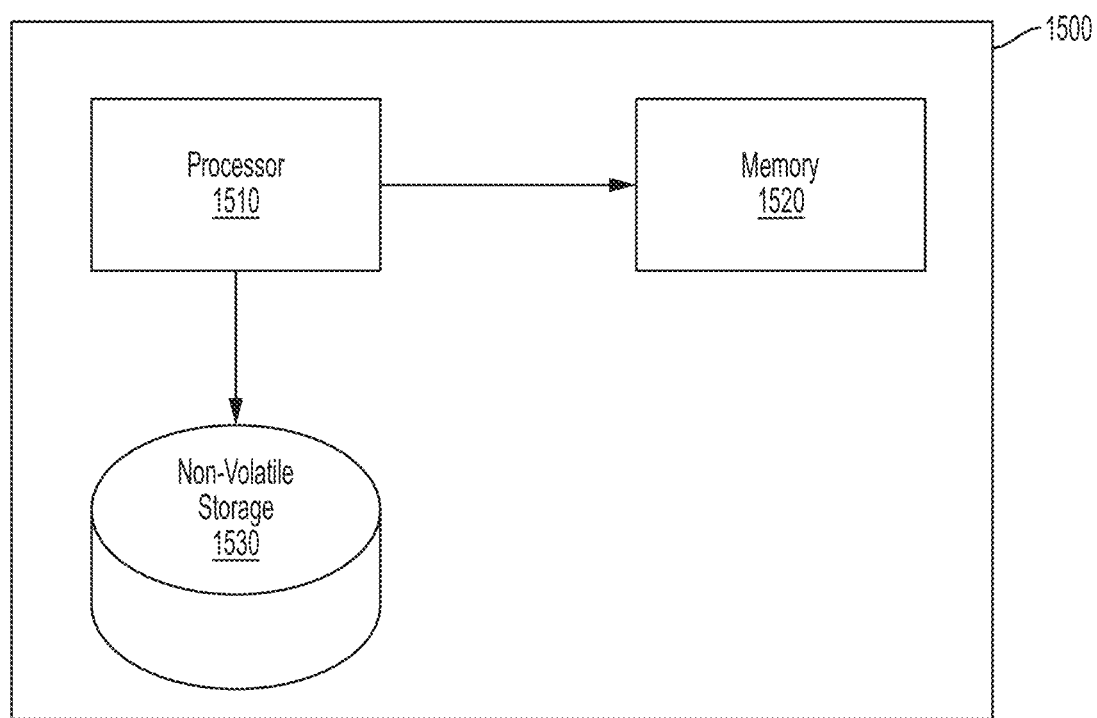
FIG. 15 is a block diagram of an illustrative computer system that may be used in implementing some embodiments of the technology described herein.

An illustrative implementation of a computer system 1500 that may be used in connection with any of the embodiments of the technology described herein is shown in FIG. 15. The computer system 1500 may include one or more computer hardware processors 1510 and one or more articles of manufacture that comprise non-transitory computer-readable storage media (e.g., memory 1520 and one or more non-volatile storage devices 1530). The processor(s) 1510 may control writing data to and reading data from the memory 1520 and the non-volatile storage device(s) 1530 in any suitable manner. To perform any of the functionality described herein, the processor(s) 1510 may execute one or more processor-executable instructions stored in one or more non-transitory computer-readable storage media (e.g., the memory 1520), which may serve as non-transitory computer-readable storage media storing processor-executable instructions for execution by the processor(s) 1510.

Figure 2A:
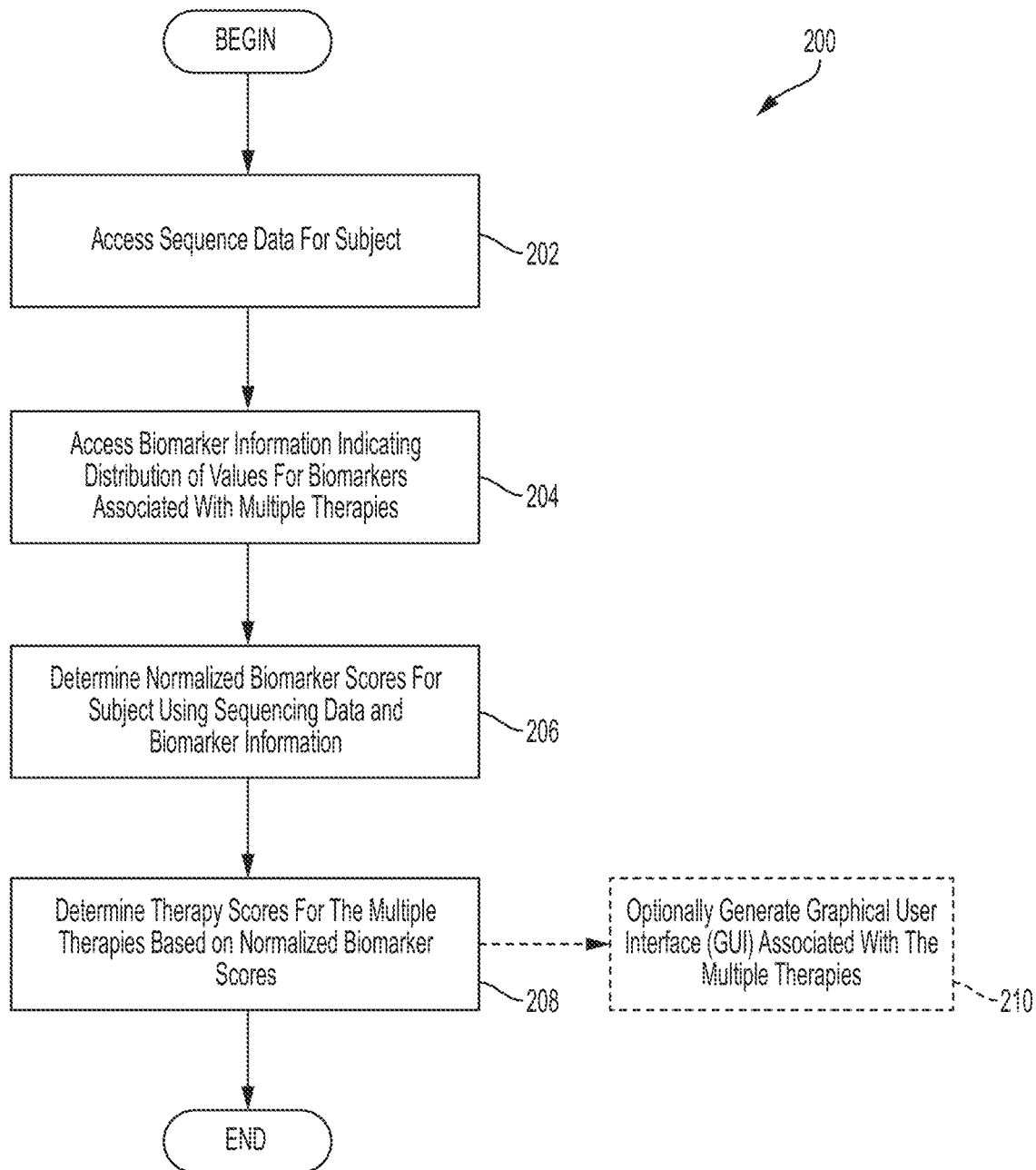
FIG. 2A is a flow chart of an illustrative process for determining therapy scores for multiple therapies based normalized biomarker scores, in accordance with some embodiments of the technology described herein.

FIG. 2A is a flowchart of an illustrative computer-implemented process 200 for determining therapy scores for multiple therapies based on normalized biomarker scores, in accordance with some embodiments of the technology described herein. A therapy score provided herein may be indicative of a patient's response to a particular therapy based on the patient's normalized biomarker scores for biomarkers associated with the particular therapy. Process 200 may be performed by any suitable computing device(s). For example, process 200 may be performed by a laptop computer, a desktop computer, one or more servers, in a cloud computing environment, or in any other suitable way.

Process 200 begins at act 202, where sequencing data for a subject is obtained. Any type of sequencing data may be obtained, for example, sequencing data from transcriptome, exome, and/or genome sequencing of a patient's tumor biopsy. In some embodiments, obtaining sequencing data comprises obtaining sequencing data from a biological sample obtained from the subject and/or from a database storing such information. Further aspects relating to obtaining sequencing data are provided in section "Sample Analysis" and "Obtaining Biomarker Information".

Next, process 200 proceeds to act 204, where biomarker information indicating distribution of values for biomarkers associated with multiple therapies is accessed. In some embodiments, for each particular one of multiple therapies, information indicating a respective distribution of values (in a reference population) for each one of one or more biomarkers associated with the particular therapy may be accessed. Such biomarker information may be obtained from one or more databases, in some embodiments.

Next, process 200 proceeds to act 206, where normalized biomarker scores for the subject are determined using sequencing data obtained at act 202 and the biomarker information obtained at act 204. Normalized biomarker scores for the subject are determined, in some embodiments, using a reference subset of biomarkers comprising any number of biomarkers from any number of reference subjects. In that way, the subject's biomarker score is adjusted (e.g., normalized) to a common scale based on a distribution of biomarker values in a reference subset of biomarkers. Further aspects relating to determining normalized biomarker scores are provided in section "From Biomarker Values To Normalized Biomarker Scores".

Next, process 200 proceeds to act 208, where therapy scores for each particular one of the multiple therapies are determined based on normalized biomarker scores for the biomarkers associated with the each particular one therapy. A therapy score may be calculated using multiple normalized biomarker scores as a sum, as a weighted sum, using a linear or generalized linear model, using a statistical model, or combinations thereof. The therapy score may be calculated using any suitable number of normalized biomarker scores, e.g., 2, 10, 50, or 100 normalized biomarker scores. Further aspects relating to determining therapy scores are provided in section "Predicting Therapy Response".

Therapy scores for any number of therapies may be output to a user, in some embodiments, by displaying the information to the user in a graphical user interface (GUI), including the information in a report, sending an email to the user, and/or in any other suitable way. For example, therapy scores and other patient related information may be provided to a user in a GUI as shown in FIGS. 9-14.

Systems and methods described herein may be used to assess the effectiveness of a therapy over time. Such systems and methods involve determining an impact score for a candidate therapy indicative of an impact of the candidate therapy on the patient based on the patient's biomarker information obtained prior to and subsequent to administration of the candidate therapy.

Figure 2B:
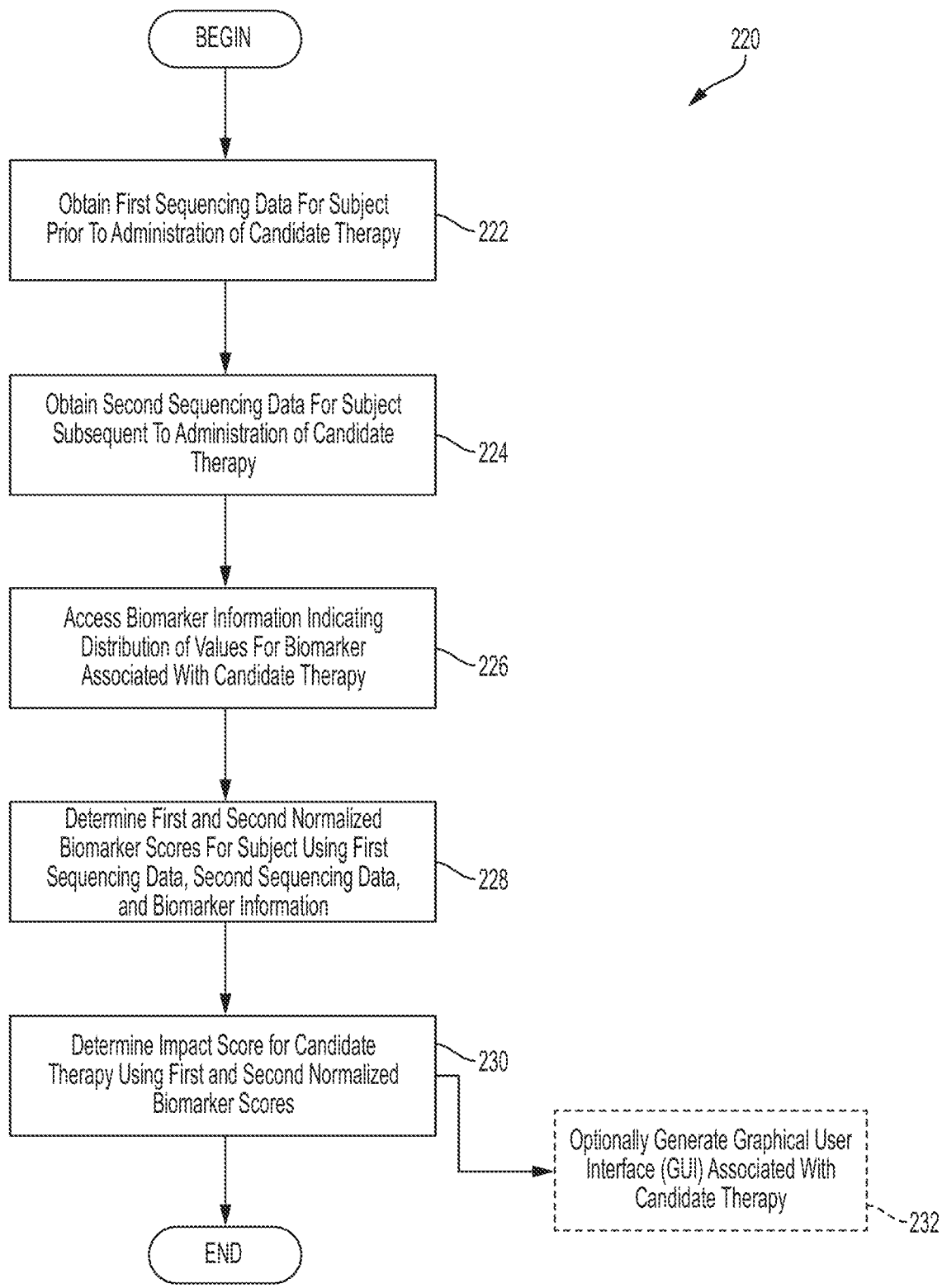
FIG. 2B is a flow chart of an illustrative process for determining impact score for a candidate therapy using a first normalized biomarker score and a second normalized biomarker score, in accordance with some embodiments of the technology described herein.

FIG. 2B is a flowchart of an illustrative computer-implemented process 220 for determining an impact score for a candidate therapy using first and second normalized biomarker scores, in accordance with some embodiments of the technology described herein. An impact score provided herein is indicative of a patient's response to a candidate therapy over time based on the patient's normalized biomarker scores obtained before, during and/or after treatment. In some embodiments, a first normalized biomarker score may be obtained before treatment and a second normalized biomarker score may be obtained during and/or after treatment.

Process 220 begins at act 222, where first sequencing data for a subject prior to administration of a candidate therapy is obtained. Sequencing data for a subject prior to treatment includes any sequencing data obtained for that subject any amount of time prior to treatment. Any type of sequencing data may be obtained, for example, sequencing data from transcriptome, exome, and/or genome sequencing of a patient's tumor biopsy. Sequencing data for the subject may be obtained minutes, days, months, or years prior to treatment. Further aspects relating to obtaining sequencing data are provided in section "Sample Analysis".

Next, process 220 proceeds to act 224, where second sequencing data for a subject subsequent to administration of a candidate therapy is obtained. Sequencing data for a subject subsequent to treatment includes any sequencing data obtained for that subject any amount of time subsequent to treatment. Sequencing data for the subject may be obtained minutes, days, months, or years subsequent to treatment. The second sequencing data may be a different type of sequencing data than the first sequencing data obtained prior to treatment. Further aspects relating to obtaining sequencing data are provided in section "Sample Analysis".

Next, process 220 proceeds to act 226, where biomarker information indicating a distribution of values for each of multiple biomarkers associated with the candidate therapy is accessed. Accessing biomarker information includes obtaining biomarker information associated with the candidate therapy from a variety of sources including from one or more databases. Biomarker information associated with the candidate therapy may be obtained from a subject prior to administration of a therapy and/or after administration of a therapy.

Next, process 220 proceeds to act 228, where first and second normalized biomarker scores for the subject are determined using first and second sequencing data and biomarker information. First and second normalized biomarker scores for the subject are determined, in some embodiments, using a reference subset of biomarkers comprising sets of biomarker values for the same biomarkers in multiple reference subjects. In that way, the subject's first and second biomarker score is adjusted (e.g., normalized) to a common scale based on a distribution of biomarker values in a reference subset of biomarkers. Further aspects relating to determining normalized biomarker scores are provided in section "From Biomarker Values To Normalized Biomarker Scores".

Next, process 220 proceeds to act 230, where an impact score for the candidate therapy is determined based on first and second normalized biomarker scores. Such impact scores, in some embodiments, may be indicative of efficacy of the candidate therapy. In some embodiments, impact scores may be used to select an additional therapy, stop administration of an ongoing therapy, and/or adjust how an ongoing therapy is being administered for the patient. Further aspects relating to determining impact scores are provided in section "Impact Scores".

Impact scores for any number and/or any type of candidate therapies may be output to a user, in some embodiments, by displaying the information to the user in a graphical user interface (GUI), including the information in a report, sending an email to the user, and/or in any other suitable way. For example, impact scores and other patient related information may be provided to a user in a GUI as shown in FIGS. 9-14.

Systems and methods described herein provide a multiple biomarker analysis that provides a more accurate prediction of a patient's response to therapy than that provided by a single biomarker analysis.

Figure 2C:
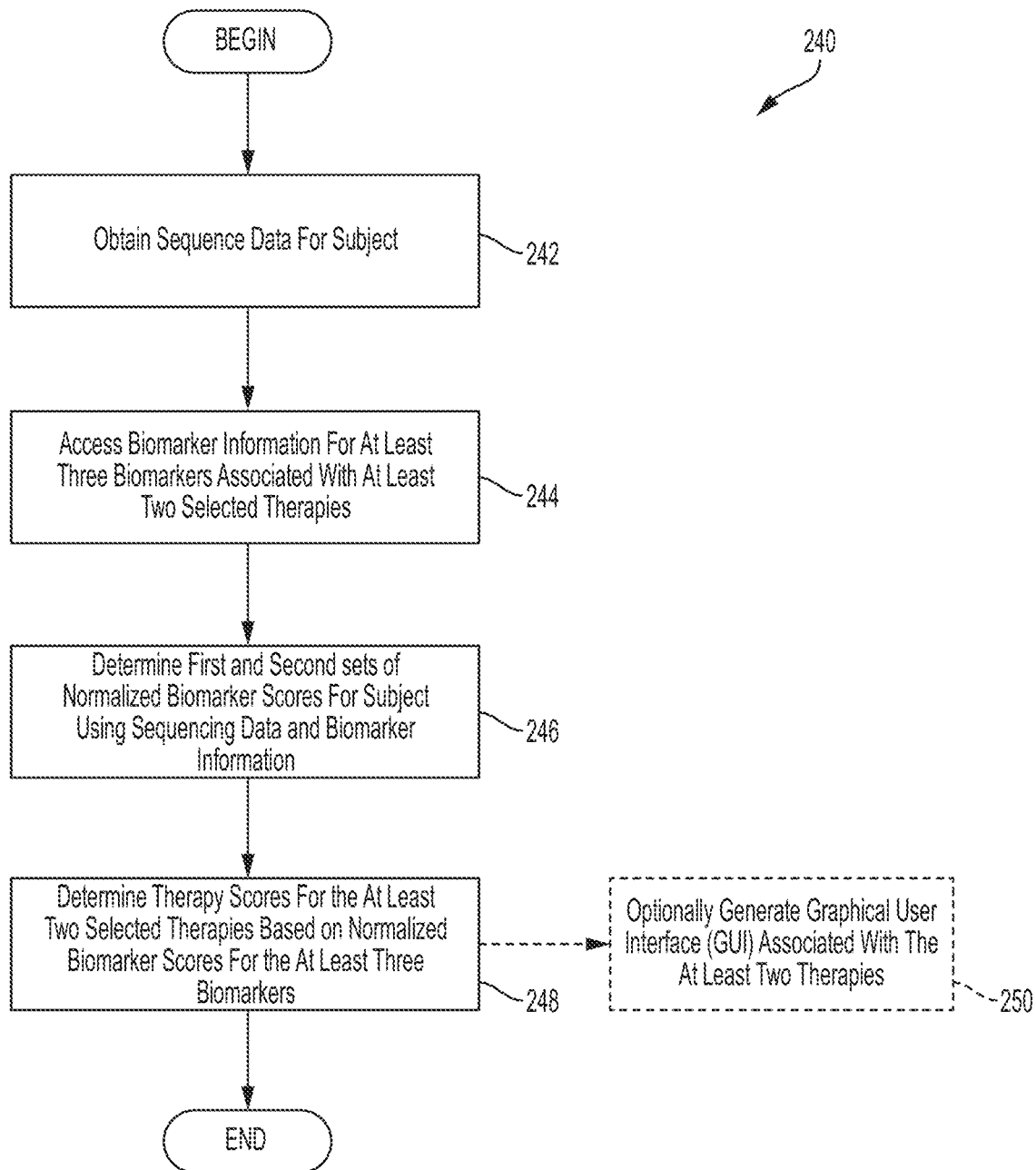
FIG. 2C is a flow chart of an illustrative process for determining therapy scores for that at least two selected therapies based on normalized biomarker scores for the at least three biomarkers, in accordance with some embodiments of the technology described herein.

FIG. 2C is a flowchart of an illustrative computer-implemented process 240 for determining therapy scores for at least two selected therapies based on respective normalized biomarker scores for at least three biomarkers, in accordance with some embodiments of the technology described herein. Therapy scores may be determined for selected therapies of any suitable type. For example, therapy scores may be determined for an immune checkpoint blockade therapy (e.g., anti-PD1 therapy) and a kinase inhibitor therapy (e.g., Sunitinib). In another example, therapy scores may be determined for two different immune checkpoint blockade therapies (e.g., anti-PD1 therapy and anti-CTLA4 therapy). Therapy scores may also be determined using any type of three biomarkers. For example, therapy scores may be determined from at least three different genetic biomarkers or therapy scores may be determined from a genetic biomarker, a cellular biomarker, and an expression biomarker.

Process 240 begins at act 242, where sequencing data for a subject is obtained. Any type of sequencing data may be obtained, for example, sequencing data from transcriptome, exome, and/or genome sequencing of a patient's tumor biopsy. In some embodiments, obtaining sequencing data comprises obtaining sequencing data from a biological sample obtained from the subject and/or from a database storing such information. Further aspects relating to obtaining sequencing data are provided in section "Sample Analysis".

Next, process 240 proceeds to act 244, where biomarker information indicating distribution of values for the at least three biomarkers associated with the at least two therapies is accessed. For each therapy, information indicating a distribution of values for each of at least three biomarkers associated with each particular therapy may be accessed. Thus, in some embodiments, at least six distributions of values may be accessed (e.g., at least three biomarker value distributions for three biomarkers associated with a first selected therapy and at least three biomarker value distributions for three biomarkers associated with a second selected therapy). Accessing biomarker information may include obtaining biomarker information from a variety of sources including one or more databases.

Next, process 240 proceeds to act 246, where first and second sets of normalized biomarker scores for the subject are determined using the sequencing data obtained at act 242 and biomarker information obtained at act 244. First and second sets of normalized biomarker scores for the subject are determined, in some embodiments, using a reference subset of biomarkers comprising sets of biomarker values for the same biomarkers in multiple reference subjects. In that way, the subject's first and second sets of biomarker scores are adjusted (e.g., normalized) to a common scale based on a distribution of biomarker values in a reference subset of biomarkers. Since the first set of biomarkers is associated with one therapy and the second set of biomarkers is associated with another therapy, the first and second sets of normalized biomarkers may differ from each other, for example, in number of biomarkers and/or types of biomarkers. For example, the first set of normalized biomarker scores may be associated with a first therapy and the second set of normalized biomarker scores may be associated with a second therapy. Further aspects relating to determining normalized biomarker scores are provided in section "From Biomarker Values To Normalized Biomarker Scores". Next, process 240 proceeds to act 248, where therapy scores for the at least two therapies are determined based on at least three normalized biomarker scores for each therapy. A therapy score may be calculated using the at least three normalized biomarker scores as a sum, as a weighted sum, using a linear or generalized linear model, using a statistical model, or combinations thereof. The therapy score may be calculated using any suitable number of normalized biomarker scores, e.g., 2, 10, 50, or 100 normalized biomarker scores. Further aspects relating to determining therapy scores are provided in section "Predicting Therapy Response".

Therapy scores for the at least two therapies and/or biomarker information used for determining therapy scores may be output to a user, in some embodiments, by displaying the information to the user in a graphical user interface (GUI), including the information in a report, sending an email to the user, and/or in any other suitable way. For example, therapy scores and other patient related information may be provided to a user in a GUI as shown in FIGS. 9-14.

Systems and methods described herein provide for determining more than one therapy score for a particular therapy. For example, a first and a second therapy score may be determined for a first therapy, and a first and second therapy score may be determined for a second therapy.

Figure 2D:
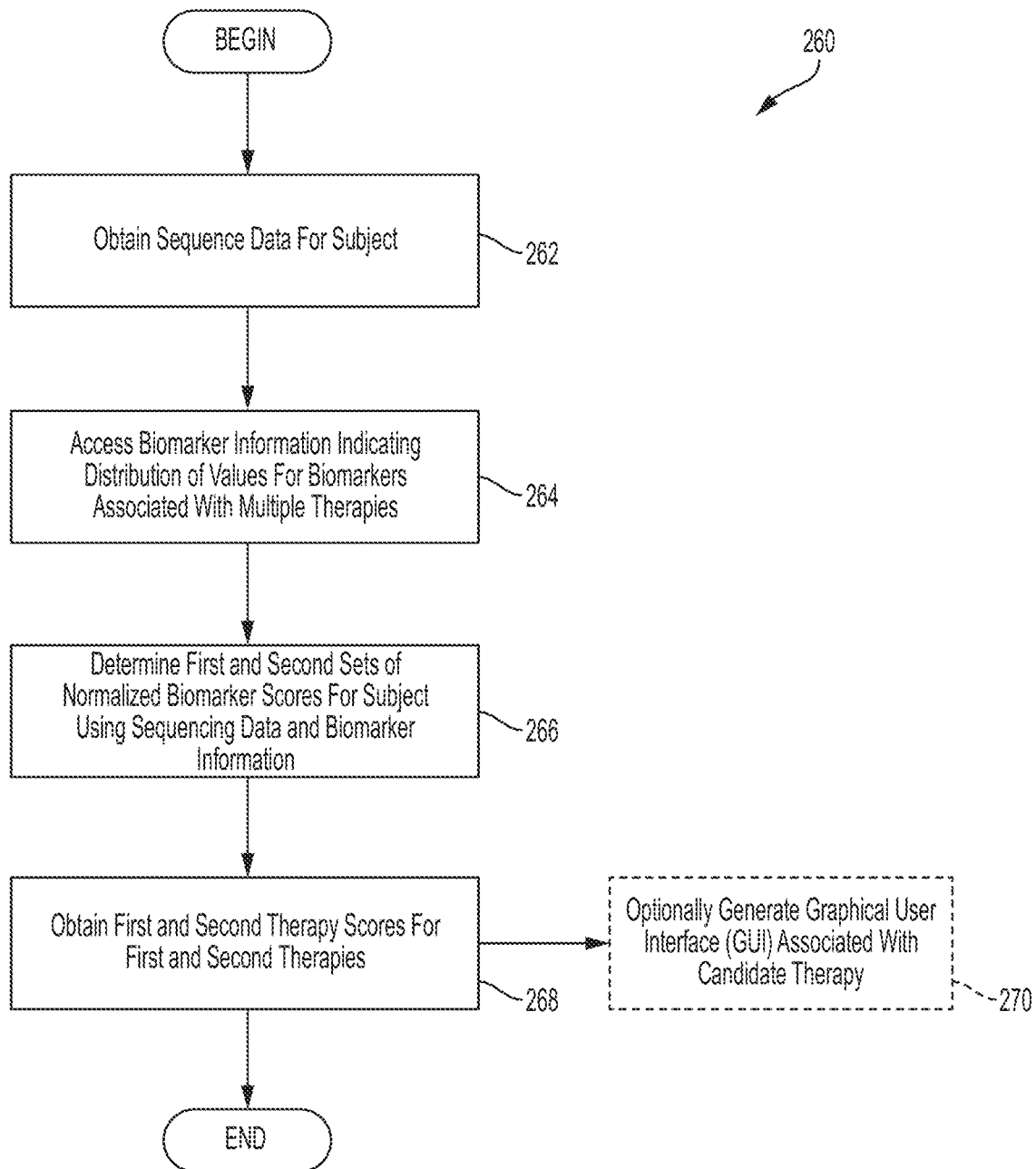
FIG. 2D is a flow chart of an illustrative process for obtaining first and second therapy scores for first and second therapies, in accordance with some embodiments of the technology described herein.

FIG. 2D is a flowchart of an illustrative computer-implemented process 260 for determining first and second therapy scores for a first and second therapy, respectively, based on normalized biomarker scores, in accordance with some embodiments of the technology described herein. First and second therapy scores may be determined using different biomarkers or different combinations of biomarkers. For example, a first therapy score is determined based on a patient's genetic biomarkers and a second therapy score is based on the patient's expression biomarkers. In another example, a first therapy score is determined based on a patient's genetic biomarkers and a second therapy score is based on the patient's genetic biomarkers and expression biomarkers. First and second therapy scores may be determined for different therapies and/or different types of therapies. For example, first and second therapy scores may be determined for an immune checkpoint blockade therapy (e.g., anti-PD1 therapy) and a kinase inhibitor therapy (e.g., Sunitinib), respectively. In another example, first and second therapy scores may be determined for two different immune checkpoint blockade therapies (e.g., anti-PD1 therapy and anti-CTLA4 therapy).

Process 260 begins at act 262, where sequencing data for a subject is obtained. Any type of sequencing data may be obtained, for example, sequencing data from transcriptome, exome, and/or genome sequencing of a patient's tumor biopsy. In some embodiments, obtaining sequencing data comprises obtaining sequencing data from a biological sample obtained from the subject and/or from a database storing such information. Further aspects relating to obtaining sequencing data are provided in section "Sample Analysis".

Next, process 260 proceeds to act 264, where biomarker information indicating distribution of values for biomarkers associated with at least two therapies. In some embodiments, information indicating a distribution of values is obtained for each of one or more biomarkers associated with a first therapy, and information indicating a distribution of values is obtained for each of one or more biomarkers associated with a second therapy different from the first therapy. Accessing biomarker information may include obtaining biomarker information from a variety of sources including, for example, one or more databases Next, process 260 proceeds to act 266, where first and second sets of normalized biomarker scores for the subject are determined using sequencing data obtained at act 262 and biomarker information obtained at act 264. First and second sets of normalized biomarker scores for the subject are determined, in some embodiments, using a reference subset of biomarkers comprising sets of biomarker values for the same biomarkers in multiple reference subjects. In that way, the subject's first and second sets of biomarker scores are adjusted (e.g., normalized) to a common scale based on a distribution of biomarker values in a reference subset of biomarkers. Since the first set of biomarkers is associated with one therapy and the second set of biomarkers is associated with another therapy, the first and second sets of normalized biomarkers may differ from each other, for example, in number of biomarkers and/or types of biomarkers. Further aspects relating to determining normalized biomarker scores are provided in section "From Biomarker Values To Normalized Biomarker Scores".

Next, process 260 proceeds to act 268, where first and second therapy scores for the first and second therapies are determined based on normalized biomarker scores for each therapy. A therapy score may be calculated using the normalized biomarker scores as a sum, as a weighted sum, using a linear or generalized linear model, using a statistical model, or combinations thereof. The therapy score may be calculated using any suitable number of normalized biomarker scores, e.g., 2, 10, 50, or 100 normalized biomarker scores. Further aspects relating to determining therapy scores are provided in section "Predicting Therapy Response".

First and second therapy scores for first and second therapies and/or biomarker information used for determining therapy scores may be output to a user, in some embodiments, by displaying the information to the user in a graphical user interface (GUI), including the information in a report, sending an email to the user, and/or in any other suitable way. For example, therapy scores and other patient related information may be provided to a user in a GUI as shown in FIGS. 9-14.

Systems and methods described herein may be used to select patients for a clinical trial for a particular therapy based on the patient's predicted response to that therapy determined using the patient's biomarkers as described herein. The systems and methods described herein may be used to identify a patient as a member of a cohort for participation in a clinical trial.

Figure 2E:
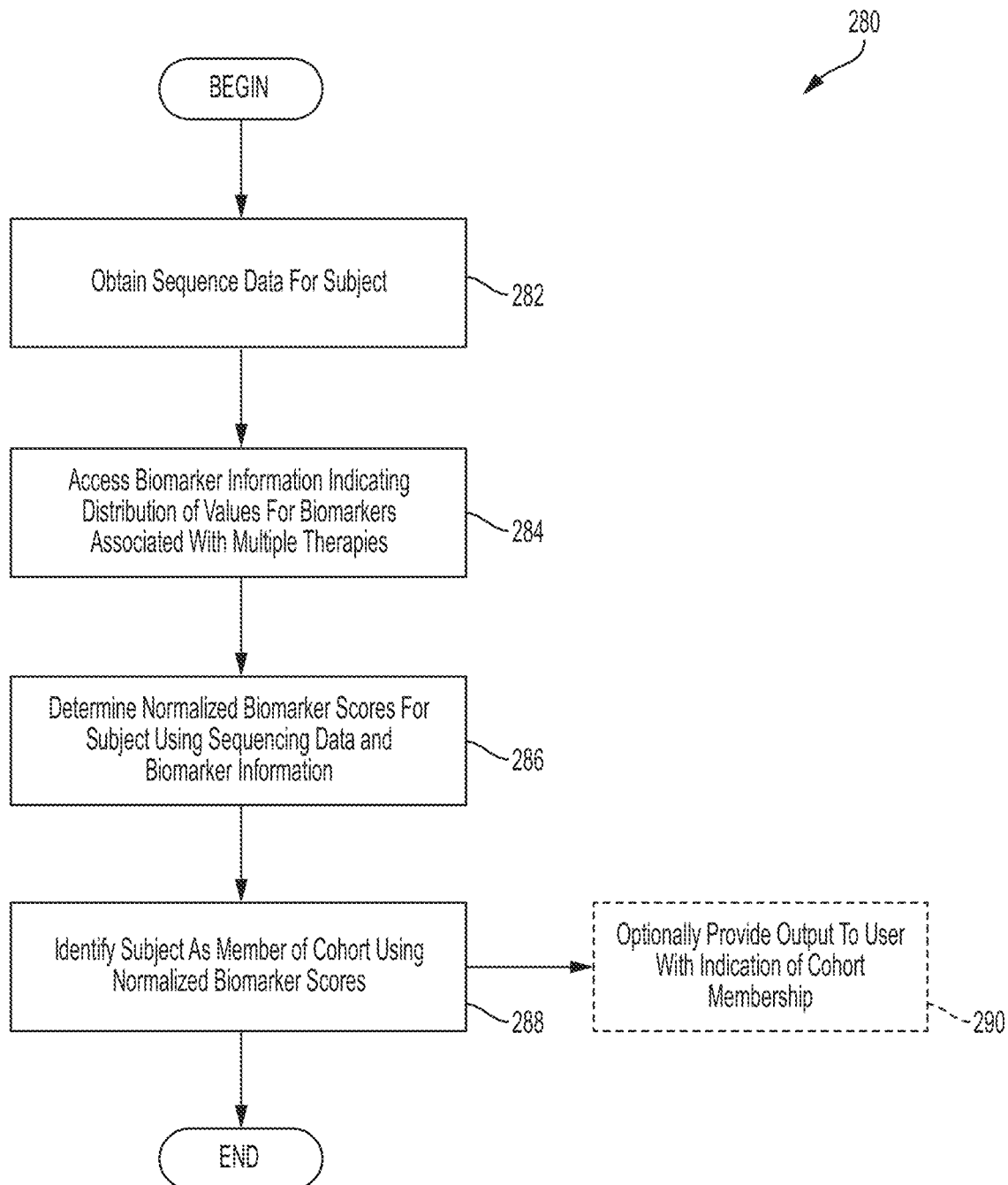
FIG. 2E is a flow chart of an illustrative process for identifying a subject as a member of a cohort using normalized biomarker scores, in accordance with some embodiments of the technology described herein.

FIG. 2E is a flowchart of an illustrative computer-implemented process 280 for identifying a subject as a member of a cohort using normalized biomarker scores, in accordance with some embodiments of the technology described herein. A subject may be identified as a member of a cohort for a clinical trial of any type of therapy, for example, a chemotherapy, an immunotherapy, an antibody therapy, and/or any combination thereof. The patient may be identified as a member of a cohort that will be administered the treatment or as a member of a cohort that will be administered a placebo. In some embodiments, the patient may be not be identified as a member of a cohort, and thus may be excluded from participation in a clinical trial. Patients may be excluded from a clinical trial, in some embodiments, if those patients have been predicted to have an adverse reaction to a therapy determined using the patient's biomarkers as described herein and/or the patient's gene expression data as described in International patent application number PCT/US18/37018, entitled "Systems and Methods for Identifying Responders and Non-Responders to Immune Checkpoint Blockade Therapy," filed Jun. 12, 2018, the entire contents of which are incorporated herein by reference.

Process 280 begins at act 282, where sequencing data for a subject is obtained. Any type of sequencing data may be obtained, for example, sequencing data from transcriptome, exome, and/or genome sequencing of a patient's tumor biopsy. In some embodiments, obtaining sequencing data comprises obtaining sequencing data from a biological sample obtained from the subject and/or from a database storing such information. Further aspects relating to obtaining sequencing data are provided in section "Sample Analysis".

Next, process 280 proceeds to act 284, where biomarker information indicating a distribution of values for each of one or more biomarkers associated with a therapy is accessed. Accessing biomarker information may include obtaining biomarker information from a variety of sources, for example, one or more databases.

Next, process 280 proceeds to act 286, where normalized biomarker scores for the subject are determined using sequencing data and biomarker information. Normalized biomarker scores for the subject are determined, in some embodiments, using a reference subset of biomarkers comprising sets of biomarker values for the same biomarkers in multiple reference subjects. In that way, the subject's biomarker score is adjusted (e.g., normalized) to a common scale based on a distribution of biomarker values in a reference subset of biomarkers. Further aspects relating to determining normalized biomarker scores are provided in section "From Biomarker Values To Normalized Biomarker Scores".

Next, process 280 proceeds to act 288, where a subject is identified as a member of a cohort for participating in a clinical trial using biomarker scores. An identified subject, in some embodiments, may be a subject that is likely to respond positively to the therapy being administered in the clinical trial. Such information may be output to a user, in some embodiments, by displaying the information to the user in a graphical user interface (GUI), including the information in a report, sending an email to the user, and/or in any other suitable way.

In this way, a patient can be identified and selected for participation in a clinical trial based on the patient's biomarker scores. Patients can also be identified for exclusion from the clinical trial, for example, patients predicted not likely to respond positively to the therapy and/or patients predicted to have an adverse reaction to the therapy.

Presentation of Predicted Therapy Response or Impact score

In some embodiments, a software program may provide a user with a visual representation presenting information related to a patient's biomarker values (e.g., a biomarker score, and/or a therapy score, and/or an impact score), and predicted efficacy or determined efficacy of one or more therapies using a graphical user interface (GUI).

Figures 6A, 6B:
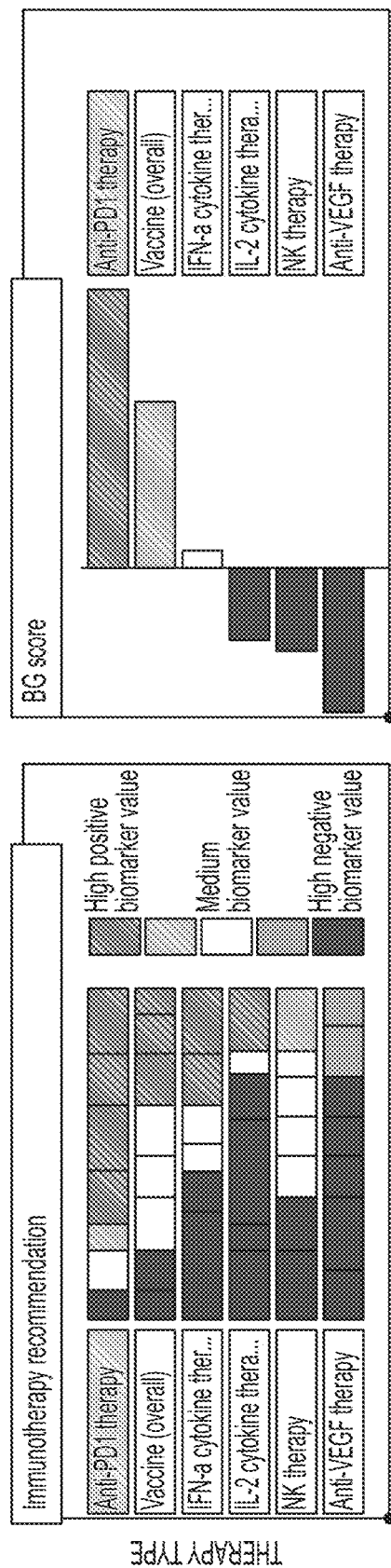
FIG. 6A is a screenshot presenting normalized biomarker values calculated for different immunotherapies, in accordance with some embodiments of the technology described herein.
FIG. 6B is a screenshot presenting patient therapy scores for different immunotherapies calculated using normalized biomarker values, in accordance with some embodiments of the technology described herein.
Figure 6C:
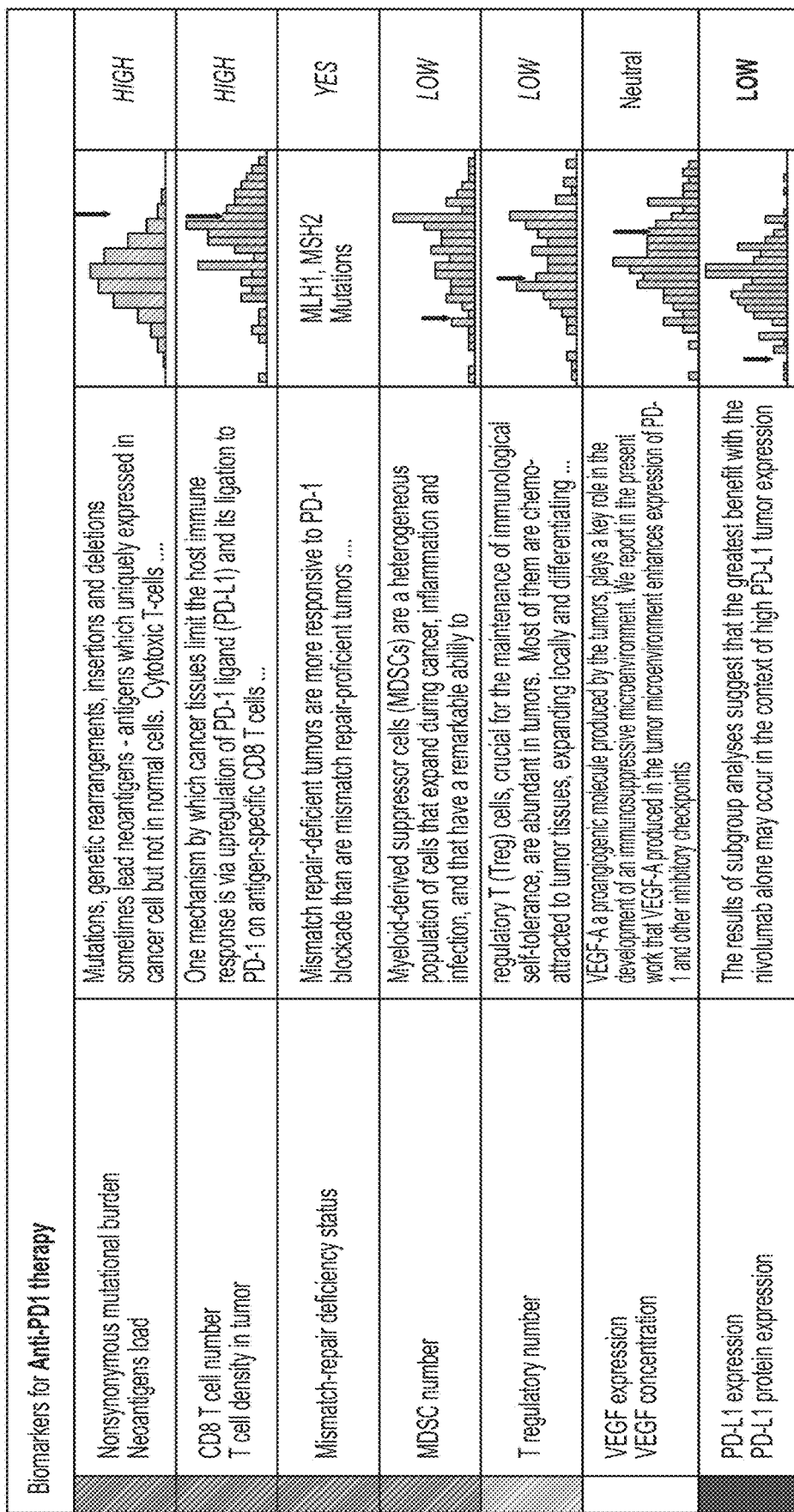
FIG. 6C is a screenshot presenting information related to biomarkers used to calculate patient therapy scores, in accordance with some embodiments of the technology described herein.

In response to being launched, the interactive GUI may provide the user of the software program with a visual representation of a patient's biomarker values and/or additional information related to the biomarker. FIGS. 6A-6C are screenshots presenting such information to a user of the software program.

FIG. 6A is a screenshot presenting a patient's biomarker information associated with different immunotherapies that may be used to treat the patient. Shading reflects normalized biomarker value in terms of gradient from −1 to 1. Shading intensity increasing as the biomarker value is increased. Shading with lines is assigned to positive biomarker values to distinguish them from negative biomarker values. Numeric "weight" of a biomarker is reflected in the width of the block with larger block width indicating a higher numeric weight.

As shown in FIG. 6A, a greater number of biomarkers with positive scores were calculated for anti-PD1 therapy indicating a predicted positive therapeutic effect of anti-PD1 therapy for a patient. By contrast, a greater number of biomarkers with negative scores were calculated for anti-VEGF therapy indicating a predicted negative therapeutic effect of anti-VEGF therapy for a patient. Numbers of positive biomarkers and negative biomarkers for a particular therapy may be similar for a patient. In such a case, the therapeutic effects of that therapy for the patient may not be predicted (i.e., may not be accurately predicted). Medium biomarker values for a particular therapy may also indicate that the therapeutic effects of that therapy for the patient may not be predicted (i.e., may not be accurately predicted).

FIG. 6B is a visual representation illustrating therapy scores calculated using normalized biomarker values shown in FIG. 6A. Negative therapy scores are shown on the left side of the y-axis, and positive therapy scores are shown on the right side of the y-axis. Positive therapy scores are also differentiated from negative therapy scores by shading with lines.

A user may interact with the GUI to obtain additional information about a biomarker. FIG. 6C is a screenshot presenting information related to each biomarker and patient specific information related to that biomarker. Information presented includes, from left to right, a block representing each biomarker, a description of the biomarker, a graph showing the distribution of biomarker values, and a general description of the biomarker value as "high," "low," or "neutral". The arrow in the graph indicates the patient's biomarker value. In some embodiments a normalized biomarker score may be labeled as a high score when the normalized biomarker score is in the top threshold percent (e.g., 1%, 5%, 10%, 15%, 20%, 25%, 30%, 35%, 40%, 45%, 50%) of a distribution of values. In some embodiments, a normalized biomarker score may be labeled as a low score when the normalized biomarker score is in the bottom threshold percent (e.g., 1%, 5%, 10%, 15%, 20%, 25%, 30%, 35%, 40%, 45%, 50%) of a distribution of values. In certain embodiments, a normalized biomarker score may be considered neutral if it is not in the top threshold or the bottom threshold of a distribution of values.

Figure 9:
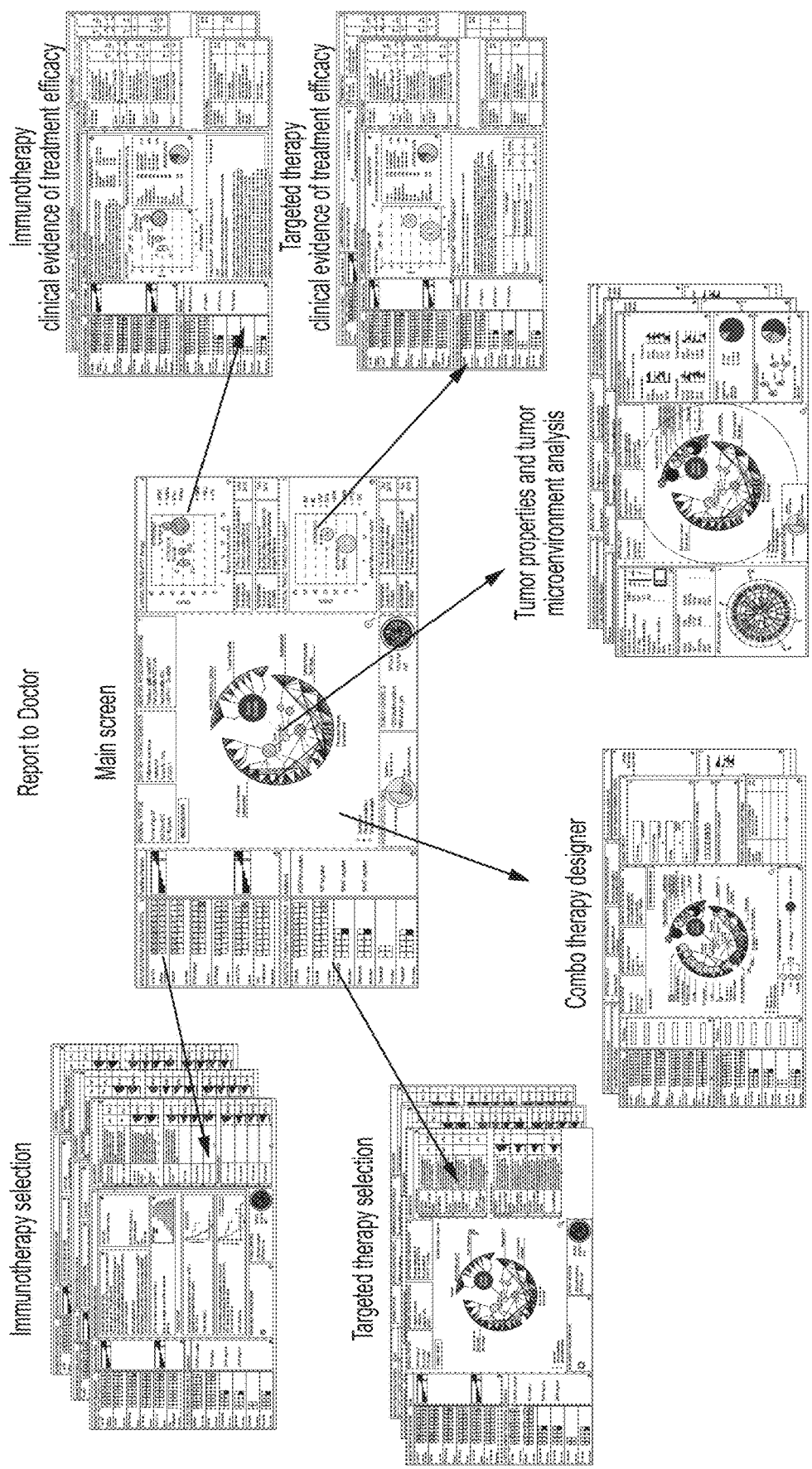
FIG. 9 is a graphic illustrating different types of screens that may be shown to a user of the software program.

FIG. 9 is a graphic illustrating different types of screens that may be shown to a user of the software program. Each of the different screens illustrated in FIG. 9 may be used to present different types of information to the user. A screenshot of a control screen of the software program is shown in the middle of FIG. 9. The control screen includes portions for presenting information relating to treatment selection, tumor properties, and clinical evidence of treatment efficacy and is described further with respect to FIGS. 10-15.

A user may interact with the control screen to obtain additional information about, for example, immunotherapy selection, targeted therapy selection, combination therapy design, tumor properties and tumor microenvironment, clinical evidence of targeted therapy efficacy, and clinical evidence of immunotherapy efficacy. The user may select a portion of the control screen (e.g., the immunotherapy portion) to view one or more additional screens presenting information relating to the selected portion. As shown in FIG. 9, arrows point from a portion of the control screen that may be selected toward the screens presenting additional information related to the selected portion.

For example, the user may select the immunotherapy selection portion of the control screen to view one or more screens presenting information relating to various immunotherapies, biomarkers associated with an immunotherapy (e.g., genetic biomarkers, cellular biomarkers, and expression biomarkers), immune cell properties of the patient's tumor, and clinical trials (e.g., information from and/or regarding published clinical trials and ongoing clinical trials).

In another example, the user may select the targeted therapy selection portion of the control screen to view one or more screens presenting information relating to various targeted therapies, biomarkers associated with targeted therapies (e.g., genetic biomarkers, cellular biomarkers, and/or expression biomarkers), properties of the patient's tumor associated with the targeted therapy, and clinical trials (e.g., published clinical trials and ongoing clinical trials).

In another example, the user may select the molecular-functional portrait (MF profile) portion of the control screen to view one or more screens presenting information relating to the patient's tumor microenvironment. Such information may include information about tumor properties (e.g., proliferation rate), angiogenesis, metastasis, cellular composition, cancer associated fibroblasts, pro-tumor immune environment, and anti-tumor immune environment.

In yet another example, the user may select the clinical evidence of treatment efficacy portion of the control screen to view one or more screens presenting information relating to a therapy (e.g., an immunotherapy or targeted therapy). Such information may include description of the therapy, therapy efficacy, potential adverse effects, related publications, treatment regimen, and patient survival data.

In a further example, the user may select a portion of the control screen to view one or more screens associated with an impact score for one or more candidate therapies, wherein the impact score is indicative of response of the subject to administration of the one or more candidate therapies.

A user of the software program may interact with the GUI to log into the software program. The user may select a stored report to view a screen presenting information relating to the selected report. The user may select the create new report portion to view a screen for creating a new report.

Figure 10:
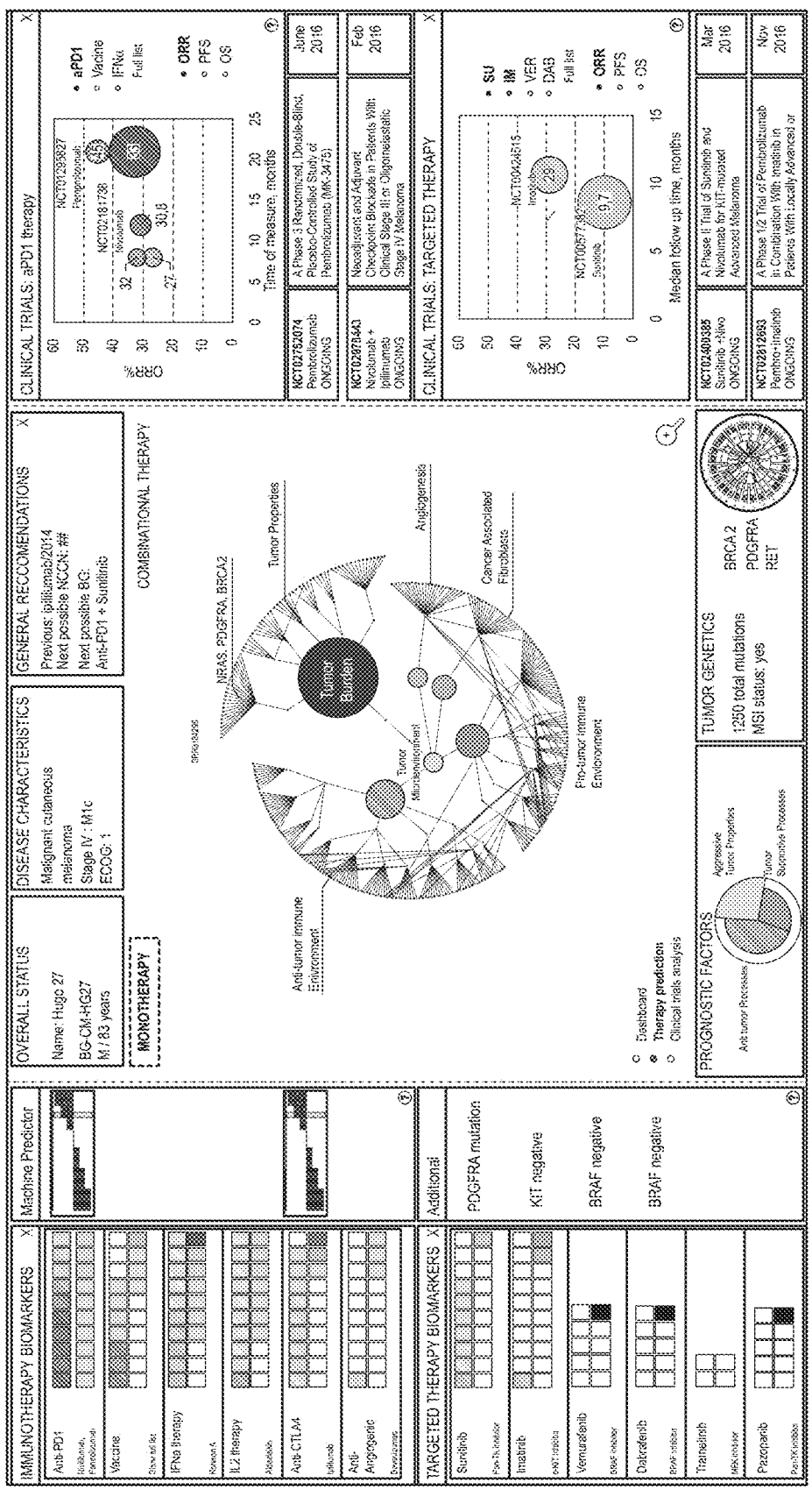
FIG. 10 is a screenshot presenting the selected patient's report including information related to the patient's sequencing data, the patient, and the patient's cancer.

FIG. 10 is a screenshot presenting the selected patient's report including information related to the patient's sequencing data, the patient, and the patient's cancer. The therapy biomarkers portion (as shown in the left panel) presents information related to available therapies (e.g., immunotherapies and targeted therapies) and their predicted efficacy in the selected patient. Additional predictions of the efficacy of a therapy in the patient are provided in the machine predictor portion and additional portion (as shown in the left panel). The MF profile portion presents information relating to the molecular characteristics of a tumor including tumor genetics, pro-tumor microenvironment factors, and anti-tumor immune response factors (as shown in the middle panel). The clinical trials portion provides information relating to clinical trials (as shown in the right panel). The monotherapy or combinational therapy portion (as shown in the middle panel) may be selected by the user to interactively design a personalized treatment for a patient.

A user may select various portions of the screen to view additional information. For example, a user may select anti-PD1 in the immunotherapy biomarkers portion of the screen (as shown in the left panel) to view information relating to anti-PD1 treatment including biomarkers associated with anti-PD1 and tumor cell processes associated with anti-PD1 treatment.

Figure 11:
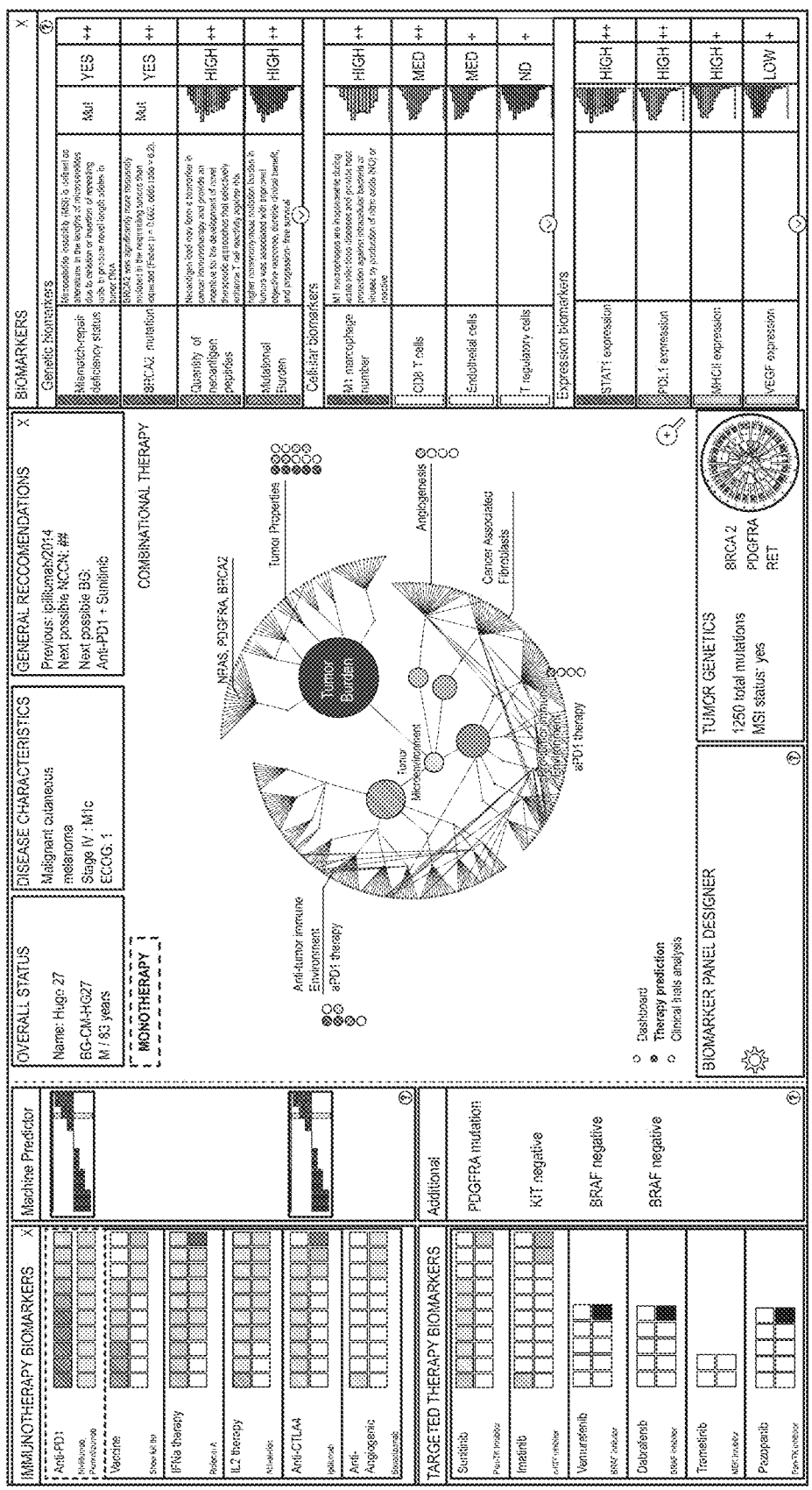
FIG. 11 is a screenshot presenting information related to anti-PD1 immunotherapy provided in response to selecting anti-PD1 immunotherapy (as shown by highlighting) in the immunotherapy biomarkers portion of the screen (as shown in the left panel).

FIG. 11 is a screenshot presenting information related to anti-PD1 immunotherapy provided in response to selecting anti-PD1 immunotherapy (as shown by highlighting) in the immunotherapy biomarkers portion of the screen (as shown in the left panel). Information relating to biomarkers associated with anti-PD1 immunotherapy is provided in the biomarkers portion (as shown in the right panel). The biomarkers portion presents genetic biomarkers, cellular biomarkers, and expression biomarkers, as well as patient specific information related to those biomarkers.

The user may select any one of the biomarkers presented in the biomarkers markers portion to view additional information relating to that biomarker including general information about the selected biomarker, patient specific information relating to the selected biomarker, information relating to tumor molecular processes associated with the selected biomarker, and treatment related information associated with the selected biomarker.

Figure 12:
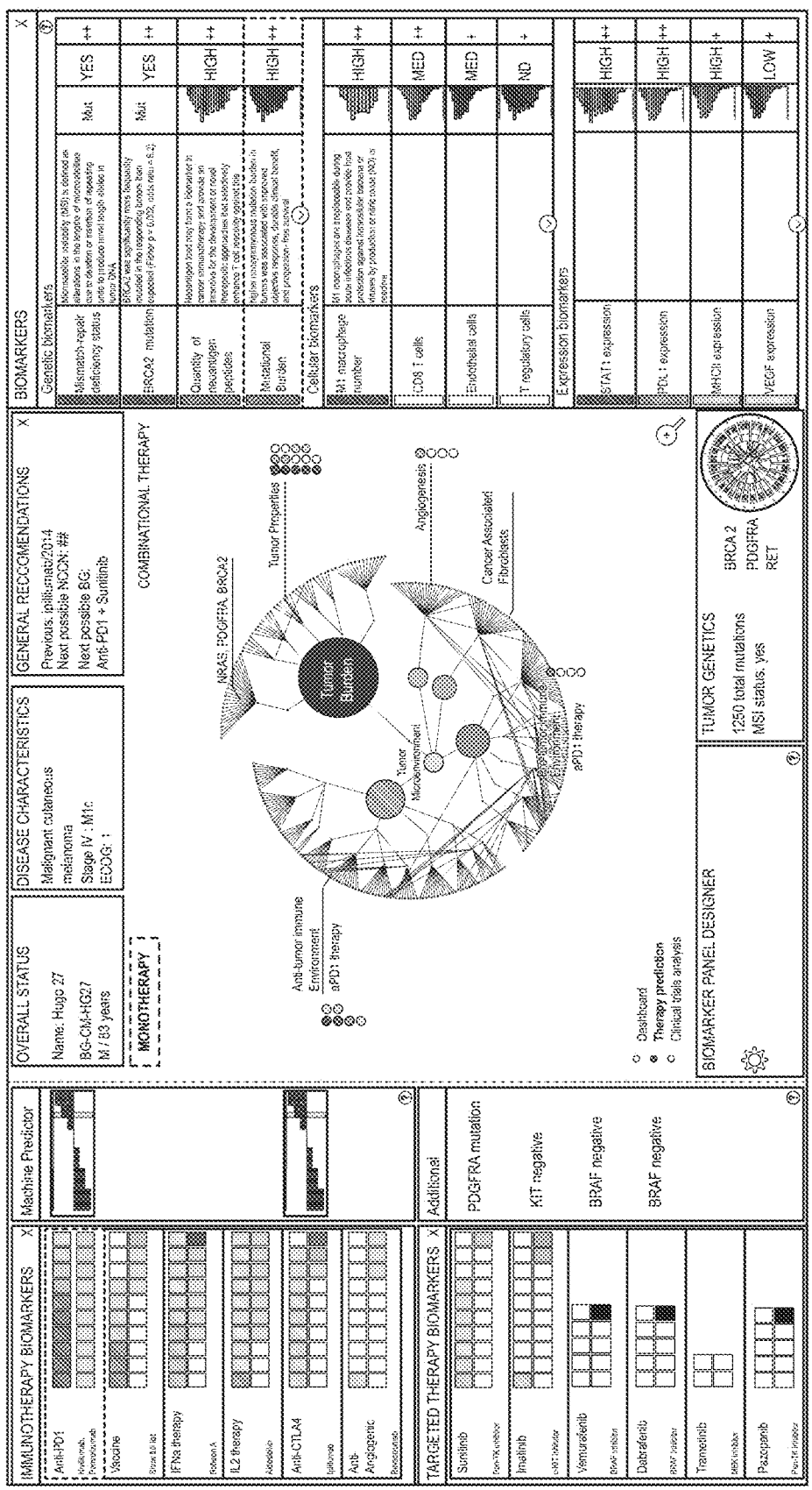
FIG. 12 is a screenshot presenting selection of mutational burden biomarker by a user.

In response to selection by a user, the selected biomarker may be visually highlighted. As a set of non-limiting examples, a "visually highlighted" element may be highlighted through a difference in font (e.g., by italicizing, bolding, and/or underlining), by surrounding the section with a visual object (e.g., a box), by "popping" the element out (e.g., by increasing the zoom for that element), by changing the color of an element, by shading the element, by incorporation of movement into the element (e.g., by causing the element to move), any combination of the foregoing in a portion or the whole of the element, or in any other suitable way. FIG. 12 is a screenshot presenting the mutational burden biomarker (as shown by highlighting) was selected by the user. The user may select another portion of the mutational burden biomarker to view a screen presenting information relating to the mutational burden biomarker such as relevant publications.

Figure 13:
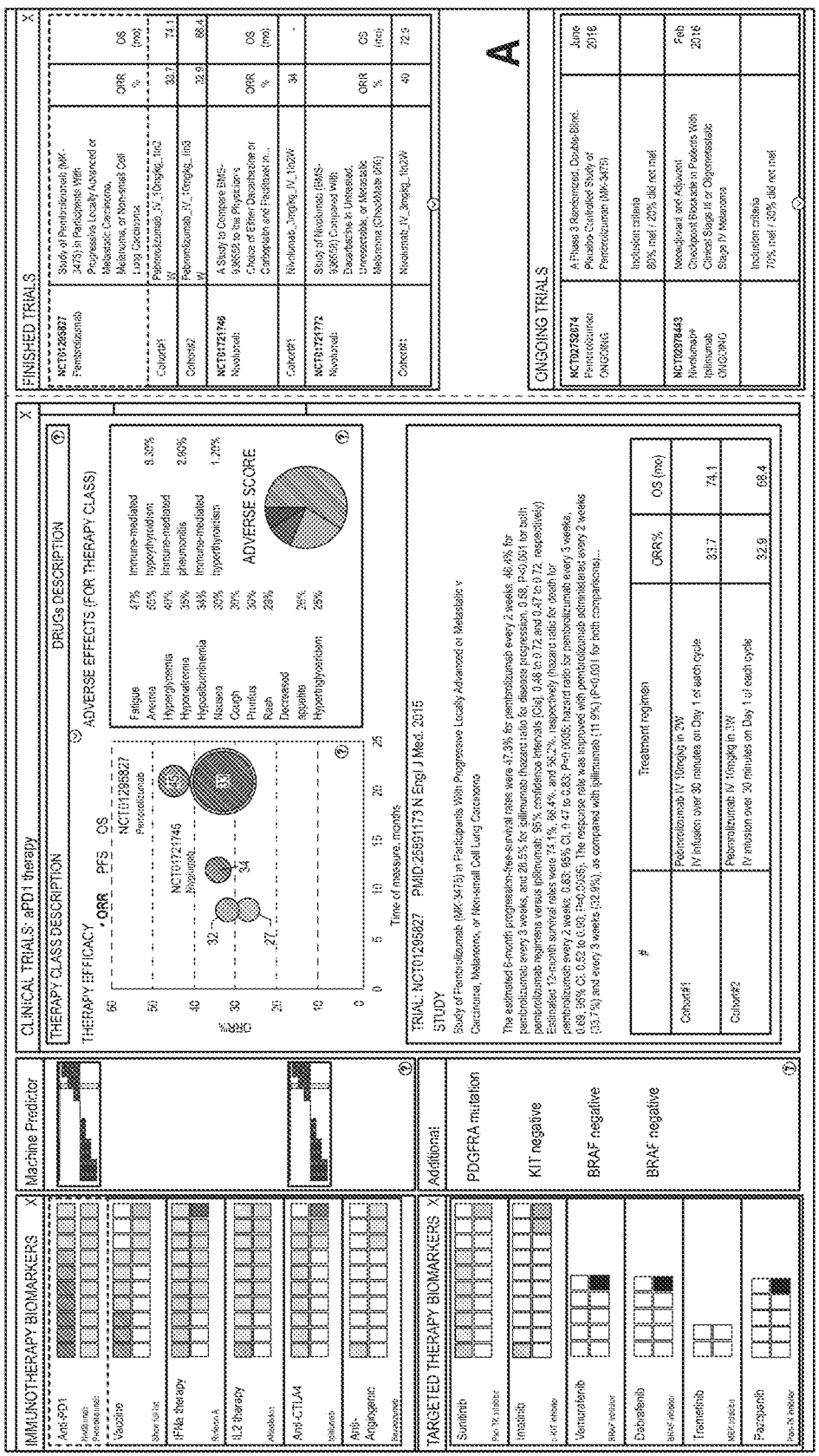
FIG. 13 is a screenshot presenting information relating to the mutational burden biomarker (as shown in the middle panel) provided in response to the user selecting the mutational burden biomarker.

FIG. 13 is a screenshot presenting information relating to the mutational burden biomarker (as shown in the middle panel) provided in response to the user selecting the mutational burden biomarker. The information may include a description of the biomarker, how the biomarker was calculated, the patient's particular biomarker value compared to other patients (as shown in a histogram), and information from publications relating to the selected biomarker.

The system allows a user to interactively view biomarker information as it relates to a predicted response to a therapy. Clinical evidence of treatment efficacy for a therapy (e.g., an immunotherapy or a targeted therapy) may be interactively viewed by the user.

Figure 14:
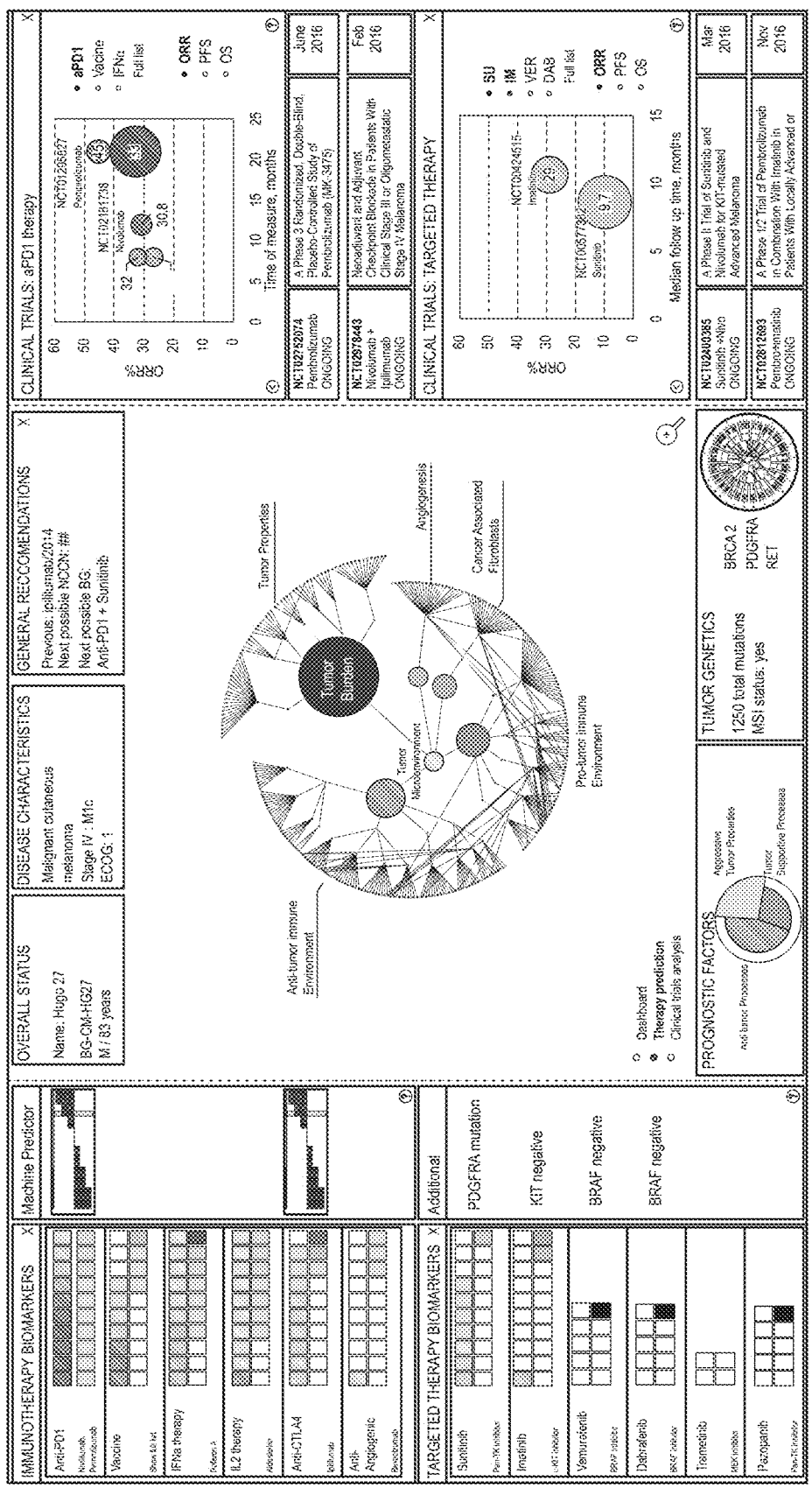
FIG. 14 is a screenshot presenting clinical trial data relating to anti-PD1 therapy effectivity in patients having stage IV metastatic melanoma (as shown in the right panel) provided in response to the user selecting anti-PD1 immunotherapy (as shown in the left panel).

FIG. 14 is a screenshot presenting clinical trial data relating to anti-PD1 therapy effectivity in patients having stage IV metastatic melanoma (as shown in the right panel) provided in response to the user selecting anti-PD1 immunotherapy (as shown in the left panel).

Therapeutics and Methods of Therapy

In certain methods or systems described herein, no recommendation is made regarding administration of a therapy to a subject (e.g., a human). In certain methods described herein, an effective amount of anti-cancer therapy described herein may be administered or recommended for administration to a subject (e.g., a human) in need of the treatment via a suitable route (e.g., intravenous administration).

The subject to be treated by the methods described herein may be a human patient having, suspected of having, or at risk for a cancer. Examples of a cancer include, but are not limited to, melanoma, lung cancer, brain cancer, breast cancer, colorectal cancer, pancreatic cancer, liver cancer, prostate cancer, skin cancer, kidney cancer, bladder cancer, or prostate cancer. The subject to be treated by the methods described herein may be a mammal (e.g., may be a human). Mammals may include, but are not limited to: farm animals (e.g., livestock), sport animals, laboratory animals, pets, primates, horses, dogs, cats, mice, and rats.

A subject having a cancer may be identified by routine medical examination, e.g., laboratory tests, biopsy, PET scans, CT scans, or ultrasounds. A subject suspected of having a cancer might show one or more symptoms of the disorder, e.g., unexplained weight loss, fever, fatigue, cough, pain, skin changes, unusual bleeding or discharge, and/or thickening or lumps in parts of the body. A subject at risk for a cancer may be a subject having one or more of the risk factors for that disorder. For example, risk factors associated with cancer include, but are not limited to, (a) viral infection (e.g., herpes virus infection), (b) age, (c) family history, (d) heavy alcohol consumption, (e) obesity, and (f) tobacco use.

Any anti-cancer therapy or anti-cancer therapeutic agent may be used in conjunction with the methods and systems described herein. In some embodiments, an anti-cancer therapeutic agent is an antibody, an immunotherapy, a molecular targeted therapy, a radiation therapy, a surgical therapy, and/or a chemotherapy.

Examples of the antibody anti-cancer agents include, but are not limited to, alemtuzumab (Campath), trastuzumab (Herceptin), Ibritumomab tiuxetan (Zevalin), Brentuximab vedotin (Adcetris), Ado-trastuzumab emtansine (Kadcyla), blinatumomab (Blincyto), Bevacizumab (Avastin), Cetuximab (Erbitux), ipilimumab (Yervoy), nivolumab (Opdivo), pembrolizumab (Keytruda), atezolizumab (Tecentriq), avelumab (Bavencio), durvalumab (Imfinzi), and panitumumab (Vectibix).

Examples of an immunotherapy include, but are not limited to, a PD-1 inhibitor or a PD-L1 inhibitor, a CTLA-4 inhibitor, adoptive cell transfer, therapeutic cancer vaccines, oncolytic virus therapy, T-cell therapy, and immune checkpoint inhibitors.

Examples of a molecular targeted therapy include, but are not limited to: Uprosertib, Alectinib, Crizotinib, Alisertib, Barasertib, Gilteritinib, Navitoclax, Bosutinib, Dasatinib, Nilotinib, Ponatinib, Imatinib, Dabrafenib, Vemurafenib, Encorafenib, Acalabrutinib, Ibrutinib, Verapamil, Tacrolimus, Abemaciclib, Ribociclib, Palbociclib, Celecoxib, Apricoxib, Selinexor, Plerixafor, Pinometostat, Rociletinib, Pyrotinib, Erlotinib, Gefitinib, Afatinib, Osimertinib, Varlitinib, Icotinib, Lapatinib, Neratinib, Tazemetostat, Tipifarnib, Dovitinib, Lucitanib, Erdafitinib, Crenolanib, Atorvastatin, Onalespib, Enasidenib, Sitagliptin, Ruxolitinib, Tofacitinib, Idasanutlin, Selumetinib, Trametinib, Cobimetinib, Binimetinib, Foretinib, Capmatinib, Tivantinib, Volitinib, Vistusertib, Everolimus, Sirolimus, Torkinib, Temsirolimus, Ridaforolimus, Metformin, Apitolisib, Dactolisib, Brontictuzumab, Omaveloxolone, Dacomitinib, Sapitinib, Poziotinib, Cabozantinib, Regorafenib, Lestaurtinib, Midostaurin, Nintedanib, Pexidartinib, Quizartinib, Sorafenib, Sunitinib, Vandetanib, Entrectinib, Pazopanib, Masitinib, Anlotinib, Brigatinib, Olaparib, Apatinib, Niraparib, Rucaparib, Veliparib, Roflumilast, Idelalisib, Copanlisib, Buparlisib, Taselisib, Pictilisib, Umbralisib, Duvelisib, Alpelisib, Volasertib, Vismodegib, Sonidegib, Saracatinib, Entospletinib, Fostamatinib, Cerdulatinib, Larotrectinib, Auranofin, Axitinib, Cediranib, Lenvatinib, and Alvocidib.

Examples of radiation therapy include, but are not limited to, ionizing radiation, gamma-radiation, neutron beam radiotherapy, electron beam radiotherapy, proton therapy, brachytherapy, systemic radioactive isotopes, and radiosensitizers.

Examples of a surgical therapy include, but are not limited to, a curative surgery (e.g., tumor removal surgery), a preventive surgery, a laparoscopic surgery, and a laser surgery.

Examples of the chemotherapeutic agents include, but are not limited to, Carboplatin or Cisplatin, Docetaxel, Gemcitabine, Nab-Paclitaxel, Paclitaxel, Pemetrexed, and Vinorelbine.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin hydrochloride, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives or derivatives thereof); Purine antagonists (Thioguanine, Fludarabine, Cladribine, 6-Mercaptopurine, Pentostatin, clofarabine, and relatives or derivatives thereof) and Pyrimidine antagonists (Cytarabine, Floxuridine, Azacitidine, Tegafur, Carmofur, Capacitabine, Gemcitabine, hydroxyurea, 5-Fluorouracil (5FU), and relatives or derivatives thereof); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives or derivatives thereof); nitrosoureas (e.g., Carmustine, Lomustine, Semustine, Fotemustine, Nimustine, Ranimustine, Streptozocin, and relatives or derivatives thereof); Triazenes (e.g., Dacarbazine, Altretamine, Temozolomide, and relatives or derivatives thereof); Alkyl sulphonates (e.g., Busulfan, Mannosulfan, Treosulfan, and relatives or derivatives thereof); Procarbazine; Mitobronitol, and Aziridines (e.g., Carboquone, Triaziquone, ThioTEPA, triethylenemalamine, and relatives or derivatives thereof); Antibiotics, such as Hydroxyurea, Anthracyclines (e.g., doxorubicin agent, daunorubicin, epirubicin and relatives or derivatives thereof); Anthracenediones (e.g., Mitoxantrone and relatives or derivatives thereof); *Streptomyces* family antibiotics (e.g., Bleomycin, Mitomycin C, Actinomycin, and Plicamycin); and ultraviolet light.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient or clinician may insist upon a lower dose or tolerable dose for medical reasons, psychological reasons, or for virtually any other reason(s).

Empirical considerations, such as the half-life of a therapeutic compound, generally contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally (but not necessarily) based on treatment, and/or suppression, and/or amelioration, and/or delay of a cancer. Alternatively, sustained continuous release formulations of an anti-cancer therapeutic agent may be appropriate. Various formulations and devices for achieving sustained release are known in the art.

In some embodiments, dosages for an anti-cancer therapeutic agent as described herein may be determined empirically in individuals who have been administered one or more doses of the anti-cancer therapeutic agent. Individuals may be administered incremental dosages of the anti-cancer therapeutic agent. To assess efficacy of an administered anti-cancer therapeutic agent, one or more aspects of a cancer (e.g., tumor formation or tumor growth) may be analyzed.

Generally, for administration of any of the anti-cancer antibodies described herein, an initial candidate dosage may be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression or amelioration of symptoms occurs or until sufficient therapeutic levels are achieved to alleviate a cancer, or one or more symptoms thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner (e.g., a medical doctor) wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy may be monitored by conventional techniques and assays and/or by monitoring the progress of the disease or cancer as described herein. The dosing regimen (including the therapeutic used) may vary over time.

When the anti-cancer therapeutic agent is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, e.g., dose, timing, and/or repetition, will depend on the particular subject and that individual's medical history, as well as the properties of the individual agents (such as the half-life of the agent, and other considerations well known in the art).

For the purpose of the present disclosure, the appropriate dosage of an anti-cancer therapeutic agent will depend on the specific anti-cancer therapeutic agent(s) (or compositions thereof) employed, the type and severity of cancer, whether the anti-cancer therapeutic agent is administered for preventive or therapeutic purposes, previous therapy, the patient's clinical history and response to the anti-cancer therapeutic agent, and the discretion of the attending physician. Typically the clinician will administer an anti-cancer therapeutic agent, such as an antibody, until a dosage is reached that achieves the desired result.

Administration of an anti-cancer therapeutic agent can be continuous or intermittent, depending, for example, upon the recipient's physiological condition, whether the purpose of the administration is therapeutic or prophylactic, and other factors known to skilled practitioners. The administration of an anti-cancer therapeutic agent (e.g., an anti-cancer antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the cancer or one or more symptoms of the cancer, or the predisposition toward a cancer. In some embodiments, the methods and systems herein may comprise recommendation of a treatment rather than treatment itself. In some embodiments, no recommendation of a treatment will be made. In certain embodiments, one or more potential treatments may be "ranked" or compared according to their predicted efficacy and/or subject or patient outcome. In certain embodiments, one or more potential treatments will not be "ranked" or compared according to their predicted efficacy and/or subject or patient outcome. In some embodiments, information about a therapy (e.g., the therapy score) for a patient will be outputted. In specific embodiments, such information may be outputted to a user (e.g., a doctor or clinician).

Alleviating a cancer includes delaying the development or progression of the disease, or reducing disease severity (e.g., by at least one parameter). Alleviating the disease does not necessarily require curative results. As used therein, "delaying" the development of a disease (e.g., a cancer) means to defer, hinder, slow, retard, stabilize, and/or postpone progression of the disease. This delay can be of varying lengths of time, depending on the history of the disease and/or individuals being treated. A method that "delays" or alleviates the development or progress of a disease, or delays the onset of one or more complications of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detected and assessed using clinical techniques known in the art. Alternatively or in addition to the clinical techniques known in the art, development of the disease may be detectable and assessed based on biomarkers described herein. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the anti-cancer therapeutic agent (e.g., an antibody) described herein is administered to a subject in need of the treatment at an amount sufficient to reduce cancer (e.g., tumor) growth by at least 10% (e.g., 20%, 30%, 40%, 50%, 60%, 70%, 80%, 90% or greater). In some embodiments, the anti-cancer therapeutic agent (e.g., an antibody) described herein is administered to a subject in need of the treatment at an amount sufficient to reduce cancer cell number or tumor size by at least 10% (e.g., 20%, 30%, 40%, 50%, 60%, 70%, 80%, 90% or more). In other embodiments, the anti-cancer therapeutic agent is administered in an amount effective in altering cancer type (e.g., from a more severe to a less severe type; or from a worse prognosis to a better prognosis). Alternatively, the anti-cancer therapeutic agent is administered in an amount effective in reducing tumor formation, size, or metastasis.

Conventional methods, known to those of ordinary skill in the art of medicine, may be used to administer the anti-cancer therapeutic agent to the subject, depending upon the type of disease to be treated or the site of the disease. The anti-cancer therapeutic agent can also be administered via other conventional routes, e.g., administered orally, parenterally, by inhalation spray, topically, rectally, nasally, buccally, vaginally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, an anti-cancer therapeutic agent may be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (e.g., glycerol, propylene glycol, liquid polyethylene glycol, and the like). For intravenous injection, water soluble anti-cancer therapeutic agents can be administered by the drip method, whereby a pharmaceutical formulation containing the antibody and a physiologically acceptable excipients is infused. Physiologically acceptable excipients may include, for example, 5% dextrose, 0.9% saline, Ringer's solution, and/or other suitable excipients. Intramuscular preparations, e.g., a sterile formulation of a suitable soluble salt form of the anti-cancer therapeutic agent, can be dissolved and administered in a pharmaceutical excipient such as Water-for-Injection, 0.9% saline, and/or 5% glucose solution.

In one embodiment, an anti-cancer therapeutic agent is administered via site-specific or targeted local delivery techniques. Examples of site-specific or targeted local delivery techniques include various implantable depot sources of the agent or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568, the contents of each of which are incorporated by reference herein for this purpose.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., *Gene Therapeutics: Methods And Applications Of Direct Gene Transfer* (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. The contents of each of the foregoing are incorporated by reference herein for this purpose.

Therapeutic compositions containing a polynucleotide may be administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

Therapeutic polynucleotides and polypeptides can be delivered using gene delivery vehicles. The gene delivery vehicle can be of viral or non-viral origin (e.g., Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). The contents of each of the foregoing are incorporated by reference herein for this purpose. Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698;

WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adenoassociated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. The contents of each of the foregoing are incorporated by reference herein for this purpose.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581. The contents of each of the foregoing are incorporated by reference herein for this purpose.

It is also apparent that an expression vector can be used to direct expression of any of the protein-based anti-cancer therapeutic agents (e.g., an anti-cancer antibody). For example, peptide inhibitors that are capable of blocking (from partial to complete blocking) a cancer causing biological activity are known in the art.

In some embodiments, more than one anti-cancer therapeutic agent, such as an antibody and a small molecule inhibitory compound, may be administered to a subject in need of the treatment. The agents may be of the same type or different types from each other. At least one, at least two, at least three, at least four, or at least five different agents may be co-administered. Generally anti-cancer agents for administration have complementary activities that do not adversely affect each other. Anti-cancer therapeutic agents may also be used in conjunction with other agents that serve to enhance and/or complement the effectiveness of the agents.

Treatment efficacy can be predicted as described herein for a patient prior to a treatment. Alternatively or in addition to, treatment efficacy can be predicted and/or determined as described herein over the course of treatment (e.g., before, during, and after treatment). See, e.g., Example 4 and Example 5 below.

Combination Therapy

Compared to monotherapies, combinations of treatment approaches showed higher efficacy in many studies, but the choice of remedies to be combined and designing the combination therapy regimen remain speculative. Given that the number of possible combinations is now extremely high, there is great need for a tool that would help to select drugs and combinations of remedies based on objective information about a particular patient. Use of biomarkers as described herein for designing or electing a specific combination therapy establishes a scientific basis for choosing the optimal combination of preparations.

As noted above, also provided herein are methods of treating a cancer or recommending treating a cancer using any combination of anti-cancer therapeutic agents or one or more anti-cancer therapeutic agents and one or more additional therapies (e.g., surgery and/or radiotherapy). The term combination therapy, as used herein, embraces administration of more than one treatment (e.g., an antibody and a small molecule or an antibody and radiotherapy) in a sequential manner, that is, wherein each therapeutic agent is administered at a different time, as well as administration of these therapeutic agents, or at least two of the agents or therapies, in a substantially simultaneous manner.

Sequential or substantially simultaneous administration of each agent or therapy can be affected by any appropriate route including, but not limited to, oral routes, intravenous routes, intramuscular, subcutaneous routes, and direct absorption through mucous membrane tissues. The agents or therapies can be administered by the same route or by different routes. For example, a first agent (e.g., a small molecule) can be administered orally, and a second agent (e.g., an antibody) can be administered intravenously.

As used herein, the term "sequential" means, unless otherwise specified, characterized by a regular sequence or order, e.g., if a dosage regimen includes the administration of an antibody and a small molecule, a sequential dosage regimen could include administration of the antibody before, simultaneously, substantially simultaneously, or after administration of the small molecule, but both agents will be administered in a regular sequence or order. The term "separate" means, unless otherwise specified, to keep apart one from the other. The term "simultaneously" means, unless otherwise specified, happening or done at the same time, i.e., the agents of the disclosure are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents or therapies described herein.

Combination therapy can also embrace the administration of the anti-cancer therapeutic agent (e.g., an antibody) in further combination with other biologically active ingredients (e.g., a vitamin) and non-drug therapies (e.g., surgery or radiotherapy).

It should be appreciated that any combination of anti-cancer therapeutic agents may be used in any sequence for treating a cancer. The combinations described herein may be selected on the basis of a number of factors, which include but are not limited to the effectiveness of altering a biomarker, reducing tumor formation or tumor growth, and/or alleviating at least one symptom associated with the cancer, or the effectiveness for mitigating the side effects of another agent of the combination. For example, a combined therapy as provided herein may reduce any of the side effects associated with each individual members of the combination, for example, a side effect associated with an administered anti-cancer agent.

EXAMPLES

In order that the systems and methods described herein may be more fully understood, the following examples are set forth. The examples described in this application are offered to illustrate the methods and systems provided herein and are not to be construed in any way as limiting their scope.

Example 1: Calculating Normalized Biomarker Values

Obtaining Biomarker Sets

Any number of biomarkers may be used to predict therapy efficacy using a technique provided herein. Biomarkers used herein were obtained from published clinical studies shown in Table 1.

TABLE 1

Datasets used for calculating therapy scores.

| Therapy | Dataset | Diagnosis | Number of biomarkers |
|---|---|---|---|
| aPD1 therapy | Hugo et al. | Melanoma | 46 |
| aCTLA4 therapy | Van Allen et al. | Melanoma | 17 |
| IFNa therapy | TCGA SKCM | Melanoma | 43 |
| MAGEA-3 vaccine | MAGEA3 dataset GSE35640 | Melanoma | 13 |
| Bevacizumab | BEV-bladder-GSE60331 | Melanoma | 11 |
| Rituximab Based | MALY-DE ICGC | Follicular lymphoma | 18 |

In the instant example, biomarkers that split the patient cohorts treated with a particular therapy by a clinical measure (e.g., overall survival (OS), progression-free survival (PFS), objective response rate (ORR), ect.) were used. For example, in patients treated with an anti-PD1 therapy, the PFS for patients having a high number of mutations was 14.5 months and the PFS for patients having a low number of mutations was 3.6 months. Thus, the number of mutations was used as a parameter for predicting therapy efficacy.

Biomarkers were defined as either positive biomarkers or negative biomarkers based on whether the parameter value of the biomarker corresponds to an increase or decrease in therapy response. Biomarkers were defined as positive biomarkers if their biomarker parameter value correlating to a positive therapy outcome was high. Biomarkers were defined as negative biomarkers if their biomarker parameter value correlating to a negative therapy outcome was high.

A detailed set of biomarkers for each therapy is presented in Table 2.

TABLE 2

Biomarkers obtained from published datasets.

| Therapy | Biomarkers | | | |
|---|---|---|---|---|
| aPD1 therapy | Affinity of neontigens | AXL | B2M LOF mutation | BRAF mutation |
| | BRCA2 mutation | Cancer gene panels (CGPs) FM-CGP | Cancer gene panels (CGPs) HSL-CGP | CCL13 |
| | CCL2 | CCL7 | CCL8 | CD8+ cell density in the tumor invasive margin |
| | CD8+ cell number | CDH1 | CVEGFC | CX3CL1 expression |
| | CXCR2 expression | Dendritic cell number | EGFR expression | Endothelial cells |
| | Eosinophil number | ESRP1 expression | Fibroblasts | Granzyme B expression |
| | JAK1 LOF mutation | JAK2 LOF mutation | LDH level | Lymphocyte number |
| | M1 macrophage number | M1/M2 macrophage ratio | MDSC % | MHC-II expression |
| | MHC-II expression (HLA-DRA) | Missmatch-repair deficiency status | MITF expression | Mutational Burden |
| | Pattern of distant metastases | PD-L1 expression | PD-L1 expression on infiltrating leukocytes | PTEN loss |
| | Quantity of neoantigen peptides | ROR2 | STAT1 expression | T reg cell % |
| | TAGLN | TCR clonality | TGFbeta level | TIL number in tumor |
| | TWIST2 | VEGF level | VEGFA | |
| aCTLA4 therapy | Absolute lymphocyte count | CD8+ cell number | CXCL11 expression | CXCL9 expression |
| | CXCR3 expression | Dendritic cell number | EOMES+CD8+ cells number | FOXP3+ cells number |
| | IDO expression | LDH expression | M1 macrophage number | M1/M2 macrophage ratio |
| | MDSC % | Mutational Burden | NY-ESO-1 seropositive | PTEN loss |
| | T reg cell % | TCR clonality | TGFbeta level | TIL number in tumor |
| | VEGF level | | | |
| IL-2 therapy | Bone metastasis | concomitant regional lymphadenopathy | Leucocytes number | LNPEP expression |
| | C-reactive protein level | Delta32 CCR5 Polymorphism | BCAT2 expression | BDNFOS expression |
| | IL-10 (−1082G−>A) polymorphism | CAIX expression | LOC130576 expression | CCR5 LOF mutation |

TABLE 2-continued

Biomarkers obtained from published datasets.

| Therapy | Biomarkers | | | |
|---|---|---|---|---|
| | ERCC1 (codon 118) polymorphism | IFN-g (+874A->T) polymorphism | LOC399900 expression | ATP6V0A2 expression |
| | Ki-67 expression | Alkaline phosphatase level | ARHGAP10 expression | CD56+ or CD57+ cells number |
| | Liver metastasis | CD83+ TIDC cells number | cDNA FLJ37989 expression | LDH level |
| | Fibronectin level | HLA-DQB1 expression | GBF1 expression | amount of alveolar component |
| | Albumin level | clear cell histology | FOXP3+ cells number | HLA-DQA1 expression |
| | granular features | MAP3K5 expression | MDSC number | Mediastinum metastasis |
| | MEF2A expression | MTUS1 expression | Neutrophil number | NK cell number |
| | non clear cell histology | NR1H2 expression | NRAS mutations | Number of metastatic sites |
| | papillary features | PH-4 expression | Platelets Number | RABL2B expression |
| | RC3H2 expression | rs12553173 | Sedimentation rate | SUPT6H expression |
| | TACC1 expression | TDP1 expression | TFPI expression | Time from tumor to occurrence of metastases |
| | Transferrin level Weight loss | TSH level α-antitrypsin level | VCAM1 expression | VEGF level |
| IFNa therapy | CAIX level | Delta32 CCR5 Polymorphism | Leucocytes count | LNPEP expression |
| | ERCC1 (codon 118) polymorphism | GBF1 expression | Bone metastasis | Breslow thickness |
| | IL-6 expression level | CCR5 LOF mutation | LOC130576 expression | CD4+ cells number |
| | Hepatic RIG-1 expression | IL-1β expression level | LOC399900 expression | BDNFOS expression |
| | Interval from initial diagnosis to treatment | ARHGAP10 expression | BCAT2 expression | CD8+ CD57+ cells number |
| | Liver metastasis | CD83+ TIDC cells number | cDNA FLJ37989 fis expression | Ki-67 expression |
| | HLA-Cw06 allele | IL-1α expression level | HLA-DQB1 expression | ATP6V0A2 expression |
| | Alkaline phosphatase level | collagen IV level | HLA-DQA1 expression | IL-10 (-1082G->A) polymorphism |
| | IFN-g (+874A->T) polymorphism | MAP3K5 expression | Mediastinum metastasis | MEF2A expression |
| | MIP-1α expression level | MIP-1β expression level | MTAP gene expression | MTUS1 expression |
| | Neutrophil count | NR1H2 expression | Number of metastatic sites | Osteopontin level |
| | Performance status | PH-4 expression | Platelets Number | RABL2B expression |
| | RC3H2 expression | Sedimentation rate | Serum calcium level | Serum hemoglobin level |
| | STAT1 gene expression | SUPT6H expression | TACC1 expression | TDP1 expression |
| | TFPI expression | Time from tumor to occurrence of metastases | TNF-α expression level | TRAIL level |
| | Ulceration of primary | VCAM1 expression | VEGF level | VEGFR2 level |
| Anti-cancer vaccine therapy | Cancer-Testis Antigens' Genes expression | CD16+CD56+CD69+ lymphocytes number | CD4+CD45RO+ cell number | CD4+CTLA-4+ T cell number |
| | CD4+PD-1+ T cell number | C-reactive protein level | ECOG performance score | EGF level |
| | I/II high-grade or III T1/2/3a low-grade disease intermediate risk | IFN-gamma-induced tumor cell apoptosis | IgM for Blood Group A trisaccharide level | IL-6 level |
| | Intratumoral versus peritumoral T cell density | LDH level | Lin-CD14+HLA-DR-/lo MDSC level | lymphocyte number |
| | lymphocytes in PBMC % | M1/M2 macrophage ratio | MDSC number | Mean Corpuscular Hemoglobin Concentration (MCHC) |
| | Number of CD27-CD45RA+ and | Patient's age | Predictive gene signature in MAGE A3 | PTEN loss |

TABLE 2-continued

Biomarkers obtained from published datasets.

| Therapy | Biomarkers | | | |
|---|---|---|---|---|
| | CD27−CD45RA− and CD27+CD45RA− T-cells | | antigen-specific cancer immunotherapy | |
| | Serum amyloid A level | Serum S100B concentration | Syndecan-4 mRNA expression level | T reg cell % |
| | TGFbeta level | Toll-like receptor 4 gene polymorphism | WT1 expression | |
| Anti-angiogenic therapy | Acneiform rash | Adrenomedullin Repeat Polymorphism | angiopoietin-2 expression levels | Bioactive Peptide Induced Signaling Pathway |
| | CD133 expression | CDC16 level | Child-Pugh class | CXCL10 plasma level |
| | CXCR1 rs2234671 G > C | CXCR2 C785T | CXCR2 rs2230054 T > C | ECOG Performance Status |
| | EGF A-61G | EGF rs444903 A > G | EGFR expression levels | EGFR rs2227983 G > A |
| | Endothelin-1 expression levels | Expression of CD31 | Expression of PDGFR-beta | HBV status |
| | HGF plasma level | History of alcohol intake | ICAM1 T469C | IFN-α2 plasma level |
| | IGF-1 rs6220 A > G | IL-12 plasma level | IL-16 plasma level | IL-2Rα plasma level |
| | IL-3 plasma level | IL-6 plasma level | IL-8 251 T > A | IL-8 plasma level |
| | Lck and Fyn tyrosine kinases in initiation of TCR Activation pathway activation | Liver metastasis | M-CSF plasma level | mucinous histology |
| | NO2-dependent IL 12 Pathway activation in NK cells | Number of resting circulating endothelial cells | Number of total circulating endothelial cells | PIGF plasma level |
| | portal vein thrombosis | rs12505758 in VEGFR2 | rs2286455 | rs3130 |
| | rs699946 in VEGFA | SDF-1α plasma level | Sex | sVEGFR1 |
| | T Cell Receptor Signaling Pathway activation | T Helper Cell Surface Molecules expression | TRAIL plasma level | VEGF -1154 A > G |
| | VEGF -1498 C > T | VEGF C936T | VEGF G-634C | VEGF-1154 G/A |
| | VEGF-2578 C/A | VEGFR1 rs9582036 | VEGFR-2 rs2305948 C > T | WNK1-rs11064560 |
| Rituximab | BCL2 expression | BCL6 expression | Beclin-1 expression level | C1qA Gene Polymorphism |
| | Carbohydrate antigen-125 level | CD163-positive macrophages | CD20 expression | CD37 expression level |
| | CD5 expression level | CXCR4 expression level | Cytotoxic T lymphocyte-associated Granzyme B expression level | FcγRIIIa 158H/H genotypes |
| | Galectin-1 expression | HIP1R mRNA level | IL-12 level | IL-1RA level |
| | Ki-67 expression | MARCO expression | Mast cell number 1 | miR-155 expression |
| | MYC expression | Number of macrophages | p21 protein expression | sLR11 level |
| | SMAD1 expression | STAT3 mRNA level | T cells | TAM number |
| | TIM3 expression | | | |

Calculating Normalized Biomarker Values

To analyze different parameters (e.g., T cell number, MHC protein expression, BRAF mutation, etc.) or parameters for which biomarker "threshold" values could not be clearly interpreted, methods to normalize biomarker values were developed. Normalized biomarker values are herein described in terms of "high," "medium" and "low," where mathematically high values correspond to 1 and mathematically low values correspond to −1.

Biomarkers with digital properties, such as certain mutations (e.g., BRAFV600E), were normalized using a binary system, where presence of a biomarker corresponded to 1 and absence of a biomarker corresponded to 0. Biomarkers associated with protein expression such as those determined from tissue staining experiments, were assigned their corresponding gene expression (e.g., target protein assigned target mRNA expression level). Biomarkers associated with cellular composition in the tumor microenviroment were recalculated with bioinformatics cell deconvolution packages based on RNAseq data (e.g., MCPcounter, CIBERSORT).

Normalized biomarker scores were calculated for a large patient cohort in which patients were diagnosed based on their tumor biopsy. Data was obtained from publicly available databases of human cancer biopsies, and data was normalized for a particular patient using one of the below formulas according to the distribution of biomarker values calculated for the large patient cohort.

Normalized parameter values in terms of "high" and "low" were calculated based on the Z-score of the parameter value using predefined mathematical functions where the normalized parameter value ranges from −1 to 1 depending on Z-score. Mean and standard deviation were taken from a previously calculated distribution of parameter values for the large patient cohort to which the patient belonged.

The function was set so that a zero value of the parameter fell in the middle of the distribution, and the highest values were assigned to parameters at the extreme upper end of the distribution.

Unit step function a):

$$\begin{cases} 1, & \text{if } Z-\text{score value} > C^{+cutoff} \\ 0, & \text{if } C^{-cutoff} < Z-\text{score value} < C^{+cutoff} \\ -1, & \text{if } Z-\text{score value} < C^{-cutoff} \end{cases}$$

Where $C^{+cutoff}$=normalized threshold value representing a "high" parameter value, and $C^{-cutoff}$=normalized threshold value representing a "low" parameter value.

Or:

Flattened unit step function b):

$$\begin{cases} \dfrac{|Z-\text{score value}|^a}{|Z-\text{score value}|^a + |C^{+cutoff}|^a}, & \text{if } Z-\text{score value} \geq 0 \\ \dfrac{|Z-\text{score value}|^a}{|Z-\text{score value}|^a + |C^{-cutoff}|^a}, & \text{if } Z-\text{score value} < 0 \end{cases}$$

Where $a>1$=parameter defining the slope of the unit step function. With $a>\infty$ function b) transforms to function a).

Threshold value $C^{+cutoff}$ ($C^{-cutoff}$) was equal to 1 (−1), indicating that 15% of patients had a high biomarker value, and 15% of patients had a low biomarker value. Different cut-offs may be used depending on the biomarkers involved in the calculation.

Figure 3:
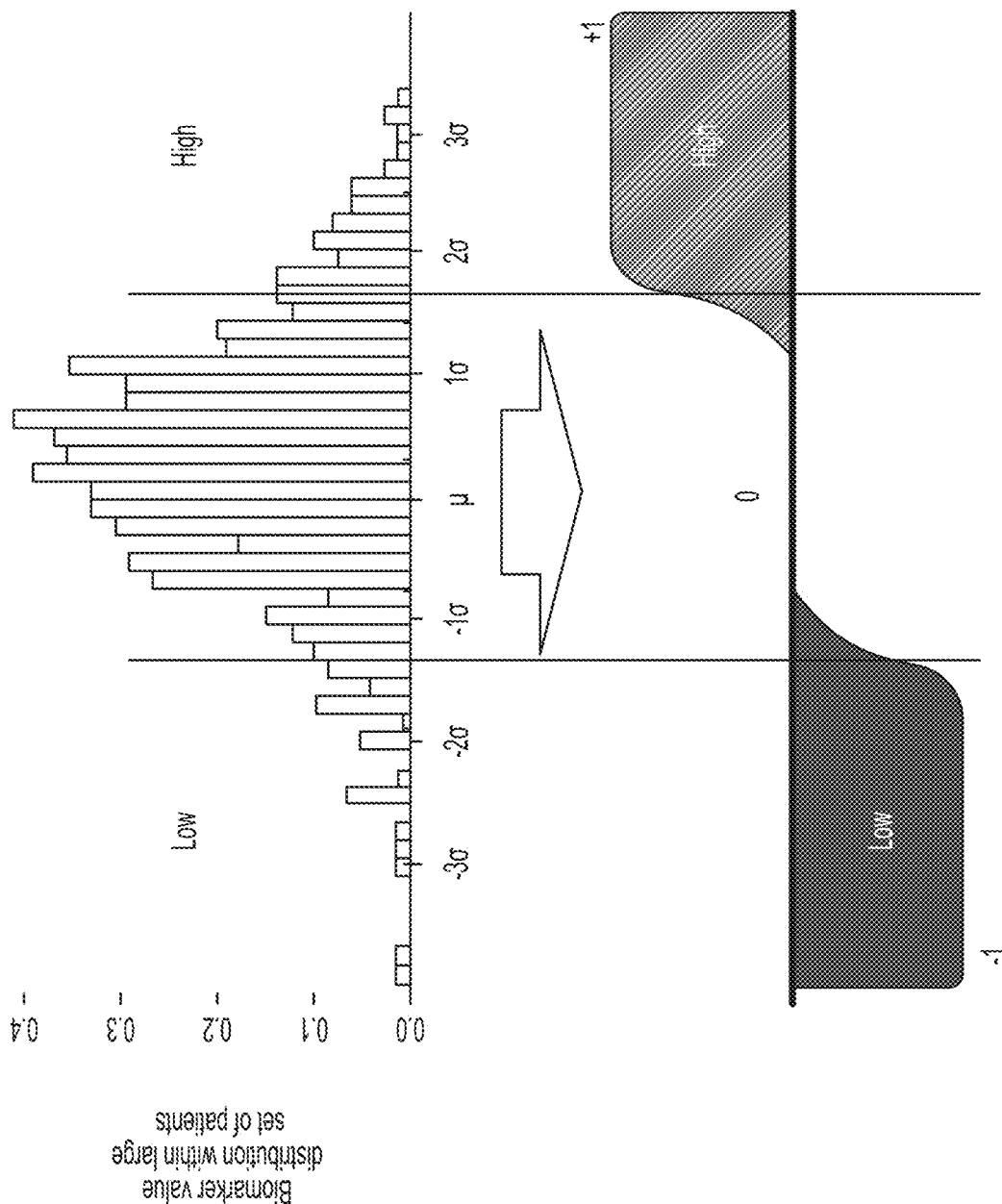
FIG. 3 is a graphical representation of biomarker value distribution for a large patient cohort, as determined in accordance with some embodiments of the technology described herein.

After normalization, each biomarker was transformed to the same range scale. Thus, a value equal to 1 represents a "high" parameter value, and a value equal to −1 represents a "low" parameter value. Parameter values equal or close to 0 reflect median parameter values according to the distribution. A graphical representation of biomarker value distribution for a large patient cohort is shown in FIG. 3.

Defining Biomarker Significance

Biomarkers were assigned weights indicative of their predictive significance based on whether the biomarker was obtained from a large or small patient cohort. Biomarkers obtained from studies using large patient cohorts may have higher predictive significance, and therefore these biomarkers were assigned an initial numeric weight of 3. Biomarkers obtained from studies using small patient cohorts may have lower predictive significance, and therefore these biomarkers were assigned an initial numeric weight of 1.

Biomarkers were assigned weights indicative of their predictive significance based on the role of the biomarker with respect to a therapy. For example, when analyzing biomarkers for treatment with an anti-PD1 therapy, PDL expression was a significant biomarker that was assigned a higher numeric weight than a less significant biomarker such as gender.

Biomarker significance in terms of "weight" was defined by expert assessment or clinical studies where the biomarker was identified. Significance or weight was based on clinical measures (e.g., patient outcome) that split two cohorts of patients divided by biomarker value. If the difference among clinical outcomes for a biomarker was large (p-value<0.01), it was assigned a high weight. If the clinical difference for a biomarker was minimal (0.01<p-value<0.05), the biomarker weight was assigned a low weight.

Alternatively or in addition to the foregoing, biomarker significance was calculated for a biomarker within a set of biomarkers using machine learning algorithms. This approach involved extensive "training" of datasets. A set of biomarkers obtained from literature was tested mathematically to improve weights manually assigned to biomarkers. The algorithm provided a list of significant biomarkers and insignificant biomarkers. Insignificant biomarkers were excluded from the initial set without loss of prediction accuracy.

Example 2: Therapy Scores Calculated from Biomarkers

Figure 4:
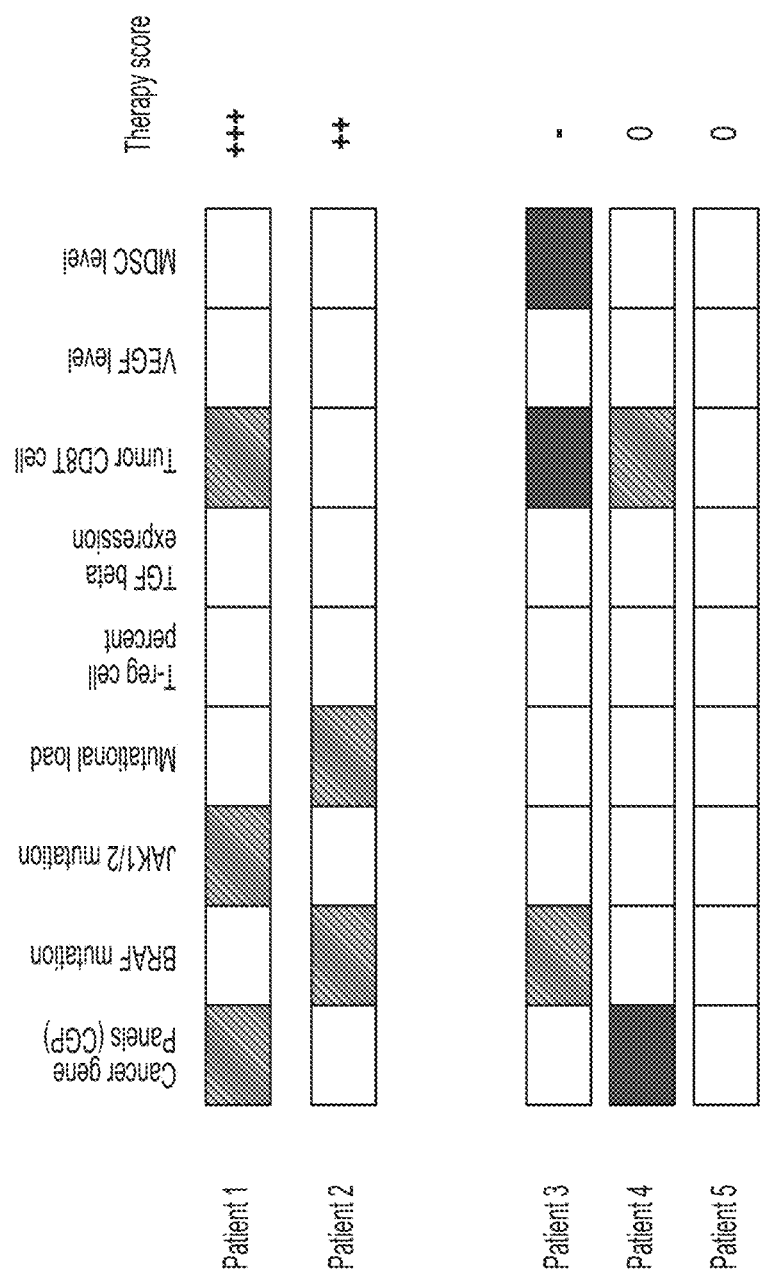
FIG. 4 is a graphical representation of patient therapy scores calculated as the sum of positive and negative biomarkers, in accordance with some embodiments of the technology described herein.

Therapy scores were calculated for five patients using a sum of normalized biomarker values multiplied by their "weight". Patient 1 and Patient 2 had more positive biomarkers, and thus had higher therapy scores (FIG. 4). Patient 4 had similar numbers of positive and negative biomarkers and Patient 5 had biomarkers with neutral values, and thus these patients had therapy scores of zero (FIG. 4). Patient 3 had a greater number of negative biomarkers, and thus has a negative therapy score (FIG. 4).

Example 3: Therapy Scores Predicted Treatment Response

Figure 5:
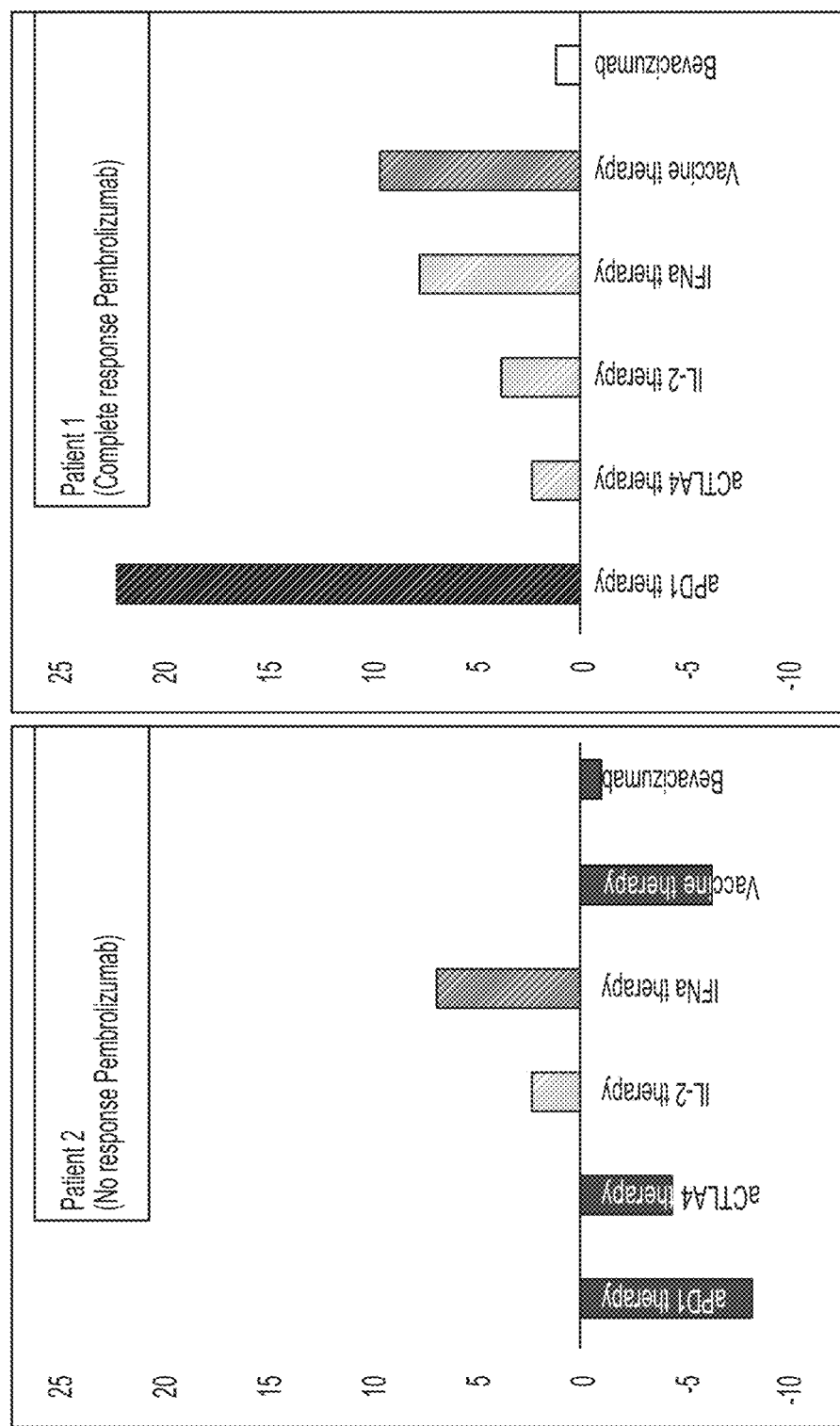
FIG. 5 is a graphical representation of patient therapy scores calculated for multiple therapies for a patient that has been determined as responsive (Patient 1) or non-responsive (Patient 2) to an anti-PD1 therapy (Pembrolizumab), in accordance with some embodiments of the technology described herein.

Therapy scores for different therapies were calculated for a non-responsive patient (Patient 1) and a responsive patient (Patient 2) with respect to their response to the anti-PD1 therapy Pembrolizumab. Based on the calculated therapy scores, Patient 1 was likely non-responsive to other treatments including anti-CTLA4 therapy, IL-2 therapy, vaccine therapy, and Bevacizumab (FIG. 5). However, Patient 1's therapy score predicted a likely response to IFN-α therapy (FIG. 5). Patient 2's therapy scores predicted a likely response to each treatment. These results demonstrated that therapy scores predicted both a response and a non-response to a therapy.

Figure 7A:
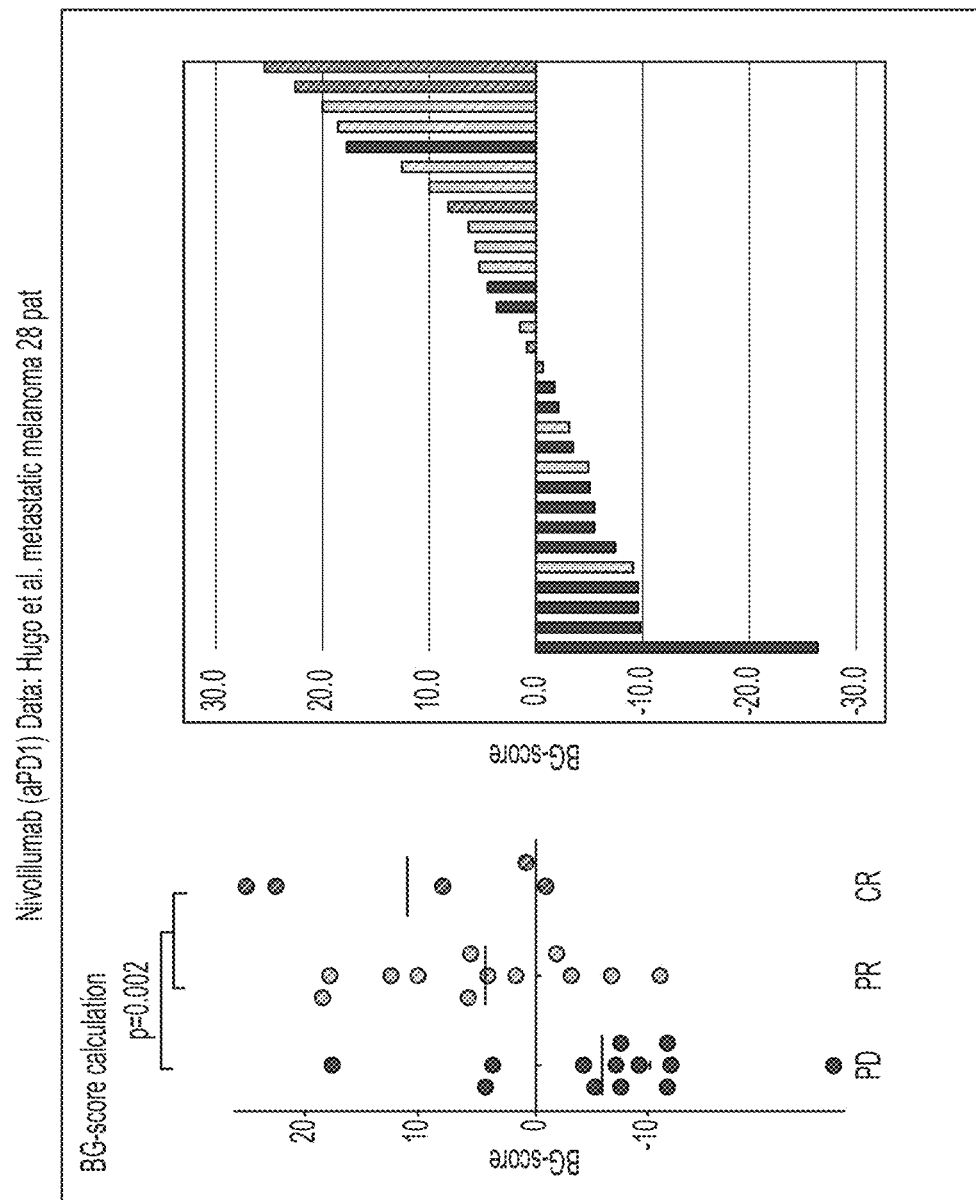
FIG. 7A is a graphical representation of therapy scores calculated for patients treated with an anti-PD1 therapy (Pembrolizumab), in accordance with some embodiments of the technology described herein. Patients with progressive disease (PD) are shown in red, patients with stable disease (SD) are shown in light blue, and patients with complete response (CR) are shown in blue.
Figure 7B:
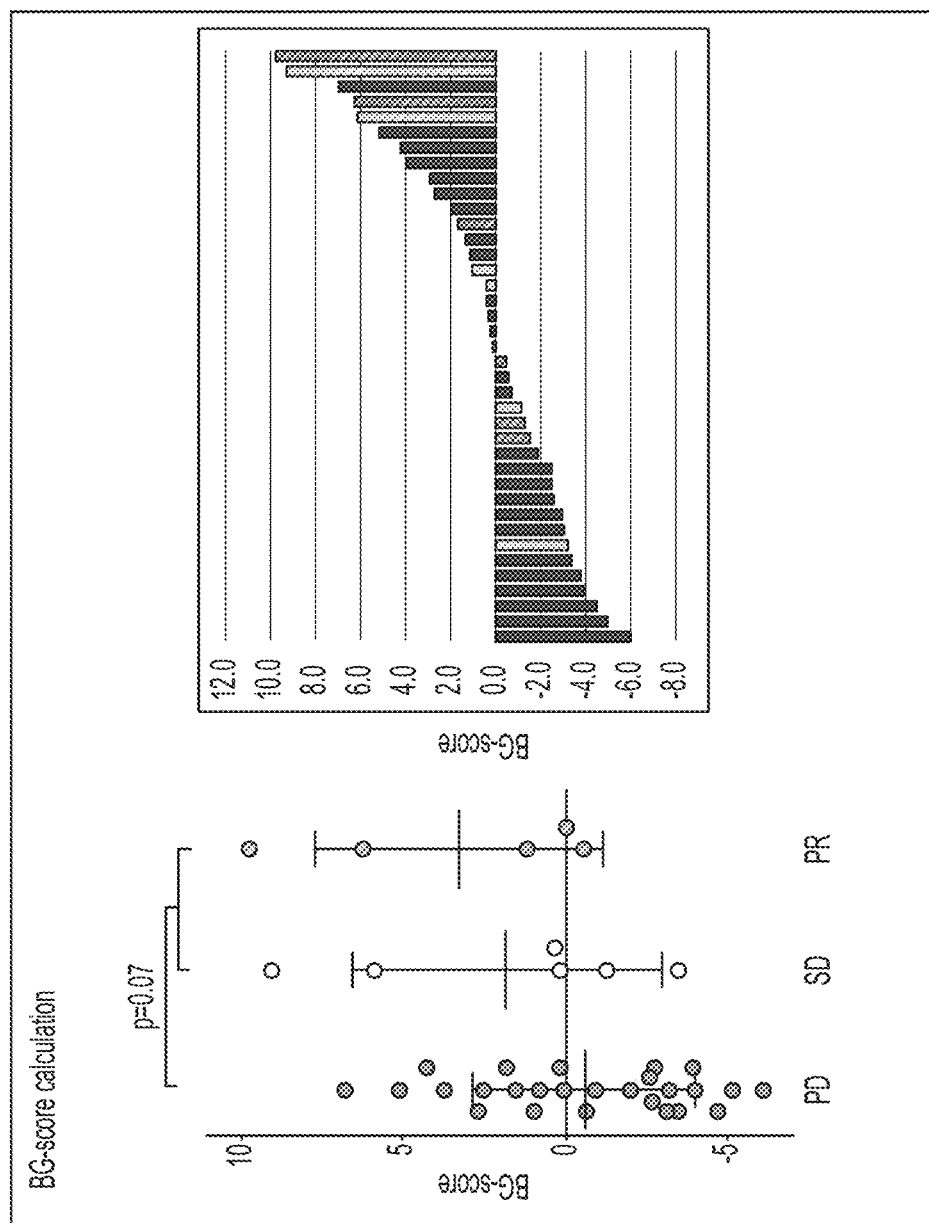
FIG. 7B is a graphical representation of therapy scores calculated for patients treated with an anti-CTLA4 therapy (Ipililumab), in accordance with some embodiments of the technology described herein. Patients with progressive disease (PD) are shown as a dark solid line, patients with stable disease (SD) are shown as a light grey striped line, and patients with partial response (PR) are shown in a dark grey striped line.

Therapy scores were calculated as described herein for an anti-PD1 therapy dataset and an anti-CTLA4 dataset. Patients treated with an anti-PD1 therapy having higher therapy scores calculated as a sum of positive and negative biomarkers were more likely to respond to therapy, and patients with negative therapy scores were unlikely to respond to therapy (FIG. 7A). Similar results were obtained for patients treated with an anti-CTLA4 therapy (FIG. 7B).

Figure 7C:
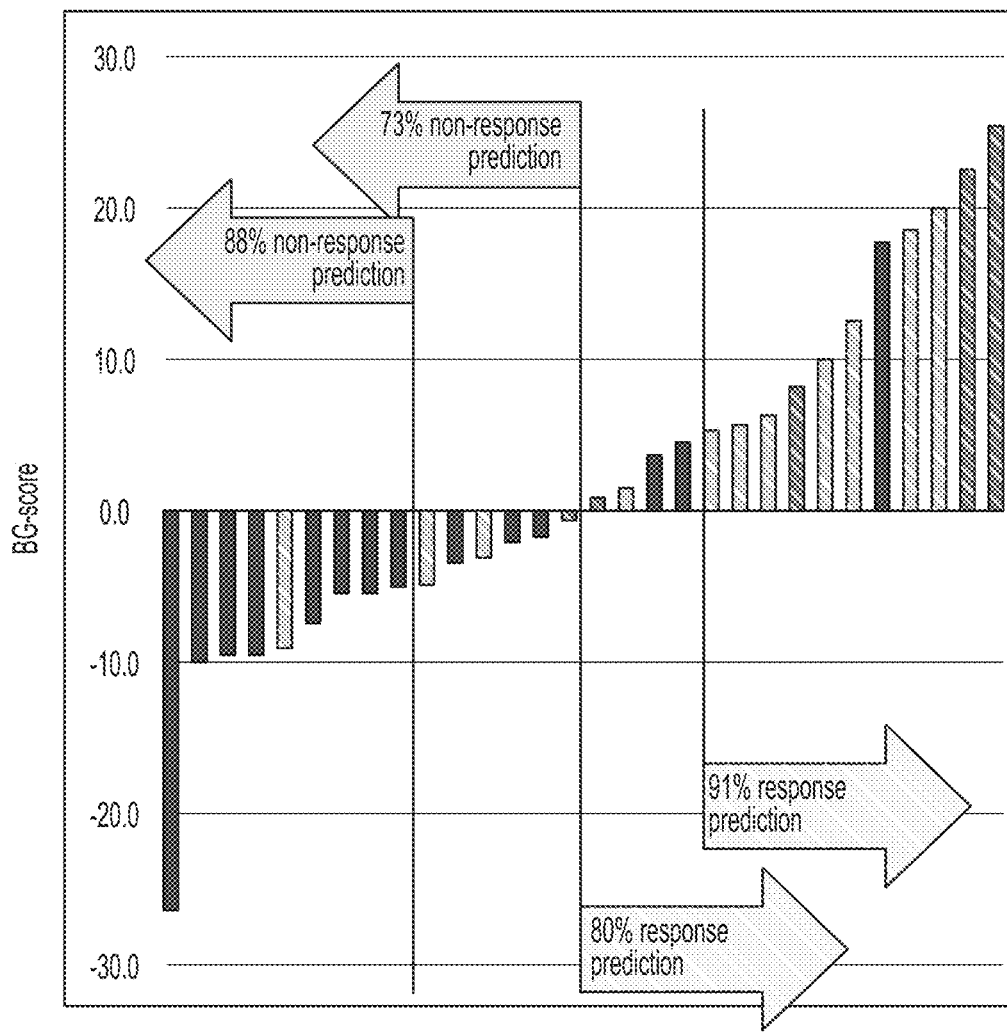
FIG. 7C is a graphical representation of therapy scores calculated for patients treated with an anti-PD1 therapy (Pembrolizumab), in accordance with some embodiments of the technology described herein. Patients with progressive disease (PD) are shown as a dark solid line, patients with stable disease (SD) are shown as a light grey striped line, and patients with partial response (PR) are shown in a dark grey striped line.

Predictive accuracy was improved by using a prediction cut-off. For example, analysis of the anti-PD1 therapy dataset showed that the prediction rate was 73% when the non-response cut-off was lower than zero and 88% when the non-response cut-off was lower than −1 (FIG. 7C). Similarly, the prediction rate was 80% when the response cut-off was higher than zero and improved to 91% when the response cut-off was higher than 1 (FIG. 7C). Therapy response rate predictions based on certain cut-offs for various therapies are shown in Table 3.

TABLE 3

Therapy response rate prediction.

| Therapy | Non-response cut-off (lower than) | Prediction rate | Response cut-off (higher than) | Prediction rate |
|---|---|---|---|---|
| aPD1 therapy | 0 | 73% | 0 | 80% |
| aCTLA4 therapy | −1 | 77% | — | — |
| IFNa therapy | 0 | 100% | 0 | 70% |
| MAGEA-3 vaccine | −2 | 94% | 0 | 50% |
| Bevacizumab | −1 | 80% | 1 | 80% |
| Rituximab Based | — | — | 0 | 100% |

Figure 8A:
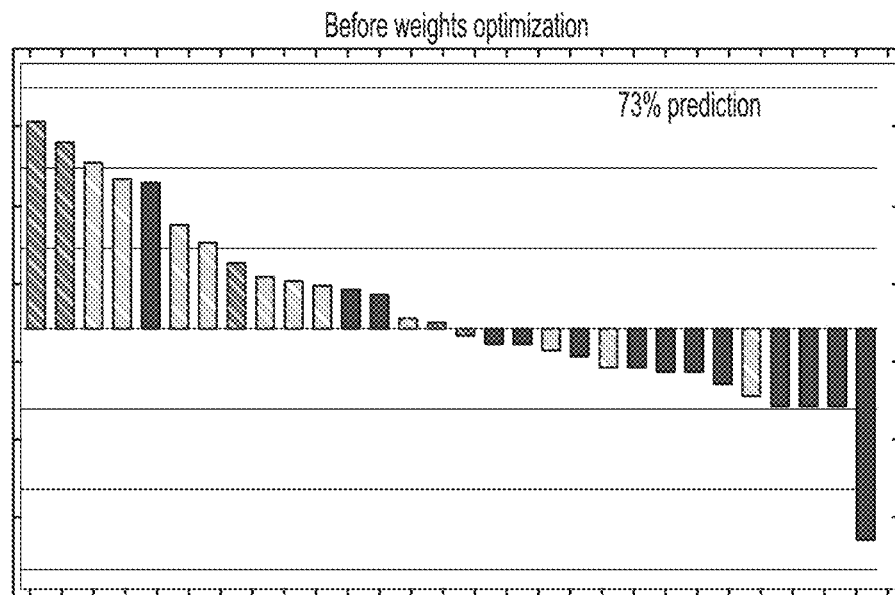
FIG. 8A is a graphical representation of therapy scores calculated without additional weight optimization in a machine learning-based optimization of biomarker importance, in accordance with some embodiments of the technology described herein. Patients with progressive disease (PD) are shown as a dark solid line, patients with stable disease (SD) are shown as a light grey striped line, and patients with partial response (PR) are shown in a dark grey striped line.
Figure 8B:
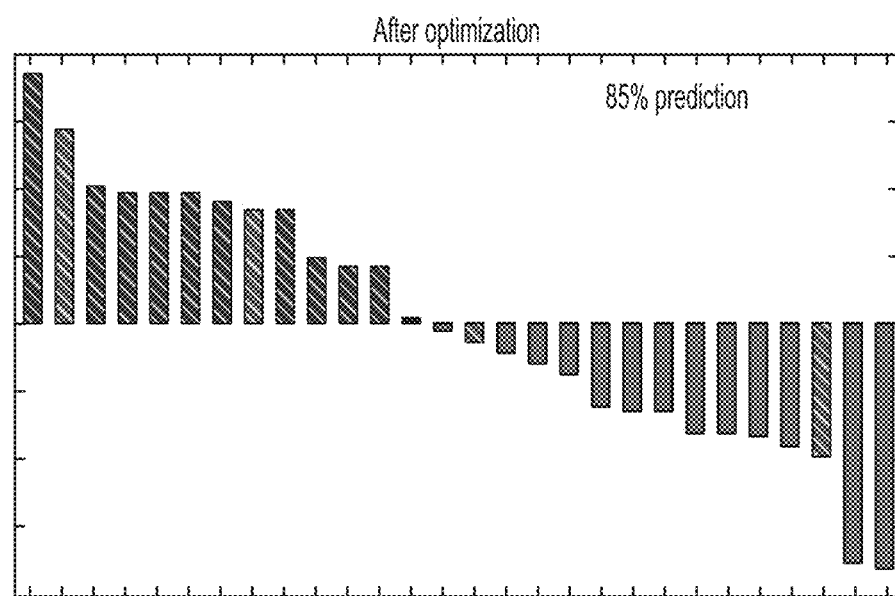
FIG. 8B is a graphical representation of therapy scores calculated with machine-adapted weights, in accordance with some embodiments of the technology described herein. Patients with progressive disease (PD) are shown as a dark solid line, patients with stable disease (SD) are shown as a light grey striped line, and patients with partial response (PR) are shown in a dark grey striped line.
Figure 8C:
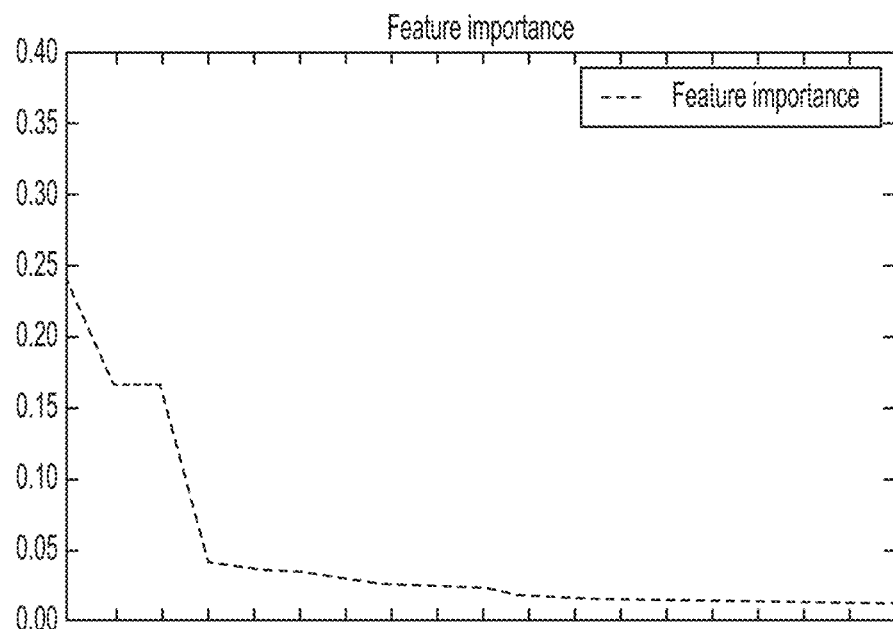
FIG. 8C is a graphical representation of biomarker importance in terms of feature importance calculated with forest regression algorithms, in accordance with some embodiments of the technology described herein.
Figure 8D:
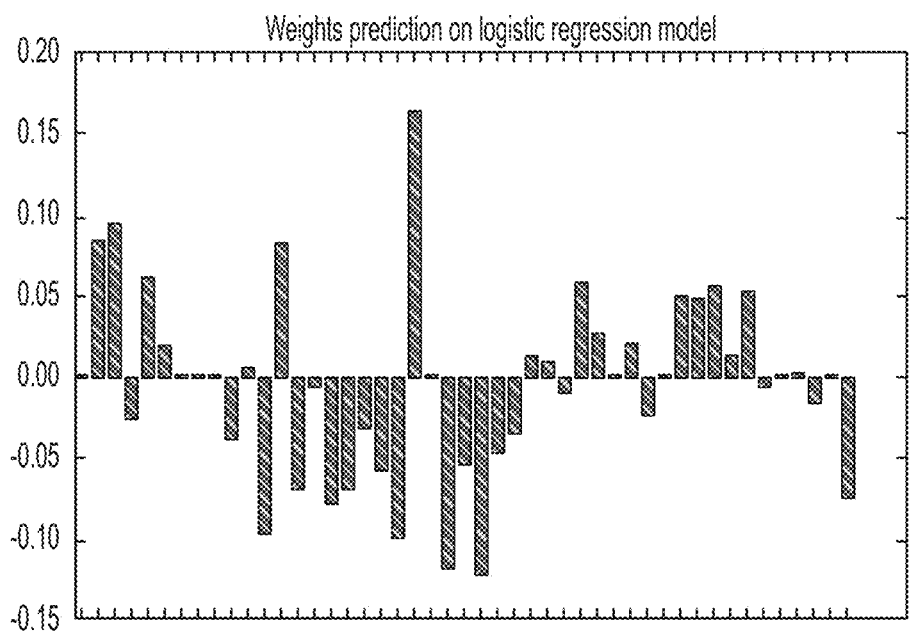
FIG. 8D is a graphical representation of biomarker weights recalculated with a logistic regression model to improve prediction of therapy response, in accordance with some embodiments of the technology described herein.

Example 4: Biomarker Weight Optimization Improved Therapy Score Prediction Accuracy Using an anti-PD1 therapy dataset obtained from Hugo et al., the prediction accuracy of therapy scores calculated with biomarker weight optimization were compared to those calculated without biomarker weight optimization. Therapy scores calculated without biomarker weight optimization accurately predicted therapy response for 73% of patients in the study (FIG. 8A). Calculating therapy scores with biomarker weight optimization improved the prediction rate to 85%. Biomarker weight optimization included calculating feature importance using random forest regression, in which abundant biomarkers were assigned higher importance for predicting a therapy response (FIG. 8C). Biomarker weights were recalculated with a logistic regression model to obtain the best prediction of therapy response (FIG. 8D).

Example 5: Calculated Therapy Scores for Different Therapies

Different combinations of biomarkers were used for calculating therapy scores for different therapies. Normalized biomarker values for each patient treated with anti-PD1 therapy (Table 4-5), aCTLA4 therapy (Table 6-7), IFNα therapy (Table 8), anti-cancer vaccine therapy (Table 9-10), and anti-angiogenic therapy (Table 11) were calculated.

TABLE 4

Set of normalized biomarker values for each patient having a negative therapy score treated with aPD1 therapy.

| ID NO: | 87 | 88 | 03 | 29.0 | 83 | 95 | 02 | 28.0 | 90 | 82 | 96 | 79 | 92 | 84 | 89 |
|---|---|---|---|---|---|---|---|---|---|---|---|---|---|---|---|
| Response | PD | PD | PD |  | PR | PD | PD |  | PD | PR | PD | PD | PD | PD | CR |
| MiR-BART9 expression | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cancer gene panels (CGPs) FM-CGP | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cancer gene panels (CGPs) HSL-CGP | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| BRAF mutation | 0.0 | 3.0 | 3.0 | 3.0 | 3.0 | 3.0 | 3.0 | 3.0 | 3.0 | 3.0 | 3.0 | 0.0 | 3.0 | 0.0 | 3.0 |
| STAT1 expression | 0.0 | 0.0 | −0.2 | −0.2 | −1.6 | 0.0 | −1.0 | −1.0 | 0.0 | −0.4 | 0.0 | 0.2 | 0.0 | −0.7 | 0.2 |
| Granzyme B expression | −0.2 | 0.0 | 0.0 | 0.0 | −0.6 | 0.0 | 0.0 | 0.0 | 0.0 | −0.9 | 0.0 | 0.0 | 0.0 | 0.0 | 0.4 |
| Hugogene/AXL | −0.5 | −0.4 | −0.2 | −0.2 | 0.0 | 0.0 | 0.0 | 0.0 | −0.5 | 0.4 | 0.0 | 0.0 | 0.0 | 0.4 | −0.4 |
| Hugogene/ROR2 | −0.5 | −0.3 | −0.5 | −0.5 | 0.0 | −0.4 | −0.4 | −0.4 | −0.1 | 0.0 | −0.1 | −0.5 | 0.0 | −0.4 | 0.0 |
| Hugogene/TAGLN | −0.2 | 0.0 | 0.0 | 0.0 | 0.3 | −0.5 | −0.5 | −0.5 | −0.2 | 0.2 | −0.4 | −0.5 | 0.0 | 0.1 | −0.5 |
| Hugogene/TWIST2 | −0.5 | −0.2 | 0.0 | 0.0 | −0.5 | −0.4 | −0.1 | −0.1 | −0.5 | 0.1 | −0.3 | −0.5 | −0.5 | 0.0 | 0.0 |
| Hugogene/CDH1 | −2.8 | −2.9 | −2.4 | −2.4 | 0.3 | 0.0 | 0.0 | 0.0 | −2.9 | 1.6 | −1.6 | 0.5 | 0.0 | −2.5 | −2.8 |
| Hugogene/CCL2 | 0.0 | −0.2 | −0.4 | −0.4 | 0.4 | −0.3 | −0.1 | −0.1 | −0.5 | 0.3 | 0.0 | −0.3 | −0.3 | 0.0 | −0.5 |
| Hugogene/CCL7 | −0.3 | 0.0 | 0.0 | 0.0 | 0.0 | 0.0 | −0.5 | −0.5 | −0.5 | 0.1 | −0.5 | 0.0 | −0.5 | 0.0 | −0.5 |
| Hugogene/CCL8 | 0.0 | 0.0 | 0.0 | 0.0 | 0.4 | −0.3 | −0.3 | −0.3 | −0.5 | 0.2 | −0.5 | 0.0 | −0.4 | 0.0 | −0.4 |
| Hugogene/CCL13 | 0.1 | 0.0 | 0.0 | 0.0 | 0.0 | 0.0 | 0.1 | 0.1 | −0.5 | 0.0 | 0.0 | −0.5 | −0.5 | 0.3 | −0.1 |
| Hugogene/CVEGFC | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Hugogene/VEGFA | −0.9 | 0.0 | 0.0 | 0.0 | 0.0 | 0.0 | 0.1 | 0.1 | −1.0 | 0.0 | 0.0 | 0.0 | −0.2 | −0.1 | −1.0 |
| EGFR expression | 0.3 | 0.0 | 0.5 | 0.5 | 0.0 | 0.0 | 0.0 | 0.0 | 0.5 | −0.2 | 0.0 | 0.2 | 0.0 | 0.0 | 0.0 |
| JAK1 LOF mutation | 0.0 | 0.0 | 0.0 | 0.0 | 0.0 | 0.0 | −1.5 | −1.5 | 0.0 | 0.0 | 0.0 | 0.0 | 0.0 | 0.0 | 0.0 |
| JAK1 LOF mutation | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| B2M LOF mutation | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| LDH level | −0.9 | 0.5 | 0.3 | 0.3 | 0.0 | 0.0 | 0.0 | 0.0 | −0.9 | 0.0 | 0.8 | 0.0 | −0.6 | −0.8 | −0.8 |
| Pattern_of_distant_metastases | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Lymphocyte number | −1.3 | −1.0 | 0.0 | 0.0 | −2.3 | 0.0 | 0.0 | 0.0 | −0.4 | −2.4 | −0.2 | 0.0 | −0.1 | −1.9 | 0.0 |
| Eosinophil number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Missmatch-repair deficiency status | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| PD-L1 expression | −0.7 | −0.6 | −0.5 | −0.5 | −0.3 | 0.0 | 0.0 | 0.0 | 3.0 | 0.0 | 0.0 | 0.0 | 0.0 | −0.1 | 0.1 |
| TCR clonality | −1.6 | −0.6 | 0.0 | 0.0 | −1.6 | 1.8 | 0.0 | 0.0 | 1.6 | −1.6 | 0.0 | −0.5 | 3.0 | 2.4 | 3.0 |
| Quantity of neoantigen peptides | −0.2 | −0.6 | −0.2 | −0.2 | −0.2 | −0.7 | 0.0 | 0.0 | 0.4 | −0.1 | −0.1 | 1.1 | 0.0 | 0.0 | 0.0 |
| Affinity of neontigens | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| CXCR2 expression | −0.5 | 0.0 | −0.4 | −0.4 | −0.5 | −0.3 | 0.0 | 0.0 | 0.0 | 0.0 | −0.5 | 0.0 | −0.5 | 0.0 | 0.0 |
| ESRP1 expression | 1.0 | 0.0 | 1.0 | 1.0 | 0.3 | 0.0 | 0.5 | 0.5 | 1.0 | −0.1 | 0.0 | 0.0 | 0.5 | 1.0 | 1.0 |
| MITF expression | 0.8 | 0.5 | 0.9 | 0.9 | −0.2 | 0.0 | 0.0 | 0.0 | 1.0 | 0.0 | 0.0 | 0.0 | −0.2 | 0.0 | 0.6 |
| Mutational Burden | −0.1 | −0.4 | −0.1 | −0.1 | −0.1 | −0.7 | 0.0 | 0.0 | 0.5 | −0.1 | −0.1 | 0.5 | 0.0 | 0.0 | 0.0 |
| BRCA2 mutation | 0.0 | 0.0 | 0.0 | 0.0 | 0.0 | 0.0 | 0.0 | 0.0 | 0.0 | 0.0 | 3.0 | 0.0 | 0.0 | 0.0 | 0.0 |
| CD8+ cell density in the tumor invasive margin | −2.4 | −2.2 | 0.0 | 0.0 | −2.1 | 0.0 | 0.0 | 0.0 | −0.1 | −2.3 | 0.0 | 0.1 | −0.7 | −0.1 | 0.4 |
| MHC-II expression | −2.6 | 0.0 | 0.0 | 0.0 | 0.0 | 0.0 | −0.7 | −0.7 | 0.0 | −0.7 | 0.0 | 0.1 | −0.1 | −0.2 | 2.2 |
| EGFR expression | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| CX3CL1 expression | 0.3 | −0.2 | 0.0 | 0.0 | 0.0 | 0.0 | 0.7 | 0.7 | 0.5 | −1.0 | 0.7 | −0.8 | 1.0 | 1.0 | 0.9 |
| PD-L1 expression on infiltrating leukocytes | −2.2 | −1.7 | −1.5 | −1.5 | −0.8 | 0.0 | 0.0 | 0.0 | 3.0 | −0.1 | 0.0 | 0.0 | 0.0 | −0.3 | 0.1 |
| VEGF level | −2.2 | 0.0 | −0.8 | −0.8 | 0.1 | 0.0 | 0.0 | 0.0 | −3.0 | 0.0 | −0.1 | −1.8 | 0.0 | −3.0 |  |
| TGFbeta level | −0.8 | 0.0 | −3.0 | −3.0 | 0.0 | −2.9 | 0.0 | 0.0 | −2.6 | 0.4 | 0.0 | −1.4 | 0.0 | −1.1 |  |

TABLE 4-continued

Set of normalized biomarker values for each patient having a negative therapy score treated with aPD1 therapy.

| ID NO: | 87 | 88 | 03 | 29.0 | 83 | 95 | 02 | 28.0 | 90 | 82 | 96 | 79 | 92 | 84 | 89 |
|---|---|---|---|---|---|---|---|---|---|---|---|---|---|---|---|
| M1/M2 macrophage ratio | −0.3 | −0.1 | −0.1 | −0.1 | −0.3 | 0.0 | 0.0 | 0.0 | 0.0 | −0.3 | 0.0 | 0.0 | −0.3 | −0.1 | 0.0 |
| T reg cell % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| MDSC % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| TIL number in tumor | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| CD8+ cell number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| M1 macrophage number | −2.4 | −0.1 | −0.2 | −0.2 | −2.4 | 0.3 | 0.0 | 0.0 | 0.0 | −2.4 | 0.5 | 0.0 | −2.4 | 0.0 | 1.4 |
| Dendritic cell number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Mutational Burden | 0.0 | −0.1 | 0.0 | 0.0 | 0.0 | −0.2 | 0.0 | 0.0 | 0.5 | 0.0 | 0.5 | 0.0 | 0.0 | 0.0 | 0.0 |
| TCR clonality | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| PTEN loss | 0.0 | 0.1 | 0.0 | 0.0 | −0.3 | 0.0 | −2.4 | −2.4 | 0.0 | 0.8 | 0.0 | 1.5 | 1.6 | −0.5 | −0.2 |
| Fibroblasts | −2.9 | −2.0 | −3.0 | −3.0 | 0.0 | −3.0 | −2.4 | −2.4 | −3.0 | 0.3 | −1.5 | −2.9 | 0.0 | 0.0 | −2.9 |
| Endothelial cells | −1.6 | −0.2 | −2.0 | −2.0 | 0.0 | −3.0 | −0.1 | −0.1 | −3.0 | 0.0 | −2.7 | −3.0 | −2.2 | 0.4 | −0.1 |
| Therapy Score | −26.2 | −9.9 | −9.6 | −9.6 | −9.0 | −7.5 | −5.6 | −5.6 | −5.2 | −5.0 | −3.5 | −3.4 | −2.4 | −2.0 | −0.9 |

Abbreviations; PR—partial response, SD—stable disease, CR—complete response, and CPD—clinical progressive disease.

TABLE 5

Set of normalized biomarker values for each patient having a positive therapy score treated with aPD1 therapy.

| ID NO: | 285 | 300 | 297 | 301 | 291 | 293 | 304 | 286 | 305 | 280 | 294 | 281 | 306 | 299 | 298 |
|---|---|---|---|---|---|---|---|---|---|---|---|---|---|---|---|
| Response | CR | PR | PD | PD | PR | PR | PR | CR | PR | PR | PD | PR | PR | CR | CR |
| MiR-BART9 expression | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cancer gene panels (CGPs) FM-CGP | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cancer gene panels (CGPs) HSL-CGP | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| BRAF mutation | 3.0 | 0.0 | 0.0 | 0.0 | 0.0 | 0.0 | 3.0 | 3.0 | 0.0 | 0.0 | 0.0 | 0.0 | 3.0 | 0.0 | 0.0 |
| STAT1 expression | −0.1 | −2.5 | 0.0 | 0.0 | 0.0 | −2.8 | 0.2 | 0.0 | −1.1 | 0.3 | 1.1 | 0.0 | 1.1 | 0.3 | 2.0 |
| Granzyme B expression | −0.1 | −0.5 | 0.0 | 0.0 | 0.0 | −0.6 | 0.0 | 0.0 | 0.0 | −0.3 | 0.8 | 0.0 | 1.0 | 0.0 | 0.0 |
| Hugogene/AXL | 0.0 | 0.4 | 0.0 | 0.0 | 0.0 | 0.4 | 0.0 | 0.0 | 0.3 | 0.0 | 0.0 | 0.0 | 0.0 | 0.0 | −0.1 |
| Hugogene/ROR2 | 0.0 | 0.0 | 0.2 | 0.0 | 0.2 | 0.0 | 0.0 | 0.0 | 0.2 | 0.3 | 0.0 | 0.2 | 0.0 | 0.0 | 0.0 |
| Hugogene/TAGLN | 0.0 | 0.0 | 0.0 | 0.0 | 0.1 | 0.0 | 0.0 | 0.0 | 0.4 | 0.1 | 0.1 | 0.0 | −0.2 | 0.3 | 0.0 |
| Hugogene/TWIST2 | −0.2 | −0.4 | −0.5 | 0.0 | 0.0 | 0.0 | 0.0 | −0.5 | 0.1 | 0.0 | 0.0 | 0.1 | 0.0 | 0.0 | −0.3 |
| Hugogene/CDH1 | 1.3 | 0.8 | −2.9 | −0.4 | 0.2 | 0.0 | 1.2 | 0.0 | −2.1 | 1.4 | −0.9 | 0.9 | 0.0 | 2.1 | 0.4 |
| Hugogene/CCL2 | −0.4 | −0.1 | 0.0 | 0.0 | 0.0 | 0.0 | 0.0 | 0.0 | 0.5 | 0.0 | −0.3 | 0.0 | −0.1 | 0.0 | 0.0 |
| Hugogene/CCL7 | −0.4 | −0.5 | 0.0 | 0.0 | 0.0 | 0.1 | 0.0 | 0.0 | 0.1 | 0.0 | 0.0 | 0.1 | 0.1 | 0.1 | 0.0 |
| Hugogene/CCL8 | −0.4 | 0.2 | 0.0 | −0.4 | −0.1 | 0.3 | 0.0 | −0.3 | 0.3 | 0.0 | −0.5 | 0.0 | 0.0 | 0.0 | 0.0 |
| Hugogene/CCL13 | −0.5 | 0.1 | 0.0 | 0.0 | 0.2 | 0.3 | 0.0 | −0.5 | 0.3 | 0.2 | −0.2 | 0.2 | 0.2 | 0.3 | 0.0 |
| Hugogene/CVEGFC | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Hugogene/VEGFA | 0.0 | 0.0 | 0.9 | 0.0 | 0.6 | 1.0 | 0.0 | 0.8 | 0.9 | 0.0 | 0.7 | 0.4 | 0.4 | 0.2 | 0.2 |
| EGFR expression | 0.0 | 0.5 | 0.0 | 0.0 | 0.0 | −0.1 | −0.1 | 0.1 | −0.2 | 0.5 | 0.0 | 0.0 | 0.0 | 0.0 | 0.0 |
| JAK1 LOF mutation | 0.0 | 0.0 | 0.0 | 0.0 | 0.0 | 0.0 | 0.0 | 0.0 | 0.0 | 0.0 | 0.0 | −1.5 | 0.0 | 0.0 | 0.0 |
| JAK1 LOF mutation | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| B2M LOF mutation | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| LDH level | 0.3 | 0.0 | 1.0 | 0.1 | 0.1 | 1.0 | 0.0 | 0.0 | −0.3 | 0.1 | 0.0 | 0.0 | 0.2 | −0.4 | −0.6 |
| Pattern_of_distant_metastases | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Lymphocyte number | −1.3 | −0.1 | 0.0 | 0.0 | 0.0 | −0.1 | −0.1 | 0.0 | 0.0 | 0.0 | −0.8 | 2.9 | −0.1 | 3.0 | −0.2 |
| Eosinophil number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Missmatch-repair deficiency status | 0.0 | 0.0 | 0.0 | 0.0 | 0.0 | 0.0 | 0.0 | 0.0 | 0.0 | 0.0 | 0.0 | 1.5 | 0.0 | 1.5 | 1.5 |
| PD-L1 expression | 0.0 | 2.8 | 0.0 | 0.0 | −0.1 | −0.1 | 0.6 | 0.0 | 0.0 | 0.2 | 2.4 | 0.0 | 2.9 | 0.6 | 1.2 |
| TCR clonality | 0.0 | −1.2 | 0.0 | −0.9 | 0.1 | 0.0 | −0.1 | 0.0 | 0.0 | 0.0 | 0.0 | 0.0 | −0.6 | 0.0 | 2.6 |
| Quantity of neoantigen peptides | 0.0 | 0.0 | −0.5 | −0.2 | 0.0 | 0.0 | −0.1 | 0.0 | 0.0 | 2.4 | 0.0 | 3.0 | −0.7 | 2.9 | 2.9 |
| Affinity of neontigens | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| CXCR2 expression | 0.0 | −0.5 | 0.0 | 0.0 | 0.0 | 0.0 | 0.0 | 0.0 | 0.0 | −0.5 | 0.0 | −0.5 | 0.0 | 0.0 | 0.0 |
| ESRP1 expression | 0.0 | −1.0 | 0.0 | 0.0 | −0.1 | 0.4 | −0.8 | 0.0 | 0.1 | 0.0 | 0.0 | 0.0 | 0.8 | 0.0 | 0.0 |
| MITF expression | 0.0 | 1.0 | 0.0 | 0.0 | 0.0 | 0.3 | −0.5 | 0.0 | 0.0 | 0.0 | −0.1 | 0.0 | 0.6 | −0.7 | −0.5 |
| Mutational Burden | 0.0 | −0.1 | −0.3 | −0.2 | 0.0 | 0.0 | −0.1 | 0.0 | 0.0 | 2.8 | 0.0 | 3.0 | −0.5 | 2.7 | 2.7 |
| BRCA2 mutation | 0.0 | 3.0 | 0.0 | 0.0 | 0.0 | 3.0 | 0.0 | 0.0 | 0.0 | 0.0 | 0.0 | 3.0 | 0.0 | 3.0 | 3.0 |
| CD8+ cell density in the tumor invasive margin | 0.0 | −1.4 | 0.7 | 1.0 | 0.0 | 0.0 | 0.0 | 0.1 | 0.0 | 0.0 | 3.0 | −0.1 | 1.7 | −0.1 | 0.0 |
| MHC-II expression | 0.0 | −0.1 | 0.0 | 0.9 | 0.0 | 0.0 | 0.0 | −0.1 | 0.0 | 0.0 | 2.5 | 0.0 | 2.4 | 0.0 | 0.9 |
| EGFR expression | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| CX3CL1 expression | 0.2 | 0.9 | 0.0 | 1.0 | 1.0 | 0.0 | −0.5 | −0.2 | −0.7 | 0.0 | 0.0 | 0.0 | 0.0 | −0.6 | −0.4 |
| PD-L1 expression on infiltrating leukocytes | 0.0 | 2.8 | 0.0 | 0.0 | −0.2 | −0.4 | 0.6 | 0.0 | 0.0 | 0.2 | 2.4 | 0.0 | 2.9 | 0.6 | 1.2 |
| VEGF level | 0.0 | 0.0 | 2.8 | 0.0 | 2.1 | 3.0 | 0.0 | 2.6 | 2.9 | 0.0 | 1.3 | 2.5 | 0.0 | 0.9 | 0.2 |
| TGFbeta level | −0.6 | 0.1 | 2.1 | 0.0 | 0.2 | 0.0 | 0.0 | 0.0 | 2.9 | 0.0 | 0.7 | 0.0 | −0.1 | 0.0 | 0.0 |
| M1/M2 macrophage ratio | 0.0 | −0.3 | 0.0 | 0.5 | 0.0 | 0.0 | 0.9 | 0.2 | 0.0 | 0.0 | 0.0 | 0.0 | 0.0 | 0.0 | 0.0 |
| T reg cell % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| MDSC % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |

TABLE 5-continued

Set of normalized biomarker values for each patient having a positive therapy score treated with aPD1 therapy.

| ID NO: | 285 | 300 | 297 | 301 | 291 | 293 | 304 | 286 | 305 | 280 | 294 | 281 | 306 | 299 | 298 |
|---|---|---|---|---|---|---|---|---|---|---|---|---|---|---|---|
| TIL number in tumor | 0.0 | 0.0 | 0.0 | 0.0 | 0.0 | 0.0 | 0.0 | 0.0 | 0.0 | 0.0 | 0.0 | 0.0 | 1.9 | 0.0 | 0.0 |
| CD8+ cell number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| M1 macrophage number | 0.0 | −2.4 | 0.0 | 3.0 | 0.0 | 0.0 | 3.0 | 2.8 | 0.0 | 0.3 | 0.0 | 0.8 | −0.1 | 2.9 | 3.0 |
| Dendritic cell number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Mutational Burden | 0.0 | 0.0 | −0.1 | −0.1 | 0.0 | 0.0 | 0.0 | 0.0 | 0.0 | 2.8 | 0.0 | 3.0 | −0.2 | 2.7 | 2.7 |
| TCR clonality | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| PTEN loss | 0.2 | 0.0 | −0.2 | 0.0 | −0.7 | −2.3 | 0.0 | 0.0 | 0.0 | 0.0 | 0.0 | 0.0 | 0.6 | 2.8 | 2.5 |
| Fibroblasts | −0.2 | 0.0 | 0.1 | 0.0 | 0.6 | 0.0 | 0.0 | −0.1 | 2.9 | 2.2 | 0.9 | 2.1 | 0.0 | 0.0 | 0.0 |
| Endothelial cells | −0.3 | 0.0 | 0.0 | 0.0 | 1.2 | 2.6 | −1.2 | −0.2 | 2.9 | 0.2 | 0.9 | 0.0 | 0.0 | 0.6 | 0.0 |
| Therapy Score | 0.8 | 1.4 | 3.5 | 4.4 | 5.3 | 5.6 | 6.1 | 7.9 | 10.2 | 12.4 | 17.6 | 18.5 | 20.0 | 22.6 | 25.1 |

Abbreviations; PR—partial response, SD—stable disease, CR—complete response, and CPD—clinical progressive disease.

TABLE 6

Set of normalized biomarker values for each patient having a negative therapy score treated with aCTLA4 therapy.

| ID NO: | PD 35 | PD 38 | PD 31 | PD 29 | PD 16 | PD 22 | SD 10 | PD 28 | PD 32 | PD 21 | PD 34 |
|---|---|---|---|---|---|---|---|---|---|---|---|
| CXCL9 expression | −0.9 | −0.9 | 0.0 | −0.8 | −0.4 | −0.9 | −0.3 | −0.9 | −0.9 | 0.0 | −0.9 |
| CXCL11 expression | −0.8 | −0.7 | 0.0 | 1.0 | −0.5 | −0.5 | −0.7 | −0.2 | −0.8 | 0.0 | −0.8 |
| CXCR3 expression | 0.0 | −0.4 | −0.4 | −0.6 | 0.0 | −0.7 | 0.8 | −0.7 | −0.7 | 0.0 | −0.5 |
| VEGF level | −3.0 | 0.0 | −2.8 | 0.0 | 0.0 | 0.0 | −2.4 | 0.0 | 0.8 | −1.2 | 2.2 |
| MDSC % | 0.0 | 0.0 | 0.0 | 0.0 | 0.0 | 0.0 | 0.0 | 0.0 | 0.0 | 0.0 | 0.0 |
| FOXP3+ cells number | 0.0 | 0.0 | 0.0 | 0.0 | 0.0 | 0.0 | 0.0 | 0.0 | 0.0 | 0.1 | 0.0 |
| Absolute lymphocyte count | 0.0 | 0.0 | 0.0 | 0.0 | 0.0 | 0.0 | 0.0 | 0.0 | 0.0 | 0.0 | 0.0 |
| IDO expression | −2.6 | −1.9 | −1.2 | −2.3 | −2.0 | −0.7 | −0.5 | −0.6 | −2.6 | 0.0 | −2.5 |
| NY-ESO-1 seropostive | 0.0 | 0.0 | 0.6 | 0.0 | 0.0 | 0.0 | 0.0 | 0.0 | 1.0 | 0.0 | 0.0 |
| EOMES+CD8+ cells number | −0.3 | −0.2 | −0.2 | −0.3 | 0.0 | −0.3 | 0.0 | −0.1 | −0.3 | 0.0 | −0.3 |
| LDH expression | −0.2 | 0.0 | 0.0 | 0.0 | 0.0 | 0.1 | 0.2 | 0.0 | 0.0 | −0.1 | 0.0 |
| VEGF level | 0.0 | 0.0 | 0.0 | 0.0 | 0.0 | 0.0 | 0.0 | 0.0 | 0.0 | 0.0 | 0.0 |
| TGFbeta level | −0.9 | 0.0 | −0.3 | −1.0 | −0.8 | 0.0 | −0.8 | 0.1 | 0.9 | −0.6 | 0.2 |
| M1/M2 macrophage ratio | 0.0 | −0.1 | −0.1 | −0.1 | −0.1 | 0.0 | −0.1 | −0.2 | −0.2 | −0.1 | −0.2 |
| T reg cell % | 0.0 | 0.0 | 0.0 | 0.0 | 0.0 | 0.0 | 0.0 | 0.0 | 0.0 | 0.0 | 0.0 |
| MDSC % | 0.0 | 0.0 | 0.0 | 0.0 | 0.0 | 0.0 | 0.0 | 0.0 | 0.0 | 0.0 | 0.0 |
| TIL number in tumor | −2.3 | −2.6 | −0.3 | −2.6 | −1.4 | −2.9 | 0.0 | −1.9 | −2.4 | 0.0 | −2.8 |
| CD8+ cell number | −0.7 | −0.7 | −0.3 | −0.1 | 0.0 | −0.7 | −0.2 | −0.7 | −0.5 | −0.6 | 0.0 |
| M1 macrophage number | 0.0 | 0.0 | 0.0 | 0.0 | 0.0 | 0.0 | 0.0 | 0.0 | 0.0 | 0.0 | 0.0 |
| Dendritic cell number | 0.0 | 0.0 | 0.0 | 0.0 | 0.0 | 0.0 | 0.0 | 0.0 | 0.0 | 0.0 | 0.0 |
| Mutational Burden | 2.1 | 0.0 | −0.1 | −0.1 | 0.0 | 0.0 | 0.0 | −0.1 | 0.0 | 0.0 | 0.0 |
| TCR clonality | 0.0 | 0.0 | 0.0 | 0.0 | 0.0 | 0.0 | 0.0 | 0.0 | 0.0 | 0.0 | 0.0 |
| PTEN loss | 1.0 | −0.4 | 0.0 | 0.0 | 0.0 | 0.0 | 0.5 | 0.0 | 0.0 | 0.0 | 0.0 |
| Therapy Score | −8.6 | −7.9 | −5.1 | −6.8 | −5.3 | −6.6 | −3.3 | −5.2 | −5.7 | −2.6 | −5.7 |

| ID NO: | PD 30 | PD 36 | CR 4 | SD 13 | PD 26 | PD 41 | PR 5 | PR 6 | PD 37 | SD 11 |
|---|---|---|---|---|---|---|---|---|---|---|
| CXCL9 expression | 0.6 | 0.0 | −0.9 | 0.1 | 0.0 | 0.0 | 0.0 | 0.2 | 0.0 | 0.0 |
| CXCL11 expression | 0.0 | 0.0 | 0.0 | 0.0 | −0.1 | 0.0 | 0.0 | 0.1 | −0.3 | 0.0 |
| CXCR3 expression | −0.2 | 0.0 | −0.3 | 0.0 | 0.0 | 0.0 | 0.0 | −0.3 | 0.0 | −0.6 |

TABLE 6-continued

Set of normalized biomarker values for each patient having a negative therapy score treated with aCTLA4 therapy.

| | | | | | | | | | | |
|---|---|---|---|---|---|---|---|---|---|---|
| VEGF level | −0.2 | −1.1 | 0.0 | −0.3 | 0.0 | 0.0 | 0.0 | 0.0 | 0.3 | 0.0 |
| MDSC % | 0.0 | 0.0 | 0.0 | 0.0 | 0.0 | 0.0 | 0.0 | 0.0 | 0.0 | 0.0 |
| FOXP3+ cells number | 0.0 | 0.0 | 0.0 | 0.0 | 0.1 | 0.0 | 0.0 | 0.0 | 0.0 | 0.0 |
| Absolute lymphocyte count | 0.0 | 0.0 | 0.0 | 0.0 | 0.0 | 0.0 | 0.0 | 0.0 | 0.0 | 0.0 |
| IDO expression | 0.0 | −0.1 | −0.1 | 0.0 | 0.0 | −0.5 | −1.1 | 0.0 | 0.0 | 0.0 |
| NY-ESO-1 seropostive | 0.0 | 0.0 | 0.0 | 0.0 | 0.0 | 0.0 | 0.0 | 0.0 | 0.0 | 0.0 |
| EOMES+CD8+ cells number | 0.0 | −0.2 | 0.0 | 0.0 | 0.0 | 0.0 | 0.0 | 0.0 | −0.2 | 0.0 |
| LDH expression | −2.2 | 0.0 | −0.1 | −0.8 | −0.2 | 0.0 | 0.0 | −0.6 | 0.0 | 0.0 |
| VEGF level | 0.0 | 0.0 | 0.0 | 0.0 | 0.0 | 0.0 | 0.0 | 0.0 | 0.0 | 0.0 |
| TGFbeta level | 0.0 | 0.0 | 0.0 | 0.0 | −0.1 | 0.1 | 0.0 | 0.5 | 0.2 | 1.0 |
| M1/M2 macrophage ratio | 0.0 | −0.1 | −0.1 | 0.0 | −0.1 | 0.0 | 0.0 | 0.2 | 0.0 | 0.0 |
| T reg cell % | 0.0 | 0.0 | 0.0 | 0.0 | 0.0 | 0.0 | 0.0 | 0.0 | 0.0 | 0.0 |
| MDSC % | 0.0 | 0.0 | 0.0 | 0.0 | 0.0 | 0.0 | 0.0 | 0.0 | 0.0 | 0.0 |
| TIL number in tumor | 0.0 | −0.1 | −0.1 | 0.0 | 0.0 | 0.0 | −0.5 | −0.1 | 0.0 | −0.5 |
| CD8+ cell number | −0.6 | −0.7 | 0.0 | 0.0 | −0.3 | 0.0 | 0.6 | 0.0 | 0.0 | 0.7 |
| M1 macrophage number | 0.0 | 0.0 | 0.0 | 0.0 | 0.0 | 0.0 | 0.0 | 0.0 | 0.0 | 0.0 |
| Dendritic cell number | 0.0 | 0.0 | 0.0 | 0.0 | 0.0 | 0.0 | 0.0 | 0.0 | 0.0 | 0.0 |
| Mutational Burden | 0.0 | 0.0 | 0.0 | 0.0 | −0.1 | −0.1 | 0.0 | 0.0 | 0.0 | 0.0 |
| TCR clonality | 0.0 | 0.0 | 0.0 | 0.0 | 0.0 | 0.0 | 0.0 | 0.0 | 0.0 | 0.0 |
| PTEN loss | 0.0 | 0.0 | 0.0 | −0.2 | 0.0 | 0.0 | 0.0 | −0.1 | 0.0 | −0.7 |
| Therapy Score | −2.6 | −2.2 | −1.6 | −1.3 | −0.8 | −0.6 | −0.9 | 0.0 | −0.1 | −0.2 |

Abbreviations; PR—partial response, SD—stable disease, CR—complete response, and CPD—clinical progressive disease.

TABLE 7

Set of normalized biomarker values for each patient having a positive therapy score treated with aCTLA4 therapy.

| | PD 19 | SD 14 | PD 24 | PD 33 | CR 3 | PR 8 | PD 17 | PD 20 | PD 25 | PD 27 | PD 40 | PD 18 | PD 39 | SD 12 | PR 7 | PD 23 | SD 15 | PR 9 |
|---|---|---|---|---|---|---|---|---|---|---|---|---|---|---|---|---|---|---|
| CXCL9 expression | 0.4 | 0.0 | 0.3 | 0.7 | 0.0 | 0.0 | 0.0 | 0.0 | −0.8 | 0.7 | 1.0 | 0.9 | 0.3 | 0.9 | 0.7 | 0.0 | 1.0 | 0.0 |
| CXCL11 expression | 0.0 | −0.3 | 0.0 | 0.8 | −0.8 | 0.0 | 0.7 | 0.0 | 0.0 | 0.1 | 0.7 | 0.5 | 0.0 | 0.8 | 0.3 | 0.0 | 0.9 | 1.0 |
| CXCR3 expression | 0.0 | −0.2 | 0.8 | 0.9 | 0.0 | 0.0 | 0.9 | −0.3 | 0.0 | 0.4 | 1.0 | 0.1 | 0.9 | 1.0 | 0.8 | 0.0 | 0.8 | 0.0 |
| VEGF level | 0.1 | 0.0 | 0.0 | −0.6 | −0.4 | 0.4 | 0.0 | 2.1 | 1.2 | 0.0 | 0.0 | 0.0 | 1.4 | 0.0 | 0.0 | 1.5 | 0.0 | 3.0 |
| MDSC % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| FOXP3+ cells number | 0.0 | 0.0 | 1.8 | 1.7 | 0.0 | 0.0 | 3.0 | 0.0 | 0.0 | 0.0 | 2.9 | 1.2 | 0.0 | 2.0 | 1.1 | 0.0 | 0.0 | 0.0 |
| Absolute lymphocyte count | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| IDO expression | 0.0 | 0.0 | 0.0 | 0.1 | 0.1 | 0.0 | 0.0 | 0.0 | 0.0 | 1.0 | 1.0 | 0.0 | 0.2 | 0.9 | 0.9 | 0.0 | 1.0 | 0.9 |
| NY-ESO-1 seropostive | 0.0 | 0.0 | 0.0 | 0.0 | 0.0 | 0.0 | 0.0 | 0.0 | 1.0 | 1.0 | 0.0 | 1.0 | 0.0 | 0.0 | 0.0 | 0.3 | 0.0 | 0.0 |
| EOMES+CD8+ cells number | 0.0 | −0.1 | 0.0 | 0.8 | 0.0 | 0.0 | 0.2 | 0.0 | 0.0 | 1.0 | 1.0 | 0.0 | 0.4 | 1.0 | 0.6 | 0.0 | 1.0 | 0.0 |
| LDH expression | 0.0 | 0.0 | 0.0 | 0.1 | 0.0 | 0.0 | 0.3 | 0.0 | 0.2 | −2.8 | 0.1 | 0.0 | 0.0 | 0.4 | −0.3 | 0.0 | −0.2 | 3.0 |
| VEGF level | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| TGFbeta level | −0.1 | 0.0 | −0.2 | −0.9 | 0.0 | 0.8 | 0.0 | 0.8 | 0.0 | 0.5 | −0.9 | 0.0 | 0.3 | −0.2 | 0.0 | 0.9 | 0.9 | 1.0 |
| M1/M2 macrophage ratio | 0.0 | −0.1 | 0.0 | 0.0 | −0.1 | 0.0 | 0.0 | −0.2 | 0.0 | 0.9 | 0.4 | 0.7 | 0.9 | 1.0 | 0.0 | 0.9 | 1.0 | −0.2 |
| T reg cell % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| MDSC % | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |

TABLE 7-continued

Set of normalized biomarker values for each patient having a positive therapy score treated with aCTLA4 therapy.

| | PD | | | | | | | | | | | | | | | | | |
|---|---|---|---|---|---|---|---|---|---|---|---|---|---|---|---|---|---|---|
| | PD 19 | SD 14 | PD 24 | PD 33 | CR 3 | PR 8 | PD 17 | PD 20 | PD 25 | PD 27 | PD 40 | PD 18 | PD 39 | SD 12 | PR 7 | PD 23 | SD 15 | PR 9 |
| TIL number in tumor | 0.0 | −0.1 | 1.3 | 0.4 | 2.9 | 0.0 | 2.9 | 0.0 | 0.0 | 0.0 | 2.8 | 0.0 | 0.7 | 2.9 | 1.8 | 0.0 | 2.6 | 0.3 |
| CD8+ cell number | 0.1 | 0.1 | 0.0 | 0.0 | 0.0 | 0.0 | −0.3 | 0.0 | 1.0 | 0.9 | 0.6 | 0.0 | 1.0 | 1.0 | 0.9 | 0.0 | 1.0 | 0.0 |
| M1 macrophage number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Dendritic cell number | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Mutational Burden | 0.0 | 0.0 | 0.0 | 0.0 | 0.0 | 0.0 | 0.0 | 0.0 | −0.1 | 0.1 | 0.0 | 0.0 | −0.1 | 0.2 | 3.0 | 3.0 | 2.8 | 0.0 |
| TCR clonality | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| PTEN loss | −0.3 | 0.8 | 0.0 | 0.0 | −0.4 | 0.0 | 0.0 | −0.7 | 0.0 | 0.0 | 0.0 | 0.9 | 0.0 | 0.0 | 0.0 | 0.0 | −0.2 | 1.0 |
| Therapy Score | 0.2 | 0.1 | 3.9 | 4.0 | 1.3 | 1.2 | 7.7 | 1.9 | 2.6 | 3.7 | 10.5 | 5.3 | 6.1 | 11.9 | 9.7 | 6.8 | 12.6 | 10.0 |

Abbreviations; PR—partial response, SD—stable disease, CR—complete response, and CPD—clinical progressive disease.

TABLE 8

Set of normalized biomarker values for each patient treated with IFNα therapy.

| TCGA | FR-A7U8 | FS-A1ZS | FS-A4F0 | D3-A2JP | FW-A3TV | FS-A1ZW | YG-AA3O | EB-A6QY | FW-A3R5 |
|---|---|---|---|---|---|---|---|---|---|
| Response | PR | SD | SD | PR | SD | PR | CR | CR | CR |
| ID: | 847 | 4526 | 2367 | 1812 | 411 | 1505 | 1154 | 382 | 1124 |
| ID NO: | 10 | 16 | 19 | 9 | 13 | 18 | 11 | 4 | 6 |
| Delta32 CCR5 Polymorphism | 0 | 0 | 0 | 0 | 0 | 0 | 0 | 0 | 0 |
| CCR5 LOF mutation | 0 | 0 | 0 | 0 | 0 | 0 | 0 | 0 | 0 |
| IFN-g (+874A->T) polymorphism | 0 | 0 | 0 | 0 | 0 | 0 | 0 | 0 | 0 |
| IL-10 (−1082G->A) polymorphism | 0 | 0 | 0 | 0 | 0 | 0 | 0 | 0 | 0 |
| ERCC1 (codon 118) polymorphism | 0 | 0 | 0 | 0 | 0 | 0 | 0 | 0 | 0 |
| VCAM1 expression | −0.8 | −0 | −0.8 | 1 | −0 | 0 | −0 | −0.5 | 0 |
| Platelets Number | 0 | 0 | 0 | 0 | 0 | 0 | 0 | 0 | 0 |
| Alkaline phosphatase level | 0 | 0 | 0 | 0 | 0 | 0 | 0 | 0 | 0 |
| Sedimentation rate | 0 | 0 | 0 | 0 | 0 | 0 | 0 | 0 | 0 |
| Weight loss | 0 | 0 | 0 | 0 | 0 | 0 | 0 | 0 | 0 |
| Time from tumor to occurrence of metastases | 0 | 0 | 0 | 0 | 0 | 0 | 0 | 0 | 0 |
| Number of metastatic sites | 0 | 0 | 0 | 0 | 0 | 0 | 0 | 0 | 0 |
| Bone metastasis | 0 | 0 | 0 | 0 | 0 | 0 | 0 | 0 | 0 |
| Liver metastasis | 0 | 0 | 0 | 0 | 0 | 0 | 0 | 0 | 0 |
| Mediastinum metastasis | 0 | 0 | 0 | 0 | 0 | 0 | 0 | 0 | 0 |
| GBF1 expression | 0.5 | −0.5 | −0.4 | 0.5 | −0 | 0.3 | −0.2 | −0.1 | −0.3 |
| LNPEP expression | −0.4 | 0.5 | 0.5 | −0 | 0.5 | −0 | 0 | 0 | −0 |
| MAP3K5 expression | −0.4 | 0.5 | 0 | −0 | −0 | −0.2 | 0 | 0 | −0 |
| cDNA FLJ37989 fis expression | 0 | 0 | 0 | 0 | 0 | 0 | 0 | 0 | 0 |
| RABL2B expression | 0 | 0 | −0 | 0.3 | −0.3 | 0.4 | −0.5 | −0.1 | 0 |
| MEF2A expression | −0 | 0.5 | 0.2 | −0 | 0 | 0 | −0 | 0 | 0.2 |
| LOC399900 expression | 0 | 0 | 0 | 0 | 0 | 0 | 0 | 0 | 0 |
| HLA-DQA1 expression | −0.2 | −0.4 | −0.1 | 0 | 0 | −0.2 | −0 | −0.5 | −0 |

TABLE 8-continued

Set of normalized biomarker values for each patient treated with IFNα therapy.

| | | | | | | | | | |
|---|---|---|---|---|---|---|---|---|---|
| TDP1 expression | 0 | 0.5 | 0 | −0.5 | 0.4 | 0 | 0 | −0 | 0.4 |
| RC3H2 expression | −0 | 0.4 | 0 | −0.3 | 0 | −0 | 0.2 | −0 | 0.3 |
| MTUS1 expression | −0 | −0 | 0 | 0.5 | 0 | −0 | 0 | −0 | 0 |
| NR1H2 expression | 0.1 | −0 | −0.3 | 0 | 0 | 0.5 | 0 | 0 | −0 |
| SUPT6H expression | 0 | −0.5 | −0.4 | 0 | −0.1 | 0.3 | −0 | −0 | 0.3 |
| BCAT2 expression | −0 | −0 | −0.5 | −0 | 0 | 0.5 | −0 | −0 | −0 |
| LOC130576 expression | 0 | 0 | 0 | 0 | 0 | 0 | 0 | 0 | 0 |
| PH-4 expression | 0.2 | −0.4 | 0.3 | −0 | −0.5 | 0.1 | 0.3 | −0 | 0.1 |
| ARHGAP10 expression | −0.5 | 0.1 | 0.4 | 0 | 0 | −0.1 | −0 | −0 | 0.3 |
| TACC1 expression | −0.5 | 0.5 | −0 | 0 | 0.5 | −0.2 | 0.4 | 0 | 0.3 |
| HLA-DQB1 expression | −0.4 | −0 | −0.4 | 0 | −0 | −0 | −0 | −0.1 | −0 |
| ATP6V0A2 expression | −0.4 | 0.1 | 0.2 | −0.4 | 0.5 | −0 | 0.4 | 0.5 | 0.2 |
| TFPI expression | −0.3 | 0 | −0 | −0 | −0 | −0 | −0 | −0 | 0 |
| BDNFOS expression | 0 | 0 | 0 | 0 | 0 | 0 | 0 | 0 | 0 |
| HLA-Cw06 allele | 0 | 0 | 0 | 0 | 0 | 0 | 0 | 0 | 0 |
| IL-1α expression level | −0 | −0 | −0 | −0 | −0 | −0 | −0 | 2 | −0 |
| IL-1β expression level | −0.1 | −0.1 | −2.1 | −0.9 | −1.5 | −0 | −0.1 | −0 | −0.1 |
| IL-6 expression level | −1.2 | 0.4 | −2.4 | −0 | −1.5 | 0.1 | −0.7 | −1.5 | 0.1 |
| TNF-α expression level | −1.5 | −1.6 | −0.8 | −1 | −0.1 | −0 | −0 | −0 | −0.2 |
| MIP-1α expression level (CCL3) | −0 | −0.2 | −2.8 | 0 | −2.1 | −0.2 | −0.1 | −1.4 | −0 |
| MIP-1β expression level (CCL4) | −2 | −0.2 | −2.7 | 0.6 | −0 | 0 | −0 | −0 | 0 |
| Performance status | 0 | 0 | 0 | 0 | 0 | 0 | 0 | 0 | 0 |
| Interval from initial diagnosis to treatmen | 0 | 0 | 0 | 0 | 0 | 0 | 0 | 0 | 0 |
| Serum calcium level | 0 | 0 | 0 | 0 | 0 | 0 | 0 | 0 | 0 |
| Serum hemoglobin level | 0 | 0 | 0 | 0 | 0 | 0 | 0 | 0 | 0 |
| Osteopontin level (SPP1) | −0 | −0 | 2.9 | −2.9 | −0 | −1.2 | 0 | 0 | −0 |
| TRAIL level (TNFSF10) | −1.8 | 0 | −0 | 0 | −0 | 0 | −0.1 | 0.3 | 0 |
| VEGFR2 level (KDR) | 1.5 | 0 | −0 | 0.4 | 0 | 0.2 | −0.1 | 0.4 | −0 |
| VEGF level | −1 | 0.1 | −0 | 0.4 | −0 | 0 | 0 | 0 | −0 |
| CAIX level (CA9) | −0.3 | −0 | 0.5 | 0 | −0 | −1.6 | 0.6 | −0 | 0.6 |
| collagen IV level (COL4A1; COL4A2; COL4A3; COL4A4; COL4A5) | 0 | 0 | −0 | 0.2 | −0.2 | 1.7 | 0 | 0.2 | 0 |
| Ulceration of primary | 0 | 0 | 0 | 0 | 0 | 0 | 0 | 0 | 0 |
| Breslow thickness | 0 | 0 | 0 | 0 | 0 | 0 | 0 | 0 | 0 |
| STAT1 gene expression | −0 | 0.1 | 2.4 | −0 | −0 | 0.4 | −0.2 | −0 | 0 |
| MTAP gene expression | −0 | −2.9 | 1.4 | −0 | 0.4 | 0 | 2.2 | 0.9 | 2.1 |
| Ki-67 expression (MKI67) | 0.3 | −0 | 0 | 1.3 | 2.3 | −0 | 0 | −0 | −2.9 |
| Neutrophil count | 0 | 0 | 0 | 0 | 0 | 0 | 0 | 0 | 0 |
| Leucocytes count | −2.7 | −0.8 | −0.8 | −0 | 0 | 0.2 | −0 | −0.1 | 0 |
| CD8+ CD57+ cells number | −2.4 | −1.5 | −2.2 | 0 | 0 | 0 | −0 | −1 | −0 |
| CD4+ cells number | −2.6 | −1.9 | −0 | 0 | 0.6 | −0.8 | 0 | −0 | 0.3 |

TABLE 8-continued

Set of normalized biomarker values for each patient treated with IFNα therapy.

| | | | | | | | | | |
|---|---|---|---|---|---|---|---|---|---|
| CD83+ TIDC cells number | −1.9 | −3 | 0.8 | −2.9 | 0 | 0 | 0 | 2.9 | 2.9 |
| Hepatic RIG-1 expression (DDX58) | 0 | 0 | 0 | 0 | 0 | 0 | 0 | 0 | 0 |
| Therapy Score | −19 | −10 | −7.2 | −3.6 | −1 | 0.2 | 2.2 | 2 | 4.5 |

| TCGA | EB-A5SH | FS-A1ZT | W3-AA1Q | ER-A19M | GN-A4U5 | D3-A8GB | FR-A44A | HR-A2OH |
|---|---|---|---|---|---|---|---|---|
| Response | SD | CPD | CPD | CR | CR | CR | CR | CR |
| ID: | 1643 | 1617 | 2101 | 1857 | 1156 | 938 | 5299 | 2004 |
| ID NO: | 3 | 17 | 14 | 12 | 7 | 2 | 5 | 8 |
| Delta32 CCR5 Polymorphism | 0 | 0 | 0 | 0 | 0 | 0 | 0 | 0 |
| CCR5 LOF mutation | 0 | 0 | 0 | 0 | 0 | 0 | 0 | 0 |
| IFN-g (+874A−>T) polymorphism | 0 | 0 | 0 | 0 | 0 | 0 | 0 | 0 |
| IL-10 (−1082G−>A) polymorphism | 0 | 0 | 0 | 0 | 0 | 0 | 0 | 0 |
| ERCC1 (codon 118) polymorphism | 0 | 0 | 0 | 0 | 0 | 0 | 0 | 0 |
| VCAM1 expression | −0 | 0 | 0.9 | 0.6 | 0 | 0 | 0.7 | 0.5 |
| Platelets Number | 0 | 0 | 0 | 0 | 0 | 0 | 0 | 0 |
| Alkaline phosphatase level | 0 | 0 | 0 | 0 | 0 | 0 | 0 | 0 |
| Sedimentation rate | 0 | 0 | 0 | 0 | 0 | 0 | 0 | 0 |
| Weight loss | 0 | 0 | 0 | 0 | 0 | 0 | 0 | 0 |
| Time from tumor to occurrence of metastases | 0 | 0 | 0 | 0 | 0 | 0 | 0 | 0 |
| Number of metastatic sites | 0 | 0 | 0 | 0 | 0 | 0 | 0 | 0 |
| Bone metastasis | 0 | 0 | 0 | 0 | 0 | 0 | 0 | 0 |
| Liver metastasis | 0 | 0 | 0 | 0 | 0 | 0 | 0 | 0 |
| Mediastinum metastasis | 0 | 0 | 0 | 0 | 0 | 0 | 0 | 0 |
| GBF1 expression | −0.4 | −0 | 0.3 | 0 | 0 | 0.5 | −0 | −0 |
| LNPEP expression | −0.5 | −0 | −0 | 0 | 0 | −0.2 | 0 | 0 |
| MAP3K5 expression | −0.5 | −0 | 0 | 0 | 0 | −0 | 0.5 | 0 |
| cDNA FLJ37989 fis expression | 0 | 0 | 0 | 0 | 0 | 0 | 0 | 0 |
| RABL2B expression | −0 | −0.3 | 0.2 | −0.1 | 0 | 0 | 0.1 | 0 |
| MEF2A expression | −0.5 | 0 | −0.2 | 0.1 | −0 | −0.2 | 0.3 | 0 |
| LOC399900 expression | 0 | 0 | 0 | 0 | 0 | 0 | 0 | 0 |
| HLA-DQA1 expression | −0 | −0 | 0.1 | −0 | 0.4 | −0 | 0.5 | 0.3 |
| TDP1 expression | −0 | 0 | −0.1 | 0.3 | −0 | −0.4 | −0 | 0 |
| RC3H2 expression | −0 | 0.3 | −0 | 0 | −0 | −0.4 | 0.1 | 0.1 |
| MTUS1 expression | −0.4 | −0 | −0.5 | 0.1 | 0 | −0.2 | 0 | 0.4 |
| NR1H2 expression | −0.1 | 0.4 | 0 | −0 | −0 | 0 | 0 | −0 |
| SUPT6H expression | 0 | −0 | 0.5 | 0 | −0 | 0.4 | 0 | −0 |
| BCAT2 expression | −0 | 0.1 | 0.5 | 0 | 0 | −0 | 0.4 | 0 |
| LOC130576 expression | 0 | 0 | 0 | 0 | 0 | 0 | 0 | 0 |
| PH-4 expression | 0.5 | −0 | 0.5 | 0.3 | −0 | −0 | −0 | −0 |
| ARHGAP10 expression | −0.5 | 0.4 | −0 | −0.1 | −0 | 0 | −0 | −0 |
| TACC1 expression | 0 | −0.1 | −0.1 | −0 | −0 | −0.1 | 0 | 0 |
| HLA-DQB1 expression | −0 | −0 | 0 | 0.4 | 0.4 | 0 | 0.5 | 0.5 |

TABLE 8-continued

Set of normalized biomarker values for each patient treated with IFNα therapy.

| | | | | | | | | |
|---|---|---|---|---|---|---|---|---|
| ATP6V0A2 expression | −0.5 | 0 | −0 | 0.2 | −0 | −0.3 | 0 | −0 |
| TFPI expression | −0.5 | −0 | −0.4 | −0 | −0 | 0 | −0 | −0 |
| BDNFOS expression | 0 | 0 | 0 | 0 | 0 | 0 | 0 | 0 |
| HLA-Cw06 allele | 0 | 0 | 0 | 0 | 0 | 0 | 0 | 0 |
| IL-1α expression level | −0 | −0 | −0 | −0 | 0.3 | −0 | −0 | −0 |
| IL-1β expression level | −0.1 | 0 | −1.4 | −0 | −0 | −0 | 0 | 0 |
| IL-6 expression level | −1.4 | 0.9 | −0 | −0 | −0 | 2.8 | −0.1 | 0.2 |
| TNF-α expression level | −0 | 0 | −0.2 | −0.2 | 0 | −0 | 0 | 0.1 |
| MIP-1α expression level (CCL3) | −0 | −0 | −2.8 | 0 | 0 | 1.3 | 2.9 | 2.9 |
| MIP-1β expression level (CCL4) | −0.9 | 0 | −0 | 2.5 | 2.3 | 1 | 3 | 3 |
| Performance status | 0 | 0 | 0 | 0 | 0 | 0 | 0 | 0 |
| Interval from initial diagnosis to treatmen | 0 | 0 | 0 | 0 | 0 | 0 | 0 | 0 |
| Serum calcium level | 0 | 0 | 0 | 0 | 0 | 0 | 0 | 0 |
| Serum hemoglobin level | 0 | 0 | 0 | 0 | 0 | 0 | 0 | 0 |
| Osteopontin level (SPP1) | 3 | 0.2 | 2.9 | −1.6 | −0 | 0 | −0 | 0.3 |
| TRAIL level (TNFSF10) | −1.9 | 0 | −0 | 1 | 1.2 | 0 | 1.8 | 2 |
| VEGFR2 level (KDR) | 0 | 0 | −0 | 0 | 1.2 | 0.3 | 0.1 | 0.1 |
| VEGF level | 1.4 | 0 | 0.2 | −0 | 1.4 | 0.3 | 0 | 0 |
| CAIX level (CA9) | 0.6 | −0 | 0.6 | −0 | −0 | 0 | 0.2 | −0 |
| collagen IV level (COL4A1; COL4A2; COL4A3; COL4A4; COL4A5) | 1 | 0 | 1.9 | 0 | 0 | −0 | 0 | 0.4 |
| Ulceration of primary | 0 | 0 | 0 | 0 | 0 | 0 | 0 | 0 |
| Breslow thickness | 0 | 0 | 0 | 0 | 0 | 0 | 0 | 0 |
| STAT1 gene expression | −3 | 0.5 | −0 | 2.7 | 2.2 | −0 | 2.9 | 2.9 |
| MTAP gene expression | 0 | 0.9 | 0.2 | −2.8 | −2.7 | −0 | −2.5 | 0 |
| Ki-67 expression (MKI67) | 2.8 | 0 | 3 | −0.9 | 0.6 | 2.9 | 0 | −0.9 |
| Neutrophil count | 0 | 0 | 0 | 0 | 0 | 0 | 0 | 0 |
| Leucocytes count | 0 | 1.8 | −0 | −0 | −0 | 2.7 | 1 | 2.7 |
| CD8+ CD57+ cells number | −0 | 0.3 | 0 | 2.5 | 2.1 | 0.9 | 2.9 | 3 |
| CD4+ cells number | 0 | 1 | 2.6 | 2.7 | 2.7 | 0 | 0.3 | 3 |
| CD83+ TIDC cells number | 1.5 | −0.3 | −1.7 | 0.4 | 0 | 0 | 0 | −0 |
| Hepatic RIG-1 expression (DDX58) | 0 | 0 | 0 | 0 | 0 | 0 | 0 | 0 |
| Therapy Score | −0.4 | 6.4 | 7 | 8.1 | 12 | 11 | 16 | 21 |

Abbreviations; PR—partial response, SD—stable disease, CR—complete response, and CPD—clinical progressive disease.

TABLE 9

Set of normalized biomarker values for each patient having a negative therapy score treated with anti-cancer vaccine therapy.

| | Response | | | | | | | | | | | | |
|---|---|---|---|---|---|---|---|---|---|---|---|---|---|
| ID NO: | NR 21 | NR 33 | NR 17 | NR 5 | NR 26 | NR 34 | NR 25 | NR 22 | R 65 | NR 27 | NR 3 | NR 14 | NR 19 |
| TGFbeta level | −0.05 | 2.13 | −2.99 | 0.01 | 0 | −0.17 | 0 | 0.36 | 1.42 | −0.03 | 0.93 | 0.31 | 0 |
| M1/M2 macrophage ratio | −0 | −0 | −0 | −0 | −0 | −0 | −0 | −0 | 1 | −0 | 1 | −0 | −0 |
| T reg cell % | 0 | 0 | 0 | 0 | 0 | 0 | 0 | 0 | 0 | 0 | 0 | 0 | 0 |
| MDSC number | 0 | 0 | 0 | 0 | 0 | 0 | 0 | 0 | 0 | 0 | 0 | 0 | 0 |
| lymphocyte number | −2.75 | −2.76 | −2.44 | −1.24 | −1.33 | −0.07 | −2.64 | −0.09 | −2.34 | −2.74 | −1.06 | −2.64 | 0.04 |

TABLE 9-continued

Set of normalized biomarker values for each patient having a negative therapy score treated with anti-cancer vaccine therapy.

| | | | | | | | | | | | | | |
|---|---|---|---|---|---|---|---|---|---|---|---|---|---|
| ECOG performance score | 0 | 0 | 0 | 0 | 0 | 0 | 0 | 0 | 0 | 0 | 0 | 0 | 0 |
| EGF level | 0 | 0 | 0 | 0 | 0 | 0 | 0 | 0 | 0 | 0 | 0 | 0 | 0 |
| Cancer-Testis Antigens' Genes expression | 0 | 0 | 0 | 0 | 0 | 0 | 0 | 0 | 0 | 0 | 0 | 0 | 0 |
| IFN-gamma-induced tumor cell apoptosis | 0 | 0 | 0 | 0 | 0 | 0 | 0 | 0 | 0 | 0 | 0 | 0 | 0 |
| IL-6 level | 0 | 0 | 0 | 0 | 0 | 0 | 0 | 0 | 0 | 0 | 0 | 0 | 0 |
| Mean Corpuscular Hemoglobin Concentration (MCHC) | 0 | 0 | 0 | 0 | 0 | 0 | 0 | 0 | 0 | 0 | 0 | 0 | 0 |
| Patient's age | 0 | 0 | 0 | 0 | 0 | 0 | 0 | 0 | 0 | 0 | 0 | 0 | 0 |
| Predictive gene signature in MAGE A3 antigen-specific cancer immunotherapy | 0 | 0 | 0 | 0 | 0 | 0 | 0 | 0 | 0 | 0 | 0 | 0 | 0 |
| TGFbeta1 level | 0 | 0 | 0 | 0 | 0 | 0 | 0 | 0 | 0 | 0 | 0 | 0 | 0 |
| CD16+CD56+CD69+ lymphocytes number | 0 | 0 | 0 | 0 | 0 | 0 | 0 | 0 | 0 | 0 | 0 | 0 | 0 |
| CD4+PD-1+ T cell number_1 | −1.37 | 0 | −0 | −0 | −2.07 | −0.07 | 0 | −0.01 | 2.37 | −1.19 | −0.09 | 0.01 | 0.01 |
| C-reactive protein level | 0 | 0 | 0 | 0 | 0 | 0 | 0 | 0 | 0 | 0 | 0 | 0 | 0 |
| Intratumoral versus peritumoral T cell density | −2.82 | −4.02 | −4.13 | −4.13 | −4.55 | −2.25 | −4.02 | −3.26 | −3.45 | −4.06 | −3.12 | −2.97 | −0.12 |
| Serum amyloid A level | 0 | 0 | 0 | 0 | 0 | 0 | 0 | 0 | 0 | 0 | 0 | 0 | 0 |
| Toll-like receptor 4 gene polymorphism | 0 | 0 | 0 | 0 | 0 | 0 | 0 | 0 | 0 | 0 | 0 | 0 | 0 |
| Syndecan-4 mRNA expression level | 0 | 0 | 0 | 0 | 0 | 0 | 0 | 0 | 0 | 0 | 0 | 0 | 0 |
| WT1 expression | 0 | 0 | 0 | 0 | 0 | 0 | 0 | 0 | 0 | 0 | 0 | 0 | 0 |
| Serum S100B concentration | 0 | 0 | 0 | 0 | 0 | 0 | 0 | 0 | 0 | 0 | 0 | 0 | 0 |
| LDH level | 0 | 0 | 0 | 0 | 0 | 0 | 0 | 0 | 0 | 0 | 0 | 0 | 0 |
| I/II high-grade or III T1/2/3a low-grade disease_intermediate risk | 0 | 0 | 0 | 0 | 0 | 0 | 0 | 0 | 0 | 0 | 0 | 0 | 0 |
| lymphocytes in PBMC % | −0.92 | −0.92 | −0.81 | −0.41 | −0.44 | −0.02 | −0.88 | −0.03 | −0.78 | −0.91 | −0.35 | −0.88 | 0.01 |
| PTEN loss | −0.89 | 0.94 | 0 | −0.96 | 1 | 0.98 | 0.01 | −0 | −0.13 | 1 | 0.13 | 0.15 | −0.02 |
| CD4+CD45RO+ cell number | 0 | 0 | 0 | 0 | 0 | 0 | 0 | 0 | 0 | 0 | 0 | 0 | 0 |
| Number of CD27−CD45RA+ and CD27−CD45RA− and CD27+CD45RA− T-cells | 0 | 0 | 0 | 0 | 0 | 0 | 0 | 0 | 0 | 0 | 0 | 0 | 0 |
| CD4+CTLA-4+ T cell number | 0 | 0 | 0 | 0 | 0 | 0 | 0 | 0 | 0 | 0 | 0 | 0 | 0 |
| CD4+PD-1+ T cell number_1 | 0 | 0 | 0 | 0 | 0 | 0 | 0 | 0 | 0 | 0 | 0 | 0 | 0 |
| IgM for Blood Group A trisaccharide level | 0 | 0 | 0 | 0 | 0 | 0 | 0 | 0 | 0 | 0 | 0 | 0 | 0 |
| Lin-CD14+HLA-DR-/lo MDSC level | 0 | 0 | 0 | 0 | 0 | 0 | 0 | 0 | 0 | 0 | 0 | 0 | 0 |
| B2M | −2.93 | −2.56 | 0.08 | −0 | −0.08 | −2.54 | 0 | −2.25 | −0.22 | 0.79 | −0.5 | −0.04 | −2.42 |
| CD86 | −2.93 | −2.53 | −0.39 | −2.78 | −0.68 | −2.91 | −1.37 | −0 | −2.98 | −0.43 | −2.32 | −1.09 | −1.27 |
| CXCL10 | −2.92 | −2.91 | −1.62 | −2.27 | −2.96 | −2.92 | −0.35 | −2.72 | −2.48 | 0.01 | −1.97 | −0 | −0.98 |
| CXCL9 | −2.76 | −2.93 | −2.93 | −2.93 | −2.91 | −2.93 | −1.94 | −2.9 | −1.66 | 0 | −0.03 | −0 | −0.02 |
| Therapy Score | −20.3 | −15.6 | −15.2 | −14.7 | −14 | −12.9 | −11.2 | −10.9 | −9.25 | −7.56 | −7.39 | −7.15 | −4.75 |

| | Response | | | | | | | | | | | | |
|---|---|---|---|---|---|---|---|---|---|---|---|---|---|
| ID NO: | NR 20 | NR 28 | NR 35 | NR 4 | NR 15 | NR 51 | R 52 | R 2 | R 58 | R 54 | R 66 | NR 32 | |
| TGFbeta level | 1.08 | −2.91 | 0 | 0 | 1.57 | −0 | 0.91 | 0.88 | 0.19 | −0.83 | −0.15 | 1.02 | |
| M1/M2 macrophage ratio | −0 | −0 | −0 | −0 | −0 | −0 | −0 | −0 | −0 | −0 | −0 | −0 | |
| T reg cell % | 0 | 0 | 0 | 0 | 0 | 0 | 0 | 0 | 0 | 0 | 0 | 0 | |
| MDSC number | 0 | 0 | 0 | 0 | 0 | 0 | 0 | 0 | 0 | 0 | 0 | 0 | |
| lymphocyte number | −0.87 | −0 | −0.01 | −0.51 | −0.01 | 0.08 | −0.09 | −1.48 | −0 | 0 | −0.01 | −0 | |
| ECOG performance score | 0 | 0 | 0 | 0 | 0 | 0 | 0 | 0 | 0 | 0 | 0 | 0 | |
| EGF level | 0 | 0 | 0 | 0 | 0 | 0 | 0 | 0 | 0 | 0 | 0 | 0 | |
| Cancer-Testis Antigens' Genes expression | 0 | 0 | 0 | 0 | 0 | 0 | 0 | 0 | 0 | 0 | 0 | 0 | |
| IFN-gamma-induced tumor cell apoptosis | 0 | 0 | 0 | 0 | 0 | 0 | 0 | 0 | 0 | 0 | 0 | 0 | |

TABLE 9-continued

Set of normalized biomarker values for each patient having a negative therapy score treated with anti-cancer vaccine therapy.

| | | | | | | | | | | | | | |
|---|---|---|---|---|---|---|---|---|---|---|---|---|---|
| IL-6 level | 0 | 0 | 0 | 0 | 0 | 0 | 0 | 0 | 0 | 0 | 0 | 0 |
| Mean Corpuscular Hemoglobin Concentration (MCHC) | 0 | 0 | 0 | 0 | 0 | 0 | 0 | 0 | 0 | 0 | 0 | 0 |
| Patient's age | 0 | 0 | 0 | 0 | 0 | 0 | 0 | 0 | 0 | 0 | 0 | 0 |
| Predictive gene signature in MAGE A3 antigen-specific cancer immunotherapy | 0 | 0 | 0 | 0 | 0 | 0 | 0 | 0 | 0 | 0 | 0 | 0 |
| TGFbeta1 level | 0 | 0 | 0 | 0 | 0 | 0 | 0 | 0 | 0 | 0 | 0 | 0 |
| CD16+CD56+CD69+ lymphocytes number | 0 | 0 | 0 | 0 | 0 | 0 | 0 | 0 | 0 | 0 | 0 | 0 |
| CD4+PD-1+ T cell number_1 | −1.08 | −0 | 0.01 | −0 | −0.44 | 0.64 | −1.78 | 0 | −0.92 | 0 | −2.52 | −1.73 |
| C-reactive protein level | 0 | 0 | 0 | 0 | 0 | 0 | 0 | 0 | 0 | 0 | 0 | 0 |
| Intratumoral versus peritumoral T cell density | −0.69 | −0.01 | −0.45 | −0.03 | −2.17 | 0.38 | −1.34 | −0.01 | −0 | −0.12 | −0 | 0 |
| Serum amyloid A level | 0 | 0 | 0 | 0 | 0 | 0 | 0 | 0 | 0 | 0 | 0 | 0 |
| Toll-like receptor 4 gene polymorphism | 0 | 0 | 0 | 0 | 0 | 0 | 0 | 0 | 0 | 0 | 0 | 0 |
| Syndecan-4 mRNA expression level | 0 | 0 | 0 | 0 | 0 | 0 | 0 | 0 | 0 | 0 | 0 | 0 |
| WT1 expression | 0 | 0 | 0 | 0 | 0 | 0 | 0 | 0 | 0 | 0 | 0 | 0 |
| Serum S100B concentration | 0 | 0 | 0 | 0 | 0 | 0 | 0 | 0 | 0 | 0 | 0 | 0 |
| LDH level | 0 | 0 | 0 | 0 | 0 | 0 | 0 | 0 | 0 | 0 | 0 | 0 |
| I/II high-grade or III T1/2/3a low-grade disease_intermediate risk | 0 | 0 | 0 | 0 | 0 | 0 | 0 | 0 | 0 | 0 | 0 | 0 |
| lymphocytes in PBMC % | −0.29 | −0 | −0 | −0.17 | −0 | 0.03 | −0.03 | −0.49 | −0 | 0 | −0 | −0 |
| PTEN loss | −0.52 | 0 | −0.49 | 0.69 | 0.01 | −0 | 0.38 | 0.86 | −0.89 | −0.01 | −0.95 | −0 |
| CD4+CD45RO+ cell number | 0 | 0 | 0 | 0 | 0 | 0 | 0 | 0 | 0 | 0 | 0 | 0 |
| Number of CD27− CD45RA+ and CD27− CD45RA− and CD27+CD45RA− T-cells | 0 | 0 | 0 | 0 | 0 | 0 | 0 | 0 | 0 | 0 | 0 | 0 |
| CD4+CTLA-4+ T cell number | 0 | 0 | 0 | 0 | 0 | 0 | 0 | 0 | 0 | 0 | 0 | 0 |
| CD4+PD-1+ T cell number_1 | 0 | 0 | 0 | 0 | 0 | 0 | 0 | 0 | 0 | 0 | 0 | 0 |
| IgM for Blood Group A trisaccharide level | 0 | 0 | 0 | 0 | 0 | 0 | 0 | 0 | 0 | 0 | 0 | 0 |
| Lin-CD14+HLA-DR-/lo MDSC level | 0 | 0 | 0 | 0 | 0 | 0 | 0 | 0 | 0 | 0 | 0 | 0 |
| B2M | 0 | −0 | 0.04 | 0 | 0 | −2.94 | 0.53 | −0.93 | 0.15 | 0.01 | 1.33 | 0.21 |
| CD86 | −0.11 | −0.6 | −2.18 | −0.34 | 0 | −0.25 | −0 | −0.04 | 0.03 | −0 | −0 | 0 |
| CXCL10 | −0.12 | −0 | −0.07 | −1.92 | −0 | 0 | 0 | −0.08 | 0.14 | 0 | 1.61 | 0.03 |
| CXCL9 | −1.05 | 0 | −0.08 | −0.35 | −0.8 | 0.26 | −0.01 | −0 | 0.01 | −0 | 0.23 | 0.06 |
| Therapy Score | −3.65 | −3.52 | −3.23 | −2.63 | −1.84 | −1.81 | −1.43 | −1.31 | −1.3 | −0.95 | −0.46 | −0.42 |

Abbreviations; PR—partial response, SD—stable disease, CR—complete response, and CPD—clinical progressive disease.

TABLE 10

Set of normalized biomarker values for each patient having a positive therapy score treated with anti-cancer vaccine therapy.

| | Response | | | | | | | | | | | | | | | |
|---|---|---|---|---|---|---|---|---|---|---|---|---|---|---|---|---|
| ID NO: | NR 29 | NR 8 | R 55 | R 63 | R 59 | NR 11 | NR 12 | R 62 | NR 7 | NR 18 | R 45 | NR 13 | NR 31 | R 49 | R 64 | NR 23 |
| TGFbeta level | 0.01 | 0 | 0.01 | −1.7 | 0.04 | 1.42 | −1.57 | 1.25 | 0.53 | −0.27 | −0.45 | −0.12 | 1.42 | −0.04 | 0.38 | −2.69 |
| M1/M2 macrophage ratio | −0 | −0 | −0 | −0 | −0 | −0 | −0 | −0 | −0 | −0 | −0 | −0 | −0 | −0 | −0 | −0 |
| T reg cell % | 0 | 0 | 0 | 0 | 0 | 0 | 0 | 0 | 0 | 0 | 0 | 0 | 0 | 0 | 0 | 0 |
| MDSC number | 0 | 0 | 0 | 0 | 0 | 0 | 0 | 0 | 0 | 0 | 0 | 0 | 0 | 0 | 0 | 0 |
| lymphocyte number | 0.06 | 0.29 | 0.16 | −0 | 0.31 | −0 | 0 | 0.93 | −0 | 0.06 | 0.21 | 0.12 | 0.11 | 0 | 0.41 | 0 | 0.22 |
| ECOG performance score | 0 | 0 | 0 | 0 | 0 | 0 | 0 | 0 | 0 | 0 | 0 | 0 | 0 | 0 | 0 | 0 |
| EGF level | 0 | 0 | 0 | 0 | 0 | 0 | 0 | 0 | 0 | 0 | 0 | 0 | 0 | 0 | 0 | 0 |
| Cancer-Testis Antigens' Genes expression | 0 | 0 | 0 | 0 | 0 | 0 | 0 | 0 | 0 | 0 | 0 | 0 | 0 | 0 | 0 | 0 |
| IFN-gamma-induced tumor cell apoptosis | 0 | 0 | 0 | 0 | 0 | 0 | 0 | 0 | 0 | 0 | 0 | 0 | 0 | 0 | 0 | 0 |

TABLE 10-continued

Set of normalized biomarker values for each patient having a positive therapy score treated with anti-cancer vaccine therapy.

| | | | | | | | | | | | | | | | | |
|---|---|---|---|---|---|---|---|---|---|---|---|---|---|---|---|---|
| IL-6 level | 0 | 0 | 0 | 0 | 0 | 0 | 0 | 0 | 0 | 0 | 0 | 0 | 0 | 0 | 0 | 0 |
| Mean Corpuscular Hemoglobin Concentration (MCHC) | 0 | 0 | 0 | 0 | 0 | 0 | 0 | 0 | 0 | 0 | 0 | 0 | 0 | 0 | 0 | 0 |
| Patient's age | 0 | 0 | 0 | 0 | 0 | 0 | 0 | 0 | 0 | 0 | 0 | 0 | 0 | 0 | 0 | 0 |
| Predictive gene signature in MAGE A3 antigen-specific cancer immunotherapy | 0 | 0 | 0 | 0 | 0 | 0 | 0 | 0 | 0 | 0 | 0 | 0 | 0 | 0 | 0 | 0 |
| TGFbeta1 level | 0 | 0 | 0 | 0 | 0 | 0 | 0 | 0 | 0 | 0 | 0 | 0 | 0 | 0 | 0 | 0 |
| CD16+CD56+CD69+ lymphocytes number | 0 | 0 | 0 | 0 | 0 | 0 | 0 | 0 | 0 | 0 | 0 | 0 | 0 | 0 | 0 | 0 |
| CD4+PD-1+ T cell number_1 | 0 | −0.06 | −0.38 | −0.3 | 0 | −0.7 | 0.02 | −0.04 | −1.09 | 2.07 | 2.77 | −0.19 | 1.64 | −0 | −0.66 | −0.01 |
| C-reactive protein level | 0 | 0 | 0 | 0 | 0 | 0 | 0 | 0 | 0 | 0 | 0 | 0 | 0 | 0 | 0 | 0 |
| Intratumoral versus peritumoral T cell density | −0 | 1.84 | 0 | 0 | 0 | 0.23 | 0 | −0 | 0.04 | 0.01 | 0.15 | 0 | −0 | 0.11 | 0.46 | 0.86 |
| Serum amyloid A level | 0 | 0 | 0 | 0 | 0 | 0 | 0 | 0 | 0 | 0 | 0 | 0 | 0 | 0 | 0 | 0 |
| Toll-like receptor 4 gene polymorphism | 0 | 0 | 0 | 0 | 0 | 0 | 0 | 0 | 0 | 0 | 0 | 0 | 0 | 0 | 0 | 0 |
| Syndecan-4 mRNA expression level | 0 | 0 | 0 | 0 | 0 | 0 | 0 | 0 | 0 | 0 | 0 | 0 | 0 | 0 | 0 | 0 |
| WT1 expression | 0 | 0 | 0 | 0 | 0 | 0 | 0 | 0 | 0 | 0 | 0 | 0 | 0 | 0 | 0 | 0 |
| Serum S100B concentration | 0 | 0 | 0 | 0 | 0 | 0 | 0 | 0 | 0 | 0 | 0 | 0 | 0 | 0 | 0 | 0 |
| LDH level | 0 | 0 | 0 | 0 | 0 | 0 | 0 | 0 | 0 | 0 | 0 | 0 | 0 | 0 | 0 | 0 |
| I/II high-grade or III T1/2/3a low-grade disease_intermediate risk | 0 | 0 | 0 | 0 | 0 | 0 | 0 | 0 | 0 | 0 | 0 | 0 | 0 | 0 | 0 | 0 |
| lymphocytes in PBMC % | 0.02 | 0.1 | 0.05 | −0 | 0.1 | −0 | 0.31 | −0 | 0.02 | 0.07 | 0.04 | 0.04 | 0 | 0.14 | 0 | 0.07 |
| PTEN loss | 0 | 0 | 0 | −0.57 | −0 | 0.45 | −0 | 0 | −0.29 | −0.08 | 0.02 | −0.01 | −0.02 | 0 | −0 | 0.42 |
| CD4+CD45RO+ cell number | 0 | 0 | 0 | 0 | 0 | 0 | 0 | 0 | 0 | 0 | 0 | 0 | 0 | 0 | 0 | 0 |
| Number of CD27−CD45RA+ and CD27−CD45RA− and CD27+CD45RA− T-cells | 0 | 0 | 0 | 0 | 0 | 0 | 0 | 0 | 0 | 0 | 0 | 0 | 0 | 0 | 0 | 0 |
| CD4+PD-1+ T cell number_1 | 0 | 0 | 0 | 0 | 0 | 0 | 0 | 0 | 0 | 0 | 0 | 0 | 0 | 0 | 0 | 0 |
| IgM for Blood Group A trisaccharide level | 0 | 0 | 0 | 0 | 0 | 0 | 0 | 0 | 0 | 0 | 0 | 0 | 0 | 0 | 0 | 0 |
| Lin-CD14+HLA-DR-/lo MDSC level | 0 | 0 | 0 | 0 | 0 | 0 | 0 | 0 | 0 | 0 | 0 | 0 | 0 | 0 | 0 | 0 |
| B2M | −0.01 | −2.93 | 0.01 | 0.5 | 0.31 | −1.13 | 0.02 | 0 | 0.69 | 0.19 | 0 | 0.05 | 0.02 | 0.66 | 1.74 | 0.83 |
| CD86 | −0.02 | 0.05 | 0.01 | 0.72 | 0 | 0.44 | 1.75 | 0.19 | −0 | 0.04 | 0.25 | 0.05 | 0.76 | 0 | 1.15 | 1.53 |
| CXCL10 | −0 | 0 | 0.44 | 1.82 | 0.01 | 0.03 | −0.25 | 0 | 1.13 | 0.28 | −0.01 | 1.75 | 0.05 | 2.09 | 1.65 | 2.32 |
| CXCL9 | −0.01 | 1.22 | 0.53 | 0.48 | 0.22 | 0.41 | −0 | −0 | 0.62 | 0.04 | 0 | 1.5 | 0 | 1.52 | 0.87 | 2.09 |
| Therapy Score | 0.05 | 0.5 | 0.83 | 0.95 | 1 | 1.17 | 1.21 | 1.39 | 1.7 | 2.55 | 2.87 | 3.16 | 3.87 | 4.88 | 5.59 | 5.64 |

| | Response | | | | | | | | | | | | | | | |
|---|---|---|---|---|---|---|---|---|---|---|---|---|---|---|---|---|
| ID NO: | NR 10 | R 61 | NR 16 | R 56 | R 48 | NR 24 | R 50 | R 46 | NR 6 | NR 9 | R 47 | R 57 | R 53 | R 60 | NR 30 | |
| TGFbeta level | 0 | 0.22 | 2 | −1.34 | −0.23 | 1.42 | 0.49 | −0 | −2.9 | −1.05 | 0.04 | 0.26 | −0 | 0.08 | −0 | |
| M1/M2 macrophage ratio | −0 | −0 | −0 | −0 | −0 | −0 | −0 | −0 | −0 | −0 | −0 | −0 | −0 | −0 | −0 | |
| T reg cell % | 0 | 0 | 0 | 0 | 0 | 0 | 0 | 0 | 0 | 0 | 0 | 0 | 0 | 0 | 0 | |
| MDSC number | 0 | 0 | 0 | 0 | 0 | 0 | 0 | 0 | 0 | 0 | 0 | 0 | 0 | 0 | 0 | |
| lymphocyte number | 2.37 | 1.58 | 0 | −0 | 2.99 | 2.87 | 1.64 | 0.01 | 0.12 | 2.74 | 0 | 2.96 | 2.92 | 2.63 | 2.68 | |
| ECOG performance score | 0 | 0 | 0 | 0 | 0 | 0 | 0 | 0 | 0 | 0 | 0 | 0 | 0 | 0 | 0 | |
| EGF level | 0 | 0 | 0 | 0 | 0 | 0 | 0 | 0 | 0 | 0 | 0 | 0 | 0 | 0 | 0 | |
| Cancer-Testis Antigens' Genes expression | 0 | 0 | 0 | 0 | 0 | 0 | 0 | 0 | 0 | 0 | 0 | 0 | 0 | 0 | 0 | |
| IFN-gamma-induced tumor cell apoptosis | 0 | 0 | 0 | 0 | 0 | 0 | 0 | 0 | 0 | 0 | 0 | 0 | 0 | 0 | 0 | |
| IL-6 level | 0 | 0 | 0 | 0 | 0 | 0 | 0 | 0 | 0 | 0 | 0 | 0 | 0 | 0 | 0 | |
| Mean Corpuscular Hemoglobin Concentration (MCHC) | 0 | 0 | 0 | 0 | 0 | 0 | 0 | 0 | 0 | 0 | 0 | 0 | 0 | 0 | 0 | |

TABLE 10-continued

Set of normalized biomarker values for each patient having a positive therapy score treated with anti-cancer vaccine therapy.

| | | | | | | | | | | | | | | | |
|---|---|---|---|---|---|---|---|---|---|---|---|---|---|---|---|
| Patient's age | 0 | 0 | 0 | 0 | 0 | 0 | 0 | 0 | 0 | 0 | 0 | 0 | 0 | 0 | 0 |
| Predictive gene signature in MAGE A3 antigen-specific cancer immunotherapy | 0 | 0 | 0 | 0 | 0 | 0 | 0 | 0 | 0 | 0 | 0 | 0 | 0 | 0 | 0 |
| TGFbeta1 level | 0 | 0 | 0 | 0 | 0 | 0 | 0 | 0 | 0 | 0 | 0 | 0 | 0 | 0 | 0 |
| CD16+CD56+CD69+ lymphocytes number | 0 | 0 | 0 | 0 | 0 | 0 | 0 | 0 | 0 | 0 | 0 | 0 | 0 | 0 | 0 |
| CD4+PD-1+ T cell number_1 | 2.7 | −0 | 0 | 0 | 3 | −0 | −1.39 | 0 | −0 | 2.99 | 2.62 | 2.8 | −2.52 | 0 | 3 |
| C-reactive protein level | 0 | 0 | 0 | 0 | 0 | 0 | 0 | 0 | 0 | 0 | 0 | 0 | 0 | 0 | 0 |
| Intratumoral versus peritumoral T cell density | 4.69 | 2.59 | 0.75 | 0.08 | 4.99 | 2.83 | 0.42 | 3.69 | 4.17 | 4.65 | 0 | 4.93 | 4.89 | 4.69 | 4.43 |
| Serum amyloid A level | 0 | 0 | 0 | 0 | 0 | 0 | 0 | 0 | 0 | 0 | 0 | 0 | 0 | 0 | 0 |
| Toll-like receptor 4 gene polymorphism | 0 | 0 | 0 | 0 | 0 | 0 | 0 | 0 | 0 | 0 | 0 | 0 | 0 | 0 | 0 |
| Syndecan-4 mRNA expression level | 0 | 0 | 0 | 0 | 0 | 0 | 0 | 0 | 0 | 0 | 0 | 0 | 0 | 0 | 0 |
| WT1 expression | 0 | 0 | 0 | 0 | 0 | 0 | 0 | 0 | 0 | 0 | 0 | 0 | 0 | 0 | 0 |
| Serum S100B concentration | 0 | 0 | 0 | 0 | 0 | 0 | 0 | 0 | 0 | 0 | 0 | 0 | 0 | 0 | 0 |
| LDH level | 0 | 0 | 0 | 0 | 0 | 0 | 0 | 0 | 0 | 0 | 0 | 0 | 0 | 0 | 0 |
| I/II high-grade or III T1/2/3a low-grade disease_intermediate risk | 0 | 0 | 0 | 0 | 0 | 0 | 0 | 0 | 0 | 0 | 0 | 0 | 0 | 0 | 0 |
| lymphocytes in PBMC % | 0.79 | 0.53 | 0 | −0 | 1 | 0.96 | 0.55 | 0 | 0.04 | 0.91 | 0 | 0.99 | 0.97 | 0.88 | 0.89 |
| PTEN loss | −0 | 0.66 | −0.08 | 0.99 | −0.83 | −0 | 0 | −0.41 | −0.02 | 0 | −0 | −0.65 | 0 | −0.02 | −0.36 |
| CD4+CD45RO+ cell number | 0 | 0 | 0 | 0 | 0 | 0 | 0 | 0 | 0 | 0 | 0 | 0 | 0 | 0 | 0 |
| Number of CD27− CD45RA+ and CD27− CD45RA− and CD27+CD45RA− T-cells | 0 | 0 | 0 | 0 | 0 | 0 | 0 | 0 | 0 | 0 | 0 | 0 | 0 | 0 | 0 |
| CD4+PD-1+ T cell number_1 | 0 | 0 | 0 | 0 | 0 | 0 | 0 | 0 | 0 | 0 | 0 | 0 | 0 | 0 | 0 |
| IgM for Blood Group A trisaccharide level | 0 | 0 | 0 | 0 | 0 | 0 | 0 | 0 | 0 | 0 | 0 | 0 | 0 | 0 | 0 |
| Lin-CD14+HLA-DR-/lo MDSC level | 0 | 0 | 0 | 0 | 0 | 0 | 0 | 0 | 0 | 0 | 0 | 0 | 0 | 0 | 0 |
| B2M | −3 | 0.15 | 1.36 | 2.61 | −2.95 | 0.02 | 2.61 | 1.78 | 2 | −2.38 | 2.12 | 0 | 1.29 | 2.27 | 0.02 |
| CD86 | −0.03 | 0 | 0.41 | 1.28 | 0.55 | 1.36 | 2.04 | 2.27 | 2.53 | 2.7 | 2.35 | 1.79 | 2.84 | 2.2 | 2.89 |
| CXCL10 | −0.81 | 0.13 | 1.63 | 2.78 | −0 | 0.03 | 2.26 | 2.38 | 2.57 | 0.16 | 2.51 | −0 | 2.08 | 2.24 | 2.76 |
| CXCL9 | 0 | 0.98 | 1.85 | 1.66 | 0.19 | 0.04 | 2.02 | 1.04 | 2.26 | 1.25 | 2.37 | 0.02 | 2.27 | 2.02 | 2.18 |
| Therapy Score | 6.71 | 6.85 | 7.92 | 8.06 | 8.71 | 9.52 | 10.6 | 10.8 | 10.8 | 12 | 12 | 13.1 | 14.7 | 17 | 18.5 |

Abbreviations; PR—partial response, SD—stable disease, CR—complete response, and CPD—clinical progressive disease.

TABLE 11

Set of normalized biomarker values for each patient treated with anti-angiogenic therapy.

| Patient ID GSM14718 | 39 | 86 | 53 | 58 | 75 | 42 | 82 | 71 | 47 |
|---|---|---|---|---|---|---|---|---|---|
| Response: | NR | NR | NR | NR | R | R | NR | R | R |
| Timepoint: | PT | PT | PT | PT | PT | PT | PT | PT | PT |
| Number of resting circulating endothelial cells | 0.000162 | −1.97328 | −0.00283 | −1.3E−06 | −0.67291 | −0.97508 | −0.68776 | −0.00018 | 0.533442 |
| Number of total circulating endothelial cells | 0 | 0 | 0 | 0 | 0 | 0 | 0 | 0 | 0 |
| Expression of PDGFR-beta | −2.97683 | −0.00033 | −0.00618 | −0.69032 | −0.001726 | 0.000607 | 0.004197 | −1.2847 | −0.18186 |
| Expression of CD31 | 0 | 0.570456 | 0.000747 | 1.482181 | 0 | 2.460252 | 1.408502 | 0.000326 | 0 |
| CDC16 level | −9.4E−07 | −0.11814 | −1.60473 | 1.244301 | −0.09602 | 3.4E−05 | −1.0432 | −0.02895 | −1.6E−07 |
| Lck and Fyn tyrosine kinases in initiation of TCR Activation pathway activation | −0.96874 | 0.730858 | −0.38819 | −0.14019 | 1.06E−06 | −0.18482 | 1.58E−05 | 0.00172 | 0.002242 |

TABLE 11-continued

Set of normalized biomarker values for each patient treated with anti-angiogenic therapy.

| | | | | | | | | | |
|---|---|---|---|---|---|---|---|---|---|
| T Cell Receptor Signaling Pathway activation | 0 | 0 | 0 | 0 | 0 | 0 | 0 | 0 | 0 |
| T Helper Cell Surface Molecules expression | 0 | 0 | 0 | 0 | 0 | 0 | 0 | 0 | 0 |
| NO2-dependent IL 12 Pathway activation in NK cells | 0 | 0 | 0 | 0 | 0 | 0 | 0 | 0 | 0 |
| Bioactive Peptide Induced Signaling Pathway | 0 | 0 | 0 | 0 | 0 | 0 | 0 | 0 | 0 |
| sVEGFR1 | −2.99459 | −0.2038 | 1.932855 | 0.000431 | −0.01157 | −0.33766 | −2.89576 | 1.5E−08 | 0.310332 |
| CD133 expression | 0 | 0 | 0 | 0 | 0 | 0 | 0 | 0 | 0 |
| rs2286455 | 0 | 0 | 0 | 0 | 0 | 0 | 0 | 0 | 0 |
| rs3130 | 0 | 0 | 0 | 0 | 0 | 0 | 0 | 0 | 0 |
| IL-6 plasma level | 0 | 0 | 0 | 0 | 0 | 0 | 0 | 0 | 0 |
| IL-8 plasma level | 0 | 0 | 0 | 0 | 0 | 0 | 0 | 0 | 0 |
| Child-Pugh class | 0 | 0 | 0 | 0 | 0 | 0 | 0 | 0 | 0 |
| HBV status | 0 | 0 | 0 | 0 | 0 | 0 | 0 | 0 | 0 |
| portal vein thrombosis | 0 | 0 | 0 | 0 | 0 | 0 | 0 | 0 | 0 |
| Sex | 0 | 0 | 0 | 0 | 0 | 0 | 0 | 0 | 0 |
| History of alcohol intake | 0 | 0 | 0 | 0 | 0 | 0 | 0 | 0 | 0 |
| Acneiform rash | 0 | 0 | 0 | 0 | 0 | 0 | 0 | 0 | 0 |
| angiopoietin-2 expression levels | −8.4E−11 | −0.81987 | −0.2002 | −2.53227 | 0.001005 | −2.10171 | −2.94843 | −0.12168 | 3.27E−06 |
| EGFR expression levels | −0.98928 | −0.34509 | 1.07E−06 | −0.00033 | 0.045048 | 0.098944 | 0.934068 | 0.009977 | 0.068077 |
| Endothelin-1 expression levels | 0.754617 | −4.3E−08 | −0.02217 | −0.73196 | 0.198087 | −0.00242 | −0.03232 | 0.002418 | 0.170778 |
| angiopoietin-2 expression levels | 0 | 0 | 0 | 0 | 0 | 0 | 0 | 0 | 0 |
| IL-12 plasma level | 0 | 0 | 0 | 0 | 0 | 0 | 0 | 0 | 0 |
| HGF plasma level | 0 | 0 | 0 | 0 | 0 | 0 | 0 | 0 | 0 |
| IL-16 plasma level | 0 | 0 | 0 | 0 | 0 | 0 | 0 | 0 | 0 |
| CXCL10 plasma level | 0 | 0 | 0 | 0 | 0 | 0 | 0 | 0 | 0 |
| SDF-1α plasma level | 0 | 0 | 0 | 0 | 0 | 0 | 0 | 0 | 0 |
| IL-2Rα plasma level | 0 | 0 | 0 | 0 | 0 | 0 | 0 | 0 | 0 |
| IL-3 plasma level | 0 | 0 | 0 | 0 | 0 | 0 | 0 | 0 | 0 |
| IFN-α2 plasma level | 0 | 0 | 0 | 0 | 0 | 0 | 0 | 0 | 0 |
| TRAIL plasma level | 0 | 0 | 0 | 0 | 0 | 0 | 0 | 0 | 0 |
| M-CSF plasma level | 0 | 0 | 0 | 0 | 0 | 0 | 0 | 0 | 0 |
| PlGF plasma level | 0 | 0 | 0 | 0 | 0 | 0 | 0 | 0 | 0 |
| mucinous histology | 0 | 0 | 0 | 0 | 0 | 0 | 0 | 0 | 0 |
| VEGF -1498 C>T | 0 | 0 | 0 | 0 | 0 | 0 | 0 | 0 | 0 |
| Liver metastasis | 0 | 0 | 0 | 0 | 0 | 0 | 0 | 0 | 0 |
| ECOG Performance Status | 0 | 0 | 0 | 0 | 0 | 0 | 0 | 0 | 0 |
| VEGF -1154 A>G | 0 | 0 | 0 | 0 | 0 | 0 | 0 | 0 | 0 |
| VEGF G-634C | 0 | 0 | 0 | 0 | 0 | 0 | 0 | 0 | 0 |
| ICAM1 T469C | 0 | 0 | 0 | 0 | 0 | 0 | 0 | 0 | 0 |
| WNK1-rs11064560 | 0 | 0 | 0 | 0 | 0 | 0 | 0 | 0 | 0 |
| EGF A-61G | 0 | 0 | 0 | 0 | 0 | 0 | 0 | 0 | 0 |
| CXCR2 C785T | 0 | 0 | 0 | 0 | 0 | 0 | 0 | 0 | 0 |
| VEGF-1154 G/A | 0 | 0 | 0 | 0 | 0 | 0 | 0 | 0 | 0 |
| VEGF-2578 C/A | 0 | 0 | 0 | 0 | 0 | 0 | 0 | 0 | 0 |
| rs699946 in VEGFA | 0 | 0 | 0 | 0 | 0 | 0 | 0 | 0 | 0 |
| rs12505758 in VEGFR2 | 0 | 0 | 0 | 0 | 0 | 0 | 0 | 0 | 0 |

TABLE 11-continued

Set of normalized biomarker values for each patient treated with anti-angiogenic therapy.

| | | | | | | | | | |
|---|---|---|---|---|---|---|---|---|---|
| VEGFR1 rs9582036 | 0 | 0 | 0 | 0 | 0 | 0 | 0 | 0 | 0 |
| EGF rs444903 A>G | 0 | 0 | 0 | 0 | 0 | 0 | 0 | 0 | 0 |
| IGF-1 rs6220 A>G | 0 | 0 | 0 | 0 | 0 | 0 | 0 | 0 | 0 |
| CXCR1 rs2234671 G>C | 0 | 0 | 0 | 0 | 0 | 0 | 0 | 0 | 0 |
| CXCR2 rs2230054 T>C | 0 | 0 | 0 | 0 | 0 | 0 | 0 | 0 | 0 |
| EGFR rs2227983 G>A | 0 | 0 | 0 | 0 | 0 | 0 | 0 | 0 | 0 |
| VEGFR-2 rs2305948 C>T | 0 | 0 | 0 | 0 | 0 | 0 | 0 | 0 | 0 |
| IL-8 251 T>A | 0 | 0 | 0 | 0 | 0 | 0 | 0 | 0 | 0 |
| CXCR2 C785T | 0 | 0 | 0 | 0 | 6 | 0 | 0 | 0 | 0 |
| VEGF C936T | 0 | 0 | 0 | 0 | 0 | 0 | 0 | 0 | 0 |
| Adrenomedullin Repeat Polymorphism | 0 | 0 | 0 | 0 | 0 | 0 | 0 | 0 | 0 |
| VEGFA | 0 | 0 | 0 | 0 | 0 | 0 | 2.259422 | 1.028465 | 1.81E−10 |
| ICAM1 | −0.27451 | 0.000147 | −1.3524 | −1.2E−09 | −0.35542 | −0.304107 | 2.516688 | −3.6E−12 | −0.9676 |
| Therapy Score | −7.44919 | −2.15904 | −1.64309 | −1.36816 | −0.89005 | −0.73775 | −0.48458 | −0.40637 | −0.06459 |

| Patient ID GSM14718 | 50 | 64 | 67 | 60 | 80 | 74 | 77 | 55 |
|---|---|---|---|---|---|---|---|---|
| Response: | NR | NR | NR | R | R | NR | R | R |
| Timepoint: | PT | PT | PT | PT | PT | PT | PT | PT |
| Number of resting circulating endothelial cells | −0.00749 | 0.873339 | −1.67907 | 0.143095 | −1.93425 | 1.318883 | −1.7134 | 1.698203 |
| Number of total circulating endothelial cells | 0 | 0 | 0 | 0 | 0 | 0 | 0 | 0 |
| Expression of PDGFR-beta | −0.38181 | 0.00909 | −0.26866 | −0.0735 | −4.8E−09 | 0.14841 | 1.195321 | 1.614482 |
| Expression of CD31 | 3.95E−05 | 0 | 3.95E−05 | 0 | 2.986855 | 0 | 0 | 2.741311 |
| CDC16 level | −0.04842 | −0.0615 | 1.26E−06 | 3.4E−05 | 0.850735 | 1.787078 | 0.080641 | 1.974031 |
| Lck and Fyn tyrosine kinases in initiation of TCR Activation pathway activation | 1.33E−09 | −3.5E−06 | 0.097905 | 2.49E−08 | 0.949367 | −0.4284 | 0.082804 | −0.98781 |
| T Cell Receptor Signaling Pathway activation | 0 | 0 | 0 | 0 | 0 | 0 | 0 | 0 |
| T Helper Cell Surface Molecules expression | 0 | 0 | 0 | 0 | 0 | 0 | 0 | 0 |
| NO2-dependent IL 12 Pathway activation in NK cells | 0 | 0 | 0 | 0 | 0 | 0 | 0 | 0 |
| Bioactive Peptide Induced Signaling Pathway | 0 | 0 | 0 | 0 | 0 | 0 | 0 | 0 |
| sVEGFR1 | 0.974816 | 0.592048 | 0.241733 | 1.68231 | −2.93689 | −2.7E−10 | −6.2E−08 | −0.0023 |
| CD133 expression | 0 | 0 | 0 | 0 | 0 | 0 | 0 | 0 |
| rs2286455 | 0 | 0 | 0 | 0 | 0 | 0 | 0 | 0 |
| rs3130 | 0 | 0 | 0 | 0 | 0 | 0 | 0 | 0 |
| IL-6 plasma level | 0 | 0 | 0 | 0 | 0 | 0 | 0 | 0 |
| IL-8 plasma level | 0 | 0 | 0 | 0 | 0 | 0 | 0 | 0 |
| Child-Pugh class | 0 | 0 | 0 | 0 | 0 | 0 | 0 | 0 |
| HBV status | 0 | 0 | 0 | 0 | 0 | 0 | 0 | 0 |
| portal vein thrombosis | 0 | 0 | 0 | 0 | 0 | 0 | 0 | 0 |
| Sex | 0 | 0 | 0 | 0 | 0 | 0 | 0 | 0 |
| History of alcohol intake | 0 | 0 | 0 | 0 | 0 | 0 | 0 | 0 |
| Acneiform rash | 0 | 0 | 0 | 0 | 0 | 0 | 0 | 0 |
| angiopoietin-2 expression levels | −0.24052 | 0.360074 | 1.61E−14 | 0.000457 | −0.42763 | 0.000343 | −0.00322 | −2.97733 |

TABLE 11-continued

Set of normalized biomarker values for each patient treated with anti-angiogenic therapy.

| | | | | | | | | |
|---|---|---|---|---|---|---|---|---|
| EGFR expression levels | 0.001253 | 0.515136 | −0.98413 | 0.017333 | 0.376318 | −0.27847 | −0.92899 | −0.08396 |
| Endothelin-1 expression levels | −2.7E−06 | 0.890757 | 0.707517 | 0.085635 | −0.39897 | 0.077677 | −0.99431 | −0.94965 |
| angiopoietin-2 expression levels | 0 | 0 | 0 | 0 | 0 | 0 | 0 | 0 |
| IL-12 plasma level | 0 | 0 | 0 | 0 | 0 | 0 | 0 | 0 |
| HGF plasma level | 0 | 0 | 0 | 0 | 0 | 0 | 0 | 0 |
| IL-16 plasma level | 0 | 0 | 0 | 0 | 0 | 0 | 0 | 0 |
| CXCL10 plasma level | 0 | 0 | 0 | 0 | 0 | 0 | 0 | 0 |
| SDF-1α plasma level | 0 | 0 | 0 | 0 | 0 | 0 | 0 | 0 |
| IL-2Rα plasma level | 0 | 0 | 0 | 0 | 0 | 0 | 0 | 0 |
| IL-3 plasma level | 0 | 0 | 0 | 0 | 0 | 0 | 0 | 0 |
| IFN-α2 plasma level | 0 | 0 | 0 | 0 | 0 | 0 | 0 | 0 |
| TRAIL plasma level | 0 | 0 | 0 | 0 | 0 | 0 | 0 | 0 |
| M-CSF plasma level | 0 | 0 | 0 | 0 | 0 | 0 | 0 | 0 |
| PIGF plasma level | 0 | 0 | 0 | 0 | 0 | 0 | 0 | 0 |
| mucinous histology | 0 | 0 | 0 | 0 | 0 | 0 | 0 | 0 |
| VEGF -1498 C>T | 0 | 0 | 0 | 0 | 0 | 0 | 0 | 0 |
| Liver metastasis | 0 | 0 | 0 | 0 | 0 | 0 | 0 | 0 |
| ECOG Performance Status | 0 | 0 | 0 | 0 | 0 | 0 | 0 | 0 |
| VEGF -1154 A>G | 0 | 0 | 0 | 0 | 0 | 0 | 0 | 0 |
| VEGF G-634C | 0 | 0 | 0 | 0 | 0 | 0 | 0 | 0 |
| ICAM1 T469C | 0 | 0 | 0 | 0 | 0 | 0 | 0 | 0 |
| WNK1-rs11064560 | 0 | 0 | 0 | 0 | 0 | 0 | 0 | 0 |
| EGF A-61G | 0 | 0 | 0 | 0 | 0 | 0 | 0 | 0 |
| CXCR2 C785T | 0 | 0 | 0 | 0 | 0 | 0 | 0 | 0 |
| VEGF-1154 G/A | 0 | 0 | 0 | 0 | 0 | 0 | 0 | 0 |
| VEGF-2578 C/A | 0 | 0 | 0 | 0 | 0 | 0 | 0 | 0 |
| rs699946 in VEGFA | 0 | 0 | 0 | 0 | 0 | 0 | 0 | 0 |
| rs12505758 in VEGFR2 | 0 | 0 | 0 | 0 | 0 | 0 | 0 | 0 |
| VEGFR1 rs9582036 | 0 | 0 | 0 | 0 | 0 | 0 | 0 | 0 |
| EGF rs444903 A>G | 0 | 0 | 0 | 0 | 0 | 0 | 0 | 0 |
| IGF-1 rs6220 A>G | 0 | 0 | 0 | 0 | 0 | 0 | 0 | 0 |
| CXCR1 rs2234671 G>C | 0 | 0 | 0 | 0 | 0 | 0 | 0 | 0 |
| CXCR2 rs2230054 T>C | 0 | 0 | 0 | 0 | 0 | 0 | 0 | 0 |
| EGFR rs2227983 G>A | 0 | 0 | 0 | 0 | 0 | 0 | 0 | 0 |
| VEGFR-2 rs2305948 C>T | 0 | 0 | 0 | 0 | 0 | 0 | 0 | 0 |
| IL-8 251 T>A | 0 | 0 | 0 | 0 | 0 | 0 | 0 | 0 |
| CXCR2 C785T | 0 | 0 | 0 | 0 | 0 | 0 | 0 | 0 |
| VEGF C936T | 0 | 0 | 0 | 0 | 0 | 0 | 0 | 0 |
| Adrenomedullin Repeat Polymorphism | 0 | 0 | 0 | 0 | 0 | 0 | 0 | 0 |
| VEGFA | 0 | 0.007774 | 0 | 0 | 4.64E−06 | 0.182942 | 2.982064 | 0 |
| ICAM1 | −0.00017 | −2.45837 | 2.727169 | −0.06574 | −2.997447 | 0.000147 | 2.144079 | −0.00516 |
| Therapy Score | 0.297699 | 0.728342 | 0.84251 | 1.789627 | 2.462987 | 2.808607 | 2.844987 | 3.021824 |

Abbreviations; NR—no response, PR—partial response, SD—stable disease, CR—complete response, and CPD—clinical progressive disease.

REFERENCES

Hugo et al., *Genomic and Transcriptomic Features of Response to Anti-PD-1 Therapy in Metastatic Melanoma.* Cell. 165, 35-44 (2016).

Van Allen et al., *Genomic Correlates of Response to CTLA-4 Blockade in Metastatic Melanoma.* Science. 350(6257): 302-22 (2015).

Illustrative Embodiments

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information, a normalized score for each biomarker in at least a subject subset of the plurality of biomarkers to obtain a set of normalized biomarker scores for the subject, wherein the subject subset of the plurality of biomarkers is a subset of the reference subset of the plurality of biomarkers; and determining, using the set of normalized biomarker scores for the subject, therapy scores for the plurality of therapies, each of the therapy scores indicative of predicted response of the subject to administration of a respective therapy in the plurality of therapies.

In one aspect provided herein is at least one non-transitory computer-readable storage medium storing processor-executable instructions that, when executed by at least one computer hardware processor, cause the at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information, a normalized score for each biomarker in at least a subject subset of the plurality of biomarkers to obtain a set of normalized biomarker scores for the subject, wherein the subject subset of the plurality of biomarkers is a subset of the reference subset of the plurality of biomarkers; and determining, using the set of normalized biomarker scores for the subject, therapy scores for the plurality of therapies, each of the therapy scores indicative of predicted response of the subject to administration of a respective therapy in the plurality of therapies.

In one aspect provided herein is a method, comprising using at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information, a normalized score for each biomarker in at least a subject subset of the plurality of biomarkers to obtain a set of normalized biomarker scores for the subject, wherein the subject subset of the plurality of biomarkers is a subset of the reference subset of the plurality of biomarkers; and determining, using the set of normalized biomarker scores for the subject, therapy scores for the plurality of therapies, each of the therapy scores indicative of predicted response of the subject to administration of a respective therapy in the plurality of therapies.

In some embodiments, the plurality of biomarkers includes a first biomarker, and determining a normalized score for each biomarker in at least the subject subset of the plurality of biomarkers comprises: determining a first normalized score for the first biomarker using the distribution of values for the first biomarker. In some embodiments, determining the first normalized score comprises: determining a first un-normalized score for the first biomarker using the sequencing data; determining a first Z-score based on the first distribution of values for the first biomarker; and determining the first normalized score for the first biomarker based on the first un-normalized score and the first Z-score.

In some embodiments, determining therapy scores for the plurality of therapies comprises determining a first therapy score for a first therapy in the plurality of therapies as a sum of two or more scores in the set of normalized biomarker scores for the subject.

In some embodiments, determining therapy scores for the plurality of therapies comprises determining a first therapy score for a first therapy in the plurality of therapies at least in part by: determining weights for two or more scores in the set of normalized biomarker scores for the subject; and determining the first therapy score as a weighted sum of the two or more scores, summands of the sum being weighted by the determined weights.

In some embodiments, determining the weights comprises determining the weights using a statistical model. In some embodiments, determining the weights comprises determining the weights using a generalized linear model. In some embodiments, determining the weights comprises determining the weights using a logistic regression model.

In some embodiments, the plurality of therapies comprises a first therapy and a second therapy different from the first therapy, and wherein determining therapy scores for the plurality of therapies comprises: determining a first therapy score for the first therapy using a first subset of the set of normalized biomarker scores for the subject; and determining a second therapy score for the second therapy using a second subset of the set of normalized biomarker scores for the subject, wherein the second subset is different from the first subset.

Some embodiments include providing the determined therapy scores to a user. Some embodiments include ranking the plurality of therapies based on the determined therapy scores. Some embodiments include recommending at least one of the plurality of therapies for the subject based on the determined therapy scores.

In some embodiments, recommending the at least one of the plurality of therapies comprises: ranking the plurality of therapies based on the determined therapy scores; and recommending at least a threshold number of top-ranked therapies for the subject.

In some embodiments, the plurality of therapies comprises at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy.

In some embodiments, the plurality of biomarkers associated with the anti-PD1 therapy comprises at least three biomarkers selected from the group of biomarkers associated with anti-PD1 therapy in Table 2. In some embodiments, determining the normalized biomarker scores for the subject comprises determining a normalized score for each of at least three biomarkers selected from the group of biomarkers associated with anti-PD1 therapy in Table 2.

In some embodiments, the plurality of biomarkers associated with the anti-CTLA4 therapy comprises at least three biomarkers selected from the group of biomarkers associated with anti-CTLA4 therapy in Table 2. In some embodiments, determining the normalized biomarker scores for the subject comprises determining a normalized score for each of at least three biomarkers selected from the group of biomarkers associated with anti-CTLA4 therapy in Table 2.

In some embodiments, the plurality of biomarkers associated with the IL-2 therapy comprises at least three biomarkers selected from the group of biomarkers associated with IL-2 therapy in Table 2. In some embodiments, determining the normalized biomarker scores for the subject comprises determining a normalized score for each of at least three biomarkers selected from the group of biomarkers associated with IL-2 therapy in Table 2.

In some embodiments, the plurality of biomarkers associated with the IFN alpha therapy comprises at least three biomarkers selected from the group of biomarkers associated with IFN alpha therapy in Table 2. In some embodiments, determining the normalized biomarker scores for the subject comprises determining a normalized score for each of at least three biomarkers selected from the group of biomarkers associated with IFN alpha therapy in Table 2.

In some embodiments, the plurality of biomarkers associated with the anti-cancer vaccine therapy comprises at least three biomarkers selected from the group of biomarkers associated with anti-cancer vaccine therapy in Table 2. In some embodiments, determining the normalized biomarker scores for the subject comprises determining a normalized score for each of at least three biomarkers selected from the group of biomarkers associated with anti-cancer vaccine therapy in Table 2.

In some embodiments, the plurality of biomarkers associated with the anti-angiogenic therapy comprises at least three biomarkers selected from the group of biomarkers associated with anti-angiogenic therapy in Table 2. In some embodiments, determining the normalized biomarker scores for the subject comprises determining a normalized score for each of at least three biomarkers selected from the group of biomarkers associated with anti-angiogenic therapy in Table 2.

In some embodiments, the plurality of biomarkers associated with the anti-CD20 therapy comprises at least three biomarkers selected from the group of biomarkers associated with anti-CD20 therapy in Table 2. In some embodiments, determining the normalized biomarker scores for the subject comprises determining a normalized score for each of at least three biomarkers selected from the group of biomarkers associated with anti-CD20 therapy in Table 2. In some embodiments, the anti-CD20 therapy is rituximab.

Some embodiments further include generating a graphical user interface (GUI) comprising: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In some embodiments, the at least one visual characteristic comprises color of a GUI element and/or size of the GUI element.

In some embodiments, in response to receiving, via the GUI, a user selection of the first therapy, presenting, via the GUI, information about at least one biomarker with which at least one of the first plurality of GUI elements is associated.

In some embodiments, the first therapy is associated with a first therapy score and the second therapy is associated with a second therapy score, and wherein the first portion and the second portion are positioned, relative to one another in the GUI, based on relative magnitude of the first therapy score and the second therapy score.

In some embodiments, each of the plurality of biomarkers is selected from the group consisting of: a genetic biomarker, a cellular biomarker, a saccharide biomarker, a lipid biomarker, a heterocyclic biomarker, an elementary compound biomarker, an imaging biomarker, an anthropological biomarker, a personal habit biomarker, a disease-state biomarker, and an expression biomarker. In some embodiments, the one or more genetic biomarkers includes a gene or marker described in the description and/or the figures.

In some embodiments, one or more genetic biomarkers are selected from the group consisting of: interferons, cytotoxic proteins, enzymes, cell adhesion proteins, extracellular matrix proteins and polysaccharides, cell growth factors, cell differentiation factors, transcription factors, and intracellular signaling proteins. In some embodiments, the one or more genetic biomarkers is selected from the group consisting of: a cytokine, a chemokine, a chemokine receptor, and an interleukin. In some embodiments, the value of one or more cellular biomarkers is determined through analysis of the number of one or more types of cells or the percentage of one or more types of cells within the biological sample. In some embodiments, the one or more types of cells are selected from the group consisting of malignant cancerous cells, leukocytes, lymphocytes, stromal cells, vascular endothelial cells, vascular pericytes, and myeloid-derived suppressor cells (MDSCs). In some embodiments, the value of one or more expression biomarkers is determined through analysis of the expression level or enzymatic activity of the nucleic acid or protein of the expression biomarker.

In some embodiments, the sequencing data is one or more of: DNA sequencing data, RNA sequencing data, or proteome sequencing data. In some embodiments, the sequencing data is obtained using one or more of the following techniques: whole genome sequencing (WGS), whole exome sequencing (WES), whole transcriptome sequencing, mRNA sequencing, DNA/RNA-hybridization, microarray, DNA/RNA chip, PCR, and single nucleotide polymorphism (SNP) genotyping.

In some embodiments each of the at least one biological samples is a bodily fluid, a cell sample, a liquid biopsy, or a tissue biopsy. In some embodiments, the tissue biopsy comprises one or more samples from one or more tumors or tissues known or suspected of having cancerous cells.

In some embodiments, the biomarker information also comprises results from one or more of the following types of analyses: blood analysis, cytometry analysis, histological analysis, immunohistological analysis, and patient history analysis.

In some embodiments, each of the therapies are selected from the group consisting of: surgery, radiation therapy, chemotherapy, immunotherapy, viral therapy, targeted therapy, hormone therapy, transplants, phototherapy, cryotherapy, and hyperthermia. In some embodiments, each of the therapies are selected from immunotherapy and targeted therapy.

In some embodiments, the therapy scores are indicative of response of the subject to administration of one therapy in the plurality of therapies. In some embodiments, the therapy scores are indicative of predicted response of the subject to administration of multiple therapies in the plurality of therapies.

In one aspect provided herein is a system comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining first sequencing data about at least one biological sample of a subject prior to administration of a candidate therapy; obtaining second sequencing data about at least one other biological sample of the subject subsequent to administration of the candidate therapy; accessing, in the at least one database, biomarker information indicating a distribution of values for each biomarker, across a respective group of people, in at least a reference subset of a plurality of biomarkers; determining, using the first and second sequencing data and the biomarker information, a first set of normalized biomarker scores for the subject and a second set of normalized biomarker scores for the subject; and determining, using the first and second sets of normalized biomarker scores for the subject, an impact score for the candidate therapy, wherein the impact score is indicative of response of the subject to administration of the candidate therapy.

In one aspect provided herein is at least one non-transitory computer-readable storage medium storing processor-executable instructions that, when executed by at least one computer hardware processor, cause the at least one computer hardware processor to perform: obtaining first sequencing data about at least one biological sample of a subject prior to administration of a candidate therapy; obtaining second sequencing data about at least one other biological sample of the subject subsequent to administration of the candidate therapy; accessing, in at least one database, biomarker information indicating a distribution of values for each biomarker, across a respective group of people, in at least a reference subset of a plurality of biomarkers; determining, using the first and second sequencing data and the biomarker information, a first set of normalized biomarker scores for the subject and a second set of normalized biomarker scores for the subject; and determining, using the first and second sets of normalized biomarker scores for the subject, an impact score for the candidate therapy, wherein the impact score is indicative of response of the subject to administration of the candidate therapy.

In one aspect provided herein is a method, comprising: using at least one computer hardware processor to perform: obtaining first sequencing data about at least one biological sample of a subject prior to administration of a candidate therapy; obtaining second sequencing data about at least one other biological sample of the subject subsequent to administration of the candidate therapy; accessing, in at least one database, biomarker information indicating a distribution of values for each biomarker, across a respective group of people, in at least a reference subset of a plurality of biomarkers; determining, using the first and second sequencing data and the biomarker information, a first set of normalized biomarker scores for the subject and a second set of normalized biomarker scores for the subject; and determining, using the first and second sets of normalized biomarker scores for the subject, an impact score for the candidate therapy, wherein the impact score is indicative of response of the subject to administration of the candidate therapy.

In some embodiments, determining the impact score for the candidate therapy further comprises: determining, using the first and second sets of normalized biomarker scores, a difference score for each biomarker in at least a subject subset of the plurality of biomarkers to obtain a set of biomarker difference scores for the subject; and determining, using the set of biomarker difference scores, the impact score for the candidate therapy.

In some embodiments, determining the impact score for the candidate therapy further comprises: determining, using the first and second sets of normalized biomarker scores, a first and second subject subset score for the subject subset of the plurality of biomarkers determining a subject subset difference score, wherein the subject subset difference score is determined using the first and second subject subset score; and determining, using the subject subset difference score, the impact score for the candidate therapy.

In some embodiments, the candidate therapy is selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy.

In some embodiments, the plurality of biomarkers associated with the anti-PD1 therapy comprises at least three biomarkers selected from the group of biomarkers associated with anti-PD1 therapy in Table 2.

In some embodiments, determining the biomarker difference scores for the subject comprises determining a difference score for each of at least three biomarkers selected from the group of biomarkers associated with anti-PD1 therapy in Table 2.

In some embodiments, determining the subject subset difference score for the subject comprises determining a first and second subject subset score for at least three biomarkers selected from the group of biomarkers associated with anti-PD1 therapy in Table 2.

In some embodiments, the plurality of biomarkers associated with the anti-CTLA4 therapy comprises at least three biomarkers selected from the group of biomarkers associated with anti-CTLA4 therapy in Table 2. In some embodiments, determining the biomarker difference scores for the subject comprises determining a difference score for each of at least three biomarkers selected from the group of biomarkers associated with anti-CTLA4 therapy in Table 2. In some embodiments, determining the subject subset difference score for the subject comprises determining a first and second subject subset score for at least three biomarkers selected from the group of biomarkers associated with anti-CTLA4 therapy in Table 2.

In some embodiments, the plurality of biomarkers associated with the IL-2 therapy comprises at least three biomarkers selected from the group of biomarkers associated with IL-2 therapy in Table 2. In some embodiments, determining the biomarker difference scores for the subject comprises determining a difference score for each of at least three biomarkers selected from the group of biomarkers associated with IL-2 therapy in Table 2. In some embodiments, determining the subject subset difference score for the subject comprises determining a first and second subject subset score for at least three biomarkers selected from the group of biomarkers associated with IL-2 therapy in Table 2.

In some embodiments, the plurality of biomarkers associated with the IFN alpha therapy comprises at least three biomarkers selected from the group of biomarkers associated with IFN alpha therapy in Table 2. In some embodiments, determining the biomarker difference scores for the subject comprises determining a difference score for each of at least three biomarkers selected from the group of biomarkers associated with IFN alpha therapy in Table 2. In some embodiments, determining the subject subset difference score for the subject comprises determining a first and second subject subset score for at least three biomarkers selected from the group of biomarkers associated with IFN alpha therapy in Table 2.

In some embodiments, the plurality of biomarkers associated with the anti-cancer vaccine therapy comprises at least three biomarkers selected from the group of biomarkers associated with anti-cancer vaccine therapy in Table 2. In some embodiments, determining the biomarker difference scores for the subject comprises determining a difference score for each of at least three biomarkers selected from the group of biomarkers associated with anti-cancer vaccine therapy in Table 2. In some embodiments, determining the subject subset difference score for the subject comprises determining a first and second subject subset score for at least three biomarkers selected from the group of biomarkers associated with anti-cancer vaccine therapy in Table 2.

In some embodiments, the plurality of biomarkers associated with the anti-angiogenic therapy comprises at least three biomarkers selected from the group of biomarkers associated with anti-angiogenic therapy in Table 2. In some embodiments, determining the biomarker difference scores for the subject comprises determining a difference score for each of at least three biomarkers selected from the group of biomarkers associated with anti-angiogenic therapy in Table 2. In some embodiments, determining the subject subset difference score for the subject comprises determining a first and second subject subset score for at least three biomarkers selected from the group of biomarkers associated with anti-angiogenic therapy in Table 2.

In some embodiments, the plurality of biomarkers associated with the anti-CD20 therapy comprises at least three biomarkers selected from the group of biomarkers associated with anti-CD20 therapy in Table 2. In some embodiments, wherein determining the biomarker difference scores for the subject comprises determining a difference score for at least three biomarkers selected from the group of biomarkers associated with anti-CD20 therapy in Table 2. In some embodiments, wherein determining the subject subset difference score for the subject comprises determining a first and second subject subset score for at least three biomarkers selected from the group of biomarkers associated with anti-CD20 therapy in Table 2. In some embodiments, the anti-CD20 therapy is rituximab.

Some embodiments include generating a graphical user interface (GUI) comprising a first portion associated with the candidate therapy, the first portion including a first plurality of GUI elements, each of the first plurality of GUI elements being associated with a respective biomarker in the plurality of biomarkers and having at least one visual characteristic determined based on a difference score of the respective biomarker; and displaying the generated GUI.

Some embodiments include generating a graphical user interface (GUI) comprising: a first portion associated with the candidate therapy, the first portion including a first plurality of GUI elements, each of the first plurality of GUI elements being associated with a respective biomarker in the plurality of biomarkers and having at least one visual characteristic determined based on a subject subset difference score; and displaying the generated GUI. In some embodiments, the at least one visual characteristic comprises color of a GUI element and/or size of the GUI element. Some embodiments include, in response to receiving, via the GUI, a user selection of the candidate therapy, presenting, via the GUI, information about at least one biomarker with which at least one of the first plurality of GUI elements is associated.

In some embodiments, determining the difference score for each biomarker in at least the subject subset comprises: determining a first normalized score for a first biomarker using the first sequencing data; determining a second normalized score for the first biomarker using the second sequencing data; and determining a first difference score based on a difference between the first and second normalized scores.

In some embodiments, determining the difference score for each biomarker in at least the subject subset comprises: determining a first subject subset score for at least three biomarkers using the first sequencing data; determining a second subject subset score for at least three biomarkers using the second sequencing data; and determining a first subject subset difference score based on a difference between the first and second subject subset scores.

In some embodiments, the biomarker information includes a first distribution of values for the first biomarker across a first group of people, and wherein determining the first normalized score comprises: determining a first un-normalized score for the first biomarker using the first sequencing data; determining a first Z-score based on the first distribution of values for the first biomarker; and determining the first normalized score for the first biomarker based on the first un-normalized score and the first Z-score.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information: a first set of normalized scores for a first set of biomarkers associated with a first therapy in the plurality of therapies; and a second set of normalized scores for a second set of biomarkers associated with a second therapy in the plurality of therapies, wherein the first set of biomarkers is different from the second set of biomarkers; providing the first set of normalized scores as input to a statistical model to obtain a first therapy score for the first therapy; providing the second set of normalized scores as input to the statistical model to obtain a second therapy score for the second therapy; generating a graphical user interface (GUI), wherein the GUI comprises: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In one aspect provided herein is at least one non-transitory computer-readable storage medium storing processor-executable instructions that, when executed by the at least one computer hardware processor, cause the at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information: a first set of normalized scores for a first set of biomarkers associated with a first therapy in the plurality of therapies; and a second set of normalized scores for a second set of biomarkers associated with a second therapy in the plurality of therapies, wherein the first set of biomarkers is different from the second set of biomarkers; providing the first set of normalized scores as input to a statistical model to obtain a first therapy score for the first therapy; providing the second set of normalized scores as input to the statistical model to obtain a second therapy score for the second therapy; generating a graphical user interface (GUI), wherein the GUI comprises: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In one aspect provided herein is a method, comprising using the at least one computer hardware processor to perform: obtaining sequencing data about at least one biological sample of a subject; accessing, in at least one database, biomarker information indicating a distribution of values for each biomarker in at least a reference subset of a plurality of biomarkers across a respective group of people, each of the plurality of biomarkers being associated with at least one therapy in a plurality of therapies; determining, using the sequencing data and the biomarker information: a first set of normalized scores for a first set of biomarkers associated with a first therapy in the plurality of therapies; and a second set of normalized scores for a second set of biomarkers associated with a second therapy in the plurality of therapies, wherein the first set of biomarkers is different from the second set of biomarkers; providing the first set of normalized scores as input to a statistical model to obtain a first therapy score for the first therapy; providing the second set of normalized scores as input to the statistical model to obtain a second therapy score for the second therapy; generating a graphical user interface (GUI), wherein the GUI comprises: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In some embodiments, the plurality of biomarkers includes a first biomarker, and wherein determining a normalized score for each biomarker in at least the subject subset of the plurality of biomarkers comprises: determining a first normalized score for the first biomarker using the distribution of values for the first biomarker. In some embodiments, determining the first normalized score comprises: determining an un-normalized score for the first biomarker using the sequencing data; determining a Z-score based on the first distribution of values for the first biomarker; and determining a normalized score for the first biomarker based on the un-normalized score and the Z-score.

In some embodiments, determining therapy scores for the plurality of therapies comprises determining a first therapy score for a first therapy in the plurality of therapies as a sum of two or more scores in the set of normalized biomarker scores for the subject.

In some embodiments, determining therapy scores for the plurality of therapies comprises determining a first therapy score for a first therapy in the plurality of therapies at least in part by: determining weights for two or more scores in the set of normalized biomarker scores for the subject; and determining the first therapy score as a sum of the two or more scores, summands of the sum being weighted by the determined weights. In some embodiments, determining the weights comprises determining the weights using a machine learning technique. In some embodiments, determining the weights comprises determining the weights using a generalized linear model. In some embodiments, determining the weights comprises determining the weights using a logistic regression model.

In some embodiments, the plurality of therapies comprises a first therapy and a second therapy different from the first therapy, and wherein determining therapy scores for the plurality of therapies comprises: determining a first therapy score for the first therapy using a first subset of the set of normalized biomarker scores for the subject; and determining a second therapy score for the second therapy using a second subset of the set of normalized biomarker scores for the subject, wherein the second subset is different from the first subset.

Some embodiments include recommending at least one of the plurality of therapies for the subject based on the determined therapy scores. Some embodiments include ranking the plurality of therapies based on the determined therapy scores. In some embodiments, recommending the at least one of the plurality of therapies comprises: ranking the plurality of therapies based on the determined therapy scores; and recommending at least a threshold number of top-ranked therapies for the subject.

In some embodiments, the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy.

In some embodiments, the plurality of biomarkers associated with the anti-PD1 therapy comprises at least three biomarkers selected from the group of biomarkers associated with anti-PD1 therapy in Table 2. In some embodiments, determining the normalized biomarker scores for the subject comprises determining a normalized score for each of at least three biomarkers selected from the group of biomarkers associated with anti-PD1 therapy in Table 2.

In some embodiments, the plurality of biomarkers associated with the anti-CTLA4 therapy comprises at least three biomarkers selected from the group of biomarkers associated with anti-CTLA4 therapy in Table 2. In some embodiments, determining the normalized biomarker scores for the subject comprises determining a normalized score for each of at least three biomarkers selected from the group of biomarkers associated with anti-CTLA4 therapy in Table 2.

In some embodiments, the plurality of biomarkers associated with the IL-2 therapy comprises at least three biomarkers selected from the group of biomarkers associated with IL-2 therapy in Table 2. In some embodiments, determining the normalized biomarker scores for the subject comprises determining a normalized score for each of at least three biomarkers selected from the group of biomarkers associated with IL-2 therapy in Table 2.

In some embodiments, the plurality of biomarkers associated with the IFN alpha therapy comprises at least three biomarkers selected from the group of biomarkers associated with IFN alpha therapy in Table 2. In some embodiments, determining the normalized biomarker scores for the subject comprises determining a normalized score for each of at least three biomarkers selected from the group of biomarkers associated with IFN alpha therapy in Table 2.

In some embodiments, the plurality of biomarkers associated with the anti-cancer vaccine therapy comprises at least three biomarkers selected from the group of biomarkers associated with anti-cancer vaccine therapy in Table 2. In some embodiments, determining the normalized biomarker scores for the subject comprises determining a normalized score for each of at least three biomarkers selected from the group of biomarkers associated with anti-cancer vaccine therapy in Table 2.

In some embodiments, the plurality of biomarkers associated with the anti-angiogenic therapy comprises at least three biomarkers selected from the group of biomarkers associated with anti-angiogenic therapy in Table 2. In some embodiments, determining the normalized biomarker scores for the subject comprises determining a normalized score for each of at least three biomarkers selected from the group of biomarkers associated with anti-angiogenic therapy in Table 2.

In some embodiments, the plurality of biomarkers associated with the anti-CD20 therapy comprises at least three biomarkers selected from the group of biomarkers associated with anti-CD20 therapy in Table 2. In some embodiments, determining the normalized biomarker scores for the subject comprises determining a normalized score for each of at least three biomarkers selected from the group of biomarkers associated with anti-CD20 therapy in Table 2. In some embodiments, the anti-CD20 therapy is rituximab.

In some embodiments, the at least one visual characteristic comprises color of a GUI element and/or size of the GUI element.

In some embodiments, in response to receiving, via the GUI, a user selection of the first therapy, presenting, via the GUI, information about at least one biomarker with which at least one of the first plurality of GUI elements is associated.

In some embodiments, the first therapy is associated with a first therapy score and the second therapy is associated with a second therapy score, and wherein the first portion and the second portion are positioned, relative to one another in the GUI, based on relative magnitude of the first therapy score and the second therapy score.

In some embodiments, each of the plurality of biomarkers is selected from the group consisting of: a genetic biomarker, a cellular biomarker, a saccharide biomarker, a lipid biomarker, a heterocyclic biomarker, an elementary compound biomarker, an imaging biomarker, an anthropological biomarker, a personal habit biomarker, a disease-state biomarker, and an expression biomarker.

In some embodiments, the value of one or more genetic biomarkers is determined through the identification of one or more mutations, insertions, deletions, rearrangements, fusions, copy number variations (CNV), or single nucleotide variants (SNV) in the nucleic acid or protein of the genetic biomarker.

In some embodiments, the one or more genetic biomarkers includes a gene or marker described in the description and/or the figures.

In some embodiments, one or more genetic biomarkers are selected from the group consisting of: interferons, cytotoxic proteins, enzymes, cell adhesion proteins, extracellular matrix proteins and polysaccharides, cell growth factors, cell differentiation factors, transcription factors, and intracellular signaling proteins.

In some embodiments, the one or more genetic biomarkers is selected from the group consisting of: a cytokine, a chemokine, a chemokine receptor, and an interleukin.

In some embodiments, the value of one or more cellular biomarkers is determined through analysis of the number of one or more types of cells or the percentage of one or more types of cells within the biological sample.

In some embodiments, the one or more types of cells are selected from the group consisting of malignant cancerous cells, leukocytes, lymphocytes, stromal cells, vascular endothelial cells, vascular pericytes, and myeloid-derived suppressor cells (MDSCs).

In some embodiments, the value of one or more expression biomarkers is determined through analysis of the expression level or enzymatic activity of the nucleic acid or protein of the expression biomarker.

In some embodiments, the sequencing data is one or more of: DNA sequencing data, RNA sequencing data, or proteome sequencing data. In some embodiments, the sequencing data is obtained using one or more of the following techniques: whole genome sequencing (WGS), whole exome sequencing (WES), whole transcriptome sequencing, mRNA sequencing, DNA/RNA-hybridization, microarray, DNA/RNA chip, PCR, and single nucleotide polymorphism (SNP) genotyping.

In some embodiments, each of the at least one biological samples is a bodily fluid, a cell sample, a liquid biopsy, or a tissue biopsy. In some embodiments, the tissue biopsy comprises one or more samples from one or more tumors or tissues known or suspected of having cancerous cells.

In some embodiments, the biomarker information also comprises results from one or more of the following types of analyses: blood analysis, cytometry analysis, histological analysis, immunohistological analysis, and patient history analysis.

In some embodiments, each of the therapies are selected from the group consisting of: surgery, radiation therapy, chemotherapy, immunotherapy, viral therapy, targeted therapy, hormone therapy, transplants, phototherapy, cryotherapy, and hyperthermia.

In some embodiments, each of the therapies are selected from immunotherapy and targeted therapy.

In some embodiments, the therapy scores are indicative of response of the subject to administration of one therapy in the plurality of therapies. In some embodiments, the therapy scores are indicative of response of the subject to administration of multiple therapies in the plurality of therapies.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker, across a respective group of people, in at least a reference subset of the plurality of biomarkers, each of the plurality of biomarkers being associated with at least one therapy in a plurality of therapies; determining, using the sequencing data and the biomarker information: a first set of normalized biomarker scores for a first set of biomarkers associated with a first therapy in the plurality of therapies; and a second set of normalized biomarker scores for a second set of biomarkers associated with a second therapy in the plurality of therapies, wherein the first set of biomarkers is different from the second set of biomarkers; providing the first set of normalized biomarker scores as input to a statistical model to obtain a first therapy score for the first therapy; providing the second set of normalized biomarker scores as input to the statistical model to obtain a second therapy score for the second therapy; wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

In one aspect provided herein is at least one non-transitory computer-readable storage medium storing processor-executable instructions that, when executed by at least one computer hardware processor, cause the at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one therapy in a plurality of therapies; determining, using the sequencing data and the biomarker information: a first set of normalized biomarker scores for a first set of biomarkers associated with a first therapy in the plurality of therapies; and a second set of normalized biomarker scores for a second set of biomarkers associated with a second therapy in the plurality of therapies, wherein the first set of biomarkers is different from the second set of biomarkers; providing the first set of normalized biomarker scores as input to a statistical model to obtain a first therapy score for the first therapy; providing the second set of normalized biomarker scores as input to the statistical model to obtain a second therapy score for the second therapy; wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

In one aspect provided herein is a method, comprising using at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one therapy in a plurality of therapies; determining, using the sequencing data and the biomarker information: a first set of normalized biomarker scores for a first set of biomarkers associated with a first therapy in the plurality of therapies; and a second set of normalized biomarker scores for a second set of biomarkers associated with a second therapy in the plurality of therapies, wherein the first set of biomarkers is different from the second set of biomarkers; providing the first set of normalized biomarker scores as input to a statistical model to obtain a first therapy score for the first therapy; providing the second set of normalized biomarker scores as input to the statistical model to obtain a second therapy score for the second therapy; wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

In some embodiments, the plurality of biomarkers includes a first biomarker, and wherein determining a normalized score for each biomarker in at least the subject subset of the plurality of biomarkers comprises: determining a first normalized score for the first biomarker using the distribution of values for the first biomarker. In some embodiments, determining the first normalized score comprises: determining an un-normalized score for the first biomarker using the sequencing data; determining a Z-score based on the first distribution of values for the first biomarker; and determining a normalized score for the first biomarker based on the un-normalized score and the Z-score.

In some embodiments, determining therapy scores for the plurality of therapies comprises determining a first therapy score for a first therapy in the plurality of therapies as a sum of two or more scores in the set of normalized biomarker scores for the subject.

In some embodiments, determining therapy scores for the plurality of therapies comprises determining a first therapy score for a first therapy in the plurality of therapies at least in part by: determining weights for two or more scores in the set of normalized biomarker scores for the subject; and determining the first therapy score as a sum of the two or more scores, summands of the sum being weighted by the determined weights.

In some embodiments, determining the weights comprises determining the weights using a machine learning technique. In some embodiments, determining the weights comprises determining the weights using a generalized linear model. In some embodiments, determining the weights comprises determining the weights using a logistic regression model.

In some embodiments, the plurality of therapies comprises a first therapy and a second therapy different from the first therapy, and wherein determining therapy scores for the plurality of therapies comprises: determining a first therapy score for the first therapy using a first subset of the set of normalized biomarker scores for the subject; and determining a second therapy score for the second therapy using a second subset of the set of normalized biomarker scores for the subject, wherein the second subset is different from the first subset.

Some embodiments include recommending at least one of the plurality of therapies for the subject based on the determined therapy scores. In some embodiments, recommending the at least one of the plurality of therapies comprises: ranking the plurality of therapies based on the determined therapy scores; and recommending at least a threshold number of top-ranked therapies for the subject.

In some embodiments, determining the normalized biomarker scores for the subject comprises determining a normalized score for each of at least three biomarkers selected from the group of biomarkers associated with anti-PD1 therapy in Table 2.

In some embodiments, determining the normalized biomarker scores for the subject comprises determining a normalized score for each of at least three biomarkers selected from the group of biomarkers associated with anti-CTLA4 therapy in Table 2.

In some embodiments, determining the normalized biomarker scores for the subject comprises determining a normalized score for each of at least three biomarkers selected from the group of biomarkers associated with IL-2 therapy in Table 2.

In some embodiments, determining the normalized biomarker scores for the subject comprises determining a normalized score for each of at least three biomarkers selected from the group of biomarkers associated with IFN alpha therapy in Table 2.

In some embodiments, determining the normalized biomarker scores for the subject comprises determining a normalized score for each of at least three biomarkers selected from the group of biomarkers associated with anti-cancer vaccine therapy in Table 2.

In some embodiments, determining the normalized biomarker scores for the subject comprises determining a normalized score for each of at least three biomarkers selected from the group of biomarkers associated with anti-angiogenic therapy in Table 2.

In some embodiments, determining the normalized biomarker scores for the subject comprises determining a normalized score for each of at least three biomarkers selected from the group of biomarkers associated with anti-CD20 therapy in Table 2. In some embodiments, the anti-CD20 therapy is rituximab.

Some embodiments include generating a graphical user interface (GUI) comprising: a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and displaying the generated GUI.

In some embodiments, the at least one visual characteristic comprises color of a GUI element and/or size of the GUI element. Some embodiments include in response to receiving, via the GUI, a user selection of the first therapy, presenting, via the GUI, information about at least one biomarker with which at least one of the first plurality of GUI elements is associated.

In some embodiments, the first therapy is associated with a first therapy score and the second therapy is associated with a second therapy score, and wherein the first portion and the second portion are positioned, relative to one another in the GUI, based on relative magnitude of the first therapy score and the second therapy score.

In some embodiments, each of the plurality of biomarkers is selected from the group consisting of: a genetic biomarker, a cellular biomarker, a saccharide biomarker, a lipid biomarker, a heterocyclic biomarker, an elementary compound biomarker, an imaging biomarker, an anthropological biomarker, a personal habit biomarker, a disease-state biomarker, and an expression biomarker.

In some embodiments, the value of one or more genetic biomarkers is determined through the identification of one or more mutations, insertions, deletions, rearrangements, fusions, copy number variations (CNV), or single nucleotide variants (SNV) in the nucleic acid or protein of the genetic biomarker. In some embodiments, the one or more genetic biomarkers includes a gene or marker described in the description and/or the figures. In some embodiments, one or more genetic biomarkers are selected from the group consisting of: interferons, cytotoxic proteins, enzymes, cell adhesion proteins, extracellular matrix proteins and polysaccharides, cell growth factors, cell differentiation factors, transcription factors, and intracellular signaling proteins. In some embodiments, the one or more genetic biomarkers is selected from the group consisting of: a cytokine, a chemokine, a chemokine receptor, and an interleukin.

In some embodiments, the value of one or more cellular biomarkers is determined through analysis of the number of one or more types of cells or the percentage of one or more types of cells within the biological sample. In some embodiments, the one or more types of cells are selected from the group consisting of malignant cancerous cells, leukocytes, lymphocytes, stromal cells, vascular endothelial cells, vascular pericytes, and myeloid-derived suppressor cells (MDSCs).

In some embodiments, the value of one or more expression biomarkers is determined through analysis of the expression level or enzymatic activity of the nucleic acid or protein of the expression biomarker.

In some embodiments, the sequencing data is one or more of: DNA sequencing data, RNA sequencing data, or proteome sequencing data. In some embodiments, the sequencing data is obtained using one or more of the following techniques: whole genome sequencing (WGS), whole exome sequencing (WES), whole transcriptome sequencing, mRNA sequencing, DNA/RNA-hybridization, microarray, DNA/RNA chip, PCR, and single nucleotide polymorphism (SNP) genotyping.

In some embodiments, each of the at least one biological samples is a bodily fluid, a cell sample, a liquid biopsy, or a tissue biopsy. In some embodiments, the tissue biopsy comprises one or more samples from one or more tumors or tissues known or suspected of having cancerous cells.

In some embodiments, the biomarker information also comprises results from one or more of the following types of analyses: blood analysis, cytometry analysis, histological analysis, immunohistological analysis, and patient history analysis.

In some embodiments, each of the therapies are selected from the group consisting of: surgery, radiation therapy, chemotherapy, immunotherapy, viral therapy, targeted therapy, hormone therapy, transplants, phototherapy, cryotherapy, and hyperthermia. In some embodiments, each of the therapies are selected from immunotherapy and targeted therapy.

In some embodiments, the therapy scores are indicative of response of the subject to administration of one therapy in the plurality of therapies. In some embodiments, the therapy scores are indicative of response of the subject to administration of multiple therapies in the plurality of therapies.

In one aspect provided herein is a system, comprising: at least one computer hardware processor; at least one database that stores biomarker information; and at least one non-transitory computer-readable storage medium storing processor-executable instructions that, when executed by the at least one computer hardware processor, cause the at least one computer hardware processor to perform: obtaining sequencing data about at least one biological sample of a subject; accessing, in the at least one database, biomarker information indicating a distribution of values for each biomarker, across a respective group of people, in at least a reference subset of the plurality of biomarkers, each of the plurality of biomarkers being associated with at least one candidate therapy; determining, using the sequencing data and the biomarker information, a normalized score for each biomarker in at least a subject subset of the plurality of biomarkers to obtain a set of normalized biomarkers for the subject; identifying the subject as a member of one or more cohorts based on the set of normalized biomarker scores for the subject, wherein each of the one or more cohorts is associated with a positive or negative outcome of the at least one candidate therapy; and outputting an indication of the one or more cohorts in which the subject is a member.

In one aspect provided herein is at least one non-transitory computer-readable storage medium storing processor-executable instructions that, when executed by at least one computer hardware processor, cause the at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one candidate therapy; determining, using the sequencing data and the biomarker information, a normalized score for each biomarker in at least a subject subset of the plurality of biomarkers to obtain a set of normalized biomarkers for the subject; identifying the subject as a member of one or more cohorts based on the set of normalized biomarker scores for the subject, wherein each of the one or more cohorts is associated with a positive or negative outcome of the at least one candidate therapy; and outputting an indication of the one or more cohorts in which the subject is a member.

In one aspect a method comprising using at least one computer hardware processor to perform: obtaining sequencing data about at least one biological sample of a subject; accessing, in at least one database, biomarker information indicating a distribution of values for each biomarker, across a respective group of people, in at least a reference subset of the plurality of biomarkers, each of the plurality of biomarkers being associated with at least one candidate therapy; determining, using the sequencing data and the biomarker information, a normalized score for each biomarker in at least a subject subset of the plurality of biomarkers to obtain a set of normalized biomarkers for the subject; identifying the subject as a member of one or more cohorts based on the set of normalized biomarker scores for the subject, wherein each of the one or more cohorts is associated with a positive or negative outcome of the at least one candidate therapy; and outputting an indication of the one or more cohorts in which the subject is a member.

In some embodiments, the at least one candidate therapy is associated with a clinical trial, optionally wherein the clinical trial is ongoing or the clinical trial is recruiting.

In some embodiments, the positive outcome is an improvement in one or more aspects of a cancer or in one or more cancer symptoms.

In some embodiments, the improvement in one or more aspects of a cancer or one or more cancer symptoms is selected from the group consisting of: decrease in tumor size, decrease in tumor number, decrease in number or percentage of cancerous cells in the body of the subject, and slowing of cancer growth.

In some embodiments, the negative outcome is a cancer therapy-related adverse effect, an deterioration in one or more aspects of a cancer, or a deterioration in one or more cancer symptoms.

In some embodiments, the cancer therapy-related adverse effect is selected from: cutaneous toxicity, thrombocytopenia, hepatotoxicity, neurotoxicity, nephrotoxicity, cardiotoxicity, hemorrhagic cystitis, immune-related toxicity, and death.

In some embodiments, the deterioration in one or more aspects of a cancer or one or more cancer symptoms is selected from the group consisting of: increase in tumor size, increase in tumor number, increase in number or percentage of cancerous cells in the body of the subject, no slowing of cancer growth, and death.

In some embodiments, the sequencing data is one or more of: DNA sequencing data, RNA sequencing data, or proteome sequencing data. In some embodiments, the sequencing data is obtained using one or more of the following techniques: whole genome sequencing (WGS), whole exome sequencing (WES), whole transcriptome sequencing, mRNA sequencing, DNA/RNA-hybridization, microarray, DNA/RNA chip, PCR, and single nucleotide polymorphism (SNP) genotyping.

In some embodiments, the biological sample is from a tumor or tissue known or suspected of having cancerous cells. In some embodiments, each of the at least one biological samples is a bodily fluid, a cell sample, a liquid biopsy, or a tissue biopsy. In some embodiments, the biological sample is blood.

Some embodiments include generating a graphical user interface (GUI) comprising: a first portion associated with the at least one candidate therapy, the first portion including a first plurality of GUI elements, each of the first plurality of GUI elements being associated with a respective biomarker in the plurality of biomarkers and having at least one visual characteristic determined based on a difference score of the respective biomarker; and displaying the generated GUI. In some embodiments, the at least one visual characteristic comprises color of a GUI element and/or size of the GUI element. Some embodiments include in response to receiving, via the GUI, a user selection of the at least one candidate therapy, presenting, via the GUI, information about at least one biomarker with which at least one of the first plurality of GUI elements is associated.

EQUIVALENTS AND SCOPE

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the technology described herein need not reside on a single computer or processor, but may be distributed in a modular fashion among different computers or processors to implement various aspects of the technology described herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as an example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the described methods and systems encompass all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the systems and methods described herein (or aspects thereof) are referred to as comprising particular elements and/or features, certain embodiments of the systems and methods or aspects of the same consist, or consist essentially of, such elements and/or features. For purposes of simplicity, those embodiments have not been specifically set forth in haec verba herein.

It is also noted that the terms "including," "comprising," "having," "containing", "involving", are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the described systems and methods, to the tenth of the unit of the lower limit of the range, unless the context clearly dictates otherwise.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

Additionally, as used herein the terms "patient" and "subject" may be used interchangeably. Such terms may include, but are not limited to, human subjects or patients. Such terms may also include non-human primates or other animals.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that fall within the prior art may be explicitly excluded from any one or more of the claims. Because such embodiments are deemed to be known to one of ordinary skill in the art, they may be excluded even if the exclusion is not set forth explicitly herein. Any particular embodiment of the systems and methods described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:

1. A system, comprising:
   at least one computer hardware processor;
   at least one database that stores biomarker information; and
   at least one non-transitory computer-readable storage medium storing processor-executable instructions that, when executed by the at least one computer hardware processor, cause the at least one computer hardware processor to perform:
      obtaining sequencing data about at least one biological sample of a subject;
      accessing, in the at least one database, biomarker information indicating a distribution of values for each biomarker, across a respective group of people, in at least a reference subset of the plurality of biomarkers, each of the plurality of biomarkers being associated with at least one therapy in a plurality of therapies;
      determining, using the sequencing data and the biomarker information:
         a first set of normalized biomarker scores for a first set of biomarkers associated with a first therapy in the plurality of therapies; and
         a second set of normalized biomarker scores for a second set of biomarkers associated with a second therapy in the plurality of therapies, wherein the first set of biomarkers is different from the second set of biomarkers;
      providing the first set of normalized biomarker scores as input to a statistical model to obtain a first therapy score for the first therapy; and
      providing the second set of normalized biomarker scores as input to the statistical model to obtain a second therapy score for the second therapy;
   wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

2. The system of claim 1, wherein the plurality of biomarkers includes a first biomarker, and wherein determining a normalized score for each biomarker in at least the subject subset of the plurality of biomarkers comprises:
   determining a first normalized score for the first biomarker using the distribution of values for the first biomarker.

3. The system of claim 2, wherein determining the first normalized score comprises:
   determining an un-normalized score for the first biomarker using the sequencing data;
   determining a Z-score based on the first distribution of values for the first biomarker; and determining a normalized score for the first biomarker based on the un-normalized score and the Z-score.

4. The system of claim 1, wherein determining therapy scores for the plurality of therapies comprises determining a first therapy score for a first therapy in the plurality of therapies as a sum of two or more scores in the set of normalized biomarker scores for the subject.

5. The system of claim 1, wherein determining therapy scores for the plurality of therapies comprises determining a first therapy score for a first therapy in the plurality of therapies at least in part by:
   determining weights for two or more scores in the set of normalized biomarker scores for the subject; and
   determining the first therapy score as a sum of the two or more scores, summands of the sum being weighted by the determined weights.

6. The system of claim 5, wherein determining the weights comprises determining the weights using a generalized linear model.

7. The system of claim 6, wherein determining the weights comprises determining the weights using a logistic regression model.

8. The system of claim 1, wherein the plurality of therapies comprises a first therapy and a second therapy different from the first therapy, and wherein determining therapy scores for the plurality of therapies comprises:
  determining a first therapy score for the first therapy using a first subset of the set of normalized biomarker scores for the subject; and
  determining a second therapy score for the second therapy using a second subset of the set of normalized biomarker scores for the subject,
  wherein the second subset is different from the first subset.

9. The system of claim 1, wherein the processor-executable instructions further cause the at least one processor to perform:
  recommending at least one of the plurality of therapies for the subject based on the determined therapy scores.

10. The system of claim 9, wherein recommending the at least one of the plurality of therapies comprises:
  ranking the plurality of therapies based on the determined therapy scores; and
  recommending at least a threshold number of top-ranked therapies for the subject.

11. The system of claim 1, wherein determining the normalized biomarker scores for the subject comprises determining a normalized score for each of at least three biomarkers selected from the group of biomarkers associated with anti-PD1 therapy in Table 2.

12. The system of claim 1, wherein determining the normalized biomarker scores for the subject comprises determining a normalized score for each of at least three biomarkers selected from the group of biomarkers associated with anti-CTLA4 therapy in Table 2.

13. The system of claim 1, wherein determining the normalized biomarker scores for the subject comprises determining a normalized score for each of at least three biomarkers selected from the group of biomarkers associated with IL-2 therapy in Table 2.

14. The system of claim 1, wherein determining the normalized biomarker scores for the subject comprises determining a normalized score for each of at least three biomarkers selected from the group of biomarkers associated with IFN alpha therapy in Table 2.

15. The system of claim 1, wherein determining the normalized biomarker scores for the subject comprises determining a normalized score for each of at least three biomarkers selected from the group of biomarkers associated with anti-cancer vaccine therapy in Table 2.

16. The system of claim 1, wherein determining the normalized biomarker scores for the subject comprises determining a normalized score for each of at least three biomarkers selected from the group of biomarkers associated with anti-angiogenic therapy in Table 2.

17. The system of claim 1, wherein determining the normalized biomarker scores for the subject comprises determining a normalized score for each of at least three biomarkers selected from the group of biomarkers associated with anti-CD20 therapy in Table 2.

18. The system of claim 1, wherein the processor-executable instructions further cause the at least one processor to perform:
  generating a graphical user interface (GUI) comprising:
    a first portion associated with a first therapy in the plurality of therapies, the first portion including a first plurality of GUI elements, each of the first plurality of GUI elements being associated with a respective biomarker in the plurality of biomarkers and having at least one visual characteristic determined based on a normalized score of the respective biomarker in the first set of normalized scores; and
    a second portion associated with a second therapy in the plurality of therapies, the second portion including a second plurality of GUI elements different from the first plurality of GUI elements, each of the second plurality of GUI elements being associated with a respective biomarker in the plurality of biomarkers and having at least one visual characteristic determined based on a normalized score of the respective biomarker in the second set of normalized scores; and
  displaying the generated GUI.

19. The system of claim 18, wherein the at least one visual characteristic comprises color of a GUI element and/or size of the GUI element.

20. The system of claim 18, wherein the processor-executable instructions further cause the at least one processor to perform:
  in response to receiving, via the GUI, a user selection of the first therapy, presenting, via the GUI, information about at least one biomarker with which at least one of the first plurality of GUI elements is associated.

21. The system of claim 18, wherein the first therapy is associated with a first therapy score and the second therapy is associated with a second therapy score, and wherein the first portion and the second portion are positioned, relative to one another in the GUI, based on relative magnitude of the first therapy score and the second therapy score.

22. The system of claim 1, wherein each of the plurality of biomarkers is selected from the group consisting of: a genetic biomarker, a cellular biomarker, a saccharide biomarker, a lipid biomarker, a heterocyclic biomarker, an elementary compound biomarker, an imaging biomarker, an anthropological biomarker, a personal habit biomarker, a disease-state biomarker, and an expression biomarker.

23. The system of claim 1, wherein each of the therapies are selected from immunotherapy and targeted therapy.

24. The system of claim 1, wherein the therapy scores are indicative of response of the subject to administration of one therapy in the plurality of therapies.

25. At least one non-transitory computer-readable storage medium storing processor-executable instructions that, when executed by at least one computer hardware processor, cause the at least one computer hardware processor to perform:
  obtaining sequencing data about at least one biological sample of a subject;
  accessing, in at least one database, biomarker information indicating a distribution of values for each biomarker, across a respective group of people, in at least a reference subset of the plurality of biomarkers, each of the plurality of biomarkers being associated with at least one therapy in a plurality of therapies;
  determining, using the sequencing data and the biomarker information:
    a first set of normalized biomarker scores for a first set of biomarkers associated with a first therapy in the plurality of therapies; and
    a second set of normalized biomarker scores for a second set of biomarkers associated with a second therapy in the plurality of therapies, wherein the first set of biomarkers is different from the second set of biomarkers;
  providing the first set of normalized biomarker scores as input to a statistical model to obtain a first therapy score for the first therapy; and providing the second set of normalized biomarker scores as input to the statistical model to obtain a second therapy score for the second therapy;

wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

26. The at least one non-transitory computer-readable storage medium of claim 25, wherein the plurality of biomarkers includes a first biomarker, and wherein determining a normalized score for each biomarker in at least the subject subset of the plurality of biomarkers comprises:

determining a first normalized score for the first biomarker using the distribution of values for the first biomarker.

27. The at least one non-transitory computer-readable storage medium of claim 26, wherein determining the first normalized score comprises:

determining an un-normalized score for the first biomarker using the sequencing data; determining a Z-score based on the first distribution of values for the first biomarker; and determining a normalized score for the first biomarker based on the un-normalized score and the Z-score.

28. A method, comprising:
using at least one computer hardware processor to perform:
    obtaining sequencing data about at least one biological sample of a subject;
    accessing, in at least one database, biomarker information indicating a distribution of values for each biomarker, across a respective group of people, in at least a reference subset of the plurality of biomarkers, each of the plurality of biomarkers being associated with at least one therapy in a plurality of therapies;
    determining, using the sequencing data and the biomarker information:
        a first set of normalized biomarker scores for a first set of biomarkers associated with a first therapy in the plurality of therapies; and
        a second set of normalized biomarker scores for a second set of biomarkers associated with a second therapy in the plurality of therapies, wherein the first set of biomarkers is different from the second set of biomarkers;
    providing the first set of normalized biomarker scores as input to a statistical model to obtain a first therapy score for the first therapy; and
    providing the second set of normalized biomarker scores as input to the statistical model to obtain a second therapy score for the second therapy;
wherein the plurality of therapies comprise at least two therapies selected from the group consisting of: an anti-PD1 therapy, an anti-CTLA4 therapy, an IL-2 therapy, an IFN alpha therapy, an anti-cancer vaccine therapy, an anti-angiogenic therapy, and an anti-CD20 therapy, and wherein the plurality of biomarkers associated with each of the plurality of therapies comprises at least three biomarkers selected from the group of biomarkers associated with the respective therapy in Table 2.

29. The method of claim 28, wherein the plurality of biomarkers includes a first biomarker, and wherein determining a normalized score for each biomarker in at least the subject subset of the plurality of biomarkers comprises:

determining a first normalized score for the first biomarker using the distribution of values for the first biomarker.

30. The method of claim 29, wherein determining the first normalized score comprises:

determining an un-normalized score for the first biomarker using the sequencing data; determining a Z-score based on the first distribution of values for the first biomarker; and determining a normalized score for the first biomarker based on the un-normalized score and the Z-score.

* * * * *